(12) United States Patent
Scolastico et al.

(10) Patent No.: US 8,609,685 B2
(45) Date of Patent: Dec. 17, 2013

(54) SMAC MIMETIC COMPOUNDS AS APOPTOSIS INDUCERS

(75) Inventors: Carlo Scolastico, Milan (IT); Leonardo Pierpaolo Manzoni, Milan (IT); Pierfausto Seneci, Milan (IT); Laura Belvisi, Milan (IT); Domenico Delia, Milan (IT); Martino Bolognesi, Milan (IT); Eloise Mastrangelo, Milan (IT); Mario De Mayo De Mari Milani, Milan (IT); Ilaria Motto, Milan (IT); Carmelo Drago, Milan (IT)

(73) Assignee: CISI SCRL, Milan (IT)

( * ) Notice: Subject to any disclaimer, the term of this patent is extended or adjusted under 35 U.S.C. 154(b) by 484 days.

(21) Appl. No.: 12/741,862

(22) PCT Filed: Nov. 5, 2008

(86) PCT No.: PCT/IB2008/002971
§ 371 (c)(1),
(2), (4) Date: Jun. 24, 2010

(87) PCT Pub. No.: WO2009/060292
PCT Pub. Date: May 14, 2009

(65) Prior Publication Data
US 2010/0267692 A1    Oct. 21, 2010

(30) Foreign Application Priority Data
Nov. 9, 2007 (EP) ..................................... 07021843

(51) Int. Cl.
| | | |
|---|---|---|
| *A01N 43/42* | (2006.01) |
| *A01N 43/00* | (2006.01) |
| *A61K 31/44* | (2006.01) |
| *A61K 31/55* | (2006.01) |
| *C07D 451/00* | (2006.01) |
| *C07D 453/00* | (2006.01) |
| *C07D 455/00* | (2006.01) |

(52) U.S. Cl.
USPC .......................... 514/294; 514/212.07; 546/94

(58) Field of Classification Search
USPC .................................. 514/294, 212.07; 546/94
See application file for complete search history.

(56) References Cited

FOREIGN PATENT DOCUMENTS

WO    WO 2005/069894    8/2005

OTHER PUBLICATIONS

International Search Report for PCT/IB2008/002971, mailed Apr. 28, 2009.
Written Opinion of the International Searching Authority for PCT/IB2008/002971, mailed Apr. 28, 2009.

*Primary Examiner* — Samira Jean-Louis
(74) *Attorney, Agent, or Firm* — Nixon & Vanderhye P.C.

(57) ABSTRACT

The present invention relates to compounds conformationally constrained mimetics of Smac with function as inhibitors of Inhibitor of Apoptosis Proteins (IAPs), the invention also relates to the use of these compounds in therapy, wherein the induction of apoptotic cell death is beneficial, especially in the treatment of cancer, alone or in combination with other active ingredients.

19 Claims, No Drawings

SMAC MIMETIC COMPOUNDS AS APOPTOSIS INDUCERS

This application is the U.S. national phase of International Application No. PCT/IB2008/002971 filed 5 Nov. 2008, which designated the U.S. and claims priority to EP Application No. 07021843.3 filed 9 Nov. 2007, the entire contents of each of which are hereby incorporated by reference.

FIELD OF THE INVENTION

The present invention relates to compounds conformationally constrained mimetics of Smac with function as inhibitors of Inhibitor of Apoptosis Proteins (IAPs). The invention also relates to the use of these compounds in therapy, wherein the induction of apoptotic cell death is beneficial, especially in the treatment of cancer, alone or in combination with other active ingredients.

TECHNICAL BACKGROUND

Apoptosis is absolutely necessary for human development and survival, with millions of cells committing suicide daily as a way to prevent uncontrolled growth. Defects in apoptosis, together with amplified growth signals, often lead to cancer. Targeting apoptosis defects in cancer has a tremendous potential.

The first human apoptotic protein identified was BCL-2, as inhibitor of apoptosis, in 1984. The role of caspases-proteases that act as the cell's direct executioners by cleaving other cellular proteins was revealed in humans beginning in 1993. In cell ready to die, pro-apoptotic BCL-2 family members, like BAX, disrupt mitochondria, causing the release of other proteins that lead to caspase release and cell death. Activation of this so-called "intrinsic" apoptotic pathway is the goal of many of the new cancer drugs.

A second, "extrinsic", cell death pathway is also an important target, and the first so-called death receptor, DR4, was discovered around 1996.

Most of the current cancer therapies, including chemotherapeutic agents, radiation, and immunotherapy, work by indirectly inducing apoptosis in cancer cells. The inability of cancer cells to execute an apoptotic program due to defects in the normal apoptotic machinery is thus often associated with an increase in resistance to chemotherapy, radiation or immunotherapy-induced apoptosis.

In this regard, targeting crucial negative regulators that play a central role in directly inhibiting apoptosis in cancer cells represents a highly promising therapeutic strategy for new anticancer drug design.

Two classes of central negative regulators of apoptosis have been identified. The first class is the Bcl-2 family of proteins (Adams et al., Science 281:1322, 1998; Reed, Adv. Pharmacol. 41:501, 1997; Reed et al., J. Cell. Biochem. 60:23, 1996). Currently, Bcl-2 antisense therapy is in several Phase III clinical trias for the treatment of solid and not solid tumors.

The second class of central negative regulators of apoptosis is the inhibitor of apoptosis proteins (IAPs) (Deveraux et al., Genes Dev. 13:239, 1999; Salvesen et al., Nat. Rev. Mol. Cell. Biol. 3:401, 2002). IAPs potently suppress apoptosis induced by a large variety of apoptotic stimuli, including chemotherapeutic agents, radiation, and immunotherapy in cancer cells.

X-linked IAP (XIAP) is the most potent inhibitor in suppressing apoptosis among all of the IAP members (Holcik et al., Apoptosis 6:253, 2001; LaClasse et al., Oncogene 17:3247, 1998; Takahashi et al., J. Biol. Chem. 273:7787, 1998; Deveraux et al., Nature 388:300, 1997; Sun et al., Nature 401:818, 1999; Deveraux et al., EMBO J. 18:5242, 1999; Asselin et al., Cancer Res. 61:1862, 2001). XIAP plays a key role in the negative regulation of apoptosis in both the death receptor-mediated and the mitochondria-mediated pathways. XIAP functions as a potent endogenous apoptosis inhibitor by directly binding and potently inhibiting three members of the caspase family enzymes, caspase-3, -7, and -9 (Takahashi et al., J. Biol. Chem. 273:7787, 1998; Deveraux et al., Nature 388:300, 1997; Sun et al., Nature 401:818, 1999; Deveraux et al., EMBO J. 18:5242; Asselin et al., Cancer Res. 61:1862, 2001; Riedl et al., Cell 104:791, 2001; Chai et al., Cell 104:769, 2001; Huang et al., Cell 104:781, 2001). XIAP contains three baculovirus inhibitor of apoptosis repeat (BIR) domains. The third BIR domain (BIR3) selectively targets caspase-9, the initiator caspase in the mitochondrial pathway, whereas the linker region between BIR1 and BIR2 inhibits both caspase-3 and caspase-7 (Salvesen et al., Nat. Rev. Mol. Cell. Biol. 3:401, 2002). While binding to XIAP prevents the activation of all three caspases, it is apparent that the interaction with caspase-9 is the most critical for its inhibition of apoptosis (Ekert et al., J. Cell Biol. 152:483, 2001; Srinivasula et al., Nature 410:112, 2001). Because XIAP blocks apoptosis at the downstream effector phase, a point where multiple signalling pathways converge, strategies targeting XIAP may prove to be especially effective to overcome resistance of cancer cells to apoptosis (Fulda et al., Nature Med. 8:808, 2002; Arnt et al., J. Biol. Chem. 277:44236.2002).

There are evidence to indicate that XIAP is widely overexpressed in many types of cancer and may ply an important role in the resistance of cancer cells to a variety of current therapeutic agents (Holcik et al., Apoptosis 6:253, 2001; LaClasse et al., Oncogene 17:3247, 1998).

Recently, Smac/DIABLO (second mitochondria-derived activator of caspases) was identified as a protein released from mitochondria into the cytosol in response to apoptotic stimuli (Budihardjo et al., Annu. Rev. Cell Dev. Biol. 15:269, 1999; Due t al., Cell 102:33, 2000). Smac is synthesized with an N-terminal mitochondrial targeting sequence that is proteolytically removed durino maturation to the mature polipeptide. Smac was shown to directly interact with XIAP and other IAPs and to disrupt their binding to caspases and facilitate caspases activation. Smac is a potent endogenous inhibitor of XIAP.

Smac/DIABLO interacts with both the BIR2 and BIR3 domains of XIAP (Chai. J. et al. Nature 406:855, 2000). The crystal structure of Smac/DIABLO reveals that it forms a homodimer through a large, hydrophobic interface, and that homodimerization is essential for its binding to the BIR2, but not BIR3, domain of XIAP (Chai. J. et al. Nature 406:855, 2000). The four amino-terminal residues of Smac/DIABLO (Ala-Val-Pro-Ile) make specific contact with a surface groove of the BIR2 and BIR3 domains, but not with the BIR1 domain, of XIAP (Wu, G. et at Nature 408:1008, 2000; Liu, Z. et al. Nature 408:1004, 2000). Significantly, the conserved tetrapeptide motif has remarkable homology to the IAP-interacting motif found in the p12 amino-terminal sequence of caspase-9 (Ala-Thr-Pro-Phe) and the *Drosophila* proteins Hid (Ala-Val-Pro-Phe), Reaper (Ala-Val-Ala-Phe) and Grim (Ala-Ile-Ala-Tyr).

The Kd value of Smac peptide AVPI to XIAP (Kd=0.4 μM) is essentially the same as the mature Smac protein (Kd=0.42 μM).

OBJECTS OF THE INVENTION

One object of the present invention is to overcome the intrinsic limitations of peptide-based inhibitors by providing non-peptidic compounds based on conformationally constrained azabicyclo alkanes as dipeptide mimics. Another object of the present invention is to provide non-peptide, small molecules that mimic the binding of Smac to XIAP.

DESCRIPTION OF THE INVENTION

According to one of its aspects, a first subject-matter of the present invention is a compound of formula (I)

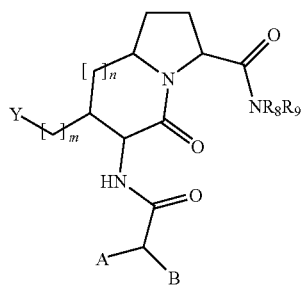

(I)

or a pharmaceutically acceptable salt or prodrug thereof, wherein:
n is 1 or 2
m is an integer from 0 to 3
A is $NR_1R_2$, or $N^+R_1R_2R_3$
$R_1$, $R_2$ and $R_3$ are, each independently,
  hydrogen;
  $C_{1-8}$ alkyl or heteroalkyl; $C_{2-8}$ alkenyl or heteroalkenyl; $C_{2-8}$ alkynyl or heteroalkynyl;
  optionally substituted aryl, alkylaryl, heteroaryl, alkylheteroaryl;
  or
  any two of $R_1$, $R_2$, and $R_3$ taken together with the nitrogen to which they are attached form a heterocyclic group, optionally substituted by one or more oxo, thioxo, and optionally comprising a heteroatom selected from O, S, and N, provided that the heteroatom is separated from the nitrogen atom by a least two carbon atoms;

$R_4$ and $R_5$ are each independently
  hydrogen;
  $C_{1-4}$ alkyl or heteroalkyl; $C_{2-5}$ alkenyl or heteroalkenyl; $C_{2-5}$ alkynyl or heteroalkynyl;
  optionally substituted aryl, alkylaryl, heteroaryl, or alkylheteroaryl;
B is
  $C_{1-4}$ alkyl; $C_{2-4}$ alkenyl; $C_{2-4}$ alkynyl;
  aryl, alkylaryl, heteroaryl or alkylheteroaryl; all optionally substituted by one or more halogen;
Y is selected among $OR_6$, $NHR_6$, $NR_6R_7$, $NH-S(O)_2-R_6$, $N^+(R_6)_3$, $SR_6$, $N_3$, $C(O)OR_6$, $CN$, $C(S)OR_6$, $C(S)NHR_6$, $C(NH)NHR_6$, $NH(CNH)NHR_6$, $NH(CS)NHR_6$, $NH(CO)NHR_6$ or

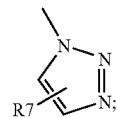

or
Y is a group of formula (II), (III) or (IV):

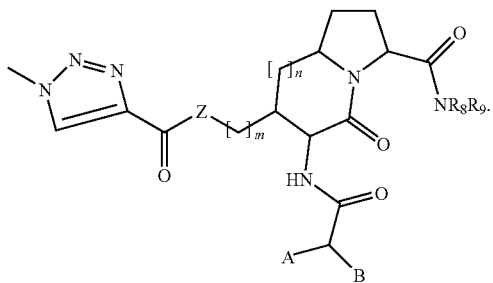

(II)

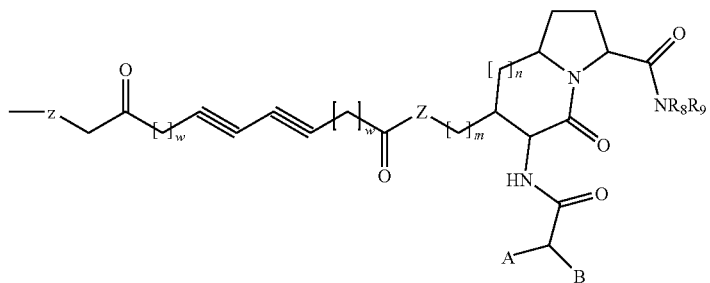

(III)

-continued

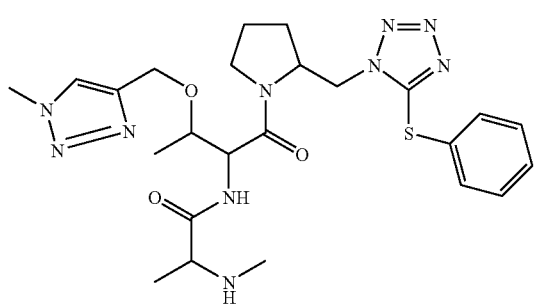

(IV)

wherein A, B, n and m are, each independently, as previously defined; and each z is independently O, NH or S; each w is independently an integer from 1 to 4;

$R_6$ is
  hydrogen;
  optionally substituted $C_{1-8}$ alkyl; $C_{2-8}$ alkenyl; $C_{2-8}$ alkynyl;
  optionally substituted aryl; heteroaryl;

$R_7$ is
  optionally substituted $C_{1-8}$ alkyl; $C_{2-8}$ alkenyl; or $C_{2-8}$ alkynyl;
  optionally substituted aryl or heteroaryl.

$R_8$ and $R_9$ are each independently
  hydrogen;
  optionally substituted $C_{1-18}$ alkyl; $C_{2-18}$ alkenyl; $C_{2-18}$ alkynyl;
  optionally substituted aryl; heteroaryl.

According to another of its aspects, the present invention also relates to a compound of formula (V)

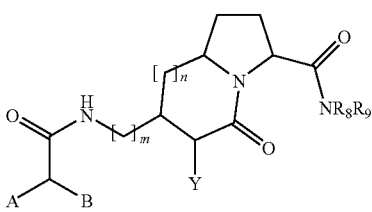

(V)

or a pharmaceutically acceptable salt or prodrug thereof, wherein the substituents are as previously defined.

According to the present invention, the terms "heteroalkyl", "heteroalkenyl", "heteroalkynyl" and "heteroaryl" define alky, alkenyl, alkynyl and aryl groups, respectively, wherein one or more carbon atoms are replaced by a heteroatom selected among O, S and N.

According to the present invention, the alkyl, alkenyl, alkynyl groups can be linear or branched; such groups may be for example methyl, ethyl, propyl, isopropyl, butyl, tert-butyl, ethenyl, propenyl, isopropenyl, butenyl, isobutenyl, hexenyl, ethynyl, propynyl, butynyl.

Unless otherwise indicated, alkyl groups are lower alkyl groups, i.e. they have 1 to 6 carbon atoms and alkenyl and alkynyl groups are lower alkenyl and alkynyl groups, i.e. they have 2 to 6 carbon atoms.

According to the present invention, the term "optionally substituted", if not expressly defined, means that any substitution is possible, provided that the resulting molecule is chemically stable. Preferably, unless otherwise indicated, the expression "optionally substituted" means that the designated groups may be optionally substituted for instance by alkyl, cycloalkyl, optionally substituted aryl, alkylaryl, heteroaryl, alkylheteroaryl, $OR_4$, $SR_4$, $NR_4R_5$ or $COOR_4$.

According to another preferred embodiment, the optionally substituted alkyl, heteroalkyl, alkenyl, heteroalkenyl, alkynyl, heteroalkynyl, alkylaryl or alkylheteroaryl groups are substituted on the aliphatic chains by oxo or thioxo groups.

According to another preferred embodiment, A is $NH_2$ or —NH-Alkyl or —N(Alkyl)$_2$.

According to another preferred embodiment, B is an alkyl group, more preferably ethyl or an optionally substituted alkylaryl group, such as a benzyl group.

According to another preferred embodiment, n is 2.

According to another preferred embodiment, m is 1.

According to another preferred embodiment, m is 2.

The expression "each independently" means that each designated groups represents any of the given definitions and can therefore be equal or different to the others.

According to another preferred embodiment, $NR_8R_9$ is a NH-alkyl group, said alkyl being preferably substituted by one or more aryl group, such as for instance a benzhydrilamino group, i.e. a group of formula

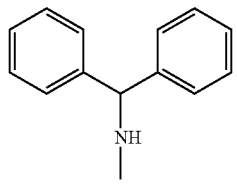

When Y is a radical of formula (II) or (III), the resulting compound of formula (I) is a "dimer", said compound may be either "heterodimeric" or "homodimeric"; that is to say, the substituents on the two structures may be equal or different.

The compounds of the invention present some chiral carbons and therefore may exist in the form of racemates or diastereoisomers, all being encompassed by the scope of the invention.

According to a preferred embodiment, the present invention relates to compounds of formula (I) having the following configuration

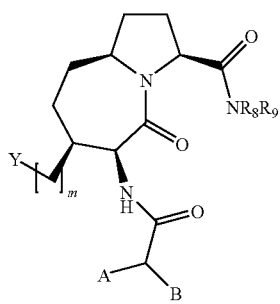

wherein the substituents are as defined above and the wedge-shaped bonds indicate that the substituents are positioned above the plane.

According to another preferred embodiment, when Y is a group of formula (II), the resulting compound of formula (I) has the following configuration

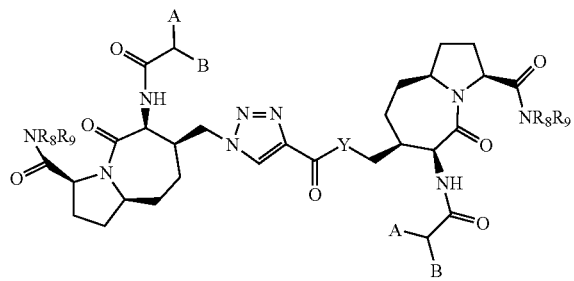

wherein the substituents are as defined above and the wedge-shaped bonds indicate that the substituents are positioned above the plane.

According to another preferred embodiment, when Y is a group of formula (III), the resulting compound of formula (I) has the following configuration

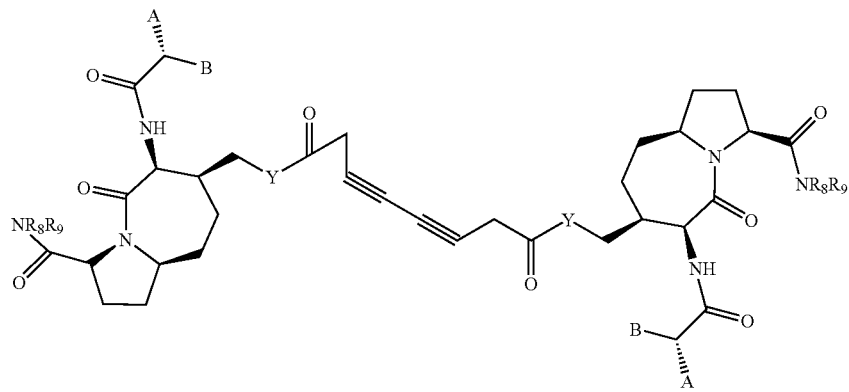

wherein the substituents are as defined above and the wedge-shaped bonds indicate that the substituents are positioned above the plane.

According to another preferred embodiment, when Y is a group of formula (IV), the resulting compound of formula (I) has the following configuration:

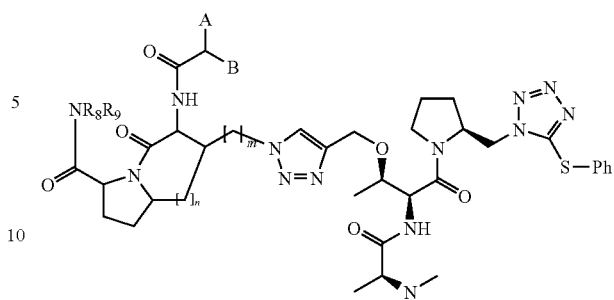

and more preferably the following, configuration:

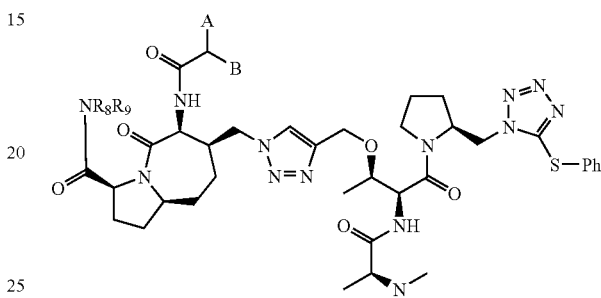

wherein the substituents are as defined above and the wedge-shaped bonds indicate that the substituents are positioned above the plane.

According to the present invention the term "prodrug" means that compounds of the invention are in the form of a precursor of the active ingredient, said precursor being metabolized after administration to the active compound of formula (I).

According to another of its aspects, the present invention also relates to a compound of formula (VI)

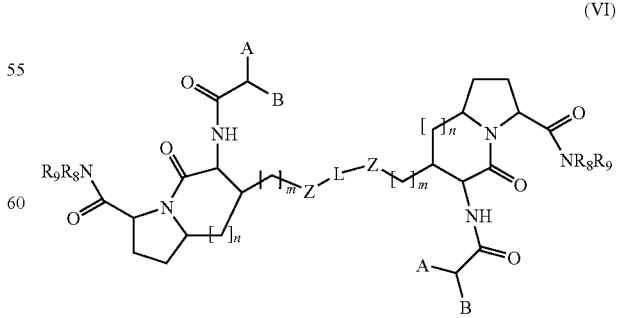

(VI)

or a pharmaceutically acceptable salt or prodrug thereof, wherein the substituents are as previously defined and L is a "linker", preferably a linker as listed in Table I.

TABLE 1
| LINKER | | |
|---|---|---|
| A1 | 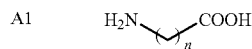 | |
| | n = 1-6, 11 | |
| A2 |  | |
| | n = 1-4 | |
| A3 | 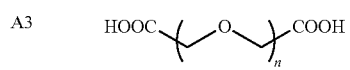 | |
| | n = 1-3 | |
| A4 | 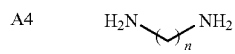 | |
| | n = 2-6 | |
| A5 | 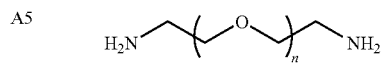 | |
| | n = 1-5 Tetrahedron Lett. 1998, 39, 6277; Makromol. Chem. 1979, 180, 2539. | |
| A6 | 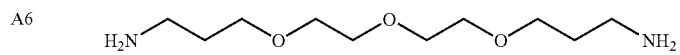 | |
| A7 | 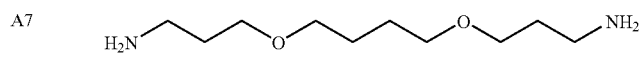 | |
| A8 |  | |
| | n = 1-4; J. Org. Chem. 2001, 66, 4799; Org. Prep. Proced. Int. 2002, 34, 326 | |
| A9 |  | |
| | n = 1-6; Bioconjugate Chem. 1999, 10, 1021. | |
| A10 | 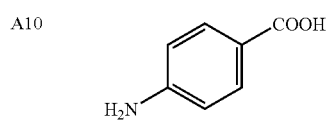 | |
| A11 | 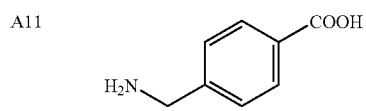 | |
| A12 | 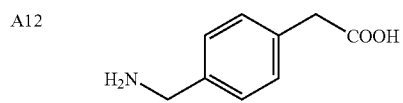 | |
| A13 | 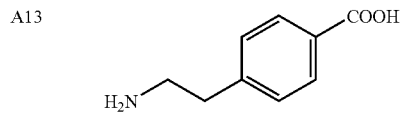 | |
| A14 | 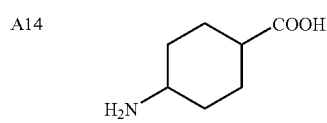 | |

TABLE 1-continued
| LINKER | |
|---|---|
| A15 | 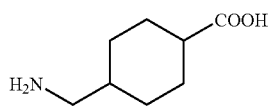 |
| A16 | 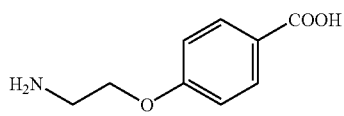 [SMILES: NCCOc1ccc(C(=O)O)cc1] |
| A17 | 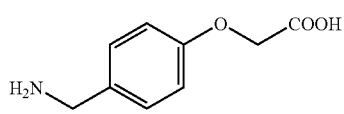 [SMILES: NCc1ccc(OCC(=O)O)cc1] |
| A18 | 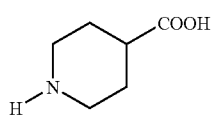 |
| A19 |  |
| A20 | 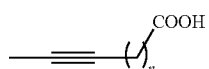<br>n = 0-4 |
| A21 | 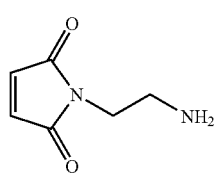<br>Bioconjugate Chem. 1990, 1, 431 |
| A22 | 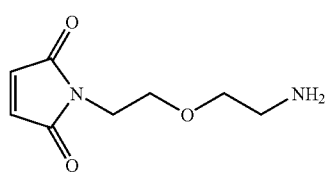<br>Bioconjugate Chem. 1990, 1, 431 |
| A23 | 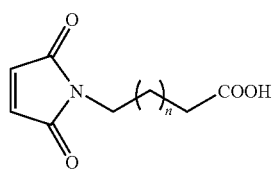<br>n = 0-3 |
| A24 | 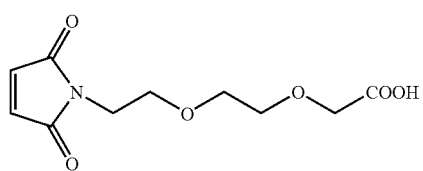<br>Bioconjugate Chem. 1996, 7, 180 |

TABLE 1-continued

| LINKER | | |
|---|---|---|
| A25 | H₂N~~O~~O~~O~~N₃ | |
| | J. Org. Chem. 1991, 56, 4326 | |
| A26 | HOOC~~O~~O~~O~~N₃ | |
| | Bioconjugate Chem. 1999, 10, 1021. | |
| A27 | HOOC~~O~~O~~O~~O~~N₃ | |
| | Bioconjugate Chem. 2000, 11, 14. | |
| A28 | HS−(−)$_n$−COOH | |
| | n = 0-1 | |
| A29 | HS~~O~~O~~COOH | |
| | Bioconjugate Chem. 1996, 7, 180 | |
| A30 | HS~~O~~O~~NH₂ | |
| | Tetrahedron 1997, 53, 10939 | |
| A31 | HS~~NH₂ | |

Alternatively, said linker may be obtained from a suitable combination thereof thus providing modified and/or elongated compounds such as, for example,

A32

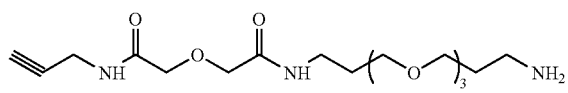

Most of the linkers of table 1 are well known and commercially available from, for example, Aldrich Neosystem and Peptides International catalogues. The other linkers may be easily prepared according to known methods, for example as per the accompanying bibliographic references. Details are given in the experimental section of this description.

Illustrative preferred embodiments of the invention are the following compounds:

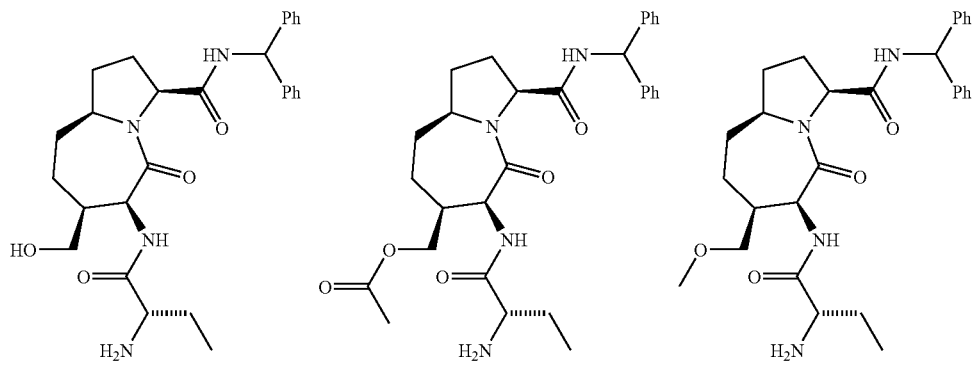

-continued
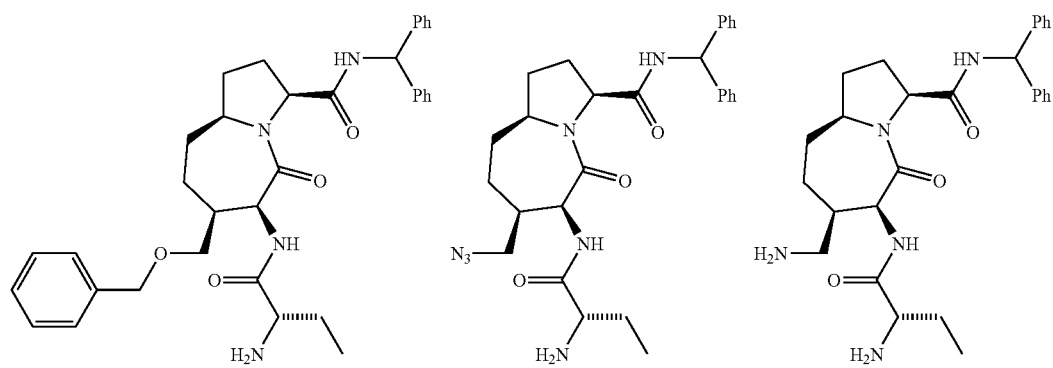
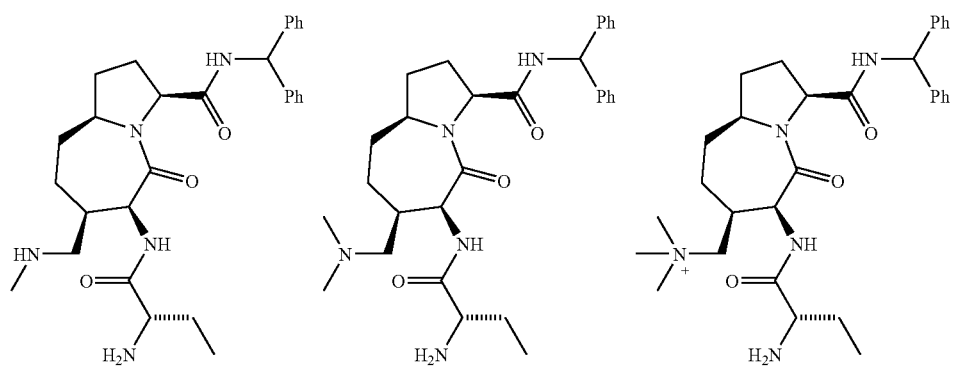
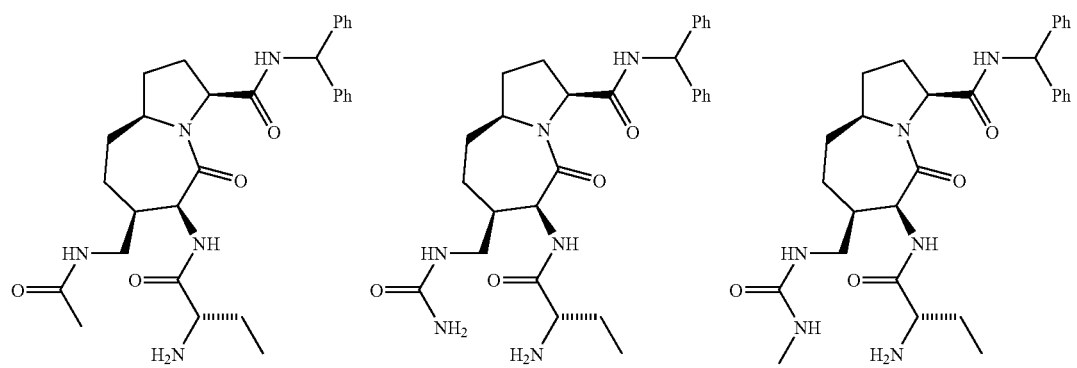
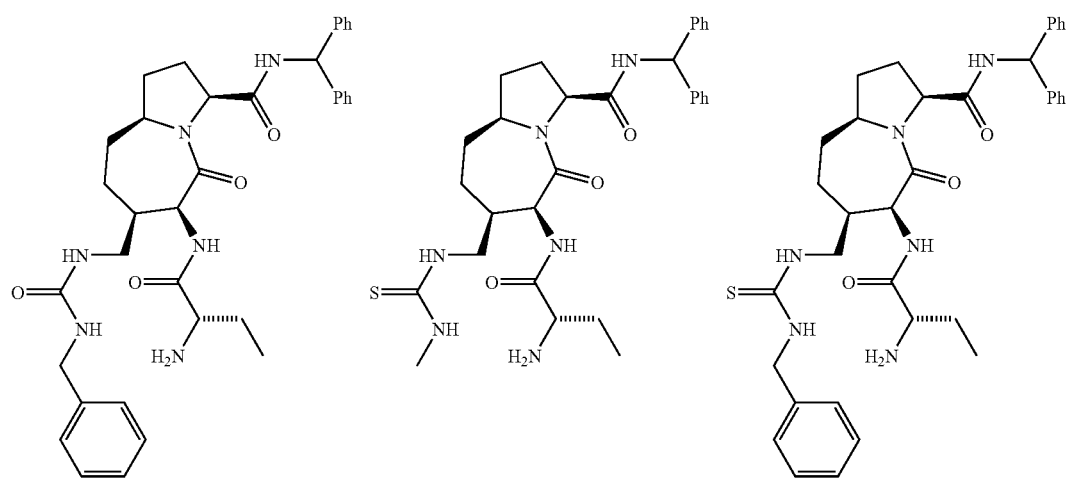

-continued
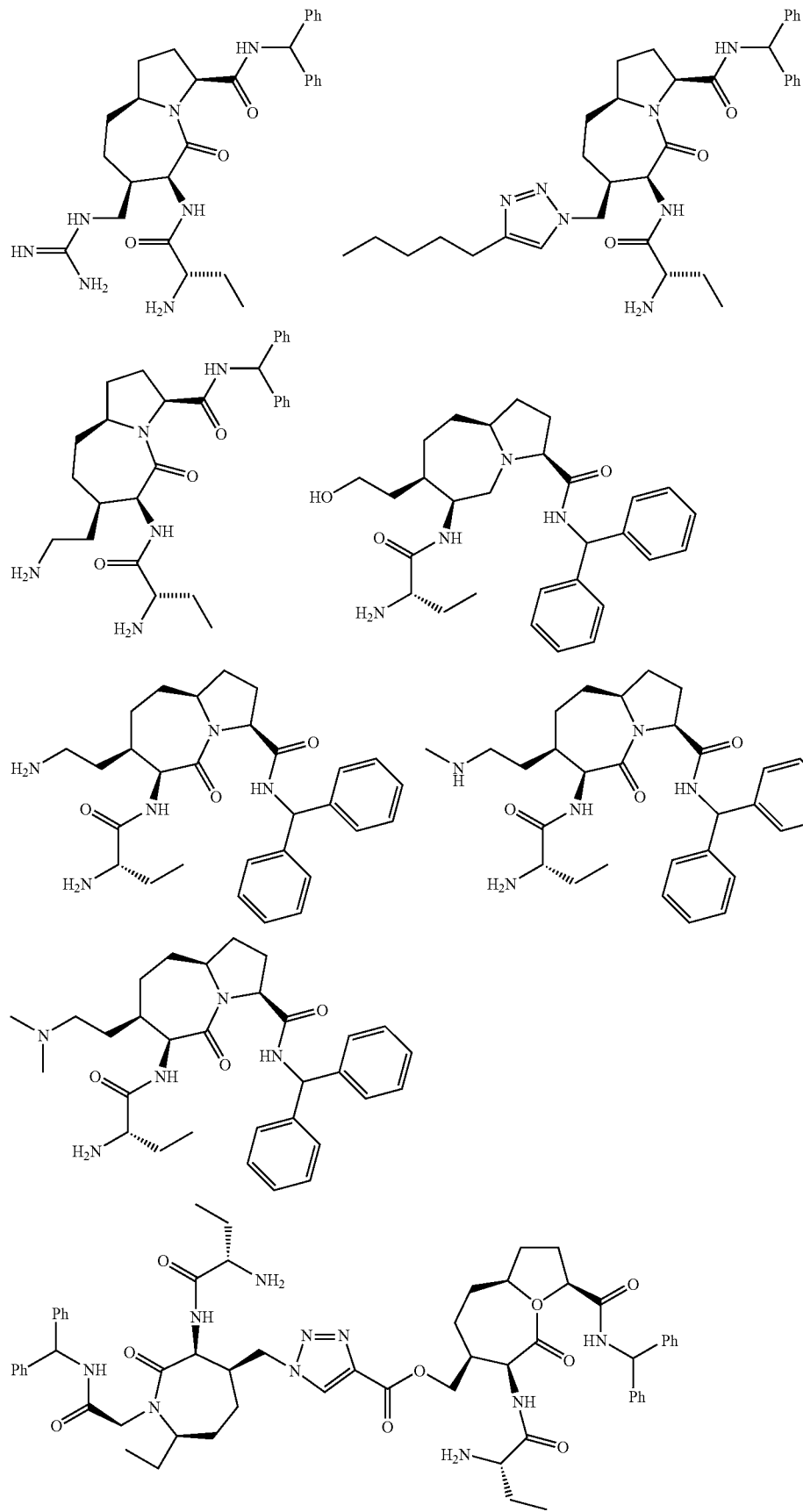

-continued
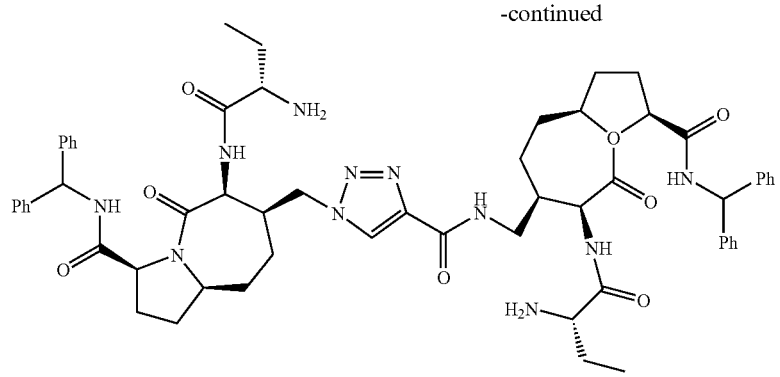
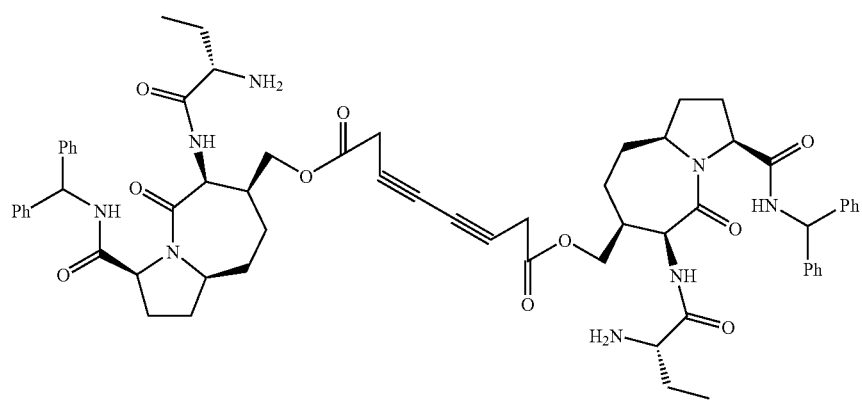
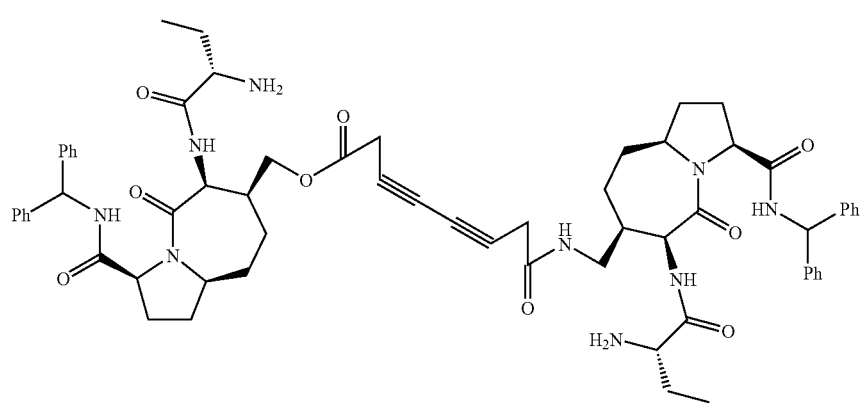
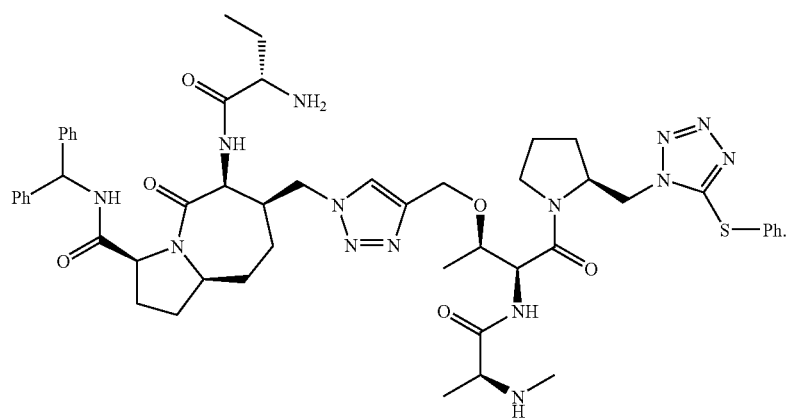

Other preferred compounds are those of the following table
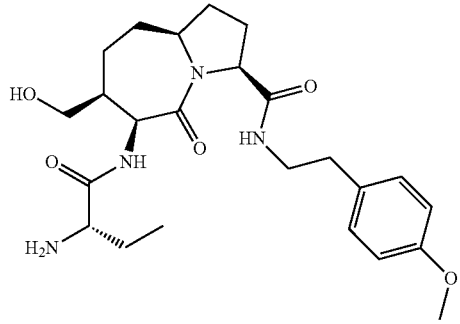
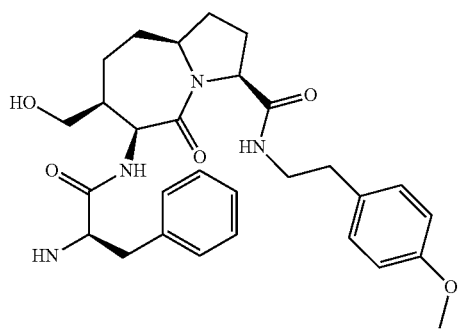
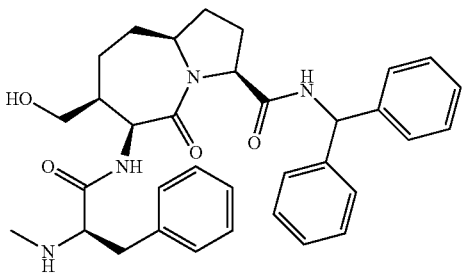
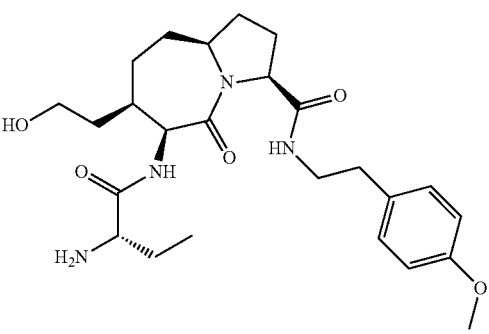
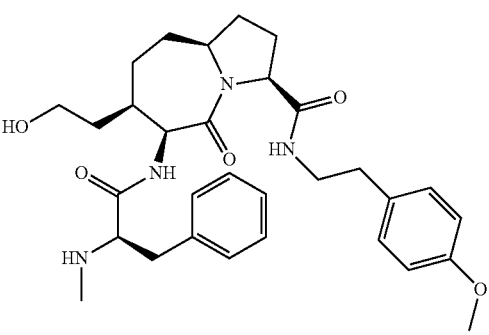
-continued
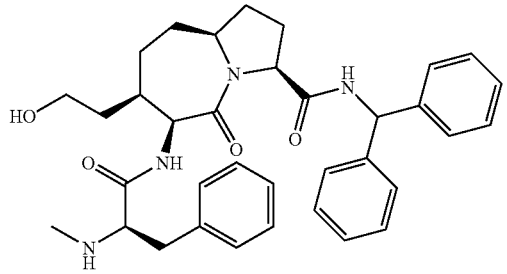
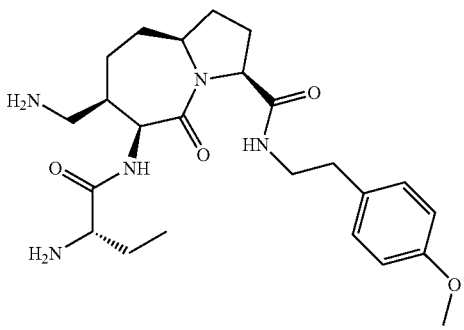
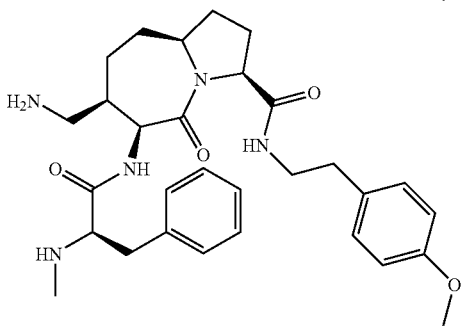
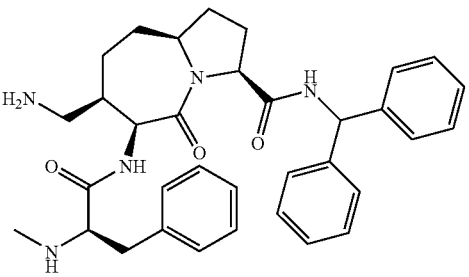
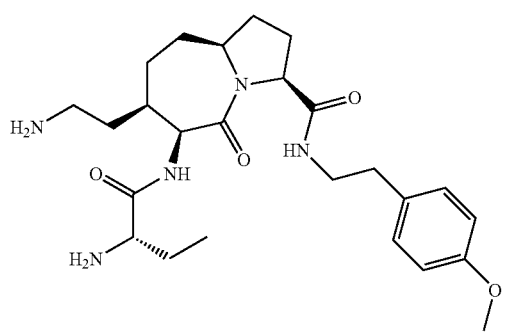

23
-continued
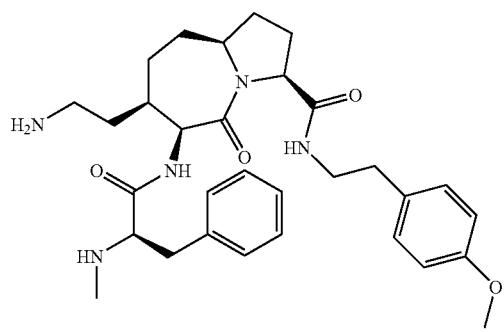
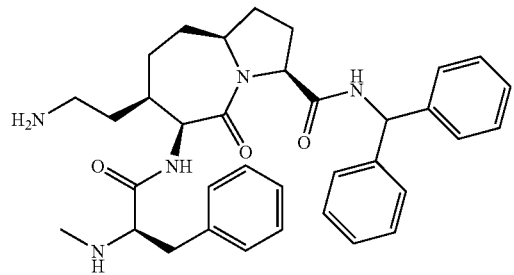
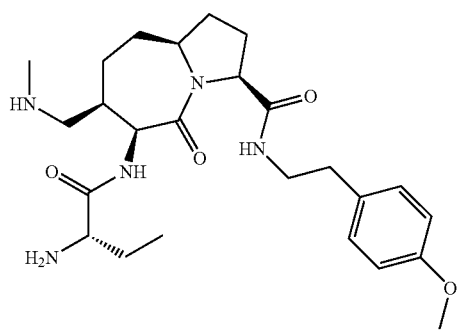
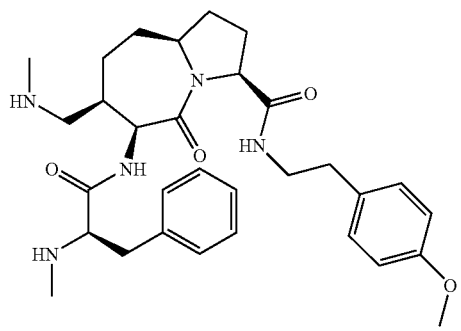
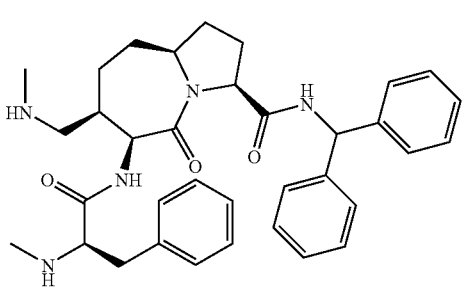
24
-continued
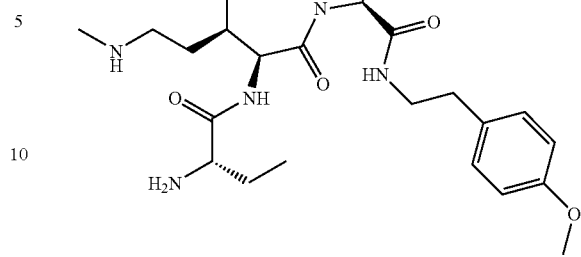
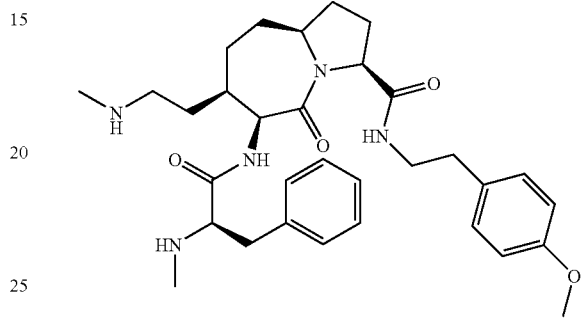
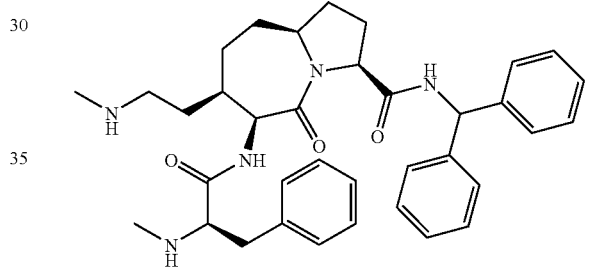
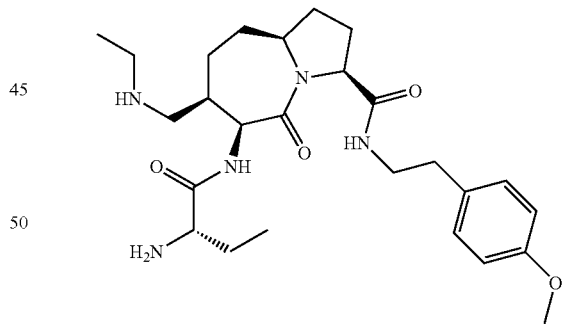
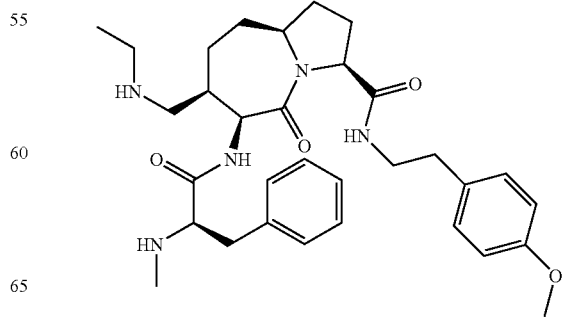

25
-continued
26
-continued
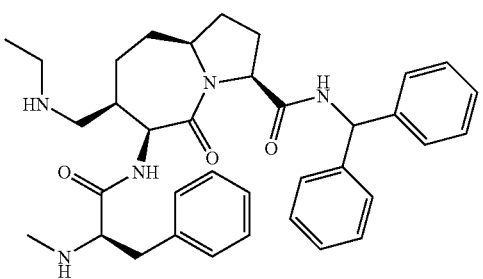
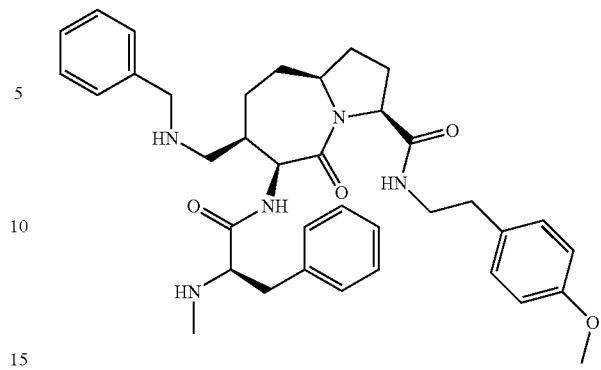
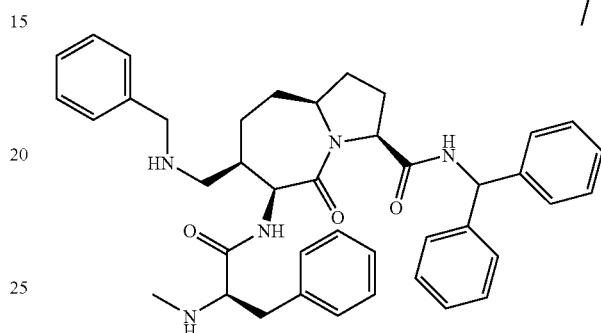
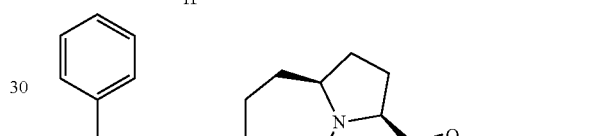
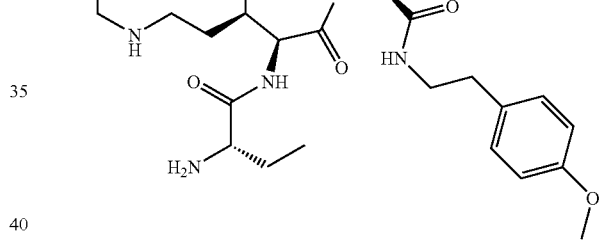
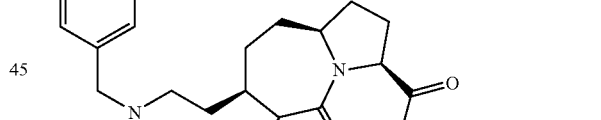
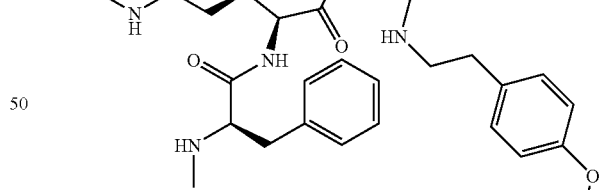
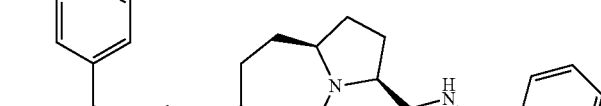
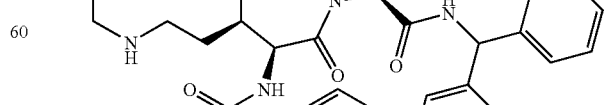
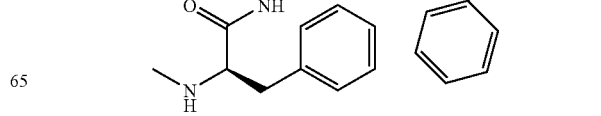

27
-continued
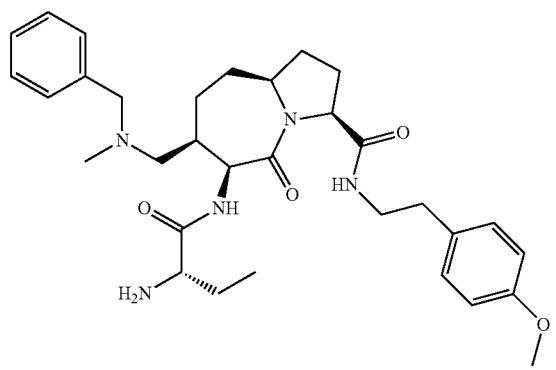
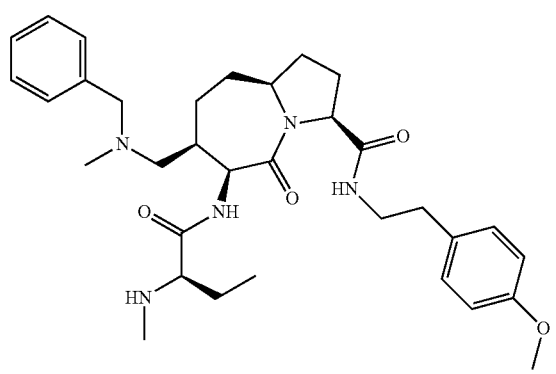
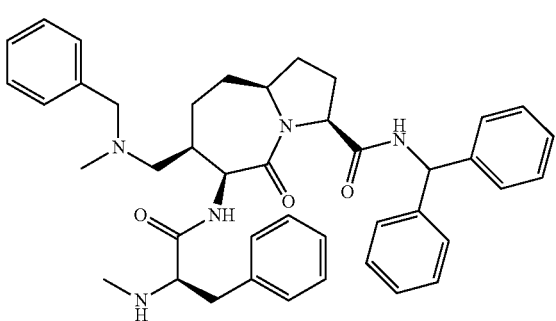
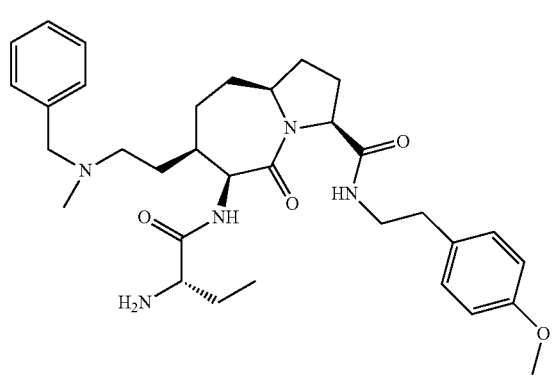
28
-continued
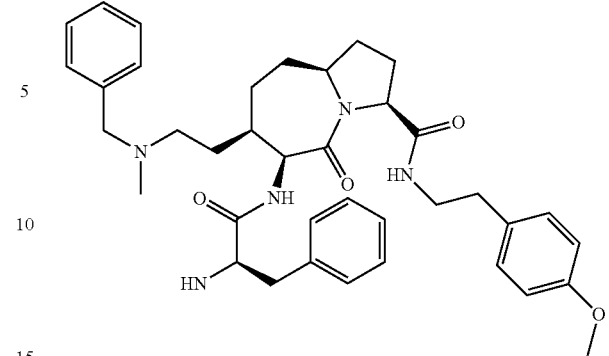
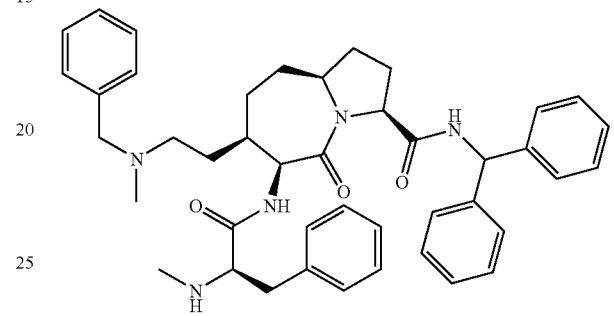
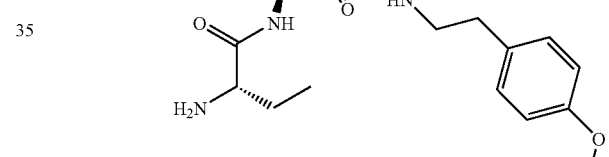
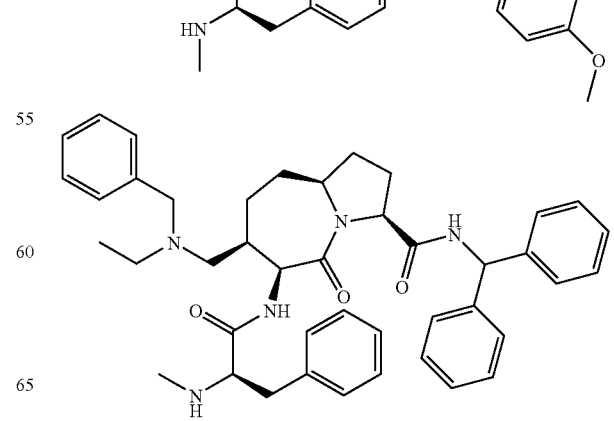

29
-continued
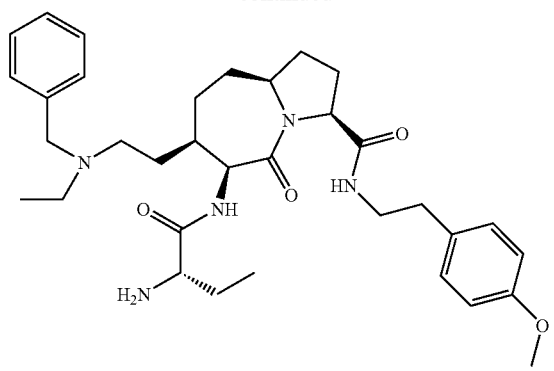
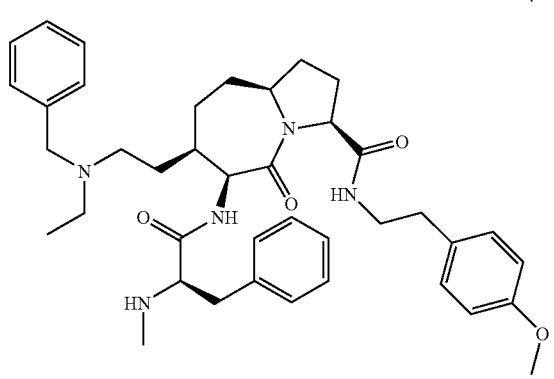
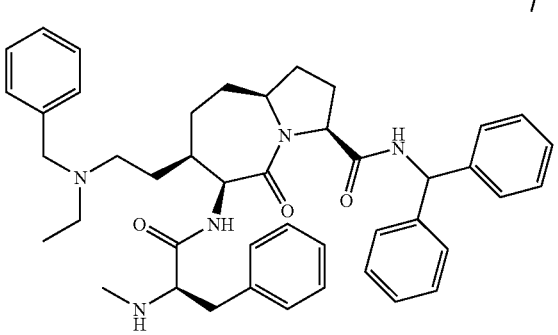
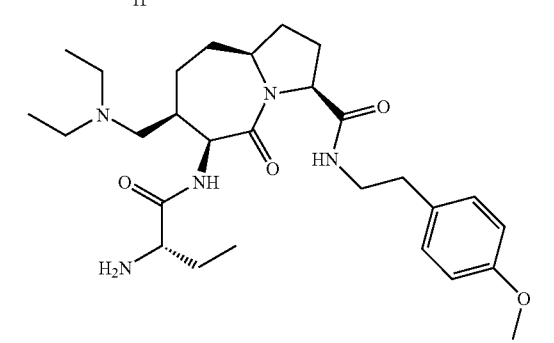
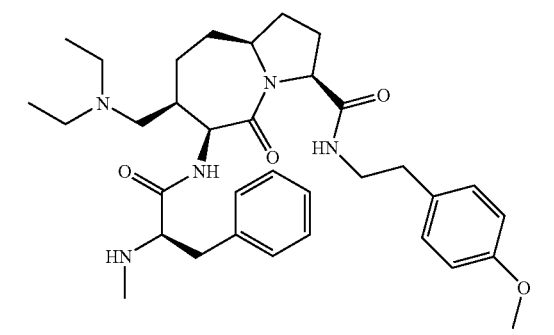
30
-continued
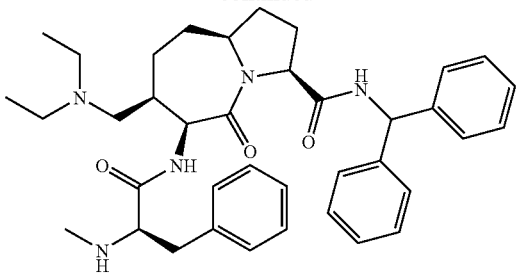
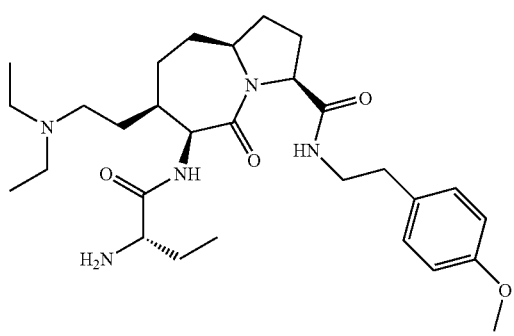
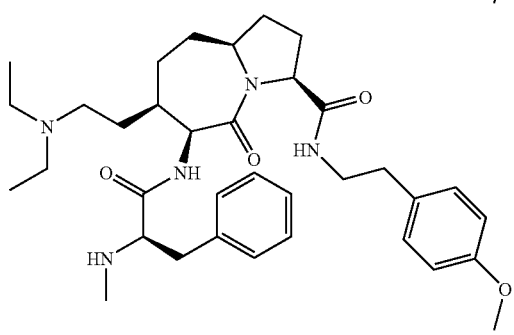
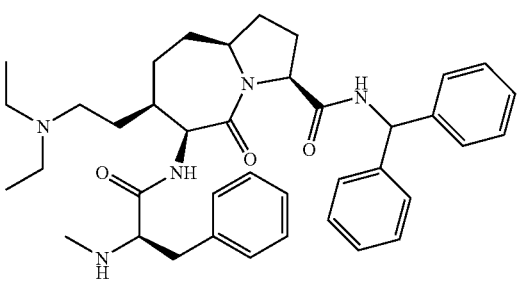
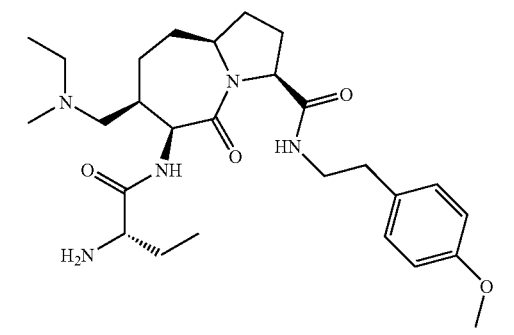

31
-continued
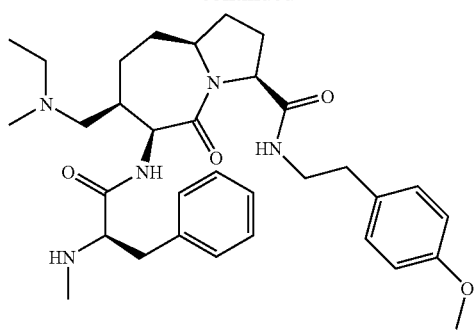
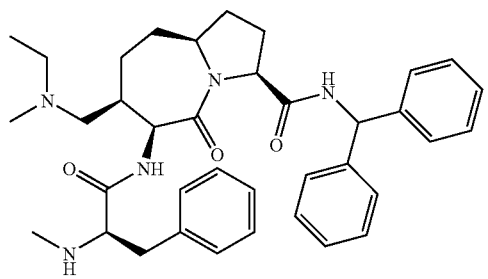
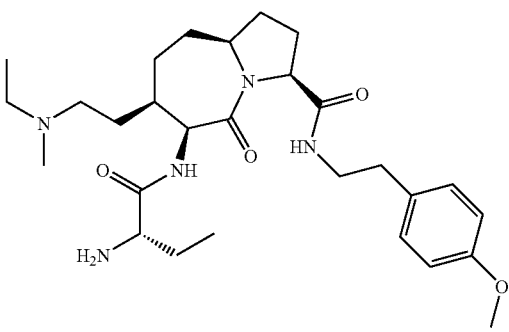
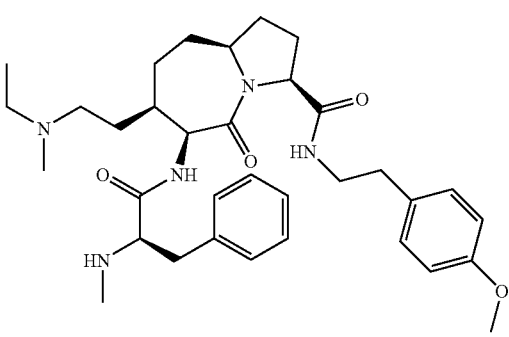
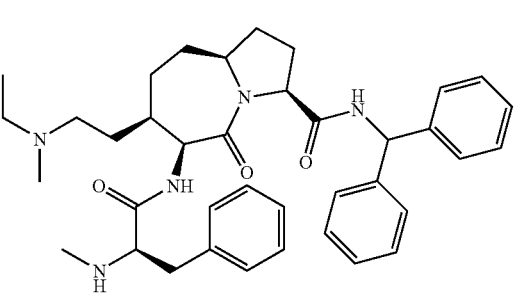
32
-continued
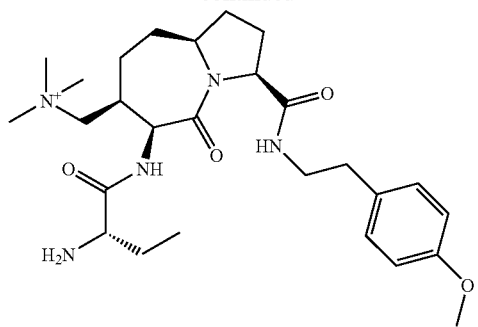
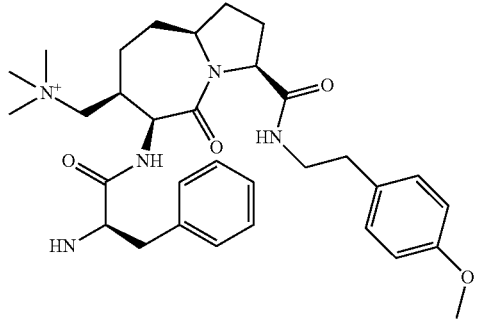
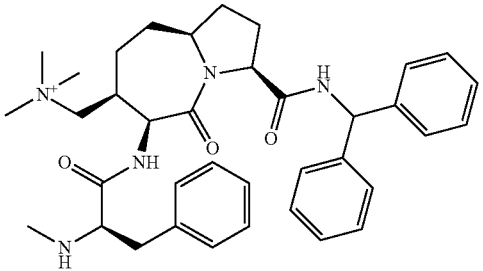
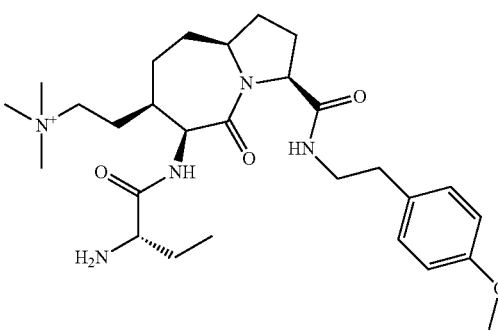
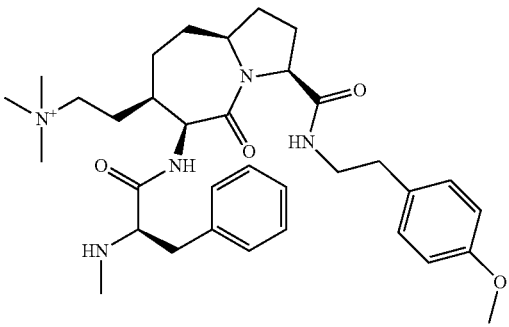

| 33 | 34 |
|---|---|
| 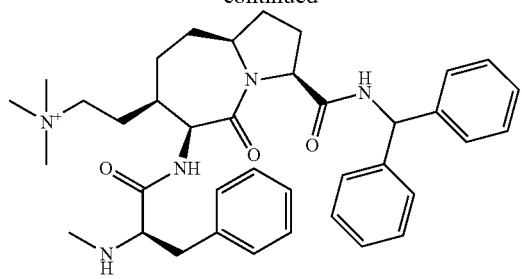 | 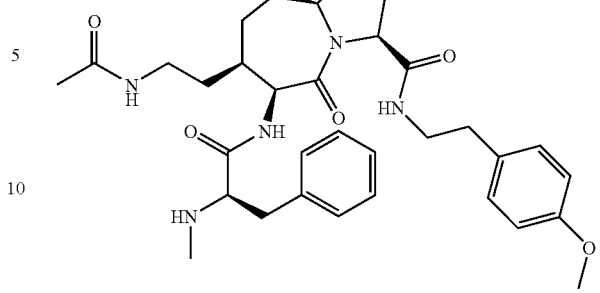 |
| 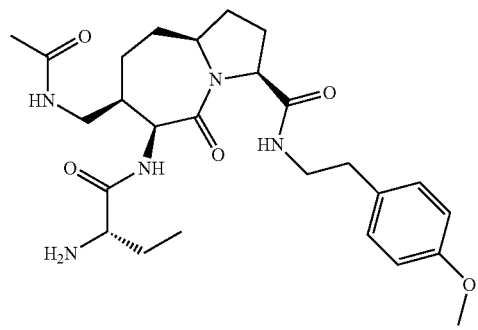 | 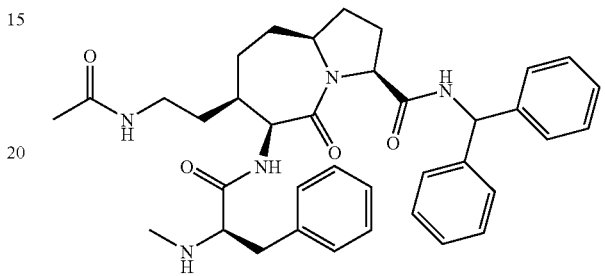 |
| 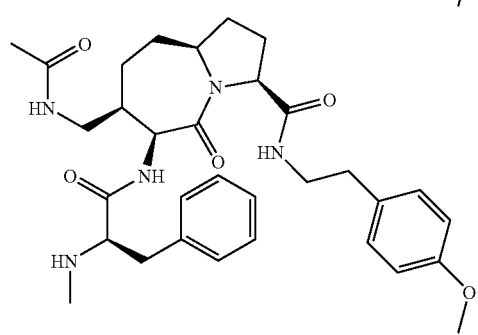 | 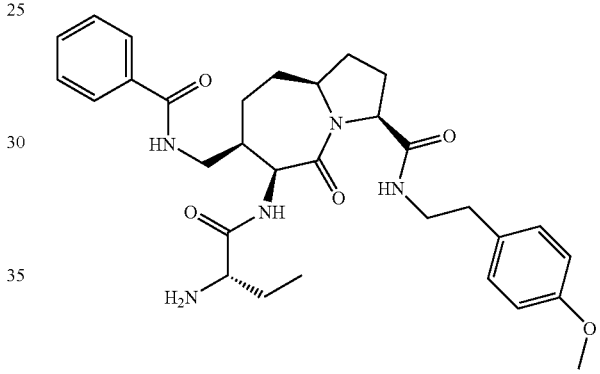 |
| 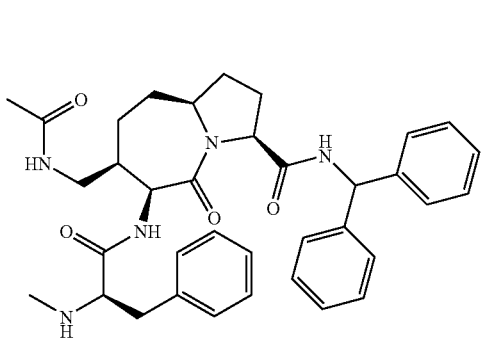 | 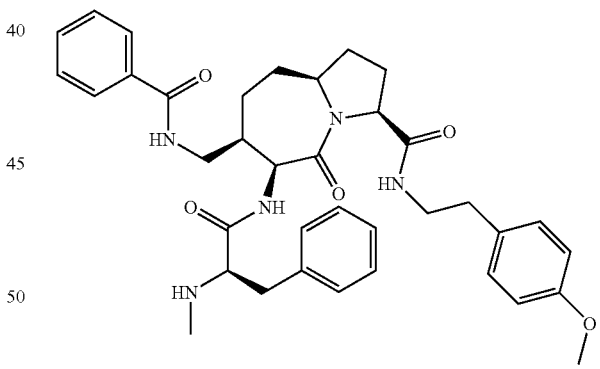 |
| 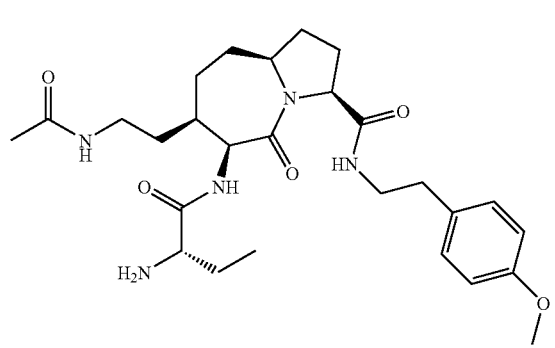 | 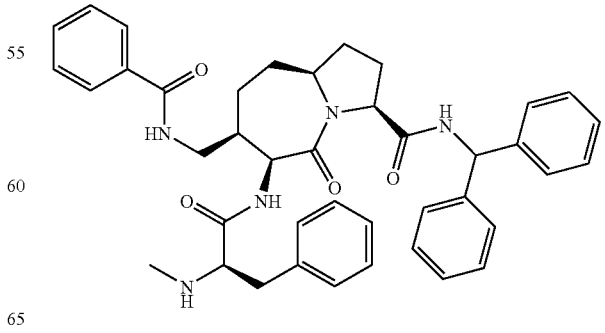 |

35
-continued
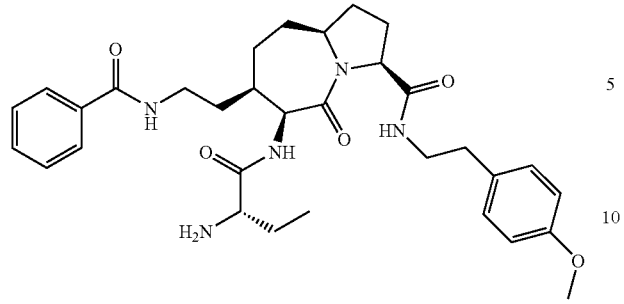
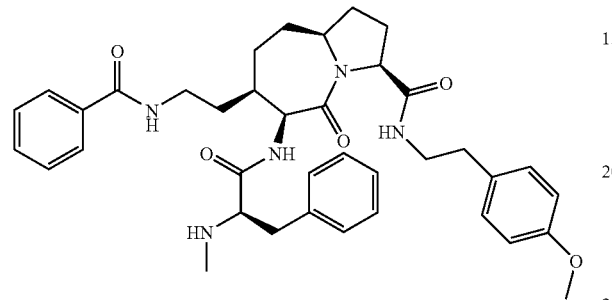
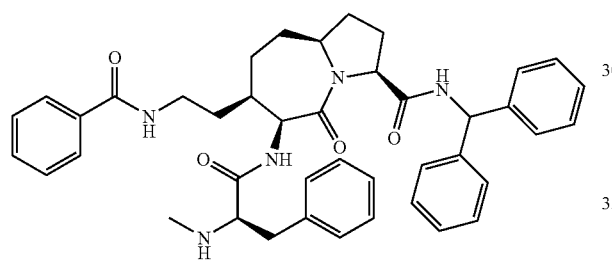
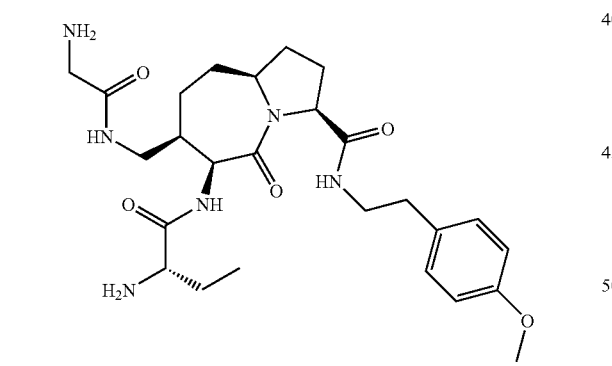
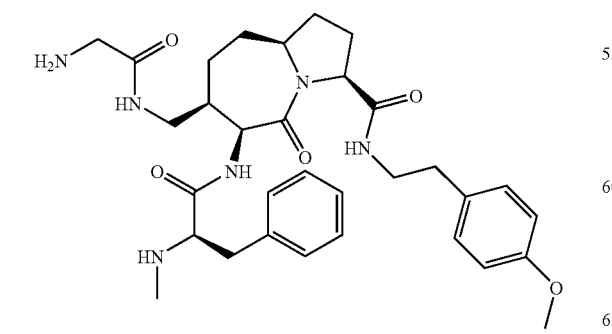
36
-continued
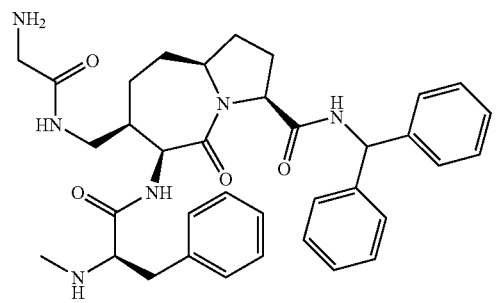
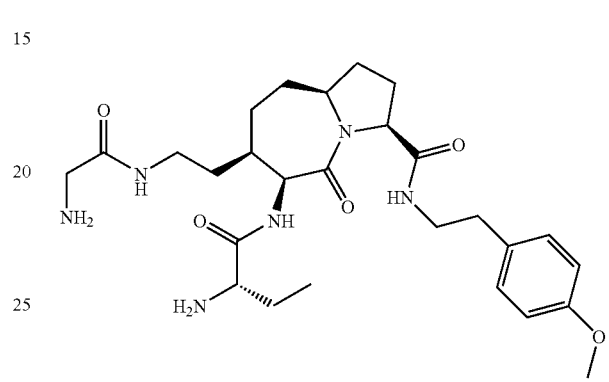
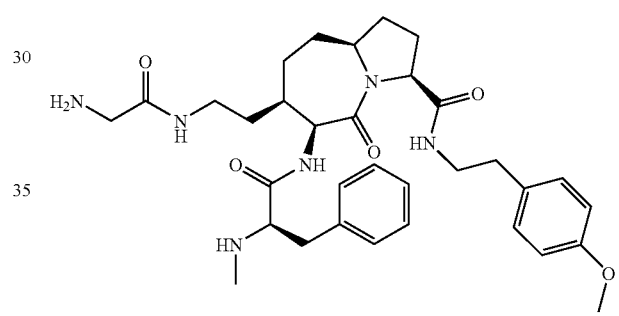
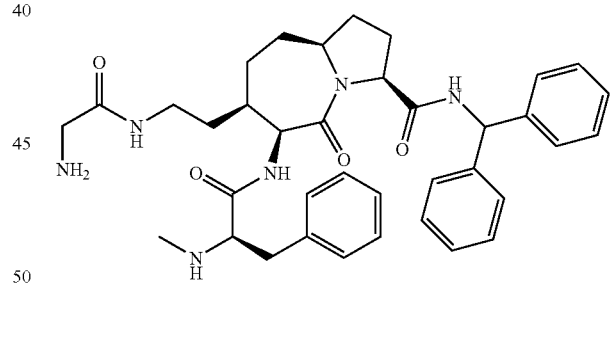
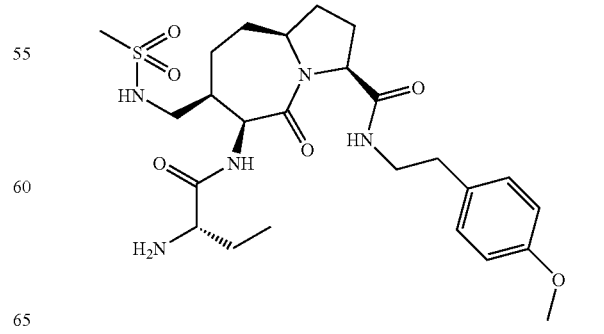

| 37 | 38 |
|---|---|
| -continued | -continued |
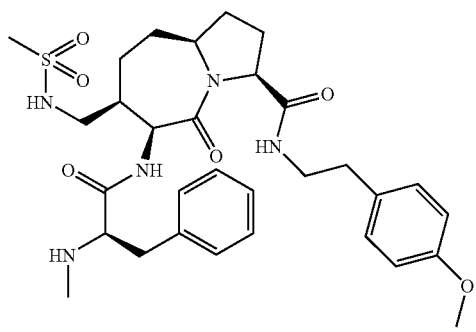 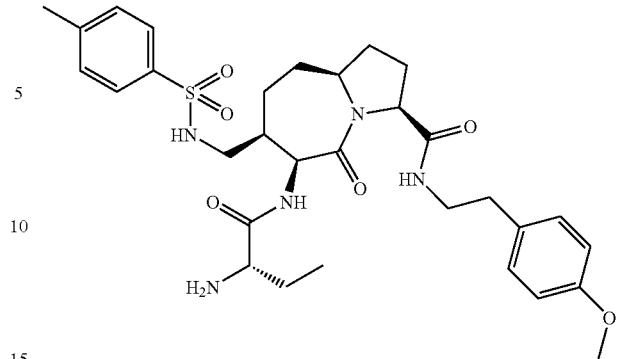
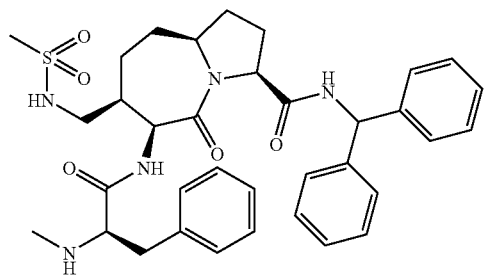 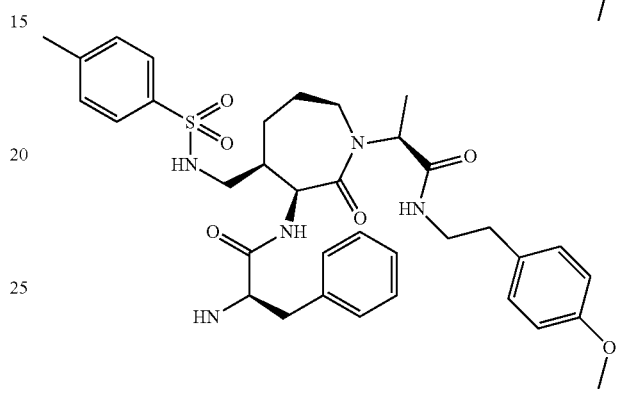
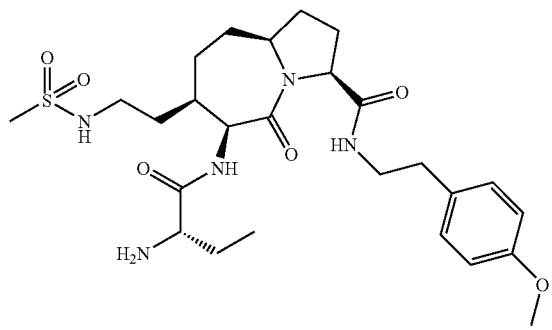 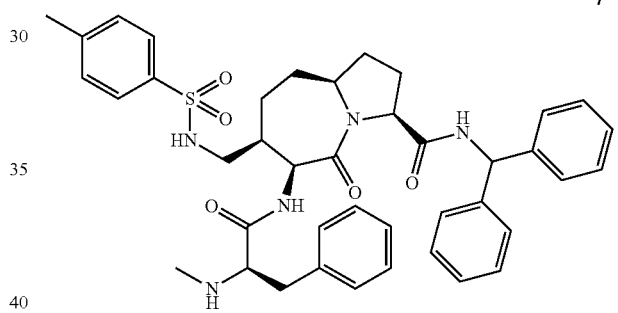
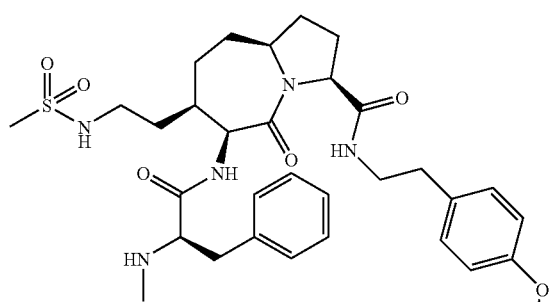 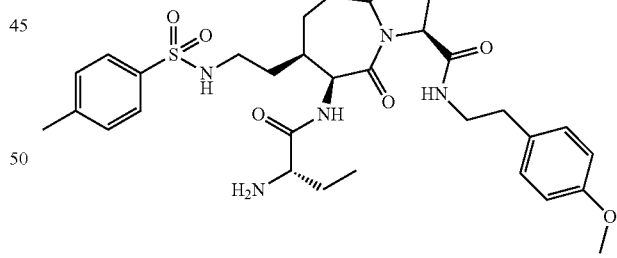
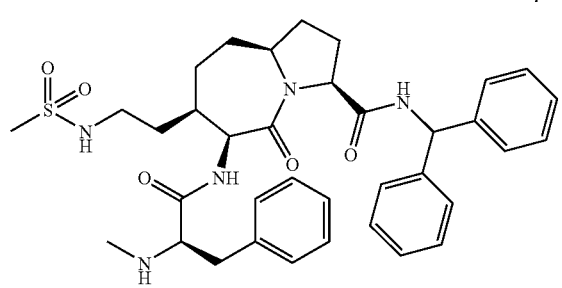 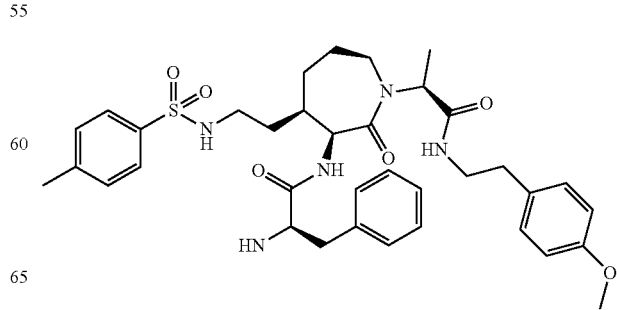

39
-continued
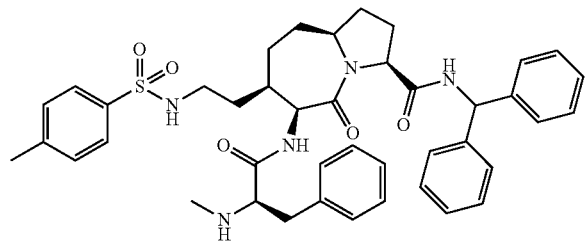
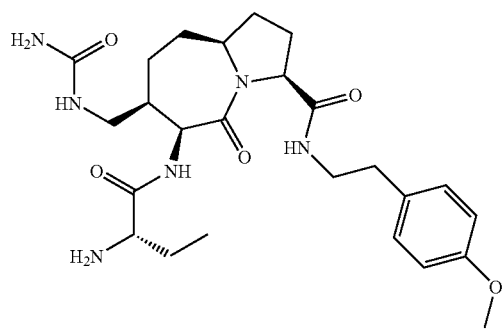
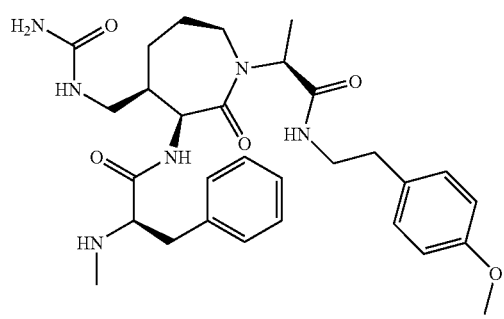
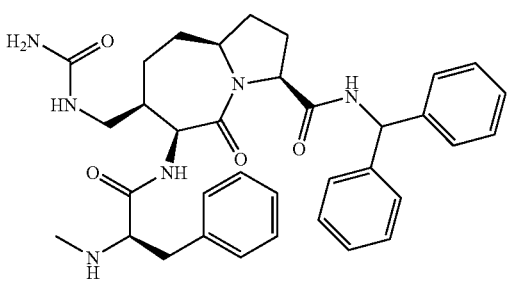
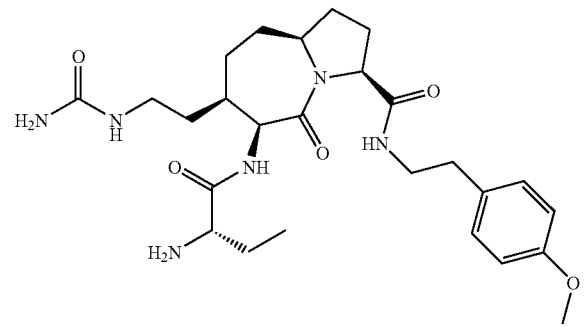
40
-continued
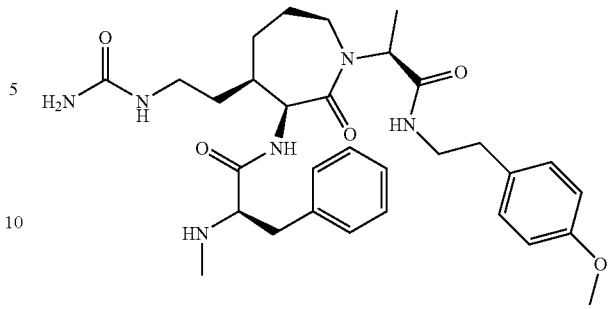
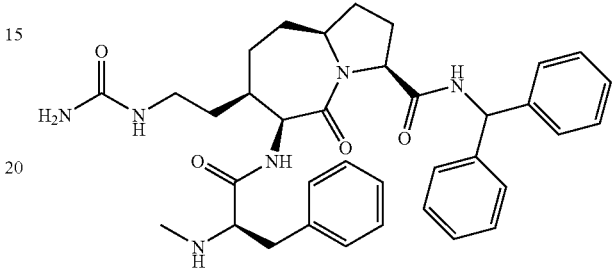
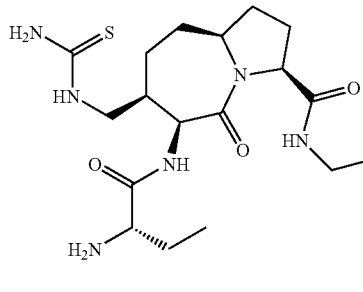
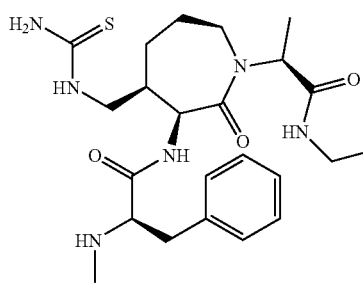
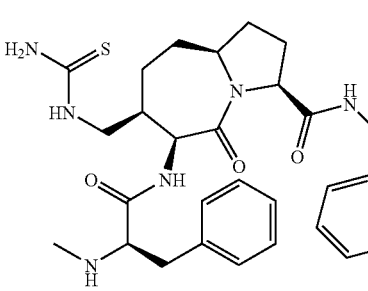

41
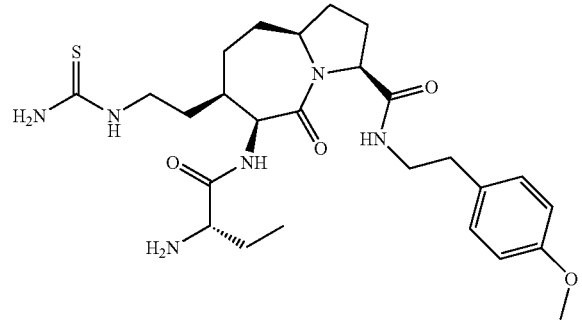
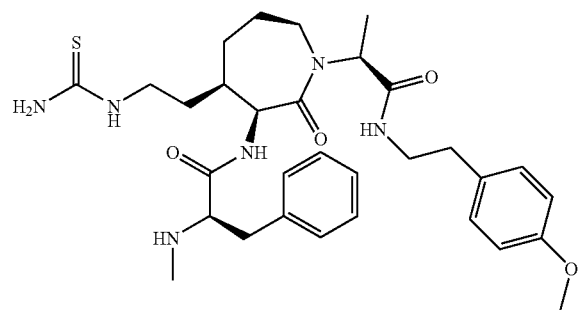
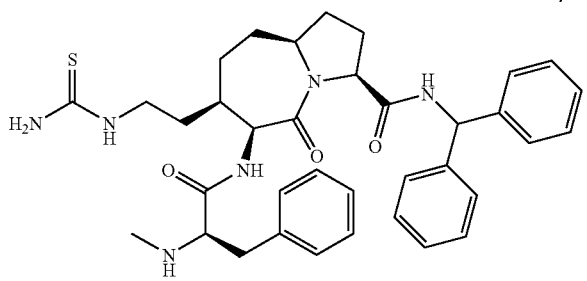
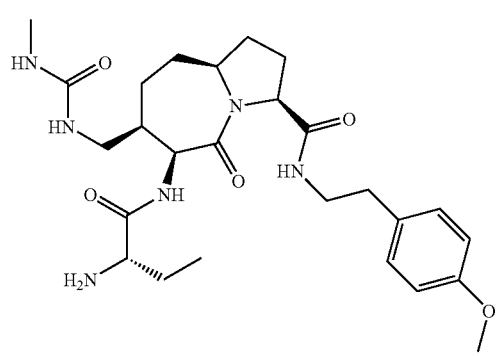
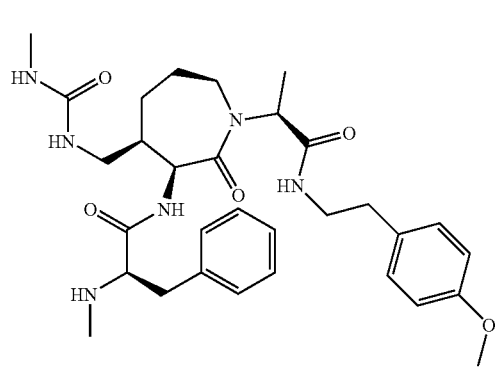
42
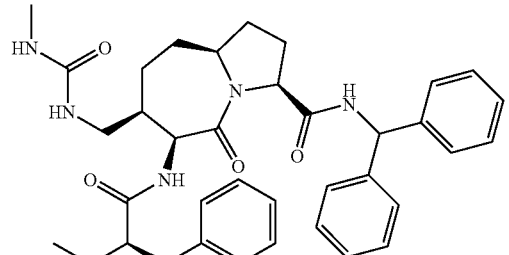
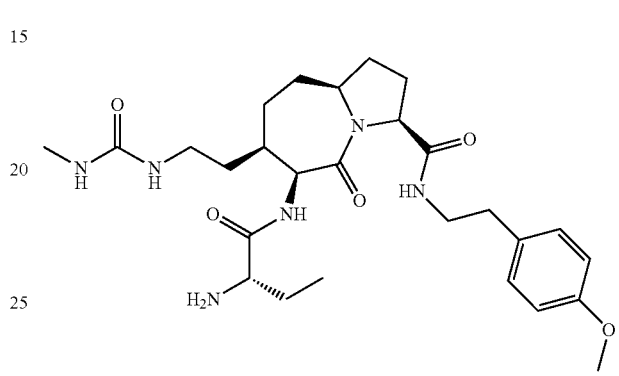
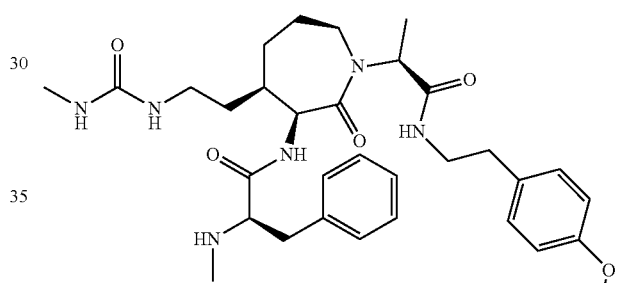
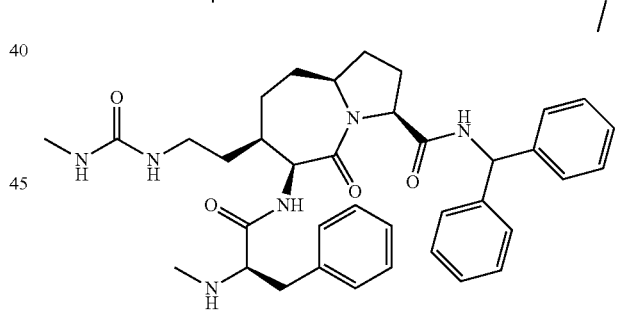
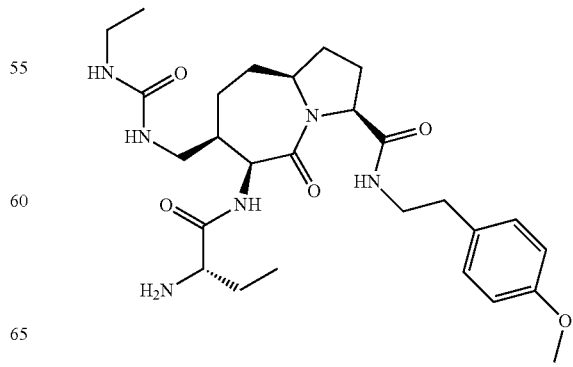

43
-continued
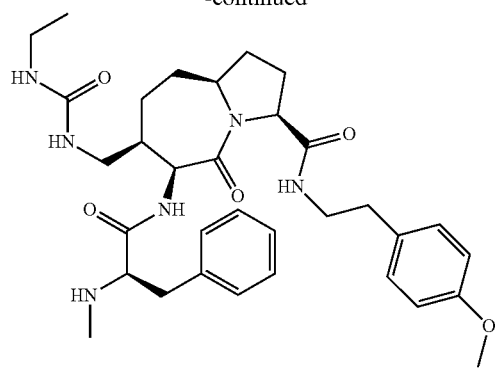
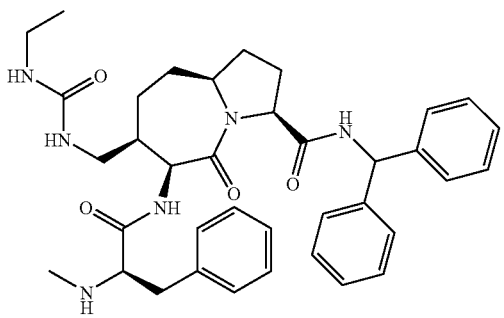
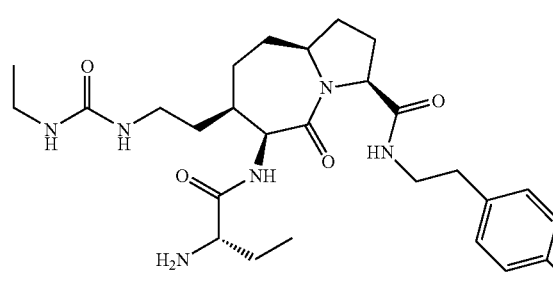
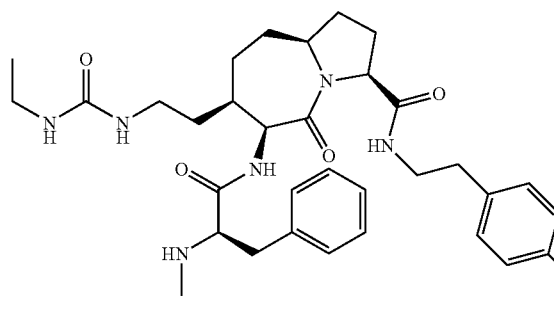
44
-continued
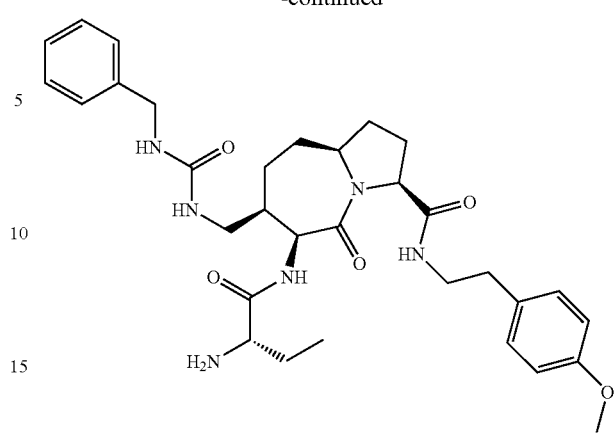
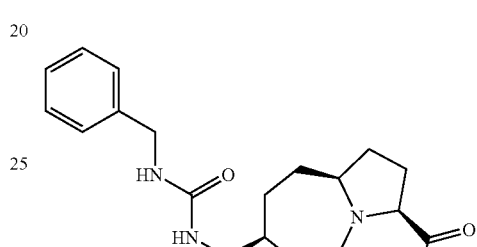
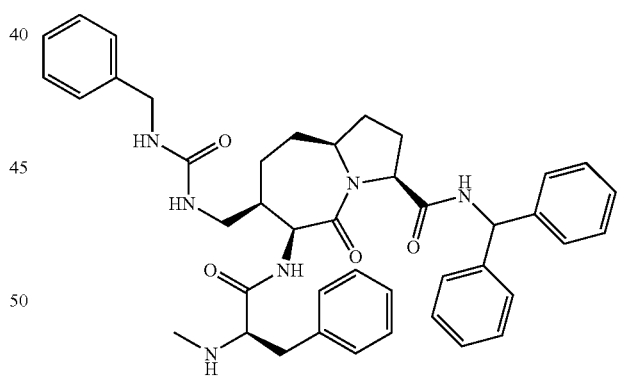
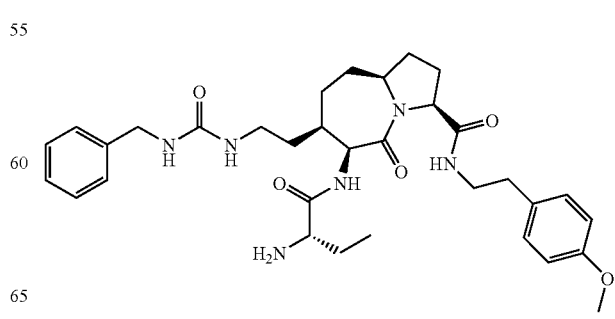

45
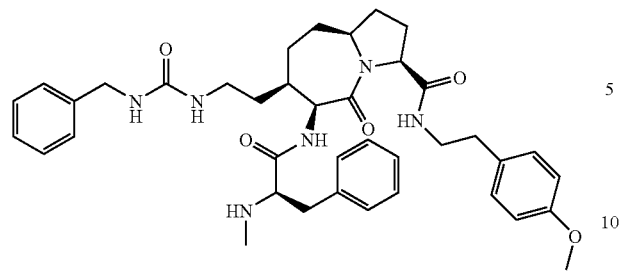
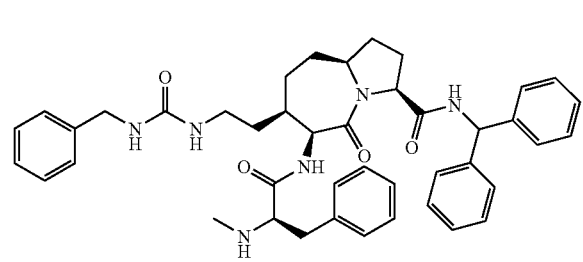
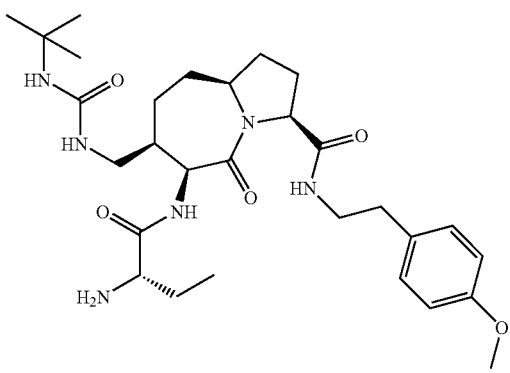
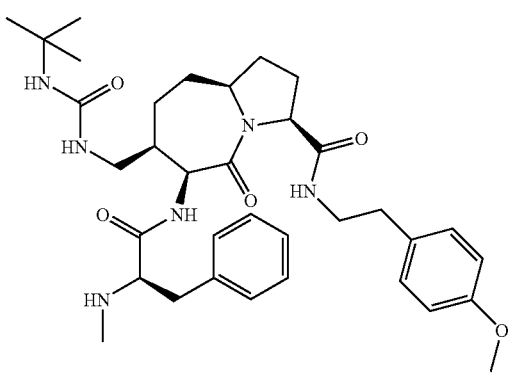
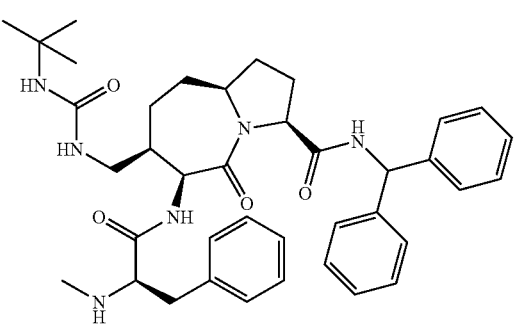
46
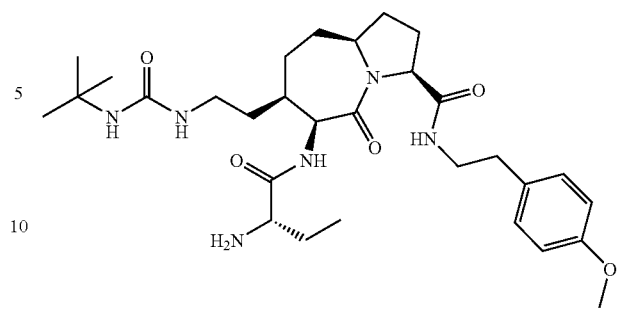
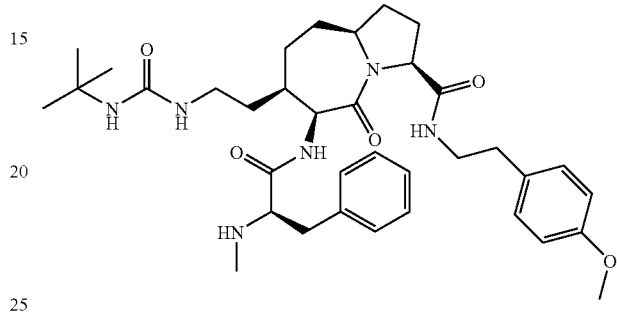
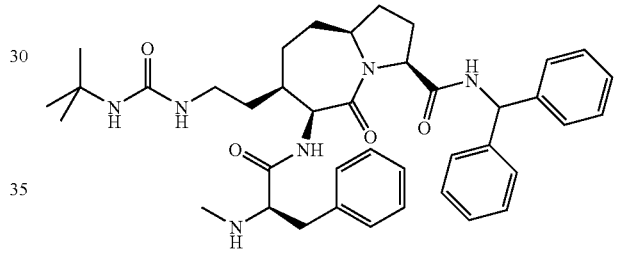
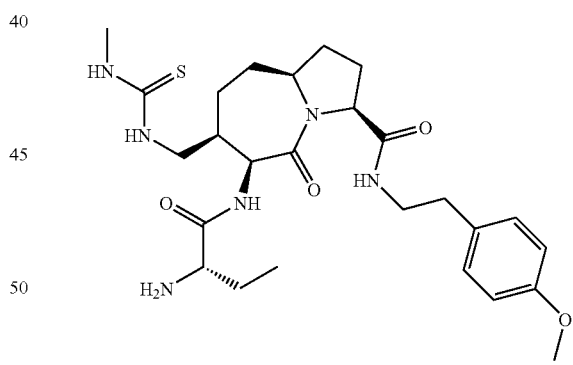
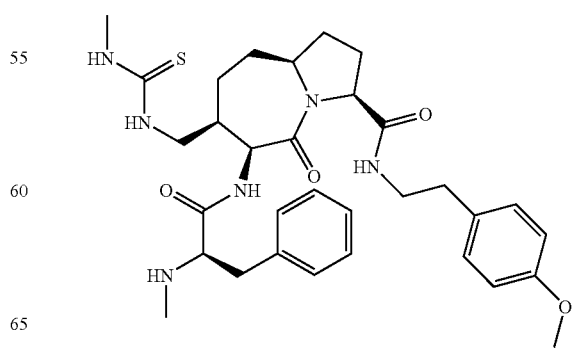

47
-continued
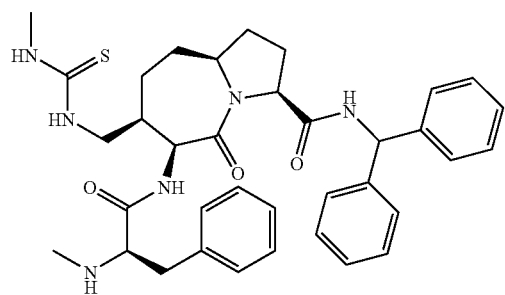
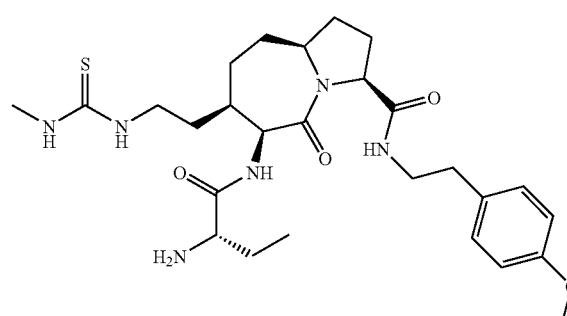
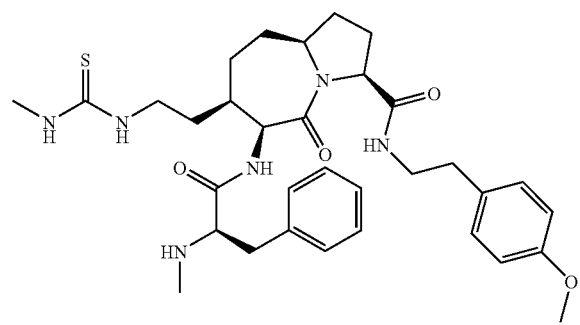
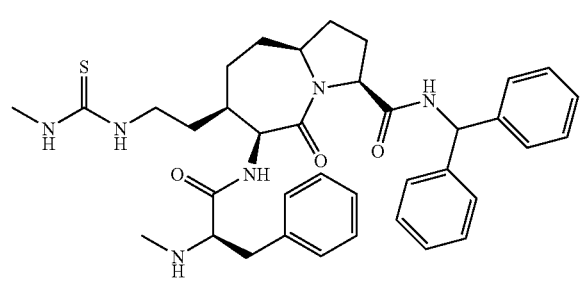
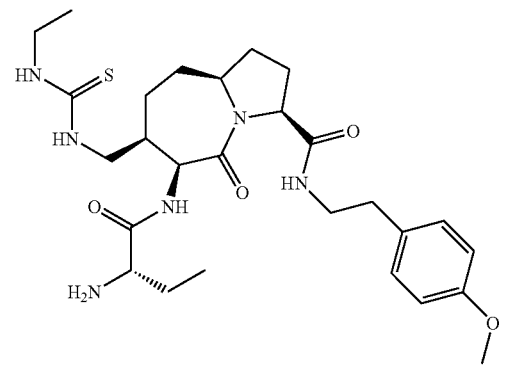
48
-continued
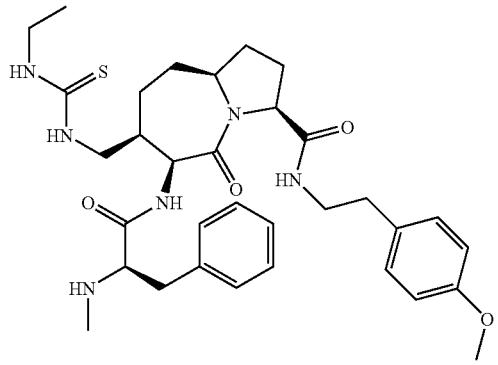
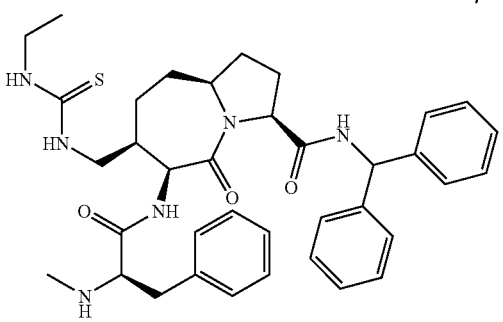
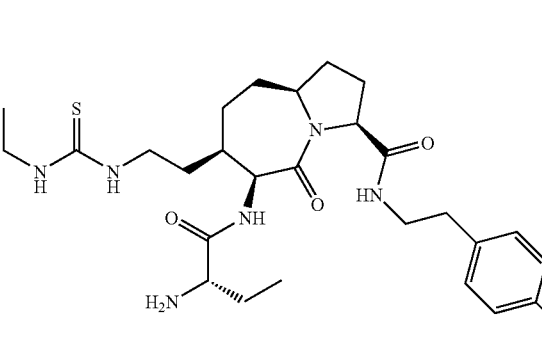
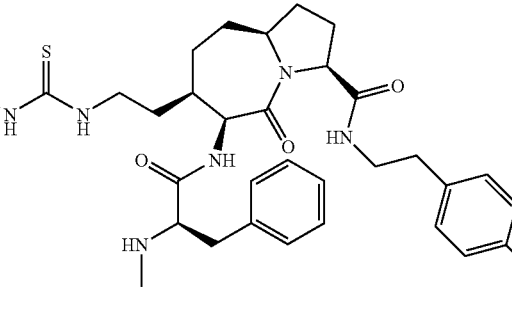
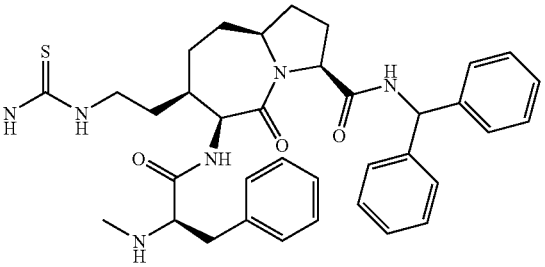

49
-continued
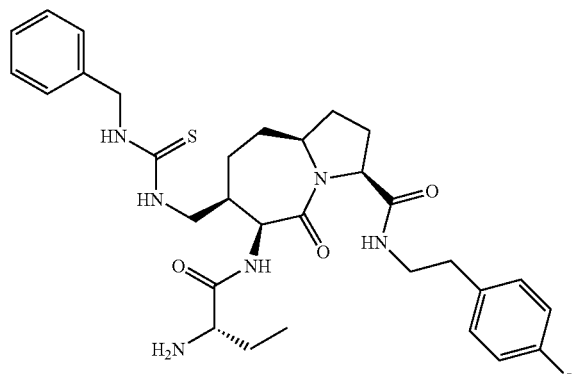
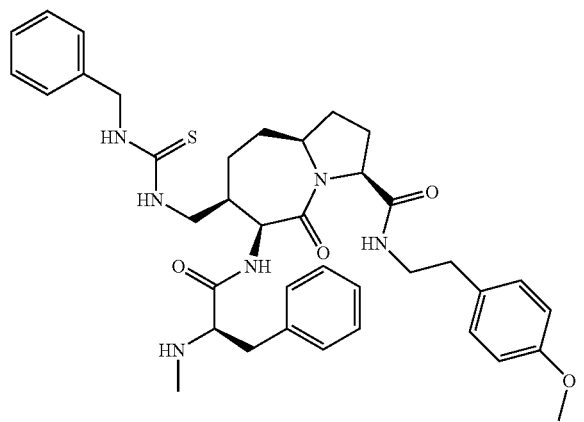
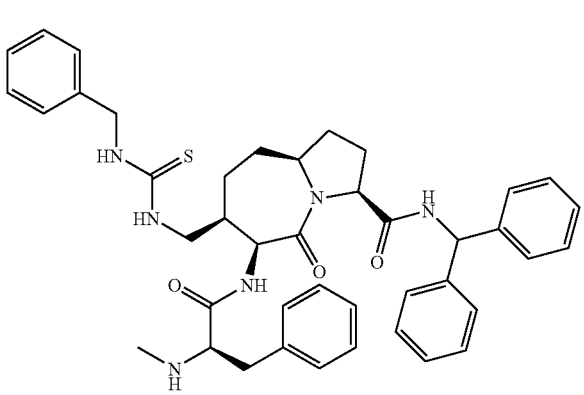
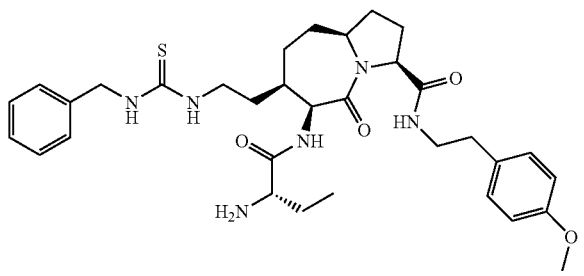
50
-continued
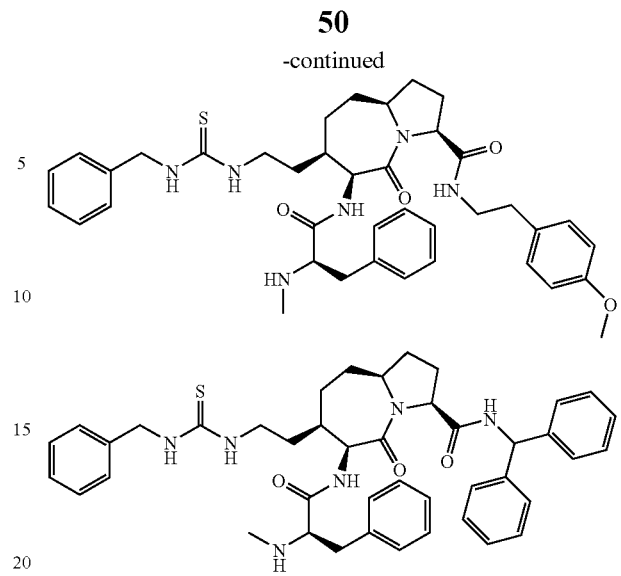
Other preferred compounds of the invention are the following:
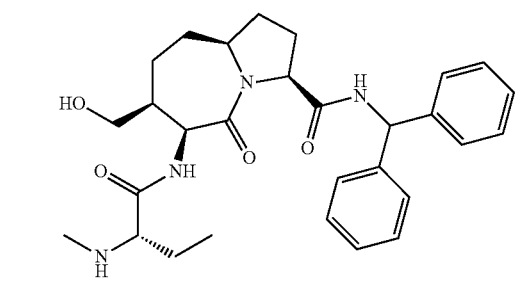
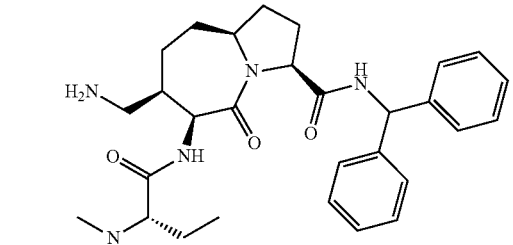
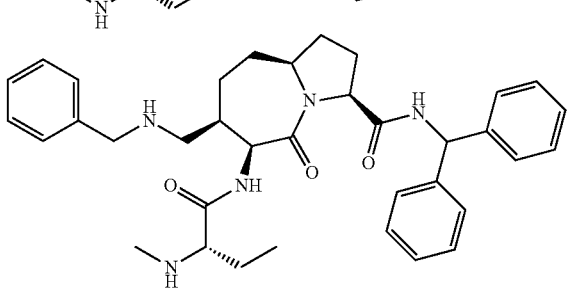

51
-continued
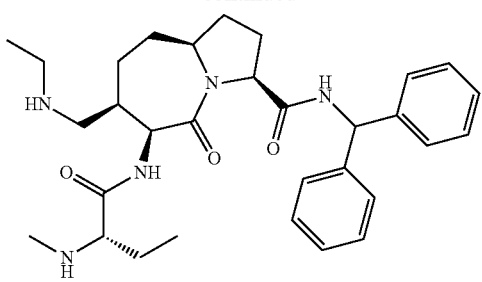
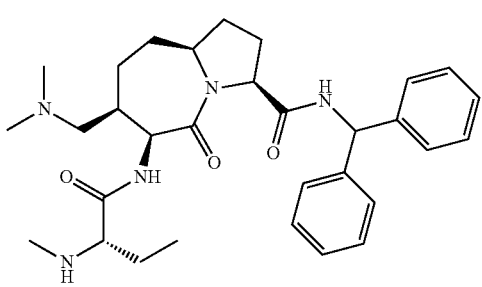
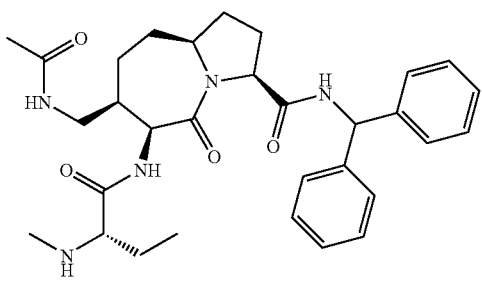
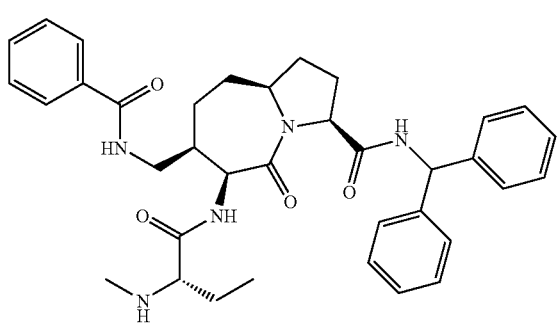
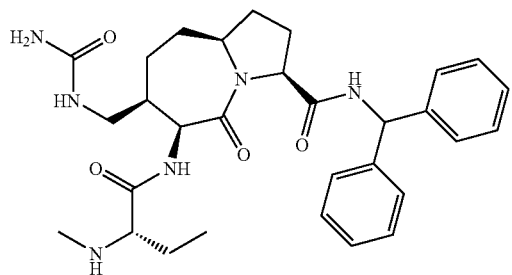
52
-continued
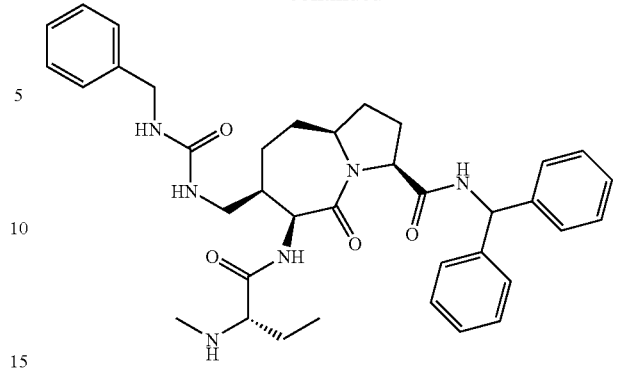
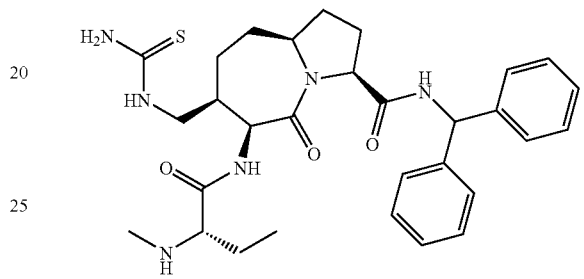
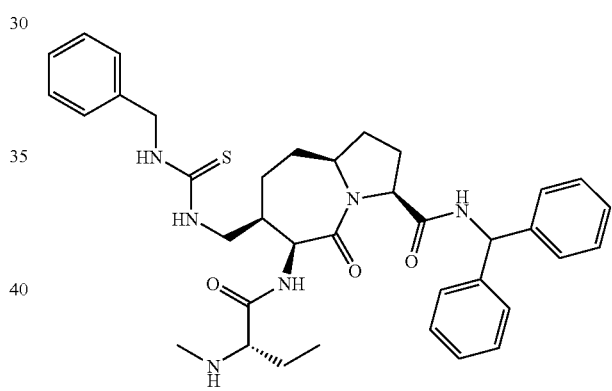
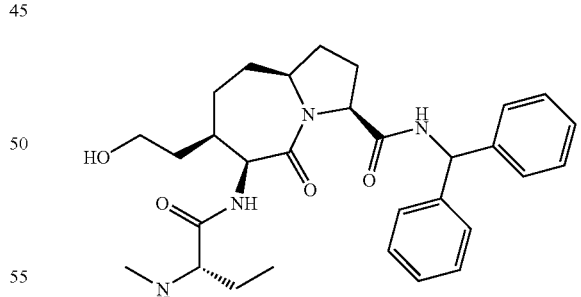
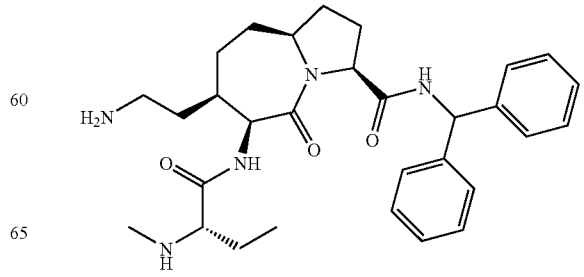

53
-continued
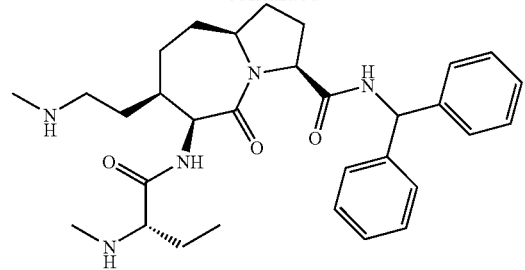
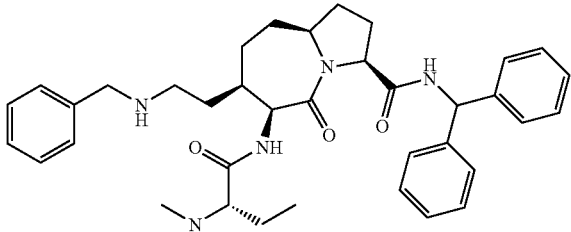
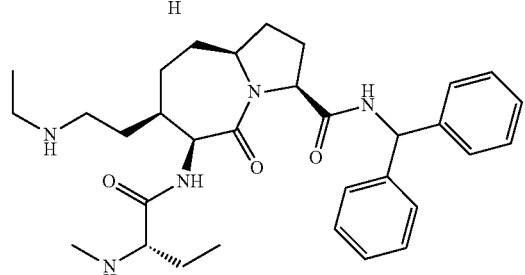
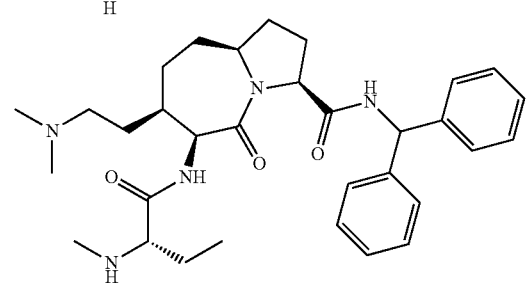
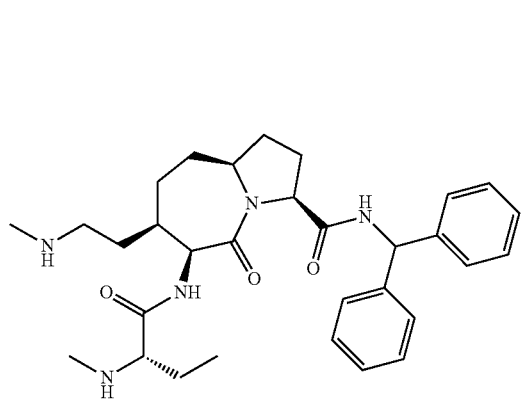
54
-continued
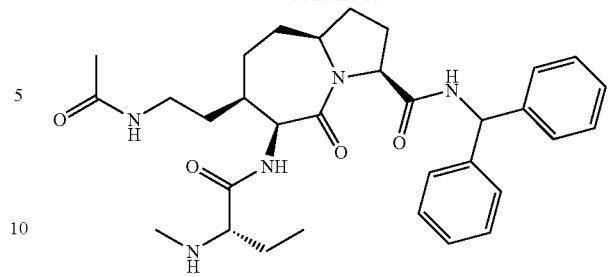
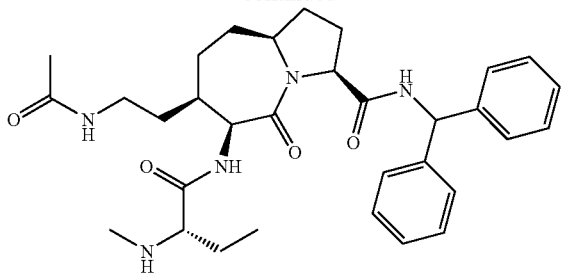

-continued

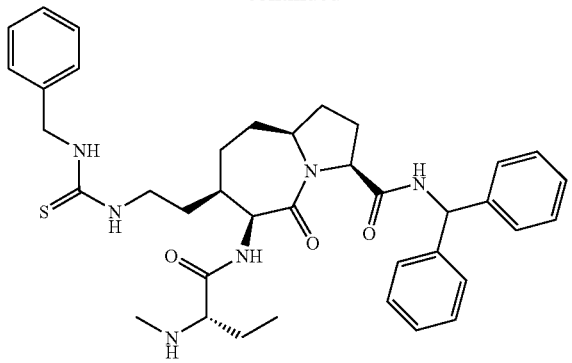 [SMILES: CC[C@H](NC)C(=O)N[C@@H]1C(=O)N2[C@@H](CC[C@@H]1CCNC(=S)NCc1ccccc1)CC[C@H]2C(=O)NC(c1ccccc1)c1ccccc1]

Other preferred compounds of the invention are disclosed in the examples.

The compounds of this invention may be prepared using experimental methods known to those skilled in the art, and according to the methods and reactions described in details in the experimental section of the present description.

The compounds of formula (I) induce apoptosis as standalone treatments, and also potentiate the induction of apoptosis as a response to proapoptotic signals. Thus, the compounds may sensitize cells to inducers of apoptosis, including cells that are resistant to these inducers.

These compounds can be used to induce or restore apoptosis in any disease that can be prevented, ameliorated or fully treated by induction or restoration of apoptosis. Thus, the present invention also provides compositions and methods for targeting mammals characterized as overexpressing an IAP family protein member. In some embodiments, the diseased cells (such as cancer cells) show elevated expression levels of IAP proteins as compared to non-pathological counterparts (such as non-cancerous cells).

In other embodiments, the cells operationally confirm to possess elevated expression levels of IAP proteins due to their entering the apoptosis program and dying in response to an inhibiting effective amount of a compound of the invention, such response being at least in part due to their IAP protein function-dependent survival.

In another embodiment, the invention pertains to modulating an apoptosis associated state which is connected with one or more apoptosis modulators. Examples of apoptosis modulating agents include, but are not limited to, Fas/CD95, TRAMP, TNF R1, DR1, DR2, DR3, DR4, DR5, DR6, FADD, RIP, TNFa, Fas ligand, TRAIL, antibodies to TRAILR1 or TRAILR2, Bcl-2, p53, BAX, BAD, Akt, CAD, PI3 kinase, PP1, and caspase proteins in general. Preferred apoptosing modulators are inducers of apoptosis such as TNF or a TNF-related ligand, particularly a TRAMP ligand, a Fas/CD95 ligand, a TNFR-1 ligand, or TRAIL.

So according to another of its aspects, the present invention relates to the use of the compounds of formula (I), (V) and (VI) for the preparation of medicaments to treat diseased cells, tissues, organs, or pathological conditions and/or disease states in an animal (for example, a mammalian subject including, but not limited to, humans and veterinary mammals), more specifically for the treatment and/or prophylaxis of cancer and related conditions, such as lymphoma, melanoma, glioma, glioblastoma, myeloma, insulinoma, hypercalcemia, leukaemia, neuroblastoma, sarcoma, polycythemia, thrombocytosis, Hodgkin's disease, macroglobulinemia; autoimmune diseases; inflammatory diseases; infections; hyperproliferative diseases; AIDS; neurodegenerative diseases; vascular diseases. In some embodiments, treated cancer cells are metastatic.

In other embodiments, treated cancer cells are resistant to common anticancer agents. Infections suitable for treatment with the compounds of the invention include, but are not limited to, infections caused by viruses, bacteria, fungi, mycoplasma, prions. According to another of its aspects, the present invention relates to pharmaceutical compositions comprising at least one of the compounds of formula (I), (V) or (VI). According to another of its aspects, the present invention relates to combinations of an effective amount of a compound of formula (I), (V) and (VI) and at least one additional therapeutic agent (including, but not limited to, chemotherapeutics, apoptosis modulators, antimicrobials, antivirals, antifungals and anti-inflammatory agents).

A number of suitable anticancer agents are contemplated for use in the method of the present invention. Examples of chemotherapeutic compounds and anticancer therapies suitable for co-administration with compounds of formula (I), (V) and (VI) are known to those skilled in the art.

In preferred embodiments, anticancer agents comprise agents that induce or stimulate apoptosis. They include, but are not limited to, radiation therapies; TNF-related factors; kinase inhibitors; antisense molecules; antibodies; anti-estrogens; anti-androgens; COX-2 inhibitors; anti-inflammatory drugs; cancer chemotherapeutic drugs; cellular signalling molecules; ceramides and cytokines; staurosporine, and the like. Specific examples of anticancer agents suitable for co-administration with compounds of Formula (I), (V) or (VI) are known to those skilled in the art.

In still other embodiments, the composition and methods of the present invention provide a compound of Formula (I), (V) and (VI) and at least one anti-hyperproliferative or anti-neoplastic agent selected from alkylating agents, antimetabolites, and natural products (for example, plant- and/or animal-derived compounds).

In some embodiments, alkylating agents suitable for use in the present compositions and methods include, but are not limited to, nitrogen mustards; ethyleneimines and methylmelamines; alkyl sulfonates; nitrosoureas; triazenes. Specific examples of alkylating agents suitable for co-administration with compounds of Formula (I), (V) or (VI) are known to those skilled in the art.

In other embodiments, antimetabolites suitable for use in the present compositions and methods include, but are not limited to, folic acid analogues; pyrimidine analogues; purine analogues. Specific examples of antimetabolites suitable for co-administration with compounds of Formula (I), (V) or (VI) are known to those skilled in the art.

In still further embodiments, chemotherapeutic agents suitable for use in the present compositions and methods include, but are not limited to, vinca alkaloids; epipodophyllotoxins; antibiotics; enzymes; biological response modifiers; platinum coordinating complexes; anthracenediones; methylhydrazine derivatives; adrenocortical suppressants; adrenocorticosteroids; progestins; estrogens; androgens; antiandrogens; gonadotropin-releasing hormone analogues. Specific examples of chemotherapeutic agents suitable for co-administration with compounds of Formula (I), (V) or (VI) are known to those skilled in the art.

Any oncolytic agent that is routinely used in a cancer therapy context finds use in the composition and methods of the present invention. The U.S. FDA and international counterpart agencies to the U.S. FDA maintain formularies of oncolytic agents approved for use, whose listed members are suitable for co-administration with compounds of Formula (I), (V) or (VI). Those skilled in the art will appreciate that the "product labels" required on all approved chemotherapeutics describe approved indications, dosing information, toxicity data, and the like, for the agents.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" 11$^{th}$ Edition, Eds. Hardman et al., 2005. According to another of its aspects, the present invention relates to a combination of an effective amount of a compound of formula (I), (V) and (VI) and at least one treatment for cancer, for instance, surgical intervention or radiotherapy.

Therefore the present invention also provides methods for administering a compound of formula (I), (V) and (VI) with radiation therapy. The invention is not limited by the types, amounts, or delivery and administration systems used to deliver the therapeutic dose of radiation to an animal.

The source of radiation can be external or internal to the animal. External radiation therapy is most common and involves directing a beam of high-energy radiation to a tumour site through the skin using, for instance, a linear accelerator. Internal radiation therapy involves implanting a radiation-emitting source inside the body at or near the tumour site, including the use of delivery systems that specifically target cancer cells.

The animal may optionally receive radiosensitizers or radioprotectors. Radiosensitizers enhance the killing of tumour cells. Radioprotectors protect healthy tissues from the harmful effect of radiation.

Any type of radiation may be administered to a patient, as long as its dosage is tolerated without unacceptable side effects. Suitable radiotherapies include ionizing/electromagnetic radiotherapy and particle beam radiation therapy.

The total dose of radiation administered to an animal is preferably about 0.01 Gray (Gy) to about 100 Gy. More preferably, about 10 Gy to about 65 Gy are administered during the course of the treatment. While in some embodiments a complete dose of radiation can be administered over the course of one day, the total dose is ideally fractionated and administered over several days. Desirably, radiotherapy is administered at intervals of at least about 3 days, in a period of 1 to 8 weeks. Accordingly, a daily dose of radiation will comprise approximately 1-5 Gy, and preferably 1-2 Gy. The daily dose of radiation should be sufficient to induce destruction of the targeted cells, but days of rest from therapy should be included. For example, radiation desirably is administered on 5 consecutive days, and not administered for 2 days, for each week of treatment, thereby allowing 2 days of rest per week. These exemplary radiotherapy administration schedules are not intended, however, to limit the present invention.

In some embodiments of the present invention, a compound of Formula (I), (V) and (VI) and one or more therapeutic or anticancer agents are administered to an animal under one or more of the following conditions: at different periodicities, at different durations, at different concentrations, by different administration routers, and so on. In some embodiments, the compound is administered prior to the therapeutic or anticancer agent, i.e. 0.5, 1, 2, 3, 4, 5, 10, 12, or 18 hours, 1, 2, 3, 4, 5, or 6 days, 1, 2, 3 or 4 weeks prior to the administration of the therapeutic or anticancer agent. In other embodiments, the compound is administered after the therapeutic or anticancer agent, i.e. 0.5, 1, 2, 3, 4, 5, 10, 12, or 18 hours, 1, 2, 3, 4, 5, or 6 days, 1, 2, 3 or 4 weeks after the administration of the therapeutic or anticancer agent. In some embodiments, the compound and the therapeutic or anticancer agent are administered concurrently but on different schedules, i.e. the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Pharmaceutical compositions within the scope of this invention include all compositions wherein the compounds of the present invention are comprised in an amount which is effective to achieve its intended purpose. While individual needs vary, determination of optimal ranges of effective amounts of each component is within the skill of the art. Typically, the compounds may be administered to mammals, and in particular humans, orally at a dose of 0.0025 to 50 mg/kg, or an equivalent amount of the pharmaceutically acceptable salt thereof, per day of the body weight of the mammal being treated for disorders responsive to induction or restoration of apoptosis. Preferably, about 0.01 to about 10 mg/kg is orally administered to treat, ameliorate, or prevent such disorders. For intramolecular injections, the dose is generally one half of the oral dose. For example, a suitable i.m. dose would be about 0.0025 to about 25 mg/kg, and most preferably, from about 0.01 to about 5 mg/kg. In a topical formulation, the compound may be present at a concentration of about 0.01 to 100 mg per gram of carrier. In a preferred embodiment, the compound is present at a concentration of about 0.07-1.0 mg/mL, more preferably, about 0.1-0.5 mg/mL, most preferably, about 0.4 mg/mL.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragées, slow release lozenges and capsules, mouth rinses and washes, gels, liquid suspensions, hair rinses, hair gels, shampoos and other preparations which can be administered rectally, such as suppositories, as well as suitable solutions for administration by injection, topically or orally, contain from about 0.01 to 99 percent, preferably from 0.25 to 75 percent of active compound(s), together with the excipient.

The compounds and pharmaceutical compositions thereof may be administered by any means that achieve their intended purpose. For example, administration may be by parenteral, subcutaneous, intravenous, intramuscular, intraperitoneal, transdermal, buccal, intratechal, intracranial, intranasal or topical routes. Alternatively, or concurrently, administration may be by the oral route. The dosage administered will be dependent upon the age, health, and weight of the recipient, kind of concerned treatment, if any, frequency of treatment, and the nature of the desired effect.

The pharmaceutical preparations of the present invention are manufactured in a manner which is itself known, for example, by means of conventional mixing, granulating, dragée-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragée cores.

Suitable excipients are, in particular, filters such as saccharides, cellulose preparations and/or calcium phosphates, as well as binders as starch paste, using, for example, starch, gelatine, cellulose, and/or polyvinyl pyrrolidone. If desired, disintegrating agents may be added such as the above mentioned starches, cross-linked polyvinyl pyrrolidone, agar, or alginic acid or a salt thereof. Auxiliaries are, above all, flow-regulating agents and lubricants, for example, silica, talc, stearic acid or salts thereof, and/or polyethylene glycol. Dragée cores are provided with suitable coatings which, if desired, are resistant to gastric juices. In order to produce coatings resistant to gastric juices, solutions of suitable cellulose are used.

Other pharmaceutical preparations which can be used orally include push-fit capsule made of gelatine, as well as soft, sealed capsules made of gelatine and a plasticizer such as glycerol or sorbitol. The push-fit capsules can contain the active compounds in the form of granules which may be mixed with fillers, binders and/or lubricants and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more active compounds with a suppository base. Suitable suppository bases are, for example, natural or synthetic triglycerides, or paraffin hydrocarbons.

Suitable formulations for parenteral administration include aqueous solutions of the active compounds in water-soluble form. In addition, suspensions of the active compounds as appropriate oily injection suspensions may be administered. Suitable lipophilic solvents or vehicles include fatty oils or synthetic fatty acid esters. Aqueous injections may contain substances which increase the viscosity of the suspension, such as sorbitol and/or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white soft paraffin, fats and high molecular weight alcohol. The preferred carriers are those in which the active ingredient is soluble. Creams are preferably formulated from a mixture of mineral oil, self-emulsifying beeswax and water in which mixture the active ingredient, dissolved in a small amount of an oil is admixed. A typical example includes about 40 parts water, about 20 parts beeswax, about 40 parts mineral oil and about 1 part almond oil.

Ointments may be formulated by mixing a solution of the active ingredient in a vegetable oil with warm soft paraffin and allowing the mixture to cool. A typical example of such an ointment includes about 30% almond oil and about 70% white soft paraffin by weight.

Lotions may be conveniently prepared by dissolving the active ingredient, in a suitable high molecular weight alcohol.

The following examples are illustrative, but not limiting, of the method and compositions of the present invention. Other suitable modifications and adaptations of the variety of conditions and parameters normally encountered in clinical therapy and which are obvious to the those skilled in the art are within the scope and the spirit of the invention.

The invention is now disclosed by way of non-limiting examples.

EXPERIMENTAL SECTION

General Synthesis

Preparation A

Compounds of formula (I) may be in general prepared according to a synthetic process outlined in Scheme 1, comprising the following stages:
a) Trans-esterification from tert-butyl-ester to methyl ester;
b) hydrogenation of the isoxazolidine ring;
c) coupling with the suitable protected aminoacid derivative;
d) cleavage of the methyl ester;
e) coupling with suitable amine;
f) if m=2, for example, transformation of hydroxyl into cyanide group followed by reduction to afford the amino group;
g) cleavage of the protecting groups.

Preparation B

Compounds of formula (I) wherein Y is a group of formula (II) (homodimeric compounds), may be prepared according to a synthetic process outlined in Scheme 1, comprising the following stages:
a) Trans-esterification from tert-butyl-ester to methyl ester;
b) hydrogenation of the isoxazolidine ring;
c) coupling with the suitable protected aminoacid derivative;
d) cleavage of the methyl ester;
e) coupling with suitable amine; dimerization via "Click reaction" of the suitable protected monomers;
g) cleavage of the protecting groups.

Preparation C

Compounds of formula (I) wherein Y is a group of formula (III) (homodimeric compounds), may be prepared according to a synthetic process outlined in Scheme 1, comprising the following stages:
a) Trans-esterification from tert-butyl-ester to methyl ester;
b) hydrogenation of the isoxazolidine ring;
c) coupling with the suitable protected aminoacid derivative;
d) cleavage of the methyl ester;
e) coupling with suitable amine;
(f) dimerization via coupling between two terminal acetylenic suitable protected monomers;
g) cleavage of the protecting groups.

Preparation D

Compounds of formula (I) wherein Y is a group of formula (IV) (homodimeric compounds), may be prepared according to a synthetic process outlined in Scheme 1, comprising the following stages:
a) Trans-esterification from tert-butyl-ester to methyl ester;
b) hydrogenation of the isoxazolidine ring;
c) coupling with the suitable protected aminoacid derivative;
d) cleavage of the methyl ester;
e) coupling with suitable amine;
f) dimerization via "Click reaction" of the suitable protected monomers;
g) cleavage of the protecting groups.

Preparation E

Compounds of formula (V), may be prepared according to a synthetic process outlined in Scheme 1, comprising the following stages:
a) Trans-esterification from tert-butyl-ester to methyl ester;
b) hydrogenation of the isoxazolidine ring;
c) protection of the nitrogen with a suitable protective group;
d) transformation of the hydroxyl group of compounds into the corresponding azides according to known procedures, for example through the Mitsunobu reaction, or mesylation and subsequent nucleophilic substitution with sodium azide, to give compounds, followed by subsequent reduction by means of catalytic hydrogenation or Staudinger reaction;

e) coupling with the suitable protected aminoacid derivative;
f) cleavage of the methyl ester;
g) coupling with suitable amine;
h) cleavage of the protecting groups.

Compounds of formula (VI) containing linkers, may be in general prepared connecting one compound of formula (I) wherein Y is different from a group of formula (II), (III); and (IV), to another molecule, from the other side, by use of cross-linking or coupling reactions well known in the art.

When one Y is an azide group, for example, one approach, may be based on the so called "click chemistry" 1,3-dipolar cycloaddition reaction, (see, f.e., Kolb, H et al, Angew. Chem. Int. Ed. 2001, 40, 2004-20021), between the said azide group and a terminal acetilenic group of the bifunctional moiety. This kind of approach is best detailed in the experimental section below. This same kind of reaction, obviously allows to connect an acetylenic group on the peptide side with a linker bearing a terminal azido group.

When Y is SH—, a suitable reaction may occur with a bifunctional linker including, for example, a maleimido terminal group such as, for instance those listed as A22-A24 in Table 1.

When Y is SH—, a suitable reaction of oxidation can transform the thio-derivative into the disulfide bridged dimers.

When X is $NH_2$, the linker may suitably include a C terminus, i.e. a carboxylic terminal group.

The connection between L and $R_6$ may be through a number of arrangements, including, e.g., (a) from C-terminus to C-terminus; (b) from N-terminus (i.e. a terminal amine group) to C-terminus; (c) from C-terminus to N-terminus; or (d) from N-terminus to N-terminus depending on the binding groups of L and our molecule involved in the cross-linking reaction.

Example 1

Synthesis of Monomeric Smac Mimetics with [4.3.0] and [5.3.0] Bicyclic Lactam Systems The general synthesis of key intermediates is showed in Scheme 1. Intermediates 2 are easily prepared using the procedure already reported in the literature. Compounds of general structure 6 were prepared efficiently using standard methods outlined in Scheme 1.

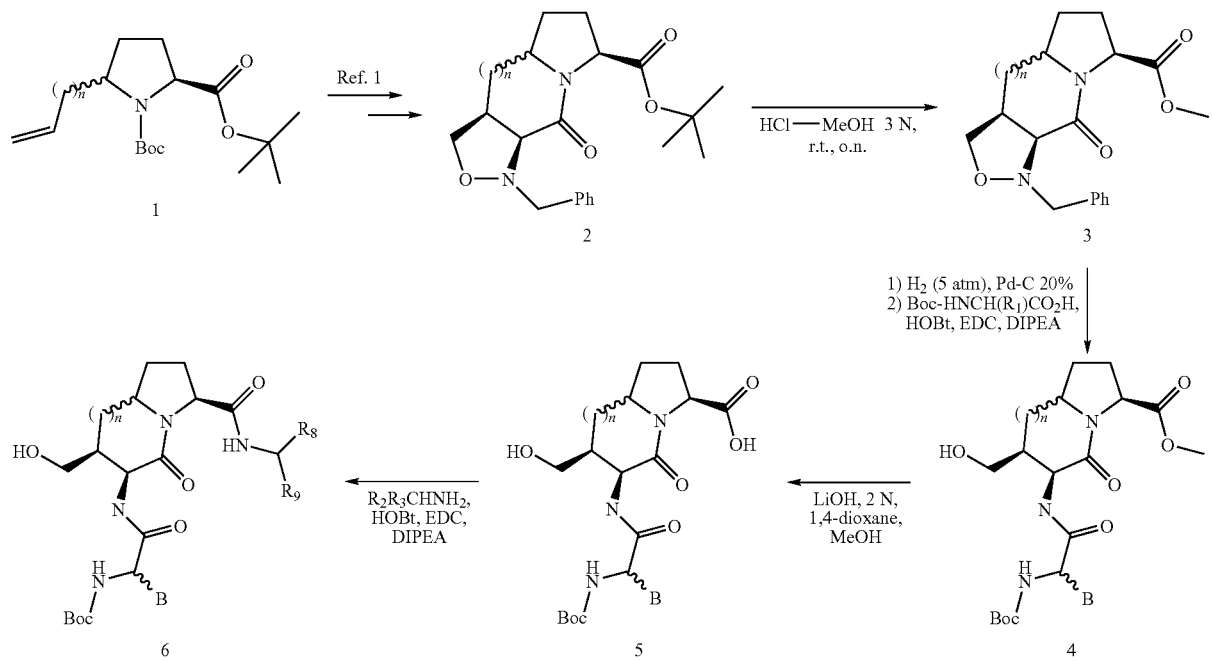

Scheme 1

Intermediates 6 are the synthetic gateway to functionalized monomeric, homodimeric and heterodimeric Smac mimetics.

1.1 General Methods:

$^1$H-NMR spectra were recorded in $CDCl_3$ or $D_2O$ as solvent at 400 MHz. $^{13}$C-NMR spectra were recorded in $CDCl_3$ or $D_2O$ as solvent at 100 MHz. Coupling constants are given in hertz and are rounded to the nearest 0.1 Hz. Purifications were carried out either by flash chromatography on silica gel (particle size 60 μm, 230-400 mesh), Kieselgel, or by Biotage™ flash chromatography: Biotage columns Si-12-M (150×12 mm; silica gel (40-63 μm), flow rate 12 ml/min; and Si-25-M columns (150×25 mm; silica gel (40-63 μm), flow rate 25 ml/min. Final products were purified by $C_{18}$ reverse phase semi-preparative HPLC column ($C_{18}$ X-Terra Waters; 0.46 cm ϕ×5 cm). Solvents were distilled and dried according to standard procedures, and reactions requiring anhydrous conditions were performed under nitrogen or argon. Organic extracts were dried over anhydrous $Na_2SO_4$, filtered, and the solvent then removed using a rotary evaporator. Solvents for the reactions were used directly from the bottle if not specified.

1.2 General Procedure for the Synthesis of Compounds 3

Compounds 2 (1.0 mmol) were dissolved in 5 mL of a 3N methanolic HCl solution. The resulting mixtures were stirred at room temperature for 48 hours and then condensed under reduced pressure. The crude products were dissolved in CH₂Cl₂ (5 ml) and washed with a saturated solution of NaHCO₃ (3×10 ml). The extracts were combined and dried over with Na₂SO₄, and the solvent was removed under reduced pressure. Finally, the crude products were purified by flash chromatography.

Compound 3a was synthesized by the general procedure described above.

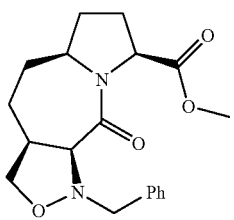

3a

3a. Eluant mixture petroleum ether/EtOAc 40:60. Yield 81% (279 mg, MW 344.17, 0.81 mmol) of pure 3a. Analytical characterization: $[\alpha]_D^{20}$-142.0 (c 1.15, MeOH); ¹H-NMR (400 MHz, CDCl₃): δ: 7.44 (d, J=6.8 Hz, 2H), 7.35-7.23 (m, 3H), 4.74 (dd, J=7.2, 4.4 Hz, 1H), 4.46 (d, J=13.6 Hz, 1H), 4.13 (dd, J=9.2, 7.6 Hz, 1H), 3.87 (m, 1H), 3.74, (s, 3H), 3.65 (d, J=13.6 Hz, 1H), 3.52 (dd, J=7.6, 6.0 Hz, 1H), 3.18 (d, J=10.0 Hz, 1H), 2.78 (m, 1H), 2.30 (m, 1H), 2.14-2.01 (m, 3H), 1.95-1.63 (m, 4H); ¹³C-NMR (100 MHz, CDCl₃): δ: 172.6, 168.8, 137.4, 129.0, 128.2, 127.2, 73.2, 71.4, 61.4, 59.9, 58.8, 52.4, 44.9, 33.9, 33.3, 32.2, 27.4.

1.3 General Procedure for the Synthesis of Compounds 4

Catalytic amounts of 10% Pd—C were added to solutions of compounds 3 (1 mmol) in MeOH (10 ml). The resulting mixtures were stirred at room temperature for ca. 72 hours under hydrogen (5 atm). After reaction completion, the mixtures were filtered through a Celite pad, and then washed with MeOH (3×10 ml). The combined organic solutions were concentrated under reduced pressure. The crude products were dissolved in dry CH₂Cl₂ (10 ml), and then Boc-NH—CH(R₁)CO₂H (1.0 mmol), EDC (1.2 mmol), HOBt (1.2 mmol) and DIPEA (4.0 mmol) were sequentially added. The reaction mixtures were stirred at room temperature overnight and then the solvent was removed under reduced pressure. The residues were purified by flash chromatography.

Compound 4a was synthesized by the general procedure described above.

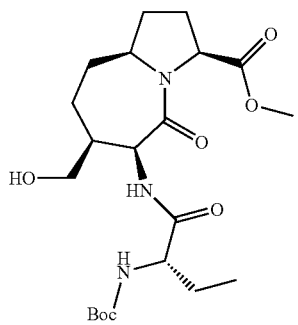

4a

4a. Eluant mixture: Petroleum ether/EtOAc 10:90. Yield 75% (331 mg, MW 441.25, 0.75 mmol) of pure 4a. Analytical characterization: $[\alpha]_D^{20}$-146.5 (c 0.71, MeOH); ¹H-NMR (400 MHz, CDCl₃): δ: 7.53 (d, J=3.5 Hz, 1H), 5.07 (d, J=7.6 Hz, 1H), 4.56 (dd, J=8.5, 4.0 Hz, 1H), 4.48 (dd, J=10.0 Hz, 7.5, 1H), 4.03 (m, 1H), 3.89 (m, 1H), 3.73 (s, 3H), 3.71 (bs, 1H), 3.31 (dd, J=12.0, 3.0 Hz, 1H), 2.30-2.23 (m, 1H), 2.15-1.97 (m, 4H), 1.90-1.75 (m, 4H), 1.69-1.58 (m, 2H), 1.43 (s, 9H), 0.95 (t, 7.5 Hz, 3H); ¹³C-NMR (100 MHz, CDCl₃): δ: 173.9, 172.4, 170.2, 155.6, 80.2, 64.3, 60.6, 58.8, 56.6, 54.1, 52.7, 41.5, 32.4, 31.7, 31.3, 29.2, 27.6, 25.7, 10.1.

Additional compounds of general structure 4 are:

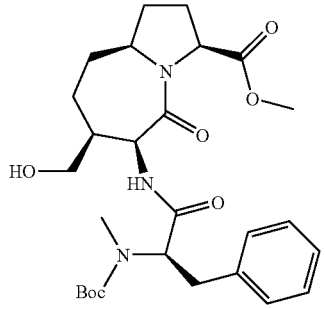

4b

4b. Biotage™ eluant conditions: 1% of MeOH and 99% of CH₂Cl₂ to 10% of MeOH and 90% of CH₂Cl₂ 10 VC. Yield 78% (404 mg, MW 517.28, 0.78 mmol) of pure 4b. Analytical characterization: $[\alpha]_D^{20}$-60.6 (c 0.85, MeOH); ¹H-NMR (400 MHz, CDCl₃) (signals are split due to amide isomerism): δ: 7.65 (m, 1H), 7.35-7.15 (m, 5H), 5.05-4.88 (2m, 1H), 4.61 (dd, J=8.4, 4.0 Hz, 1H), 4.53 (m, 1H), 3.92 (dd, J=15.6, 7.6 Hz, 1H), 3.67 (2s, 3H), 3.65 (m, 1H), 3.45-3.20 (m, 2H), 2.95 (m, 1H), 2.85-2.70 (2s, 3H), 2.25 (m, 1H), 2.15-1.60 (m, 8H), 1.31-1.35 (2 s, 9H); ¹³C-NMR (100 MHz, CDCl₃): signals are split due to amide isomerism: δ: 172.4, 172.2, 170.3, 137.5, 129.20, 129.1, 128.6, 128.4, 128.1, 127.2, 126.7, 126.5, 80.5, 73.2, 71.4, 64.5, 61.7, 61.4, 60.9, 60.6, 60.4, 59.9, 58.8, 54.2, 52.4, 44.9, 41.4, 34.4, 34.1, 33.5, 33.3, 32.8, 32.2, 31.2, 30.8, 28.2, 27.7, 27.4, 14.2.

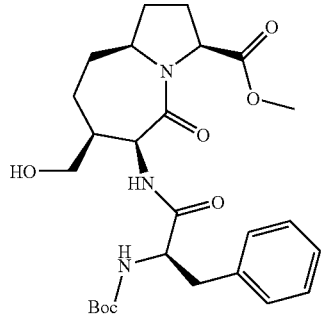

4c

4c. Biotage™ eluant conditions: 1% of MeOH and 99% of CH₂Cl₂ to 10% of MeOH and 90% of CH₂Cl₂ 10 VC. Yield 89% (448 mg, MW 503.26, 0.89 mmol) of pure 4c. Analytical characterization: $[\alpha]_D^{20}$-58.6 (c 0.91, MeOH); ¹H-NMR (400 MHz, CDCl₃): δ: 7.57 (d, J=7.2 Hz, 1H) 7.34-7.23 (m, 6H), 4.83 (bs, 1H), 4.58 (dd, J=8.0, 4.0, 1H), 4.45-4.53 (m, 2H), 3.92 (dd, J=15.6, 7.6 Hz, 1H), 3.77 (s, 3H), 3.60 (dd, J'=13.6, 1.6 Hz, 1H), 3.32 (dd, J=12.0, 2.8 Hz, 1H), 3.22 (dd, J=14, 4.8 Hz, 1H), 2.95 (dd, J=14, 8.8 Hz, 1H), 2.30 (m, 1H), 2.20-2.00 (m, 3H), 1.95-1.75 (m, 4H), 1.57 (m, 1H), 1.38-1.41 (s, 9H); ¹³C-NMR (100 MHz, CDCl₃): δ: 172.4, 172.2, 136.3, 129.4, 129.3, 129.2, 128.8, 128.6, 127.1, 80.5, 64.3, 60.7, 58.8, 54.2, 52.4, 41.4, 33.5, 32.8, 31.2, 28.3, 27.7.

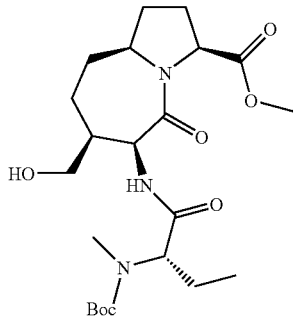

4d

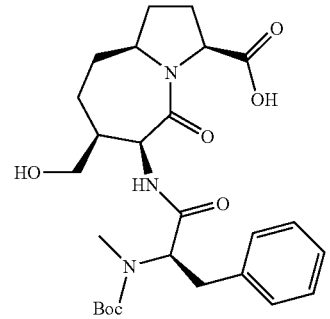

5b

5b. The crude product did not require further purification. Quantitative yield (503 mg, MW 503.26, 1.0 mmol). Analytical characterization: $[\alpha]_D^{20}$-62.7 (c 0.90, MeOH); $^1$H-NMR (400 MHz, CDCl$_3$): (signals are split due to amide isomerism): δ: 7.65 (2d, J=6.8 Hz, 1H), 7.30-7.22 (m, 5H), 4.90 (2m, 1H), 4.63 (m, 1H), 4.55 (m, 1H), 3.91 (m, 1H), 3.58 (dd, J=12, 2 Hz, 1H), 3.44 (dd, J=14, 5.6 Hz, 1H), 3.35 (m, 1H), 2.95 (m, 1H), 2.75 (2s, 3H), 2.30 (m, 2H), 2.20-1.50 (m, 7H), 1.26 (2s, 9H); $^{13}$C-NMR (100 MHz, CDCl$_3$): (signals are split due to amide isomerism) δ: 173.7, 172.2, 137.4, 129.0, 128.7, 128.5, 128.2, 126.7, 126.6, 80.5, 67.1, 64.3, 61.6, 61.0, 60.8, 59.2, 54.2, 41.1, 34.3, 34.1, 33.8, 33.0, 32.1, 31.0, 28.2, 27.0, 20.5.

4d. Biotage™ eluant conditions: 40% of EtOAc and 60% of Petroleum ether to 100% of EtOAc 10 VC. Yield 73% (700 mg; MW 455, 1.54 mmol) of pure 4d. $[\alpha]_D^{20}$-88.2 (c 0.005, CHCl$_3$). $^1$H-NMR (400 MHz, CDCl$_3$): δ: 7.51 (d, J=5.2 Hz, 1H), 4.62 (dd, J=3.8, 4.1 Hz, 1H), 4.50 (t, J=7.6 Hz, 1H), 4.42 (bs, 1H), 3.92 (dd, J=6.6, 14.5 Hz, 1H), 3.77 (s, 3H), 3.70 (d, J=12.3 Hz, 1H), 3.39 (dd, J=3.2, 12.3 Hz, 1H), 2.86 (s, 3H), 2.30 (m, 1H), 2.14-1.73 (m, 9H), 1.63 (m, 1H), 1.49 (s, 9H), 0.94 (t, J=7.3 Hz, 3H); $^{13}$C-NMR (100 MHz, CDCl$_3$): δ: 173.1, 172.4, 170.3, 80.5, 64.4, 60.9, 60.6, 58.8, 54.0, 52.4, 41.6, 33.6, 32.8, 31.3, 30.4, 28.4, 27.7, 21.6, 10.7.

1.4 General Procedure for the Synthesis of Compounds 5

2 N aqueous LiOH solutions (3.5 ml, 7.0 mmol) were added to stirred solutions of compounds 4 (1.0 mmol) in 1,4-dioxane (4 ml) at 0° C. The reaction mixtures were stirred at room temperature until complete hydrolysis of the starting material, then HCl (1N aqueous solution) was added dropwise until pH≈5. The mixtures were extracted with CH$_2$Cl$_2$ (3×20 ml), the combined organic layers were dried over Na$_2$SO$_4$, and then the solvent was removed under reduced pressure. Compound 5a was synthesized by the general procedure described above.

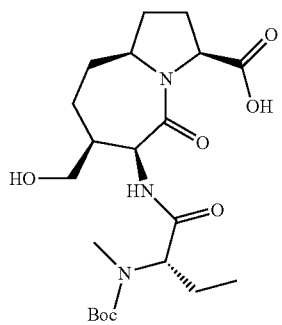

5d

5d. The crude product did not require further purification. Quantitative yield (441 mg, MW 441.20, 1.0 mmol). Analytical characterization: $[\alpha]_D^{20}$-95.0 (c 0.50, MeOH); $^1$H-NMR (400 MHz, CDCl$_3$): δ: 7.59 (bs, 1H), 4.56 (d, J=7.71 Hz, 1H), 4.45 (m, 2H), 3.84 (dd, J=8.23, 17.48 Hz, 1H), 3.59 (d, J=12.86 Hz, 1H), 3.35 (dd, J=3.09, 11.83 Hz, 1H), 2.79 (s, 3H), 2.23-1.58 (m, 11H), 1.41 (s, 9H), 0.85 (t, J=7.20 Hz, 3H); $^{13}$C-NMR (100 MHz, CDCl$_3$): δ: 173.5, 173.0, 171.8, 80.8, 64.4, 61.1, 60.5, 59.2, 54.2, 41.2, 33.8, 33.0, 31.1, 27.0, 21.6, 10.7.

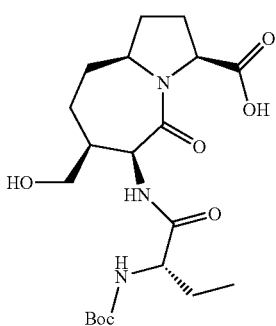

5a

5a. The crude product did not require further purification. Quantitative yield (427 mg, MW 427.23, 1.0 mmol). Analytical characterization: $[\alpha]_D^{20}$-123.0 (c 0.61, MeOH); $^1$H-NMR (400 MHz, CDCl$_3$): δ: 7.76 (d, J=6.5 Hz, 1H), 7.20 (bs, 1H), 5.33 (m, 1H), 4.56 (m, 2H), 4.09 (m, 1H), 3.91 (d, J=7.5 Hz, 1H), 3.43 (d, J=9.5 Hz, 1H), 2.26 (d, J=6.5 Hz, 1H), 2.12-1.62 (m, 10H), 1.42 (s, 9H), 0.95 (t. J=6.5 Hz, 3H); $^{13}$C-NMR (100 MHz, CDCl$_3$): δ: 173.8, 173.5, 171.0, 80.4, 64.3, 60.8, 60.4, 59.0, 56.5, 54.0, 41.2, 33.4, 32.9, 31.0, 28.2, 27.6, 25.7, 10.1.

Additional compounds of general structure 5 are:

1.5 General Procedure for the Synthesis of Compounds 6

Crude compounds 5 (1.0 mmol) were dissolved in dry CH$_2$Cl$_2$ (10 ml), and then R$_2$R$_3$CHNH$_2$ (1.2 mmol), EDC (1.2 mmol), HOBt (1.2 mmol) and DIPEA (4.0 mmol) were sequentially added. The reaction mixtures were stirred at room temperature overnight, and then the solvent was removed under reduced pressure. The residues were purified by flash chromatography.

Compound 6a was synthesized by the general procedure described above.

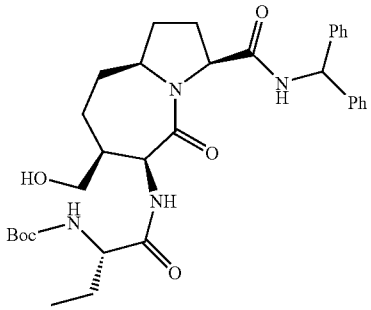

6a 3.82-3.70 (m, 4H), 3.70-3.45 (m, 4H), 3.30 (m, 1H), 2.90 (m, 1H), 2.80 (m, 5H), 2.38 (m, 1H), 2.25 (m, 1H), 2.10 (m, 1H), 2.00-1.70 (m, 4H), 1.38 (2s, 9H), 1.30-1.00 (m, 2H); $^1$H-NMR (600 MHz, DMSO-d6, 358K): δ: 7.68 (d, J=7.4 Hz, 1H), 7.58 (bs, 1H), 7.28-7.19 (m, 7H), 6.85 (d, J=7.2 Hz, 2H), 4.95 (bs, 1H), 4.45 (t, J=8.4 Hz, 1H), 4.38 (d, J=7.8 Hz, 1H), 4.23 (bs, 1H), 3.92 (m, 1H), 3.74 (s, 3H), 3.45 (dd, J=10.2, 5.4 Hz, 1H), 3.32-3.22 (m, 4H), 2.87 (t, J=12.0 Hz, 1H), 2.73 (s, 3H), 2.67 (t, J=7.8 Hz, 2H), 2.17 (dd, J=12.0, 6.0 Hz, 1H), 2.05 (m, 1H), 1.93-1.80 (m, 3H), 1.75-1.58 (m, 4H), 1.25 (s, 9H); $^{13}$C-NMR (100 MHz, CDCl$_3$): (signals are split due to amide isomerism): δ: 172.2, 170.7, 158.3, 129.7, 129.6, 129.1, 129.0, 128.7, 128.5, 126.7, 126.6, 114.1, 113.9, 80.6, 64.3, 61.8, 61.6, 60.6, 59.0, 55.3, 54.0, 41.4, 40.8, 40.2, 34.7, 34.3, 34.0, 33.1, 31.1, 28.3, 28.1, 26.1.

6a. Eluant mixture: Petroleum ether/EtOAc 10:90. Yield 79% (490 mg, MW 592.33, 0.79 mmol) of pure 6a. Analytical characterization: $[α]_D^{20}$-125.0 (c 1.48, MeOH); $^1$H-NMR (400 MHz, CDCl$_3$): δ: 7.97 (d, J=8.4 Hz, 1H), 7.62 (d, J=7.2 Hz, 1H), 7.35-7.15 (m, 10H), 6.21 (d, J=8.8 Hz, 1H), 5.17 (d, J=7.2 Hz, 1H), 4.73 (d, J=7.6 Hz, 1H), 4.49 (m, 1H), 4.10 (m, 1H), 3.77 (dd, J=17.6, 8.5 Hz, 1H), 3.67 (d, J=10.8 Hz, 1H), 3.28 (dd, J=12.0, 3.2 Hz, 1H), 2.38 (dd, J=12.0, 6.8 Hz, 1H), 2.23 (m, 1H), 2.10-1.95 (m, 2H), 1.89-1.55 (m, 6H), 1.43 (s, 9H), 1.30-1.10 (m, 3H), 0.96 (t, 7.2 Hz, 3H); $^{13}$C-NMR (100 MHz, CDCl$_3$): δ: 173.9, 171.7, 169.6, 155.8, 142.0, 141.2, 128.6, 128.4, 127.4, 127.2, 126.9, 80.3, 64.2, 61.2, 60.4, 58.9, 56.8, 53.9, 41.5, 34.0, 33.2, 31.1, 28.3, 25.8, 25.6, 21.0, 14.2, 10.2.

Additional compounds of general structure 6 are:

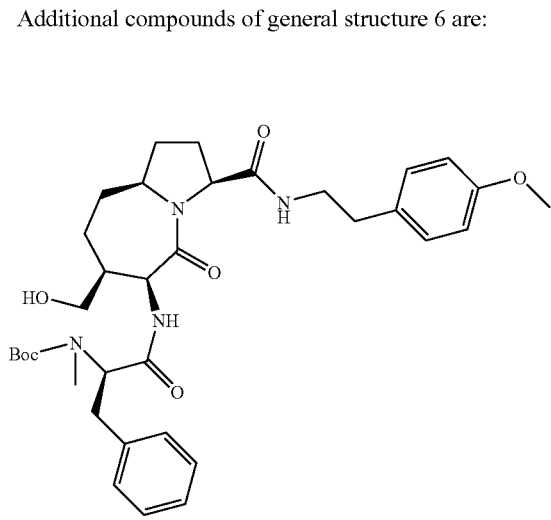

6b

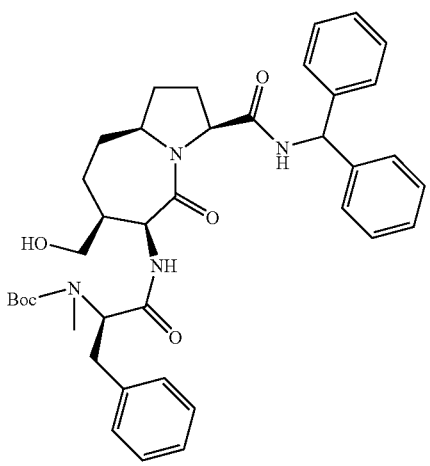

6c

6b. Biotage™ eluant conditions: 1% of MeOH and 99% of CH$_2$Cl$_2$ to 10% of MeOH and 90% of CH$_2$Cl$_2$ 10 VC. Yield 94.8% (603 mg, MW 636.35, 0.95 mmol) of pure 6b. Analytical characterization: $[α]_D^{20}$-70.12 (c 1.21, CHCl$_3$); $^1$H-NMR (400 MHz, CDCl$_3$): (signals are split due to amide isomerism): δ: 7.60 (m, 1H), 7.40-7.10 (m, 7H), 6.90-6.70 (m, 3H), 4.95 (2m, 1H), 4.55 (d, J=6.8 Hz, 1H), 4.45 (m, 1H), 6c. Biotage™ eluant conditions: 1% of MeOH and 99% of CH$_2$Cl$_2$ to 10% of MeOH and 90% of CH$_2$Cl$_2$ 10 VC. Yield 90.3% (603 mg, MW 668.36, 0.90 mmol) of pure 6c. Analytical characterization: $[α]_D^{20}$-70.1 (c 1.21, CHCl$_3$); $^1$H-NMR (400 MHz, CDCl$_3$): (signals are split due to amide isomerism): δ: 7.93 (m, 1H), 7.66 (m, 1H), 7.50-7.10 (m, 15H), 6.22 (d, 8.8 Hz, 1H), 4.95 (2m, 1H), 4.74 (d, J=7.2 Hz, 1H), 4.45 (m, 1H), 3.82 (m, 1H), 3.60-3.35 (m, 2H), 3.25 (d, J=4.2 Hz, 1H), 2.98 (m, 1H), 2.80 (2s, 3H), 2.46 (m, 1H), 2.29 (m, 1H), 2.10 (m, 1H), 2.00-1.65 (m, 4H), 1.40 (s, 9H), 1.30-1.05 (m, 2H); $^1$H-NMR (600 MHz, DMSO-d6, 358K): δ: 8.62 (d, J=7.2 Hz, 1H), 7.78 (d, J=7.4 Hz, 1H), 7.43-7.18 (m, 15H), 6.10 (d, J=8.4 Hz, 1H), 4.90 (bs, 1H), 4.63 (dd, J=7.8, 3.6 Hz, 1H), 4.48 (t, J=8.4 Hz, 1H), 4.23 (bs, 1H), 3.96 (dd, J=15.0, 7.2 Hz, 1H), 3.45 (dd, J=10.2, 4.8 Hz, 1H), 3.30 (dd, J=11.4, 6.0 Hz, 1H), 3.23 (dd, J=14.4, 4.8 Hz, 1H), 2.88 (dd, J=14.4, 10.8 Hz, 1H), 2.74 (s, 3H), 2.21 (m, 1H), 2.13-1.93 (m, 3H), 1.85 (m, 1H), 1.78-1.50 (m, 4H), 1.28 (s, 9H); $^{13}$C-NMR (100 MHz, CDCl$_3$): (signals are split due to amide isomerism): δ: 172.3, 169.5, 142.1, 137.4, 129.0, 128.7, 128.6, 128.5, 127.5, 127.4, 127.3, 127.2, 127.0, 126.9, 126.6, 109.3, 80.2, 67.1, 64.2, 61.3, 60.6, 60.0, 58.9, 57.0, 56.8, 54.0, 41.4, 34.5, 34.3, 34.0, 33.2, 31.8, 31.0, 28.2, 28.1, 25.6, 23.4.

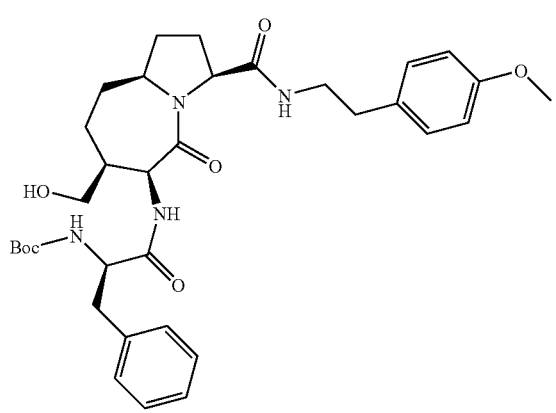

6d

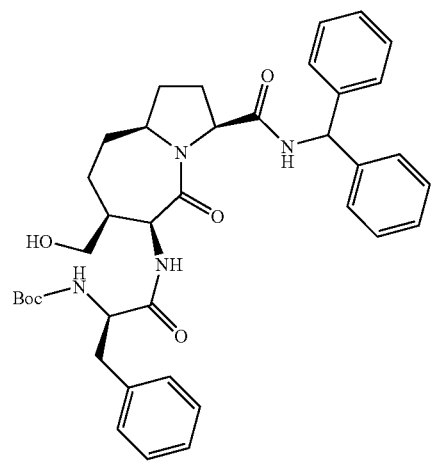

6f

6d. Biotage™ eluant conditions: 1% of MeOH and 99% of CH₂Cl₂ to 10% of MeOH and 90% of CH₂Cl₂ 10 VC. Yield 77.0% (479 mg, MW 622.10, 0.77 mmol) of pure 6d. Analytical characterization: [α]$_D^{20}$-77.1 (c 1.03, CHCl₃); ¹H-NMR (400 MHz, CDCl₃): δ: 7.55 (d, J=6.0, 1H), 7.40-7.21 (m, 5H), 7.10 (d, J=8.4 Hz, 2H), 6.83 (d, J=11.2, 2H), 6.72 (bt, J=5.6 Hz, 1H), 4.95 (bs, 1H), 4.51 (d, J=6.4 Hz, 1H), 4.43 (dd, J=10.4, 7.2 Hz, 1H), 3.78 (m, 4H), 3.65-3.38 (m, 3H), 3.25 (m, 2H), 3.00 (m, 2H), 2.75 (m, 2H), 2.35 (m, 1H), 2.24 (m, 1H), 2.05 (m, 1H), 1.95-1.65 (m, 4H), 1.40 (s, 9H), 1.27 (m, 1H), 1.10 (m, 1H); ¹³C-NMR (100 MHz, CDCl₃): δ: 172.8, 171.4, 170.7, 158.2, 136.2, 130.6, 129.7, 129.2, 128.7, 127.0, 114.0, 80.5, 64.1, 61.8, 58.9, 56.1, 55.2, 54.0, 52.7, 41.3, 40.3, 38.2, 34.4, 34.3, 33.1, 32.9, 28.0, 26.4.

6f. Biotage™ eluant conditions: 1% of MeOH and 99% of CH₂Cl₂ to 10% of MeOH and 90% of CH₂Cl₂ 10 VC. Yield 90.0% (589 mg, MW 654.20, 0.90 mmol) of pure 6f. Analytical characterization: [α]$_D^{20}$-71.2 (c 0.85, CHCl₃); ¹H-NMR (400 MHz, CDCl₃): δ: 7.86 (d, J=8.8 Hz, 1H), 7.49 (d, J=7.2 Hz, 1H), 7.39-7.22 (m, 13H), 7.17 (d, J=7.6 Hz, 2H), 6.23 (d, J=8.8 Hz, 1H), 4.95 (bs, 1H), 4.73 (d, J=7.6 Hz, 1H), 4.46 (m, 2H), 3.80 (dd, J=17.6, 7.2 Hz, 1H), 3.51 (t, J=12.4, 1H), 3.25 (m, 2H), 3.05 (m, 1H), 2.45 (dd. J=12.4, 6.8 Hz, 1H), 2.29 (dd, J=12.0, 6.8 Hz, 1H), 2.05 (m, 1H), 1.90 (m, 2H), 1.75 (m, 2H), 1.41 (s, 9H), 1.35-1.00 (m, 3H); ¹³C-NMR (100 MHz, CDCl₃): δ: 172.0, 169.4, 142.1, 137.4, 129.4, 129.0, 127.2, 126.5, 80.4, 67.1, 64.1, 61.2, 58.9, 56.8, 54.0, 41.5, 34.5, 34.0, 33.2, 31.0, 28.2, 25.6.

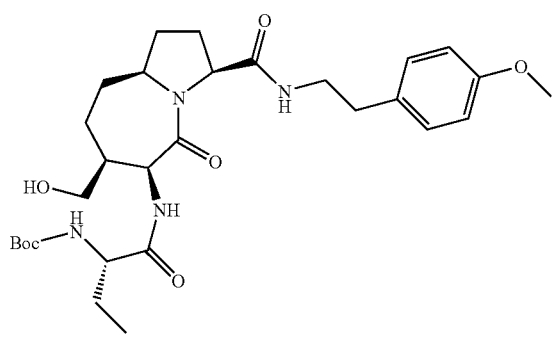

6e

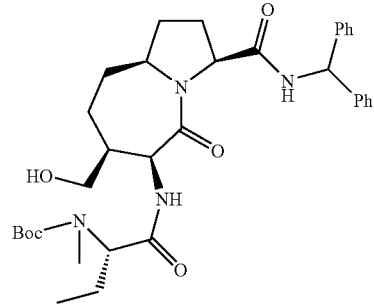

6g

6e. Biotage™ eluant conditions: 1% of MeOH and 99% of CH₂Cl₂ to 10% of MeOH and 90% of CH₂Cl₂ 10 VC. Yield 67.0% (375 mg, MW 560.32, 0.67 mmol) of pure 6e. Analytical characterization: [α]$_D^{20}$-112.0 (c 1.00, CHCl₃); ¹H-NMR (400 MHz, CDCl₃): (signals are split due to amide isomerism): δ: 7.52 (d, J=6.0 Hz, 1H), 7.12 (dd, J=8.8, 2.0 Hz, 2H), 6.85 (d, J=8.4 Hz, 2H), 6.76 (m, 1H), 5.10 (m, 1H), 4.54 (d, J=7.2 Hz, 1H), 4.45 (dd, J=10.0, 7.6 Hz, 1H), 4.10 (m, 1H), 3.80 (s, 3H), 3.78-3.55 (m, 3H), 3.45 (m, 1H), 3.35 (dd, J=11.6, 2.4 Hz, 1H), 2.75 (m, 2H), 2.35 (m, 1H), 2.25 (m, 1H), 2.05 (m, 1H), 1.95-1.60 (m, 6H), 1.48 (s, 9H), 1.31-1.19 (m, 2H), 1.00 (t, J=7.6 Hz, 3H); ¹³C-NMR (100 MHz, CDCl₃): δ: 173.8, 171.4, 170.7, 158.2, 155.7, 130.7, 129.6, 114.0, 80.4, 72.9, 64.3, 61.6, 59.0, 56.6, 55.3, 53.9, 52.8, 41.6, 40.2, 34.4, 33.1, 31.2, 28.3, 26.2, 25.7, 10.2.

6g. Biotage™ eluant conditions: 50% of EtOAc and 50% of Petroleum ether to 100% of EtOAc 7 VC. Yield 71% (620 mg, MW 606, 1.0 mmol) of pure 6g. [α]$_D^{20}$-85.3 (c 0.01, CHCl₃). ¹H-NMR (400 MHz, CDCl₃): δ: 7.87 (d, J=6.8 Hz, 1H), 7.45 (bs, 1H), 7.29-7.10 (m, 10H), 6.15 (d, J=88.63 Hz, 1H), 4.68 (d, J=7.45 Hz, 1H), 4.46 (bs, 1H), 4.39 (t. J=8.24 Hz, 1H), 3.71 (dd, J=17.3, 8.6 Hz, 1H), 3.53 (d, J=12.16 Hz, 1H), 3.20 (dd, J=3.14, 12.16 Hz, 1H), 2.79 (s, 3H), 2.38 (m, 1H), 2.20 (m, 1H), 1.98-1.67 (m, 7H), 1.42 (s, 9H), 1.10-1.02 (m, 2H), 0.85 (t, J=7.06 Hz, 3H); ¹³C-NMR (100 MHz, CDCl₃): δ: 173.1, 171.9, 169.5, 142.2, 141.2, 128.7, 128.5, 127.4, 127.3, 80.5, 64.2, 61.2, 60.2, 58.9, 56.8, 53.7, 41.7, 34.6, 33.2, 31.1, 30.2, 28.4, 25.6, 21.4, 10.7.

1.6 General Procedure for the Synthesis of Compounds 7 (Scheme 2)

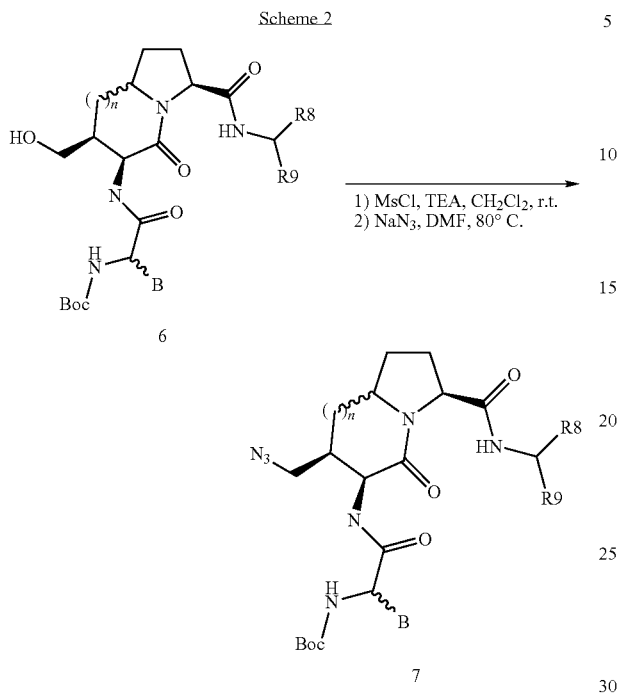

Dry TEA (4.0 mmol) and MsCl (4.0 mmol) were added to stirred solutions of compounds 6 (1.0 mmol) in dry CH$_2$Cl$_2$ (4 ml) under argon at 0° C. The reaction mixtures were stirred at room temperature overnight. After reaction completion, the resulting mixtures were diluted with CH$_2$Cl$_2$ (20 ml) and washed with saturated solutions of NH$_4$Cl (3×20 ml). The combined organic layers were dried over Na$_2$SO$_4$, and then the solvent removed under reduced pressure. The crude products were dissolved in dry DMF (10 ml) under argon at room temperature, and then NaN$_3$ (10.0 mmol) was added. The reaction mixtures were left stirring at 80° C. overnight. After reaction completion, the solvent was removed under reduced pressure, the crude products were diluted with CH$_2$Cl$_2$ (20 ml) and washed with water (3×20 ml). The organic layers were dried over Na$_2$SO$_4$, and then the solvent removed under reduced pressure. Finally, the crude products were purified by flash chromatography.

Compound 7a was synthesized by the general procedure described above.

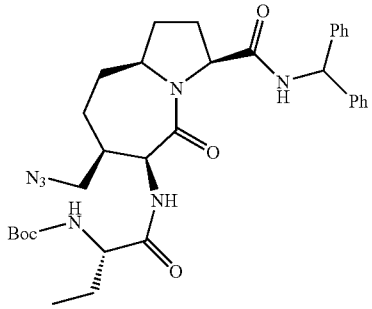

7a. Eluant mixture: Petroleum ether/EtOAc 30:70. Yield 51% (315 mg, MW 617.33, 0.51 mmol) of pure 7a. Analytical characterization: [α]$_D^{20}$-109.9 (c 0.62, MeOH); $^1$H-NMR (400 MHz, CDCl$_3$): δ: 7.82 (d. J=8.8 Hz, 1H), 7.30-7.13 (m, 8H), 7.21 (d, J=6.4 Hz, 2H), 7.11 (d. J=6.8 Hz, 1H), 6.14 (d, J=8.8 Hz, 1H), 4.92 (bd, J=7.2 Hz, 1H), 4.64 (d, J=7.6 Hz, 1H), 4.50 (dd, J=10.0 Hz, 8.0, 1H), 3.96 (dd, J=13.6, 7.2 Hz, 1H), 3.76 (dd, J=17.6, 9.2 Hz, 1H), 3.45 (dd, J=12.4, 3.6 Hz, 1H), 3.06 (dd, J=12.4, 9.2 Hz, 1H), 2.36 (dd, J=12.4, 6.8 Hz, 1H), 2.18 (m, 1H), 1.95 (m, 1H), 1.82-1.44 (m, 7H), 1.39 (s, 9H), 1.30-1.1 (m, 2H), 0.89 (t, J=7.2 Hz, 3H); $^{13}$C-NMR (100 MHz, CDCl$_3$): δ: 172.4, 171.3, 169.4, 155.8, 142.0, 141.1, 128.7, 128.6, 127.3, 127.2, 126.9, 80.3, 61.0, 58.9, 56.8, 56.4, 53.6, 53.5, 40.0, 34.2, 33.3, 32.0, 28.3, 25.5, 21.0, 10.2.

Additional compounds of general structure 7 are:

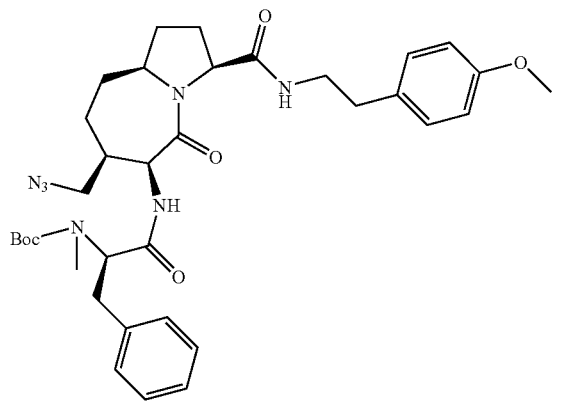

7b. Biotage™ eluant conditions: 1% of MeOH and 99% of CH$_2$Cl$_2$ to 10% of MeOH and 90% of CH$_2$Cl$_2$ 10 VC. Yield 87.6% (579 mg, MW 661.36, 0.88 mmol) of pure 7b. Analytical characterization: [α]$_D^{20}$-112.2 (c 1.25, CHCl$_3$); $^1$H-NMR (600 MHz, DMSO-d6, 358K): δ: 7.70 (d, J=8.7 Hz, 1H), 7.61 (bs, 1H), 7.35-7.20 (m, 5H), 7.13 (d, J=8.4 Hz, 2H), 6.85 (d, J=7.8 Hz, 2H), 4.90 (bs, 1H), 4.53 (t, J=9 Hz, 1H), 4.38 (d, J=4.8 Hz, 1H), 3.94 (dd, J=15, 7.2 Hz, 1H), 3.74 (s, 3H), 3.42 (dd, J=12, 3 Hz, 1H), 3.33-3.24 (m, 3H), 3.20 (t, J=8.4 Hz, 1H), 2.87 (dd, J=13.2, 10.8 Hz, 1H), 2.74 (s, 3H), 2.68 (t, J=7.2 Hz, 2H), 2.15 (m 1H), 2.05 (m, 1H), 1.92 (m, 1H), 1.83 (m, 3H), 1.75-1.58 (m, 3H), 1.28 (s, 9H); $^{13}$C-NMR (100 MHz, CDCl$_3$): (signals are split due to amide isomerism): δ: 172.2, 171.1, 169.6, 155.2, 142.4, 141.3, 129.2, 129.1, 128.8, 128.4, 126.7, 126.6, 80.4, 61.3, 60.2, 58.8, 55.2, 53.5, 40.4, 39.5, 34.5, 34.2, 34.0, 33.3, 32.0, 29.7, 28.3, 28.1, 26.1.

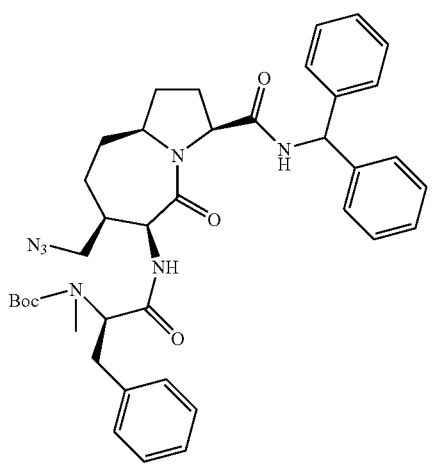

7c

7c. Biotage™ eluant conditions: 1% of MeOH and 99% of CH$_2$Cl$_2$ to 10% of MeOH and 90% of CH$_2$Cl$_2$ 10 VC. Yield 94.5% (655 mg, MW 693.36, 0.95 mmol) of pure 7c. Analytical characterization: $[\alpha]_D^{20}$-122.8 (c 0.90, CHCl$_3$); $^1$H-NMR (600 MHz, DMSO-d6, 358K): δ: 8.65 (d, J=8.5 Hz, 1H), 7.75 (d, J=7.8 Hz, 1H), 7.40-7.18 (m, 15H), 6.10 (d, J=9.0 Hz, 1H), 4.92 (bs, 1H), 4.63 (dd, J=8.4, 3.6 Hz, 1H), 4.55 (t, J=9.6 Hz, 1H), 3.97 (dd, J=15.6, 7.8 Hz, 1H), 3.41 (dd, J=12.0, 4.2 Hz, 1H), 3.25 (dd, J=14.4, 5.4 Hz, 1H), 3.18 (dd, J=11.4, 7.8 Hz, 1H), 2.88 (dd, J=13.8, 10.8 Hz, 1H), 2.75 (s, 3H), 2.20 (dd, J=12.6, 5.4 Hz, 1H), 2.07-2.00 (m, 2H), 1.98-1.87 (m, 1H), 1.85-1.77 (m, 2H), 1.75-1.65 (m, 3H), 1.33 (s, 9H); $^{13}$C-NMR (100 MHz, CDCl$_3$): (signals are split due to amide isomerism): δ: 172.4, 171.3, 169.4, 155.8, 142.1, 141.3, 129.1, 128.6, 128.4, 127.2, 126.8, 126.6, 80.2, 61.2, 61.0, 60.2, 58.8, 56.8, 53.9, 53.6, 53.5, 39.8, 39.6, 34.2, 34.0, 33.4, 32.2, 32.0, 28.3, 28.1, 25.6.

2H), 2.25 (m, 1H), 2.13 (m, 1H), 1.95 (m, 1H), 1.82-1.60 (m, 3H), 1.44 (m 1H), 1.35 (m, 1H), 1.33 (s, 9H), 1.20 (m, 1H); $^{13}$C-NMR (100 MHz, CDCl$_3$): δ: 171.5, 170.8, 170.6, 158.3, 136.6, 130.6, 129.7, 129.6, 129.2, 128.8, 127.1, 114.0, 61.5, 60.4, 58.8, 56.1, 55.3, 53.5, 53.3, 40.5, 39.5, 38.2, 34.6, 33.7, 33.2, 31.8, 28.3, 26.4.

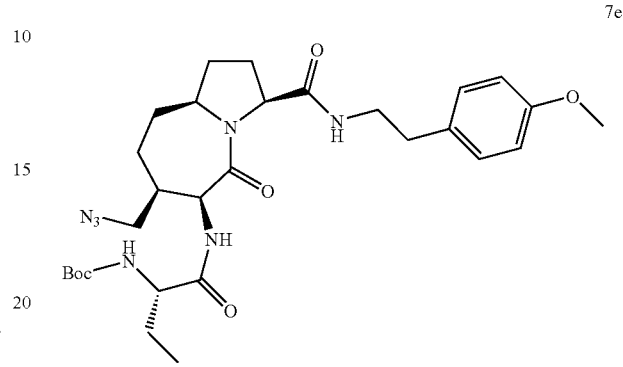

7e

7e. Biotage™ eluant conditions: 1% of MeOH and 99% of CH$_2$Cl$_2$ to 10% of MeOH and 90% of CH$_2$Cl$_2$ 10 VC. Yield 69.7% (408 mg, MW 585.33, 0.70 mmol) of pure 7e. Analytical characterization: $[\alpha]_D^{20}$-107.4 (c 0.88, CHCl$_3$); $^1$H-NMR (400 MHz, CDCl$_3$): δ: 7.45 (d, J=6.5 Hz, 1H), 7.04 (d, J=8.4 Hz, 2H), 6.74 (d, J=8.4 Hz, 2H), 6.71 (bs, 1H), 4.95 (bd, 1H), 4.46 (d, J=7.6 Hz, 1H), 4.33 (dd, J=10.4, 7.2 Hz, 1H), 3.97 (m, 1H), 3.72 (s, 3H), 3.68-3.50 (m, 2H), 3.37 (m, 1H), 3.25 (dd, J=12.0, 3.2 Hz, 1H), 2.69 (m, 2H), 2.30 (dd, J=12.0, 6.4 Hz, 1H), 2.16 (dd, J=12.4, 6.4 Hz, 1H), 1.96 (m, 1H), 1.90-1.55 (m, 6H), 1.40 (s, 9H), 1.25-1.05 (m, 2H), 0.92 (t, J=7.6 Hz, 3H); $^{13}$C-NMR (100 MHz, CDCl$_3$): δ: 173, 170.5, 170.0, 158.3, 130.6, 130.5, 114.1, 80.5, 61.4, 58.9, 56.6, 55.5, 54.2, 40.2, 37.7, 34.4, 34.1, 33.1, 28.2, 26.2, 25.4, 20.8, 10.3.

7d

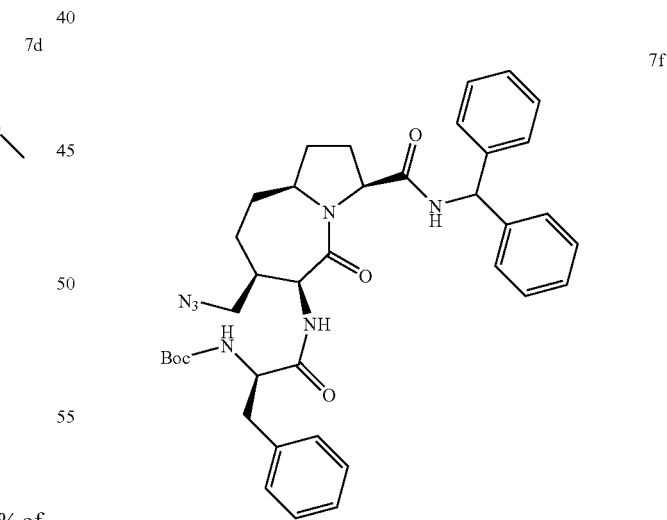

7f

7d. Biotage™ eluant conditions: 1% of MeOH and 99% of CH$_2$Cl$_2$ to 10% of MeOH and 90% of CH$_2$Cl$_2$ 10 VC. Yield 67.8% (439 mg, MW 647.34, 0.68 mmol) of pure 7d. Analytical characterization: $[\alpha]_D^{20}$-104.2 (c 1.06, CHCl$_3$); $^1$H-NMR (400 MHz, CDCl$_3$): δ: 7.27-7.15 (m, 5H), 7.03 (d, J=8.0, 2H), 6.97 (d, J=7.6 Hz, 1H), 6.76 (d, J=8.0 Hz, 2H), 6.57 (bs, 1H), 4.83 (d, J=7.6 Hz, 1H), 4.46-4.39 (m, 3H), 3.74 (m, 1H), 3.71 (s, 3H), 3.47 (m, 1H), 3.38 (m, 1H), 3.12-3.05 (m, 2H), 2.91 (bt, J=9.2 Hz, 2H), 2.67 (dd, J=13.2, 6.8 Hz, 7f. Biotage™ eluant conditions: 1% of MeOH and 99% of CH$_2$Cl$_2$ to 10% of MeOH and 90% of CH$_2$Cl$_2$ 10 VC. Yield 57.7% (392 mg, MW 679.35, 0.58 mmol) of pure 7f. Analytical characterization: $[\alpha]_D^{20}$-95.5 (c 0.88, CHCl$_3$); $^1$H-NMR (400 MHz, CDCl$_3$): δ: 7.74 (d, J=8.8 Hz, 1H), 7.29-7.17 (m, 13H), 7.09 (d, J=6.8 Hz, 2H), 6.96 (d, J=6.8 Hz, 1H), 6.13 (d, J=8.8 Hz, 1H), 4.85 (bs, 1H), 4.62 (d, J=7.2 Hz, 1H), 4.44 (dd, J=10.0, 8.0 Hz, 1H), 4.36 (m, 1H), 3.70 (dd, J=17.6, 7.6 Hz, 1H), 3.05 (m, 2H), 2.87 (m, 2H), 2.36 (dd, J=12.4, 6.8 Hz, 1H), 2.19 (m, 1H), 1.92 (dd, J=14.4, 2.8 Hz, 1H), 1.83-1.77 (m, 2H), 1.68-1.63 (m, 1H), 1.42 (m, 1H), 1.33 (s, 9H), 1.20-1.05 (m, 2H); $^{13}$C-NMR (100 MHz, CDCl$_3$): δ: 171.5, 169.4, 142.0, 136.6, 129.2, 128.8, 128.7, 128.6, 127.5, 127.4, 127.3, 127.1, 80.4, 61.0, 58.8, 56.8, 53.5, 53.3, 39.6, 34.0, 33.3, 31.8, 28.3, 25.7.

1.7 General Procedure for the Synthesis of Compounds 8 (Scheme 3)

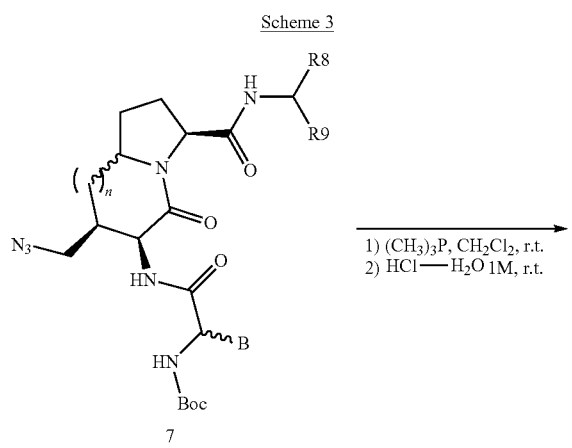

Scheme 3

7

1) (CH$_3$)$_3$P, CH$_2$Cl$_2$, r.t.
2) HCl—H$_2$O 1M, r.t.

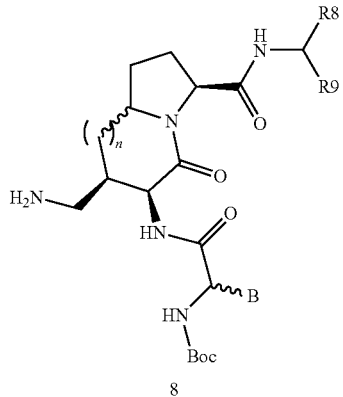

8

1 N solutions of (CH$_3$)$_3$P in toluene (1.5 mmol) were added to stirred solutions of compounds 7 (1.0 mmol) in dry CH$_2$Cl$_2$ (15 ml) under argon at room temperature. After two hours, 1N HCl solution (100 ml) was added to the reaction mixtures, which were stirred at room temperature for further 10-20 min. After reaction completion, the reaction mixtures were extracted with CH$_2$Cl$_2$ (3×100 ml), the organic layers were combined and dried over Na$_2$SO$_4$, and the solvent was removed under reduced pressure. The crude products were not requiring any further purification.

Compound 8a was synthesized by the general procedure described above.

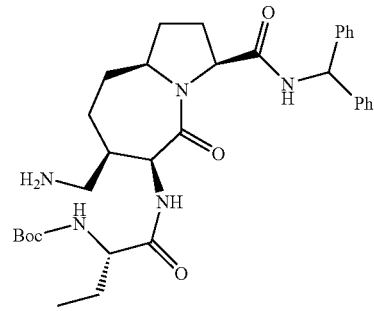

8a

8a. The crude product did not require further purification. Yield 92% (544 mg, MW 591.34, 0.92 mmol) of pure 8a. Analytical characterization: $[α]_D^{20}$-68.5 (c 1.31, MeOH); $^1$H-NMR (400 MHz, CDCl$_3$): δ: 8.39 (bs, 3H), 8.04 (bs, J=7.2 Hz, 1H), 7.82 (d, J=8.4 Hz, 1H), 7.40-7.20 (m, 10H), 6.18 (d, J=8.4 Hz, 1H), 5.12 (d, J=6.4 Hz, 1H), 4.71 (d, J=7.2 Hz, 1H), 4.49 (t, J=8.0 Hz, 1H), 4.05 (q, J=7.2 Hz, 1H); 3.74 (q, J=8.4 Hz, 1H); 2.90 (bs, 2H); 2.40 (m, 1H), 2.21 (m, 1H), 2.05-1.55 (m, 7H), 1.47 (s, 9H), 1.33 (m, 1H), 1.22 (m, 1H), 0.99 (t, J=7.6 Hz, 3H); $^{13}$C-NMR (100 MHz, CDCl$_3$): δ: 175.9, 170.1, 169.4, 142.2, 141.1, 128.7, 127.5, 127.4, 127.3, 80.3, 61.3, 58.7, 57.1, 53.8, 42.8, 38.1, 34.0, 33.3, 32.0, 29.0, 28.3, 25.8, 25.0, 10.4.

Additional compounds of general structure 8 are:

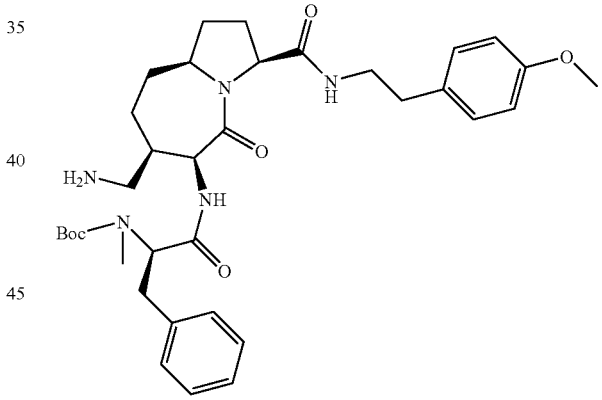

8b

8b. HPLC eluant conditions: from 70% of H$_2$O (0.1% HCOOH) and 30% of CH$_3$CN (0.1% HCOOH) to 60% of H$_2$O (0.1% HCOOH) and 40% of CH$_3$CN (0.1% HCOOH), flow rate 20 ml/min., 10 min. runs. Yield 58.0% (369 mg, MW 635.37, 0.58 mmol) of pure 8b. Analytical characterization: $[α]_D^{20}$-62.5 (c 1.40, CHCl$_3$); H-NMR (600 MHz, DMSO-d$_6$, 358K): δ: 7.71 (bs, 1H), 7.61 (bs, 1H), 7.29 (m, 2H), 7.23 (m, 3H), 7.13 (d, J=7.2 Hz, 2H), 6.86 (d, J=8.4 Hz, 2H), 4.89 (bs, 1H), 4.52 (t, J=8.4 Hz, 1H), 4.40 (m, 1H), 3.98 (m, 1H), 3.74 (s, 3H), 3.23 (m, 3H), 2.94 (m, 2H), 2.75-2.60 (m, 6H), 2.18 (m, 1H), 2.11 (m, 1H), 2.05-1.85 (m, 3H), 1.82 (m, 2H), 1.75-1.40 (m, 2H), 1.29 (s, 9H); $^{13}$C-NMR (100 MHz, CDCl$_3$): (signals are split due to amide isomerism): δ: 173.9, 170.6, 169.8, 158.3, 137.3, 130.5, 129.7, 129.1, 128.7, 128.6, 126.8, 114.0, 81.1, 80.9, 69.4, 62.1, 61.8, 58.8, 55.3, 53.8, 42.5, 40.2, 37.8, 34.2, 33.8, 32.9, 31.2, 28.2, 28.0, 26.5.

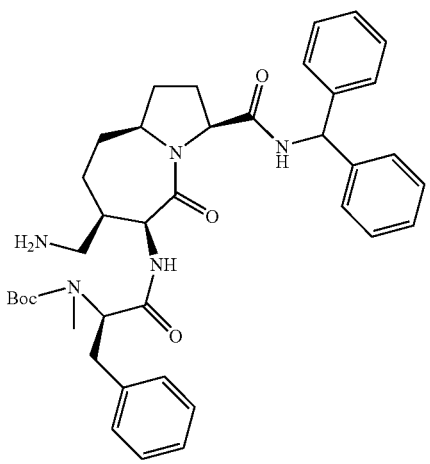

8c

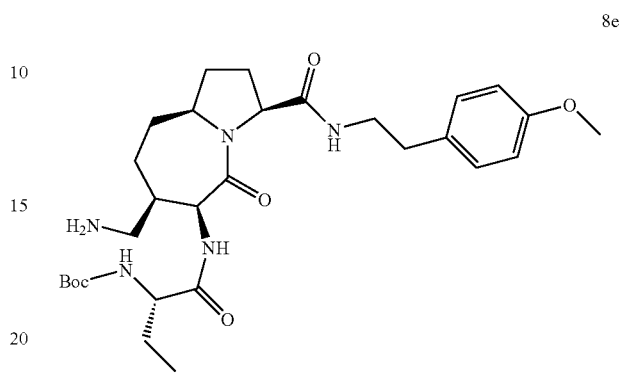

8e

8c. HPLC eluant conditions: from 70% of H$_2$O (0.1% HCOOH) and 30% of CH$_3$CN (0.1% HCOOH) to 55% of H$_2$O (0.1% HCOOH) and 45% of CH$_3$CN (0.1% HCOOH), flow rate 20 ml/min., 10 min. runs. Yield 58.3% (387 mg, MW 667.37, 0.58 mmol) of pure 8c. Analytical characterization: $[\alpha]_D^{20}$ -74.6 (c 1.40, CHCl$_3$); $^1$H-NMR (600 MHz, DMSO-d$_6$): δ: 8.71 (d, J=7.8 Hz, 1H), 7.80 (d, J=8.4 Hz, 1H), 7.45-7.20 (m, 15H), 6.09 (d, J=8.4 Hz, 1H), 4.90 (bs, 1H), 4.65 (m, 1H), 4.53 (t, J=8.4 Hz, 1H), 4.02 (m, 1H), 3.23 (bd. J=12.6 Hz, 1H), 2.94 (m, 2H), 2.70 (s, 3H), 2.68 (m, 1H), 2.21 (m, 1H), 2.07 (m, 2H), 1.95-1.65 (m, 5H), 1.61 (m, 1H), 1.30 (s, 9H); $^{13}$C-NMR (100 MHz, CDCl$_3$): (signals are split due to amide isomerism): δ: 174.3, 170.1, 169.4, 142.1, 137.5, 129.21, 128.7, 128.6, 127.5, 127.4, 127.2, 126.7, 81.0, 62.4, 61.2, 58.7, 56.9, 53.6, 42.2, 37.7, 34.0, 33.7, 33.0, 31.0, 28.2, 28.0, 25.8.

1.95-1.65 (m, 6H), 1.40 (s, 9H), 1.32-1.05 (m, 2H); $^{13}$C-NMR (100 MHz, CDCl$_3$): δ: 172.8, 171.4, 170.7, 158.2, 136.2, 130.6, 129.7, 129.2, 128.7, 127.0, 114.0, 80.5, 61.2, 61.6, 58.9, 56.1, 55.2, 54.0, 52.7, 43.5, 41.3, 40.3, 38.2, 34.4, 34.3, 33.1, 32.9, 28.0, 26.4.

8e. HPLC eluant conditions: from 80% of H$_2$O (0.1% HCOOH) and 20% of CH$_3$CN (0.1% HCOOH) to 70% of H$_2$O (0.1% HCOOH) and 30% of CH$_3$CN (0.1% HCOOH), flow rate 20 ml/min., 10 min. runs. Yield 33% (185 mg, MW 559.34, 0.33 mmol) of pure 8e. Analytical characterization: $[\alpha]_D^{20}$ -49.3 (c 0.70, CHCl$_3$); $^1$H-NMR (400 MHz, DMSO-d6, 298K): δ: 8.11 (d, J=8.4 Hz, 1H), 7.95 (t, J=4.2 Hz, 1H), 7.14 (d, J=8.4 Hz, 2H), 7.00 (d, J=8.0 Hz, 1H), 6.85 (d, J=8.4 Hz, 2H), 4.42 (t, J=8.8. Hz, 1H), 4.30 (dd, J=7.6, 3.6, 1H), 3.91 (m, 1H), 3.84 (m, 1H), 3.73 (s, 3H), 3.21 (m, 2H), 2.70-2.50 (m 4H), 2.11 (m, 1H), 2.00-1.82 (m, 2H), 1.80-1.45 (m, 8H), 1.39 (s, 9H), 0.88 (t, J=7.2 Hz, 3H); $^{13}$C-NMR (100 MHz, DMSO-d6, 298K): δ: 172.4, 171.8, 171.7, 169.8, 158.2, 155.9, 131.8, 131.7, 130.1, 114.0, 78.6, 67.4, 61.4, 58.0, 56.5, 56.1, 55.5, 55.4, 53.9, 34.7, 32.9, 32.4, 31.8, 30.9, 28.7, 28.5, 25.6, 11.0.

8d

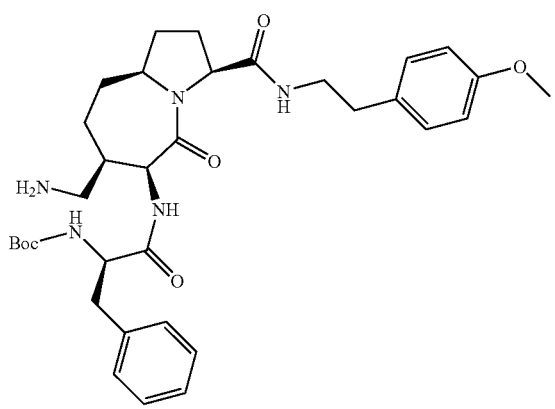

8f

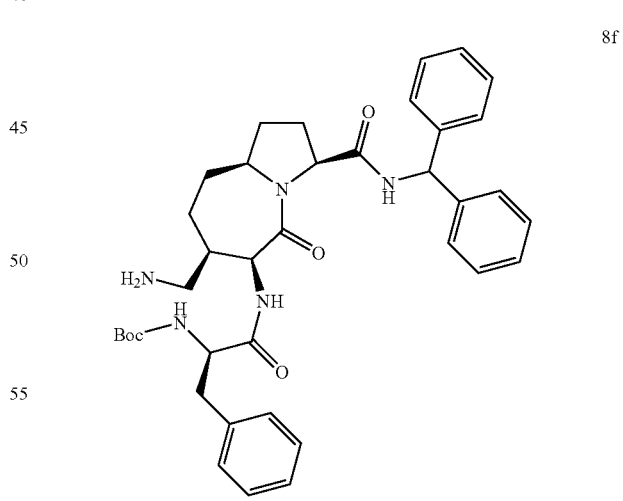

8d. HPLC eluant conditions: from 70% of H$_2$O (0.1% HCOOH) and 30% of CH$_3$CN (0.1% HCOOH) to 60% of H$_2$O (0.1% HCOOH) and 40% of CH$_3$CN (0.1% HCOOH), flow rate 20 ml/min., 10 min. runs. Yield 69.0% (428 mg, MW 621.35, 0.69 mmol) of pure 8d. Analytical characterization: $[\alpha]_D^{20}$ -67.1 (c 1.03, CHCl$_3$); $^1$H-NMR (400 MHz, CDCl$_3$): δ: 7.55 (d, J=6.0, 1H), 7.40-7.21 (m, 5H), 7.15 (d, J=8.4 Hz, 2H), 6.80 (d, J=11.2, 2H), 6.75 (m, 1H), 4.95 (m, 1H), 4.51 (m, 1H), 4.45 (m, 1H), 3.76 (m, 4H), 3.65 (m, 1H), 3.25-2.94 (m, 4), 2.75 (m, 2H), 2.35 (m, 1H), 2.22 (m, 1H), 2.07 (m, 1H), 8f. HPLC eluant conditions: from 70% of H$_2$O (0.1% HCOOH) and 30% of CH$_3$CN (0.1% HCOOH) to 60% of H$_2$O (0.1% HCOOH) and 40% of CH$_3$CN (0.1% HCOOH), flow rate 20 ml/min., 10 min. runs. Yield 65.0% (425 mg, MW 653.36, 0.65 mmol) of pure 8f. Analytical characterization: $[\alpha]_D^{20}$ -71.2 (c 0.85, CHCl$_3$); $^1$H-NMR (400 MHz, CDCl$_3$): δ: 7.85 (d, J=8.8 Hz, 1H), 7.45 (d, J=7.2 Hz, 1H), 7.40-7.15 (m, 14H), 7.17 (d, J=7.6 Hz, 2H), 6.21 (d, J=8.8 Hz, 1H), 4.73 (m, 1H), 4.46 (m, 2H), 3.80 (dd, J=17.6, 7.2 Hz, 1H), 3.25 (m, 2H), 2.45-2.14 (m, 4H), 2.05 (m, 1H), 1.90 (m, 2H), 1.75 (m, 2H), 1.41 (s, 9H), 1.35-1.00 (m, 2H); $^{13}$C-NMR (100 MHz, CDCl$_3$): δ: 172.0, 169.4, 142.1, 137.4, 129.4, 129.0, 127.2, 126.5, 80.4, 67.1, 61.2, 58.9, 56.8, 54.0, 43.5, 41.5, 34.5, 33.2, 31.0, 28.2, 25.6.

1.8 General Procedure for the Synthesis of Compounds 9 (Scheme 4)

Scheme 4

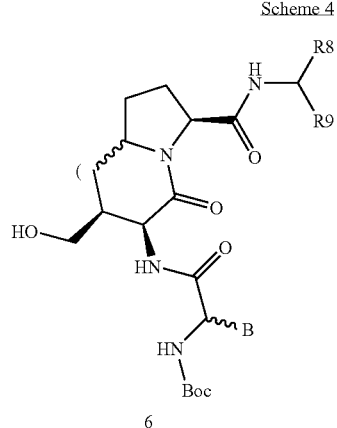

6

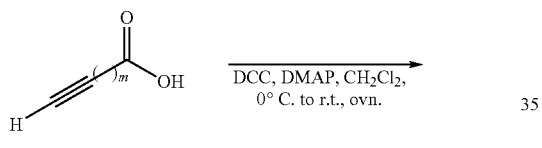

+

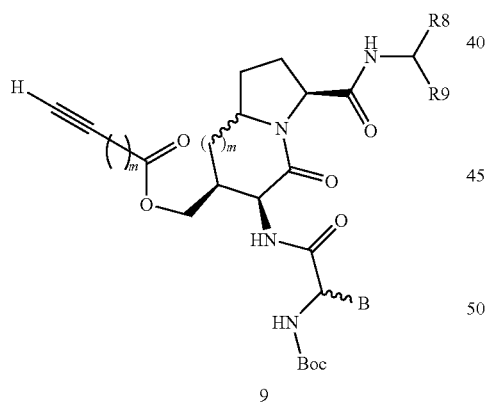

9

Combined solutions of DCC (0.10 mmol) and DMAP (0.02 mmol) were added to stirred solutions of compounds 6 (0.10 mmol) and the appropriate terminal alkyne carboxylic acid (0.10 mmol) in dry CH$_2$Cl$_2$ at 0° C. The reaction mixtures were warmed to room temperature over a period of 1 hour. After reaction completion, the reaction mixtures were filtered, and washed with diethyl ether. The solvent was removed under reduced pressure, and finally the crude products were purified by Biotage™ flash chromatography.

Compound 9a was synthesized by the general procedure described above.

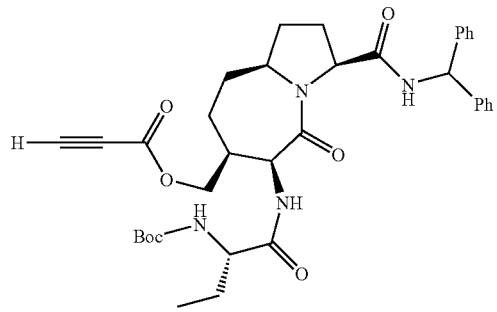

9a

9a. Biotage™ eluant conditions: 1% of MeOH and 99% of CH$_2$Cl$_2$ to 10% of MeOH and 90% of CH$_2$Cl$_2$. Yield 85% (55 mg, MW 644.32, 0.085 mmol) of pure 9a. Analytical characterization: [α]$_D^{20}$-81.4 (c 0.75, MeOH); $^1$H-NMR (400 MHz, CDCl$_3$): δ: 7.91 (d, J=8.8 Hz, 1H), 7.50-7.10 (m, 11H), 6.24 (d, J=8.4 Hz, 1H), 5.00 (d, J=6.4 Hz, 1H), 4.75 (d, J=7.2 Hz, 1H), 4.64 (t, J=9.2 Hz, 1H), 4.20 (dd, J=10.8, 7.2 Hz, 1H), 4.06 (dd, J=11.2, 7.6 Hz, 1H), 3.85 (q, J=8.4 Hz, 1H), 2.95 (s, 1H), 2.45 (m, 1H), 2.28 (m, 1H), 2.0-1.55 (m, 7H), 1.47 (s, 9H), 1.35-1.10 (m, 3H), 0.97 (t, J=7.6 Hz, 3H); $^{13}$C-NMR (100 MHz, CDCl$_3$): δ: 172.4, 171.3, 169.5, 155.5, 152.2, 142.1, 141.1, 128.7, 127.3, 80.2, 74.6, 61.0, 58.7, 56.8, 53.0, 39.1, 34.2, 34.0, 33.3, 31.3, 28.3, 25.6, 10.4.

1.9 General Procedure for the Synthesis of Compounds 10 (Scheme 5)

Scheme 5

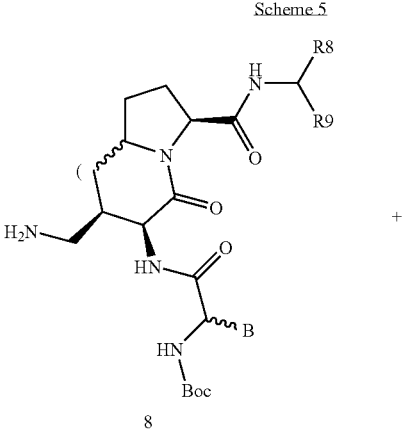

8

+

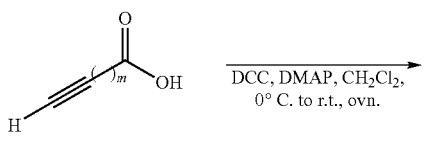

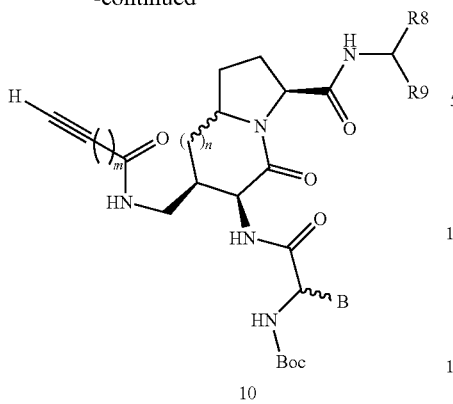

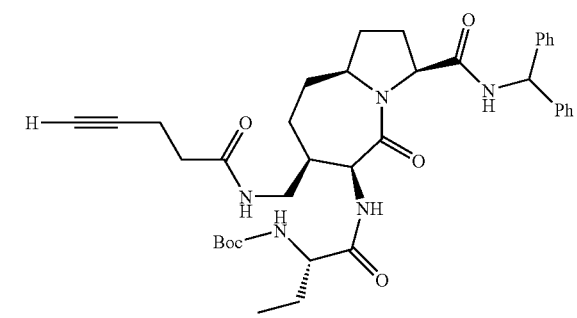 [SMILES: C#CCCC(=O)NC[C@H]1CC[C@H]2CC[C@@H](C(=O)NC(c3ccccc3)c3ccccc3)N2C(=O)[C@H]1NC(=O)[C@H](CC)NC(=O)OC(C)(C)C]

Combined solutions of DCC (0.10 mmol) and DMAP (0.02 mmol) were added to stirred solutions of compounds 8 (0.10 mmol) and the appropriate terminal alkyne carboxylic acid (0.10 mmol) in dry CH$_2$Cl$_2$ at 0° C. The reaction mixtures were warmed to room temperature over a period of 1 hour. After reaction completion, the reaction mixtures were filtered, and washed with diethyl ether. The solvent was removed under reduced pressure, and finally the crude products were purified by Biotage™ flash chromatography.

Compounds 10a and 10b were synthesized by the general procedure described above.

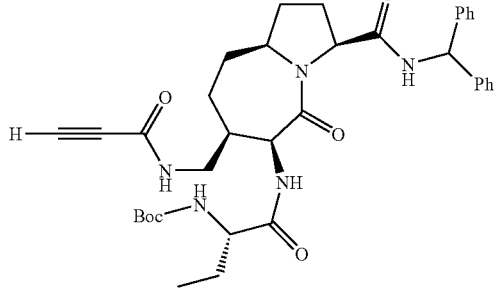

10a. Biotage™ eluant conditions: 1% of MeOH and 99% of CH$_2$Cl$_2$ to 10% of MeOH and 90% of CH$_2$Cl$_2$. Yield 87% (56 mg, MW 643.34, 0.087 mmol) of pure 10a. Analytical characterization: $[\alpha]_D^{20}$-74.2 (c 1.57, CHCl$_3$); $^1$H-NMR (400 MHz, CDCl$_3$): δ: 7.79 (d, J=8.4 Hz, 1H), 7.60 (d, J=7.6 Hz, 1H), 7.30-7.18 (m, 10H), 7.10 (d, J=6.4 Hz, 1H), 6.12 (d, J=8.8 Hz, 1H), 4.89 (d, J=6.8 Hz, 1H), 4.64 (d, J=7.2 Hz, 1H), 4.41 (t, J=9.2 Hz, 1H), 3.88 (dd, J=13.6, 7.2, 1H), 3.70 (dd, J=17.6, 8.8, 1H), 3.55 (m, 1H), 3.09 (m, 1H), 2.72 (s, 1H), 2.37 (m, 1H), 2.16 (m, 1H), 1.90-1.50 (m, 8H), 1.36 (s, 9H), 1.35-1.10 (m, 2H), 0.91 (t, J=7.6 Hz, 3H); $^{13}$C-NMR (100 MHz, CDCl$_3$): δ: 173.9, 171.4, 169.3, 152.6, 141.9, 141.0, 128.7, 127.6, 127.5, 127.3, 80.6, 73.3, 61.2, 58.9, 57.2, 56.8, 54.1, 41.5, 40.2, 34.4, 33.1, 31.8, 28.3, 25.6, 25.1, 10.4.

10b. Biotage™ eluant conditions: 1% of MeOH and 99% of CH$_2$Cl$_2$ to 10% of MeOH and 90% of CH$_2$Cl$_2$. Yield 87% (57 mg, MW 657.35, 0.087 mmol) of pure 10b. Analytical characterization: $[\alpha]_D^{20}$-95.0 (c 0.93, CHCl$_3$); $^1$H-NMR (400 MHz, CDCl$_3$): δ: 7.90 (d, J=6.8 Hz, 1H), 7.36-7.16 (m, 12H), 6.21 (d, J=8.0 Hz, 1H), 5.07 (bs, 1H), 4.71 (d, J=8.0 Hz, 1H), 4.58 (t, J=9.2 Hz, 1H), 3.98 (d, J=6.4, 1H), 3.77 (d, J=8.0, 1H), 3.40 (m, 1H), 3.13 (m, 1H), 2.71 (s, 1H), 2.60-2.40 (m, 7H), 2.22 (m, 1H), 2.10-1.40 (m, 10H), 1.45 (s, 9H), 1.35-1.10 (m, 2H), 0.91 (t, J=7.6 Hz, 3H); $^{13}$C-NMR (100 MHz, CDCl$_3$): δ: 173.5, 171.8, 171.4, 169.3, 156.1, 141.9, 141.2, 128.7, 128.6, 127.5, 127.4, 127.3, 127.2, 80.6, 69.1, 61.2, 58.9, 57.2, 56.9, 54.4, 42.1, 39.9, 35.4, 34.5, 33.3, 32.2, 28.3, 25.6, 25.1, 15.1, 14.2, 10.4.

1.10 General Procedure for the Synthesis of Compounds 11 (Scheme 6)

Scheme 6

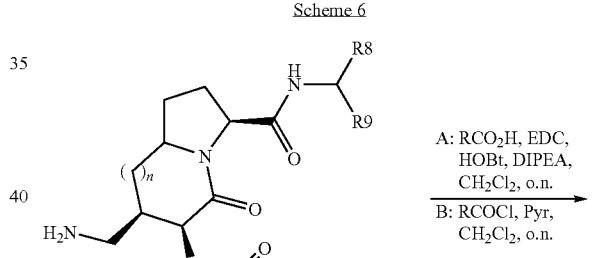

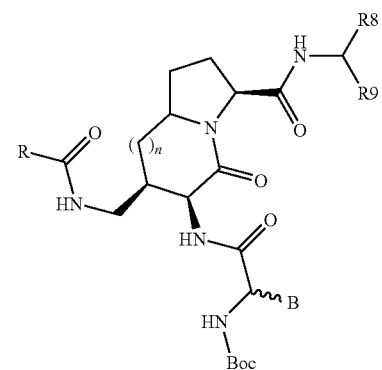

Method A: A carboxylic acid RCO$_2$H (0.10 mmol), EDC (0.12 mmol), HOBt (0.12 mmol) and DIPEA (0.40 mmol)

were sequentially added to a stirred solution of compounds 8 (0.10 mmol) in dry CH$_2$Cl$_2$ (2 ml). The reaction mixtures were stirred at room temperature overnight and then, after reaction completion, the solvent was removed under reduced pressure. Finally, the crude products were purified by Biotage™ flash chromatography.

Method B: Pyridine (1.0 mmol) and a carboxylic acid chloride RCOCl (0.10 mmol) were sequentially added to stirred solutions of compounds 8 (0.10 mmol) in CH$_2$Cl$_2$ (2 ml). The reaction mixtures were stirred at room temperature overnight and then, after reaction completion, the solvent was removed under reduced pressure. Finally the crude products were purified by Biotage™ flash chromatography.

Compounds 11a to 11c were synthesized by the general procedures described above.

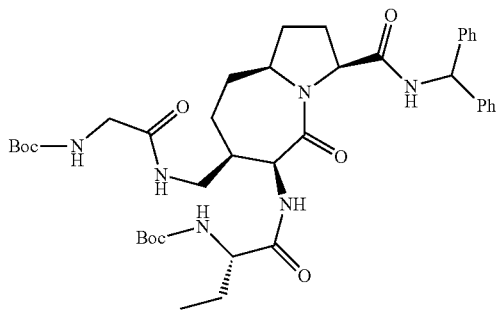

11a 11a (Method A). Biotage™ eluant conditions: 1% of MeOH and 99% of CH$_2$Cl$_2$ to 10% of MeOH and 90% of CH$_2$Cl$_2$. Yield 89% (67 mg, MW 748.42, 0.089 mmol) of pure 11a. [α]$_D^{20}$-41.0 (c 1.50, CHCl$_3$); $^1$H-NMR (400 MHz, CDCl$_3$): δ: 7.91 (d, J=7.2 Hz, 1H), 7.55-7.15 (m, 12H), 6.21 (d, J=8.8 Hz, 1H), 5.31 (bs, 1H), 5.09 (d, J=7.4 Hz, 1H), 4.71 (d, J=7.2 Hz, 1H), 4.53 (t, J=8.0 Hz, 1H), 4.04 (q, J=7.2 Hz, 1H), 3.77 (m, 3H), 3.45 (m, 1H), 3.05 (m, 1H), 2.45 (m, 1H), 2.25 (m, 1H), 1.90-1.55 (m, 8H), 1.44 (s, 9H), 1.43 (s, 9H), 1.30-1.05 (m, 2H), 0.98 (t, J=7.6 Hz, 3H); $^{13}$C-NMR (100 MHz, CDCl$_3$): δ: 173.3, 171.6, 169.6, 169.4, 165.7, 156.0, 142.1, 141.2, 128.6, 127.4, 127.3, 80.7, 79.8, 61.1, 58.8, 58.6, 56.8, 55.5, 54.0, 44.2, 39.8, 34.4, 33.3, 31.9, 25.7, 25.5, 10.9.

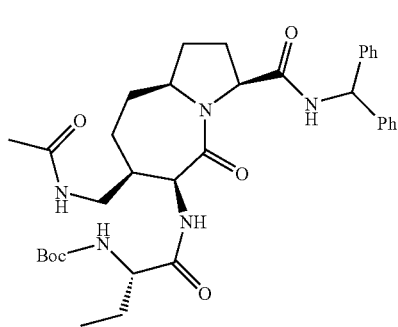

11b 11b (Method B). Biotage™ eluant conditions: 1% of MeOH and 99% of CH$_2$Cl$_2$ to 10% of MeOH and 90% of CH$_2$Cl$_2$. Yield 91% (58 mg, MW 633.35, 0.091 mmol) of pure 11b. Analytical characterization: [α]$_D^{20}$-64.0 (c 1.15, CHCl$_3$); $^1$H-NMR (400 MHz, CDCl$_3$): δ: 7.91 (d, J=8.8 Hz, 1H), 7.38-7.27 (m, 10H), 7.19 (d, J=8.4 Hz, 1H) 7.05 (bs, 1H), 6.22 (d, J=8.8 Hz, 1H), 5.98 (d, J=6.4 Hz, 1H), 4.72 (d, J=7.6 Hz, 1H), 4.49 (t, J=8.0 Hz, 1H), 3.97 (dd, J=13.2, 6.0, 1H), 3.80 (m, 1H), 3.55 (bs, 1H), 2.81 (d, J=12.0 Hz, 1H), 2.45 (m, 1H), 2.25 (m, 1H), 2.08 (s, 3H), 2.00-1.48 (m, 8H), 1.46 (s, 9H), 1.25-1.0 (m, 2H), 1.00 (t, J=7.6 Hz, 3H); $^{13}$C-NMR (100 MHz, CDCl$_3$): δ: 173.6, 171.7, 170.5, 169.3, 142.0, 141.1, 128.6, 127.5, 127.3, 127.2, 80.5, 61.2, 59.0, 57.1, 56.8, 54.1, 53.9, 41.4, 40.2, 34.5, 33.1, 31.9, 28.3, 25.6, 25.2, 23.3, 10.3.

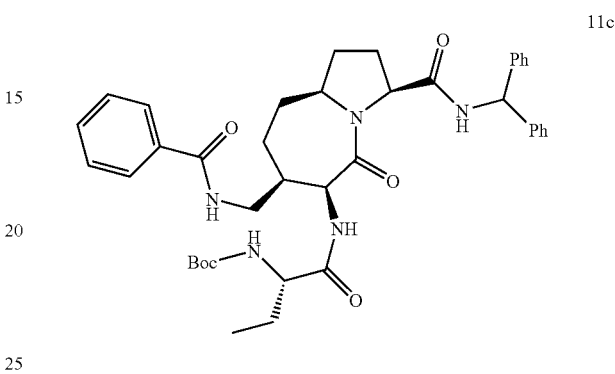

11c 11c (Method B). Biotage™ eluant conditions: 1% of MeOH and 99% of CH$_2$Cl$_2$ to 10% of MeOH and 90% of CH$_2$Cl$_2$. Yield 92% (64 mg, MW 695.37, 0.092 mmol) of pure 11c. Analytical characterization: [α]$_D^{20}$-54.1 (c 1.10, CHCl$_3$); $^1$H-NMR (400 MHz, CDCl$_3$): δ: 7.99-7.8 (m, 4H), 7.60-7.15 (m, 16H), 6.23 (d, J=8.8 Hz, 1H), 5.0 (d, J=6.8 Hz, 1H), 4.74 (d, J=7.2, 1H), 4.05 (t, J=6.0, 1H), 4.05 (dd, J=13.2, 6.2, 1H), 3.95 (bs, 1H), 4.75 (dd, J=13.2, 7.2, 1H), 3.20 (d, J=13.0, 1H), 2.45 (dd, J=12.0, 6.4 Hz, 1H), 2.21 (m, 1H), 2.05-1.48 (m, 7H), 1.45 (m, 2H), 1.37 (s, 9H), 1.25-1.0 (m, 2H), 0.87 (t. J=7.6 Hz, 3H); $^{13}$C-NMR (100 MHz, CDCl$_3$): δ: 173.9, 171.7, 170.0, 167.3, 141.7, 140.7, 134.3, 131.2, 128.6, 128.4, 127.5, 127.4, 127.3, 127.2, 80.5, 61.2, 61.0, 58.9, 57.1, 56.8, 54.1, 41.5, 40.3, 34.5, 34.3, 33.1, 31.7, 28.3, 25.9, 20.6, 10.1.

1.11 General Procedure for the Synthesis of Compounds 12 (Scheme 7)

Scheme 7

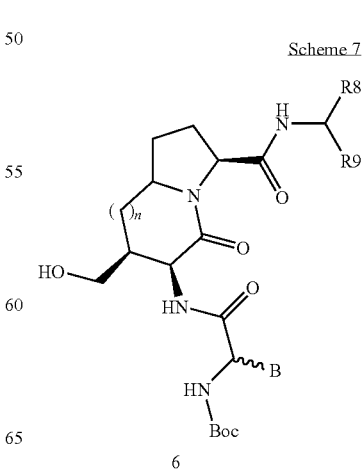

6

RCOCl, DMAP, Pyr, CH$_2$Cl$_2$, o.n.

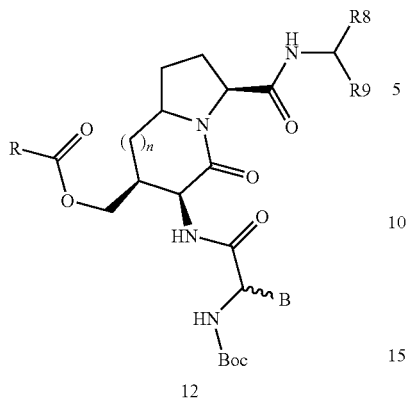

12

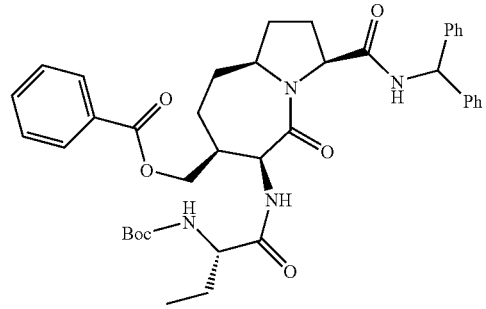

12b

Pyridine (1.0 mmol), a carboxylic acid chloride RCOCl (0.10 mmol) and DMAP (0.02 mmol) were sequentially added to stirred solutions of compounds 6 (0.10 mmol) in CH$_2$Cl$_2$ (2 ml). The reaction mixtures were stirred at room temperature overnight, then the solvent was removed under reduced pressure. Finally, the crude products were purified by Biotage™ flash chromatography. Compounds 12a to 12c were synthesized by the general procedure described above.

12b. Biotage™ eluant conditions: 1% of MeOH and 99% of CH$_2$Cl$_2$ to 10% of MeOH and 90% of CH$_2$Cl$_2$. Yield 94% (65 mg, MW 696.35, 0.094 mmol) of pure 12b. Analytical characterization: $[\alpha]_D^{20}$ -83.7 (c 0.95, MeOH); $^1$H-NMR (400 MHz, CDCl$_3$): δ: 7.98 (d, J=7.6 Hz, 1H), 7.89 (d, J=8.4 Hz, 1H), 7.52 (t, J=7.2 Hz, 1H), 7.40 (t, J=7.2 Hz, 1H), 7.30-7.10 (m, 11H), 7.05 (t, J=7.2 Hz, 1H), 6.15 (d, J=8.8 Hz, 1H), 4.92 (d, J=6.4 Hz, 1H), 4.69 (m, 2H), 4.34 (dd, J=11.2, 3.6 Hz, 1H), 4.09 (dd, J=11.2, 4.4 Hz, 1H), 4.01 (m, 1H) 3.83 (dd, J=17.2, 8.4 Hz, 1H), 2.87 (dd, J=12.0, 6.4 Hz, 1H), 2.21 (m, 1H), 2.05-1.48 (m, 8H), 1.36 (s, 9H), 1.25-1.0 (m, 2H), 0.87 (t, J=7.6 Hz, 3H); $^{13}$C-NMR (100 MHz, CDCl$_3$): δ: 172.3, 171.7, 169.6, 166.1, 155.6, 142.1, 141.1, 133.1, 130.1, 129.6, 128.7, 128.6, 128.5, 127.3, 80.2, 65.7, 61.0, 58.8, 56.8, 56.4, 53.4, 53.0, 39.3, 34.3, 33.4, 31.6, 28.3, 25.6, 10.1.

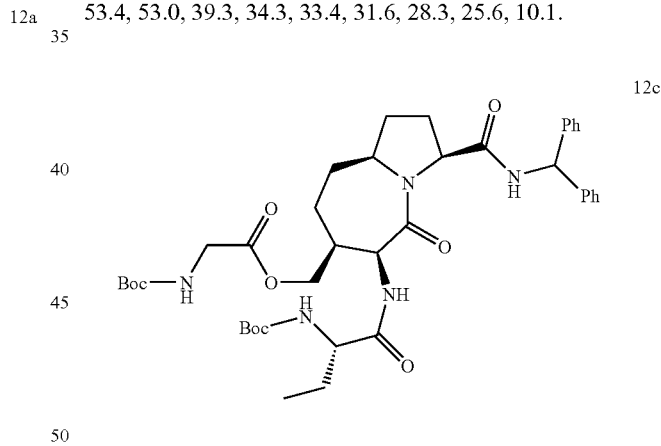

12a. Biotage™ eluant conditions: 1% of MeOH and 99% of CH$_2$Cl$_2$ to 10% of MeOH and 90% of CH$_2$Cl$_2$. Yield 92% (58 mg, MW 634.34, 0.092 mmol) of pure 12a. Analytical characterization: $[\alpha]_D^{20}$ -105.0 (c 1.28, MeOH); $^1$H-NMR (400 MHz, CDCl$_3$): δ: 7.93 (d, J=8.8 Hz, 1H), 7.38-7.19 (m, 10H), 6.21 (d, J=8.8 Hz, 1H), 7.10 (d, J=8.4 Hz, 1H), 6.23 (d, J=8.8 Hz, 1H), 5.01 (d, J=6.8 Hz, 1H), 4.73 (d, J=7.6 Hz, 1H), 4.67 (t, J=8.4 Hz, 1H), 4.06 (m, 1H), 4.01 (m, 1H), 3.87 (dd, J=17.6, 8.8 Hz, 1H), 2.44 (m, 1H), 2.26 (m, 1H), 2.06 (s, 3H), 1.88 (m, 4H), 1.80-1.60 (m, 3H), 1.55 (m, 1H), 1.47 (s, 9H), 1.22-1.10 (m, 1H), 0.967 (t, 7.6 Hz, 3H); $^{13}$C-NMR (100 MHz, CDCl$_3$): δ: 172.1, 171.7, 170.6, 169.5, 142.1, 141.2, 128.7, 128.6, 127.4, 127.3, 127.2, 65.4, 61.0, 58.7, 56.7, 52.9, 39.1, 34.3, 33.4, 31.5, 28.3, 25.6, 20.9, 10.8.

12c. Biotage™ eluant conditions: 1% of MeOH and 99% of CH$_2$Cl$_2$ to 10% of MeOH and 90% of CH$_2$Cl$_2$. Yield 89% (67 mg, MW 749.40, 0.089 mmol) of pure 12c. Analytical characterization: $[\alpha]_D^{20}$ -93.4 (c 0.55, MeOH); $^1$H-NMR (400 MHz, CDCl$_3$): δ: 7.80 (d. J=8.4 Hz, 1H), 7.35-7.15 (m, 10H), 6.14 (d, J=8.8 Hz, 1H), 5.33 (m, 1H), 4.65 (d, J=7.6 Hz, 2H), 3.94 (m, 2H), 3.81 (m, 4H), 2.32 (dd, J=11.6, 6.4 Hz, 1H), 2.18 (m, 1H), 1.90-1.55 (m, 8H), 1.37 (s, 18H), 1.30-1.10 (m, 2H), 0.96 (t, J=7.2 Hz, 3H); $^{13}$C-NMR (100 MHz, CDCl$_3$): δ: 172.6, 171.6, 170.0, 169.7, 159.5, 159.1, 156.0, 142.0, 141.0, 128.6, 127.4, 127.2, 80.1, 66.4, 61.0, 58.8, 58.7, 56.8, 56.3, 52.9, 42.6, 38.8, 34.4, 33.2, 31.6, 28.3, 25.6, 25.3, 10.3.

1.12 General Procedure for the Synthesis of Compounds 13 (Scheme 8)

Scheme 8

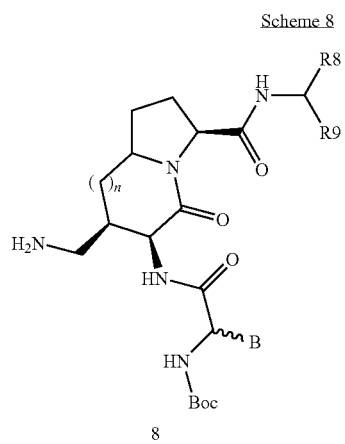

8

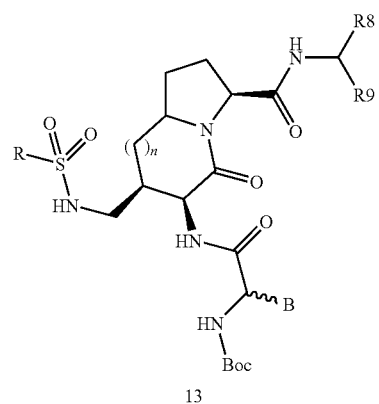

13

A 0.3 M water solution of K$_2$CO$_3$ (1.3 ml, 0.40 mmol) and a sulfonyl chloride RSO$_2$Cl (0.22 mmol) were added to stirred solutions of compounds 8 (0.10 mmol) in CH$_2$Cl$_2$ (2 ml). The reaction mixtures were stirred at room temperature overnight and then, after reaction completion, the solvent was removed under reduced pressure. Finally the crude products were purified by Biotage™ flash chromatography. Compounds 13a and 13b were synthesized by the general procedure described above.

13a

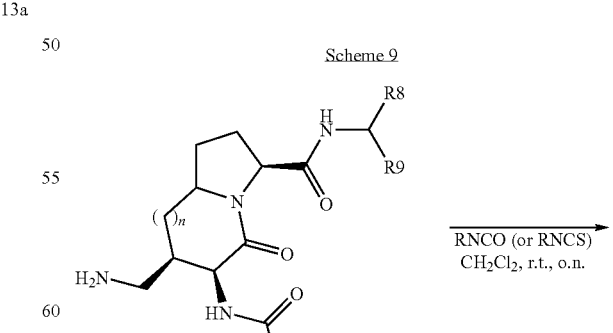

13a. Biotage™ eluant conditions: 1% of MeOH and 99% of CH$_2$Cl$_2$ to 10% of MeOH and 90% of CH$_2$Cl$_2$. Yield 74% (50 mg, MW 669.32, 0.074 mol) of pure 13a. Analytical characterization: $[\alpha]_D^{20}$-101.0 (c 1.68, CHCl$_3$); $^1$H-NMR (400 MHz, CDCl$_3$): δ: 7.74 (d, J=8.4 Hz, 1H), 7.30-7.18 (m, 10H), 7.12 (d, J=7.2 Hz, 1H), 6.13 (d, J=8.8 Hz, 1H), 5.95 (d, J=9.2 Hz, 1H), 4.92 (d, J=6.8 Hz, 1H), 4.63 (t, J=8.0 Hz, 1H), 4.40 (t, J=8.4, 1H), 3.92 (dd, J=13.6, 7.6 Hz, 1H), 3.70 (dd, J=13.6, 8.3, 1H), 3.05 (m, 2H), 2.79 (s, 3H), 2.41 (m, 1H), 2.28 (m, 1H), 1.90-1.55 (m, 8H), 1.37 (s, 9H), 1.32-1.10 (m, 3H), 0.91 (t, J=7.2 Hz, 3H); $^{13}$C-NMR (100 MHz, CDCl$_3$): δ: 173.5, 171.2, 171.1, 169.3, 155.8, 142.0, 141.1, 127.5, 127.4, 127.3, 127.2, 80.4, 61.3, 58.9, 56.8, 53.5, 45.7, 40.0, 39.8, 34.3, 33.1, 31.7, 28.3, 25.7, 25.4, 10.2.

13b

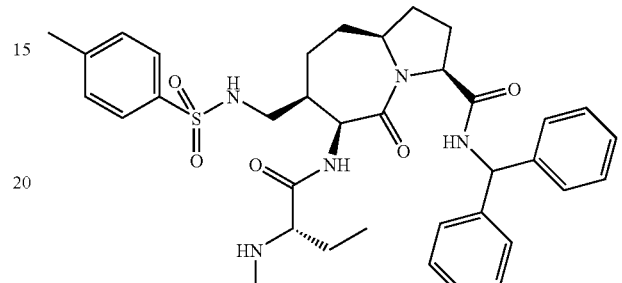

13b. Biotage™ eluant conditions: 1% of MeOH and 99% of CH$_2$Cl$_2$ to 10% of MeOH and 90% of CH$_2$Cl$_2$. Yield 82% (61 mg, MW 745.35, 0.082 mmol) of pure 13b. Analytical characterization: $[\alpha]_D^{20}$-85.0 (c 1.05, CHCl$_3$); $^1$H-NMR (400 MHz, CDCl$_3$): δ: 7.85 (d, J=8.4 Hz, 1H), 7.64 (d, J=8.8 Hz, 2H), 7.31-7.10 (m, 14H), 6.35 (d, J=6.4 Hz, 1H), 6.12 (d, J=8.8 Hz, 1H), 4.75 (bs, 1H), 4.60 (d, J=7.2 Hz, 1H), 3.38 (t, J=8.4 Hz, 1H), 3.87 (dd, J=12.8, 6.8 Hz, 1H), 3.68 (dd, J=17.6, 8.8 Hz, 1H), 2.82 (m, 1H), 2.67 (m, 1H), 2.34 (m, 1H), 2.33 (s, 3H), 2.16 (m, 1H), 1.95-1.55 (m, 7H), 1.45 (m, 2H), 1.34 (s, 9H), 1.32-1.10 (m, 2H), 0.80 (t, J=7.2 Hz, 3H); $^{13}$C-NMR (100 MHz, CDCl$_3$): δ: 173.3, 171.3, 169.4, 142.8, 142.0, 141.2, 137.8, 129.5, 128.6, 127.3, 127.2, 127.0, 80.4, 61.3, 58.8, 57.3, 56.9, 54.0, 45.8, 40.0, 34.3, 33.2, 31.9, 28.3, 25.7, 25.2, 21.4, 10.1.

1.13 General Procedure for the Synthesis of Compounds 14 (Scheme 9)

Scheme 9

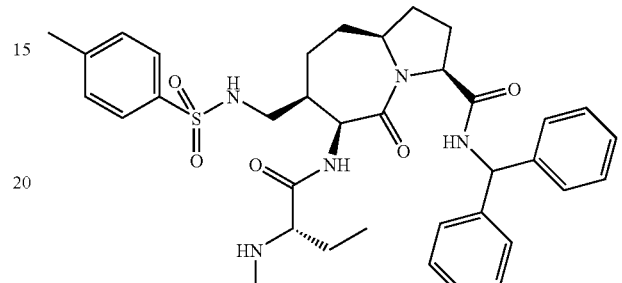

8

-continued

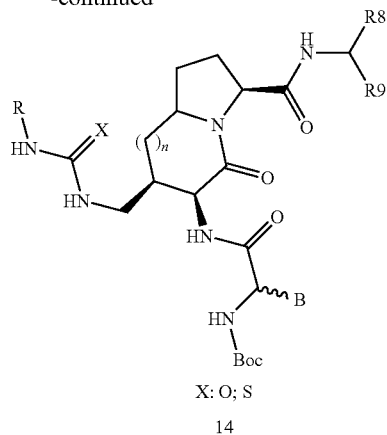

X: O; S

14

RNCO or RNCS (neat, 0.12 mmol) and DIPEA (0.12 mmol) were added to stirred solutions of compounds 8 (0.10 mmol) in CH$_2$Cl$_2$ (2 ml). The reaction mixtures were stirred at room temperature overnight and then the solvent was removed under reduced pressure. Finally the crude products were purified by Biotage™ flash chromatography.

Compounds from 14a to 14f were synthesized by the general procedure described above.

14a

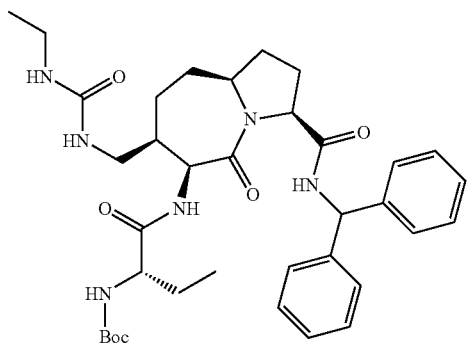

14a. Biotage™ eluant conditions: 1% of MeOH and 99% of CH$_2$Cl$_2$ to 10% of MeOH and 90% of CH$_2$Cl$_2$. Yield 89% (59 mg, MW 662.38, 0.089 mmol) of pure 14a. Analytical characterization: $[\alpha]_D^{20}$-83.3 (c 1.11, CHCl$_3$); $^1$H-NMR (400 MHz, CDCl$_3$): δ: 7.86 (d, J=7.4 Hz, 1H), 7.30-7.18 (m, 9H), 7.08 (d, J=7.2 Hz, 2H), 6.13 (d, J=8.8 Hz, 1H), 5.62 (bs, 1H), 4.93 (d, J=6.8 Hz, 1H), 4.63 (d. J=7.6 Hz, 1H), 4.46-4.37 (m, 2H), 3.89 (dd, J=13.6, 7.6 Hz, 1H), 3.68 (dd, J=17.6, 9.2 Hz, 1H), 3.29 (m, 1H), 3.14 (m, 2H), 3.05 (bd, J=12 Hz, 1H), 2.36 (m, 1H), 2.15 (m, 1H), 1.85-1.71 (m, 5H), 1.65-1.56 (m, 3H), 1.40 (m, 1H), 1.36 (s, 9H), 1.05 (t, J=7.2 Hz, 3H), 0.89 (t, J=7.6 Hz, 3H); $^{13}$C-NMR (100 MHz, CDCl$_3$): δ: 173.1, 172.0, 169.3, 169.3, 158.4, 156.0, 142.0, 141.3, 128.7, 128.6, 127.5, 127.2, 80.6, 61.2, 58.9, 57.0, 57.1 56.8, 54.5, 53.5, 42.6, 40.8, 35.2, 34.5, 33.3, 32.0, 31.5, 28.3, 25.5, 25.6, 15.6, 10.3.

14b

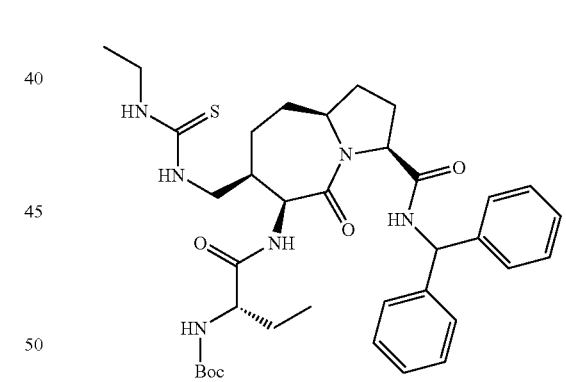

14b. Biotage™ eluant conditions: 1% of MeOH and 99% of CH$_2$Cl$_2$ to 10% of MeOH and 90% of CH$_2$Cl$_2$. Yield 95% (69 mg, MW 724.39, 0.095 mmol) of pure 14b. Analytical characterization: $[\alpha]_D^{20}$-89.6 (c 1.30, CHCl$_3$); $^1$H-NMR (400 MHz, CDCl$_3$): δ: 7.87 (d, J=8.4 Hz, 1H), 7.30-7.05 (m, 16H), 6.13 (d, J=8.0 Hz, 1H), 5.75 (bs, 1H), 4.88 (m, 2H), 4.61 (d, J=7.2 Hz, 1H), 4.41 (t, J=7.2 Hz, 1H), 4.31 (m, 2H), 3.78 (dd, J=13.6, 7.2 Hz, 1H), 3.63 (dd, J=17.6, 9.2 Hz, 1H), 3.23 (m, 1H), 3.08 (bd. J=14.4 Hz, 1H), 2.35 (m, 1H), 2.14 (m, 1H), 1.85-1.45 (m, 8H), 1.30 (m, 1H), 1.30 (s, 9H), 1.05 (m, 2H), 0.88 (t, J=7.6 Hz, 3H); $^{13}$C-NMR (100 MHz, CDCl$_3$): δ: 173.0, 171.9, 169.3, 158.3, 156.1, 141.9, 141.3, 139.8, 128.7, 128.6, 128.6, 128.4, 127.6, 127.5, 127.3, 127.2, 127.1, 80.6, 61.3, 58.9, 57.0, 54.5, 44.6, 43.0, 40.8, 34.5, 33.1, 32.2, 28.3, 25.6, 25.2, 10.1.

14c

14c. Biotage™ eluant conditions: 1% of MeOH and 99% of CH$_2$Cl$_2$ to 10% of MeOH and 90% of CH$_2$Cl$_2$. Yield 89% (60 mg, MW 678.36, 0.089 mmol) of pure 14c. Analytical characterization: $[\alpha]_D^{20}$-81.9 (c 1.09, CHCl$_3$); $^1$H-NMR (400 MHz, CDCl$_3$): δ: 7.83 (d, J=8.4 Hz, 1H), 7.35-7.05 (m, 11H), 6.13 (d, J=8.8 Hz, 1H), 5.93 (bs, 1H), 4.90 (d. J=6.0 Hz, 1H), 4.63 (d, J=7.2 Hz, 1H), 4.43 (t, J=6.0 Hz, 1H), 3.88 (dd, J=14.0, 7.2 Hz, 1H), 3.67 (dd, J=17.6, 9.2 Hz, 1H), 3.38 (m, 2H), 2.38 (m, 1H), 2.15 (m, 1H), 2.05 (m, 1H), 1.85-1.70 (m, 3H), 1.65-1.45 (m, 5H), 1.36 (s, 9H), 1.14 (t, J=6.8 Hz, 3H), 1.1 (m, 1H), 0.86 (t, J=7.2 Hz, 3H); $^{13}$C-NMR (100 MHz, CDCl$_3$): δ: 171.6, 169.4, 169.3, 141.8, 141.2, 128.7, 128.6, 127.6, 127.5, 127.3, 127.1, 80.8, 61.3, 59.0, 57.2, 56.8, 56.2, 54.8, 47.5, 40.4, 34.4, 33.3, 28.3, 25.7, 25.2, 14.2, 10.4.

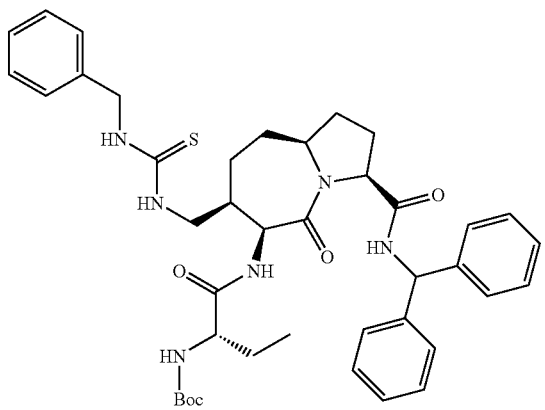

14d. Biotage™ eluant conditions: 1% of MeOH and 99% of CH$_2$Cl$_2$ to 10% of MeOH and 90% of CH$_2$Cl$_2$. Yield 88% (65 mg, MW 740.37, 0.088 mmol) of pure 14d. Analytical characterization: [α]$_D^{20}$-92.0 (c 1.30. MeOH); $^1$H-NMR (400 MHz, CDCl$_3$): δ: 7.88 (d, J=8.8 Hz, 1H), 7.34-7.04 (m, 16H), 6.40 (bs, 1H), 6.12 (d, J=8.0 Hz, 1H), 4.81 (d, J=6.0, 1H), 4.67 (m, 1H), 4.60 (d, J=7.2 Hz, 1H), 4.52 (dd, J=16.4, 4.4 Hz, 1H), 4.38 (t. J=6.0 Hz, 1H), 4.56 (m, 3H), 2.35 (m, 1H), 2.15 (m, 1H), 1.95 (m, 1H), 1.85-1.45 (m, 7H), 1.35 (m, 1H), 1.30 (s, 9H), 1.05 (m, 2H), 0.88 (t, J=7.6 Hz, 3H); $^{13}$C-NMR (100 MHz, CDCl$_3$): δ: 173.2, 171.7, 169.2, 156.2, 141.8, 141.3, 128.8, 128.7, 128.6, 128.5, 127.6, 127.4, 127.3, 127.2, 80.6, 61.3, 58.9, 57.0, 54.7, 48.1, 40.4, 34.5, 33.1, 32.3, 28.3, 25.6, 25.0, 10.4.

14e

14e. Biotage™ eluant conditions: 1% of MeOH and 99% of CH$_2$Cl$_2$ to 10% of MeOH and 90% of CH$_2$Cl$_2$. Yield 83% (61 mg, MW 738.37, 0.083 mmol) of pure 14e. Analytical characterization: [α]$_D^{20}$-91.1 (c 1.33, CHCl$_3$); $^1$H-NMR (400 MHz, CDCl$_3$): δ: 8.82 (bt, J=6.4 Hz, 1H), 8.66 (bs, 1H), 7.95 (d, J=7.2 Hz, 3H), 7.64 (t, J=7.6 Hz, 1H), 7.53 (d, J=8.0 Hz, 2H), 7.40-7.24 (m, 9H), 7.21 (m, 3H), 6.21 (d, J=8.4 Hz, 1H), 5.57 (d, J=8.8 Hz, 1H), 4.75 (d. J=7.2 Hz, 1H), 4.67 (dd, J=10, 7.6, 1H), 4.20 (bs, 1H), 3.85 (dd. J=16.8, 9.2 Hz, 1H), 3.47 (m, 1H), 3.34 (m, 1H), 2.44 (m, 1H), 2.25 (m, 1H), 2.05-1.85 (m, 4H), 1.80-1.60 (m, 6H), 1.47 (s, 9H), 1.35-1.10 (m, 2H), 0.97 (t, J=6.4 Hz, 1H); $^{13}$C-NMR (100 MHz, CDCl$_3$): δ: 172.9, 171.7, 169.5, 167.7, 153.4, 142.1, 141.2, 133.3, 132.2, 129.0, 128.9, 127.4, 127.3, 127.2, 80.1, 61.0, 58.8, 56.8, 56.4, 54.3, 42.2, 40.7, 34.5, 33.3, 32.3, 28.3, 10.2.

14f

14f. Biotage™ eluant conditions: 1% of MeOH and 99% of CH$_2$Cl$_2$ to 10% of MeOH and 90% of CH$_2$Cl$_2$. Yield 87% (66 mg, MW 754.35, 0.087 mmol) of pure 14f. Analytical characterization: [α]$_D^{20}$-78.4 (c 1.41, CHCl$_3$); $^1$H-NMR (400 MHz, CDCl$_3$): δ: 10.84 (t, J=6.4 Hz, 1H), 9.04 (s, 1H), 7.92 (m, 3H), 7.65 (m, 1H), 7.53 (m, 3H), 7.40-7.23 (m, 8H), 7.20-7.15 (m, 3H), 6.21 (d, J=8.4 Hz, 1H), 5.54 (d, J=8.0 Hz, 1H), 4.74 (d, J=7.2 Hz, 1H), 4.70 (t, J=8.0 Hz, 1H), 4.22 (m, 1H), 3.83 (m, 3H), 2.45 (m, 1H), 2.25 (m, 1H), 2.03-1.75 (m, 4H), 1.80-1.65 (m, 5H), 1.47 (s, 9H), 1.40 (m, 1H), 1.18 (m, 1H), 1.00 (t, J=7.2 Hz, 3H); $^{13}$C-NMR (100 MHz, CDCl$_3$): δ: 179.7, 173.3, 171.4, 169.5, 166.5, 142.0, 141.3, 133.7, 131, 129.2, 128.7, 128.6, 128.5, 128.4, 80.1, 61.2, 58.9, 56.8, 56.4, 54.4, 48.4, 40.1, 34.4, 33.3, 32.5, 28.3, 25.6, 10.3.

1.14 General Procedure for the Synthesis of Compounds 15 (Scheme 10)

Scheme 10

14 e, f

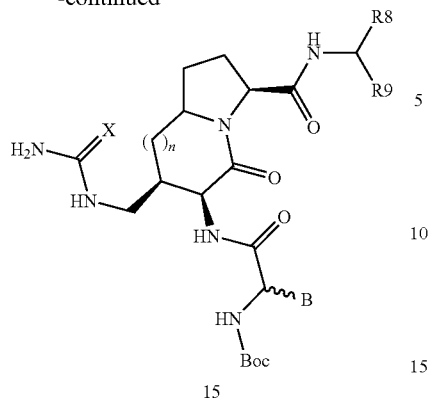

15

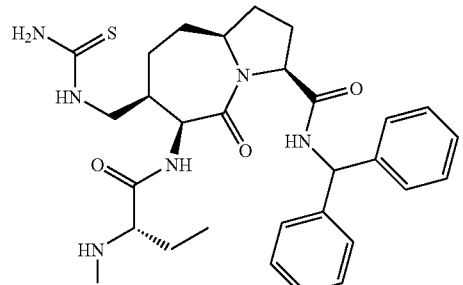

15b

15b. Yield 82% (53 mg, MW 650.33, 0.082 mmol) of pure 15b. Analytical characterization: $[\alpha]_D^{20}$-72.9 (c 1.07, MeOH); $^1$H-NMR (400 MHz, CDCl$_3$): δ: 7.91 (d, J=8.8 Hz, 1H), 7.55-7.15 (m, 11H), 6.21 (d, J=8.8 Hz, 1H), 5.09 (d, J=7.2 Hz, 1H), 4.71 (d, J=7.2 Hz, 1H), 4.61 (m, 1H), 3.95 (m, 1H), 3.78 (dd, J=17.6, 9.2 Hz, 1H), 3.70 (m, 1H), 3.50 (m, 1H), 2.46 (m, 1H), 2.23 (m, 1H), 2.05 (m, 1H), 1.95-1.55 (m, 8H), 1.43 (s, 9H), 1.35-1.15 (m, 2H), 1.00 (t, J=7.2 Hz, 3H); $^{13}$C-NMR (100 MHz, CDCl$_3$): δ: 173.1, 171.5, 169.3, 156.7, 141.6, 128.9, 128.6, 127.6, 127.4, 127.1, 81.2, 61.3, 58.9, 57.4, 56.9, 48.9, 40.4, 34.5, 33.1, 29.7, 28.3, 25.7, 25.1, 10.5.

K$_2$CO$_3$ (0.20 mmol) was added to stirred solutions of compounds 14e or 14f (0.10 mmol) in MeOH (2 ml). The reaction mixtures were stirred at room temperature overnight. After reaction completion, the reaction mixtures were extracted with CH$_2$Cl$_2$ (5 ml). The extracts were combined and dried over with Na$_2$SO$_4$, and the solvent was removed under reduced pressure. The crude products were not requiring any further purification.

Compounds 15a and 15b were synthesized by the general procedure described above.

1.15 General Procedure for the Synthesis of Compounds 16 (Scheme 11)

Scheme 11

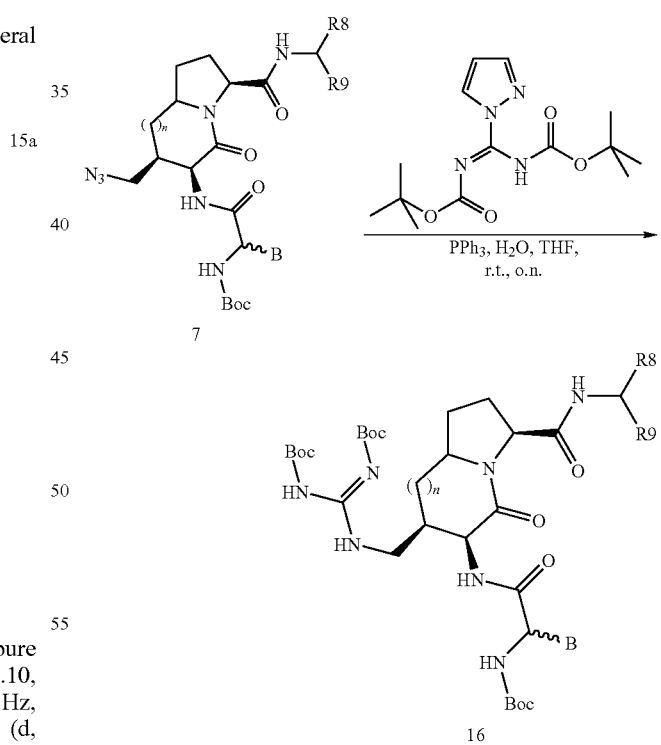

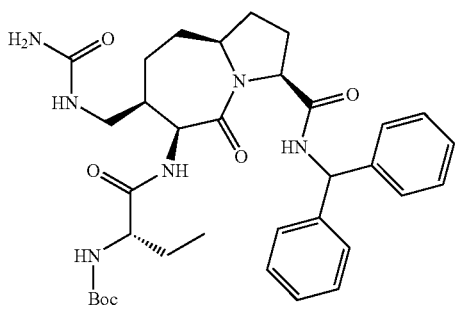

15a

15a. Yield 82% (52 mg, MW 634.35, 0.082 mmol) of pure 15a. Analytical characterization: $[\alpha]_D^{20}$-76.4 (c 1.10, MeOH); $^1$H-NMR (400 MHz, CDCl$_3$): 7.34 (d, J=8.8 Hz, 1H), 7.27-7.08 (m, 11H), 6.13 (d. J=8.8 Hz, 1H), 4.96 (d, J=7.2 Hz, 1H); 4.64 (d, J=7.2 Hz, 1H), 4.46 (m, 1H), 3.88 (dd, J=14.0, 7.2 Hz, 1H), 3.68 (dd, J=17.6, 9.2 Hz, 1H), 3.17 (m, 1H), 3.06 (m, 1H), 2.36 (m, 1H), 2.16 (m, 1H), 1.81-1.70 (m, 4H), 1.65-1.45 (m, 3H), 1.36 (s, 9H), 1.10-1.00 (m, 2H), 0.91 (t, J=7.2 Hz, 3H); $^{13}$C-NMR (100 MHz, CDCl$_3$): 173.1, 171.7, 169.3, 158.9, 141.8, 141.2, 128.7, 128.6, 127.6, 127.4, 127.3, 127.2, 80.8, 61.1, 58.9, 57.2, 56.8, 54.6, 43.2, 40.7, 34.5, 33.2, 32.3, 29.7, 28.3, 25.6, 25.2, 10.4.

N,N'-bis-Boc-1-guanylpyrazole (0.15 mmol) in a mixture of THF (1 ml) and water (0.2 ml), a 1M aqueous LiOH solution (0.2 ml) and triphenylphosphine (0.30 mmol) were sequentially added to a stirred solution of compounds 7 (0.10 mmol). The reaction mixtures were stirred at room temperature for 48 hours and then THF was removed under reduced pressure. The residues were partitioned between aqueous 10% citric acid (5 ml) and AcOEt (5 ml). The aqueous layers were extracted with AcOEt (3×5 ml) and then the organic layers were combined, washed with brine (5 ml) and dried over $Na_2SO_4$. Finally, the crude products were purified by chromatography on a $C_{18}$ reverse phase semi-preparative HPLC column.

Compound 16a was synthesized by the general procedure described above.

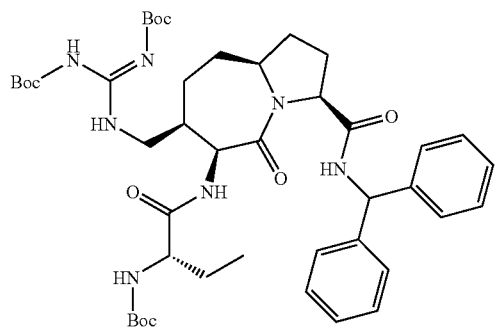

16a

16a. HPLC eluant conditions: from 45% of $H_2O$ (0.1% TFA) and 55% of $CH_3CN$ to 30% of $H_2O$ (0.1% TFA) and 70% of $CH_3CN$, flow rate 20 ml/min., 10 min. runs. Yield 31% (26 mg, MW 833.47, 0.031 mmol) of pure 16a. Analytical characterization: $[\alpha]_D^{20}$-84.2 (c 0.65, MeOH); $^1$H-NMR (400 MHz, $CDCl_3$): δ: 7.60 (m, 1H), 7.50 (m, 1H), 7.30-7.08 (m, 11H), 6.12 (d, J=8.4 Hz, 1H), 4.94 (m, 1H), 4.64 (d, J=7.2 Hz, 1H), 4.54 (m, 1H), 3.77 (m, 1H), 3.54 (m, 1H), 2.87 (m, 1H), 2.34 (m, 1H), 2.30-1.51 (m, 11H), 1.47 (s, 9H), 1.34 (s, 9H), 1.20 (s, 9H), 1.10 (m, 1H), 0.93 (t, J=7.2 Hz, 3H); $^{13}$C-NMR (100 MHz, $CDCl_3$): δ: 172.4, 171.3, 169.4, 158.1, 156.0, 154.0, 149.0, 142.0, 141.1, 128.7, 128.6, 127.3, 127.2, 126.9, 80.3, 79.5, 79.2, 61.0, 58.9, 56.8, 56.4, 53.6, 53.5, 40.0, 34.2, 33.3, 32.0, 31.2, 28.3, 27.9, 25.5, 21.0, 10.2.

1.16 General Procedure for the Synthesis of Compounds 17 (Scheme 12)

Scheme 12

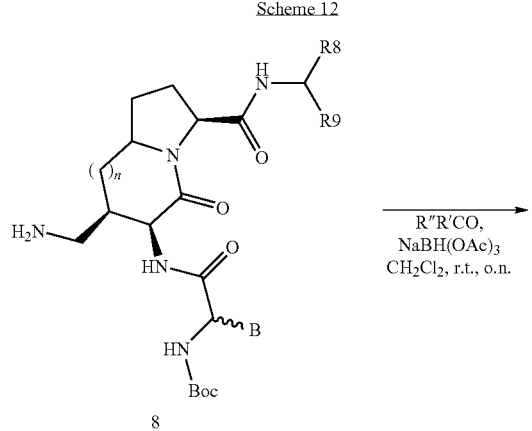

8

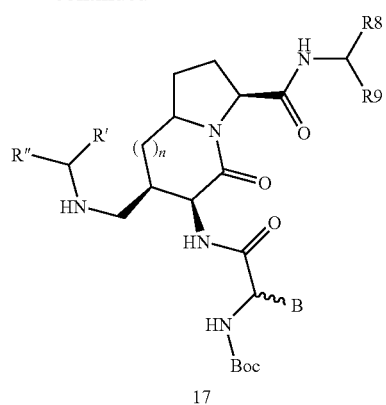

17

NaBH(OAc)$_3$ (0.13 mmol) was added to stirred solutions of compounds 8 (0.10 mmol) and of a carbonyl compound (0.11 mmol) in dry DCM (2 ml). The reaction mixtures were stirred overnight at room temperature, and then the solvent was removed under reduced pressure. Finally, the crude products were purified either by chromatography on a $C_{18}$ reverse phase semi-preparative HPLC column or by Biotage™ flash chromatography.

Compounds 17a and 17b were synthesized by the general procedure described above.

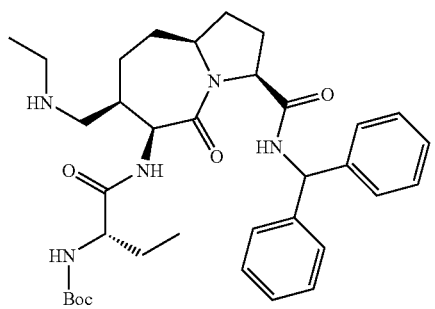

17a

17a. HPLC eluant conditions: from 80% of $H_2O$ (0.1% $NH_3$) and 20% of $CH_3CN$ to 20% of $H_2O$ (0.1% $NH_3$) and 80% of $CH_3CN$, flow rate 20 ml/min., 10 min. runs. Yield 79% (49 mg, MW 619.37, 0.079 mmol) of pure 17a. Analytical characterization: $[\alpha]_D^{20}$-88.7 (c 1.08, $CHCl_3$); $^1$H-NMR (400 MHz, $CDCl_3$): 8.60 (d, J=7.2 Hz, 1H), 8.53 (bs, 1H), 7.84 (d, J=8.8 Hz, 1H), 7.40-7.20 (m, 10H), 6.21 (d, J=8.4 Hz, 1H), 5.04 (d, J=6.4, 1H), 4.73 (d, J=7.2 Hz, 1H), 4.61 (t, J=8.4 Hz, 1H), 4.08 (dd, J=13.6, 6.8 Hz, 1H), 3.82 (dd. J=17.2, 8.8 Hz, 1H), 3.00 (m, 2H), 2.80 (m, 1H), 2.64 (bd, J=12.8 Hz, 1H), 2.43 (m, 1H), 2.22 (m, 1H), 1.95-1.60 (m, 7H), 1.45 (s, 9H), 1.31 (t, J=7.2 Hz, 3H), 1.30-1.10 (m, 2H), 1.05 (t, J=7.2 Hz, 3H); $^{13}$C-NMR (100 MHz, $CDCl_3$): 173.8, 170.7, 169.5, 142.1, 128.7, 128.5, 127.4, 127.2, 80.3, 61.2, 58.5, 57.0, 56.5, 54.5, 51.8, 44.7, 38.0, 34.4, 33.2, 32.8, 28.1, 25.7, 12.2, 10.3.

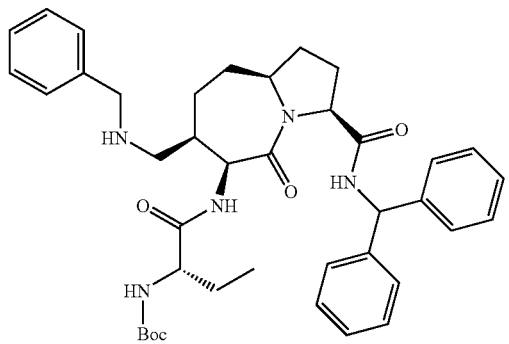

17b

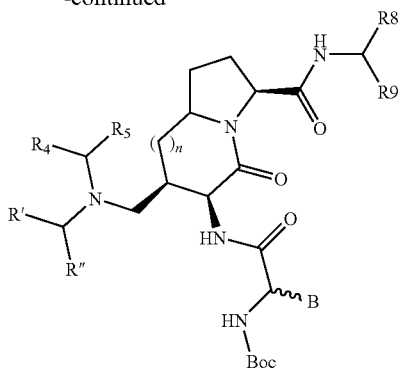

18

NaBH(OAc)$_3$ (0.13 mmol) and acetic acid (0.1 mmol) were sequentially added to stirred solutions of compounds 17 (0.10 mmol) and of a carbonyl compound (0.11 mmol) in dry DCM (2 ml). The reaction mixtures were stirred overnight at room temperature, and then the solvent was removed under reduced pressure. Finally, the crude products were purified by Biotage™ flash chromatography.

17b. Biotage™ eluant conditions: 1% of MeOH and 99% of CH$_2$Cl$_2$ to 10% of MeOH and 90% of CH$_2$Cl$_2$. Yield 78% (53 mg, MW 681.39, 0.078 mmol) of pure 17b. Analytical characterization: [α]$_D^{20}$-92.1 (c 1.27, CHCl$_3$); $^1$H-NMR (400 MHz, CDCl$_3$): δ: 8.45 (d, J=6.0 Hz, 1H), 7.89 (d, J=8.8 Hz, 1H), 7.35-7.05 (m, 13H), 6.14 (d, J=8.4 Hz, 1H), 5.00 (d, J=7.2 Hz, 1H), 4.42 (dd, J=9.6, 7.2 Hz, 1H), 3.98 (m, 1H), 3.80 (dd, J=18.0, 8.8 Hz, 1H), 3.63 (d. J=4.4 Hz, 2H), 2.55-2.40 (m, 2H), 2.34 (m, 2H), 2.16 (m, 1H), 1.90-1.45 (m, 9H), 1.37 (s, 9H), 1.25-1.1 (m, 2H), 0.92 (t. J=7.6 Hz, 3H); $^{13}$C-NMR (100 MHz, CDCl$_3$): δ: 172.2, 172.1, 170.0, 142.4, 141.3, 128.6, 128.5, 128.4, 128.2, 127.5, 127.3, 127.2, 127.1, 79.6, 60.8, 58.3, 56.7, 55.6, 53.8, 52.8, 38.2, 35.1, 29.7, 28.3, 26.4, 25.4, 10.0.

Compounds 18a to 18c were synthesized by the general procedure described above.

1.17 General Procedure for the Synthesis of Compounds 18 (Scheme 13)

Scheme 13

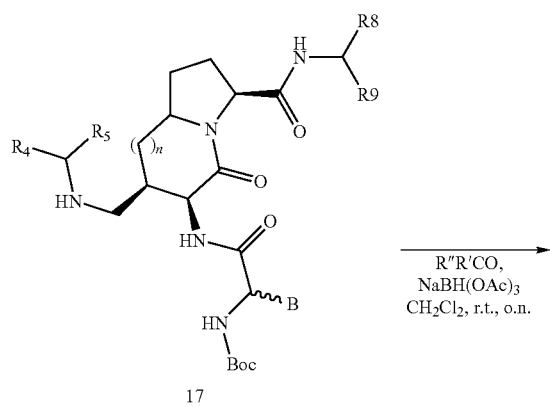

17

18a

18a. Biotage™ eluant conditions: 1% of MeOH and 99% of CH$_2$Cl$_2$ to 10% of MeOH and 90% of CH$_2$Cl$_2$. Yield 92% (64 mg, MW 695.40, 0.092 mmol) of pure 18b. Analytical characterization: [α]$_D^{20}$-84.2 (c 1.36, CHCl$_3$); $^1$H-NMR (400 MHz, CDCl$_3$): δ: 9.10 (Bs, 1H), 8.35 (bs, 1H), 7.40-7.00 (m, 15H), 6.21 (d, J=8.4 Hz, 1H), 5.15 (d, J=7.6 Hz, 1H), 4.79 (d, J=7.2 Hz, 1H), 4.49 (dd, J=9.2, 6.0 Hz, 1H), 4.03 (m, 1H), 3.93 (dd, J=17.6, 9.2 Hz, 1H), 3.60 (bs, 1H), 3.29 (bs, 1H), 2.63 (bs, 1H), 2.47 (m, 1H), 2.26 (m, 1H), 2.16 (bs, 3H), 1.95-1.85 (m, 5H), 1.80-1.50 (m, 4H), 1.44 (s, 9H), 1.25-1.1 (m, 2H), 0.92 (t, J=7.6 Hz, 3H); $^{13}$C-NMR (100 MHz, CDCl$_3$): δ: 172.2, 170.0, 142.2, 141.3, 128.6, 128.5, 128.4, 127.3, 127.2, 127.1, 79.6, 61.1, 58.3, 56.8, 35.0, 33.6, 33.4, 31.2, 28.4, 26.7, 25.5, 9.9.

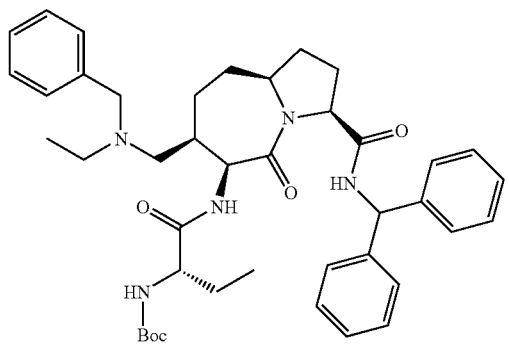

18b

18b. Biotage™ eluant conditions: 1% of MeOH and 99% of CH$_2$Cl$_2$ to 10% of MeOH and 90% of CH$_2$Cl$_2$. Yield 91% (65 mg, MW 709.42, 0.091 mmol) of pure 18b. Analytical characterization: [α]$_D^{20}$-86.0 (c 1.2, CHCl$_3$); $^1$H-NMR (400 MHz, CDCl$_3$): δ: 9.05 (bs, 1H), 8.23 (d, J=8.4 Hz, 1H), 7.35-6.95 (m, 16H), 6.20 (d, J=8.4 Hz, 1H), 5.16 (d. J=7.6 Hz, 1H), 4.79 (d, J=7.2 Hz, 1H), 4.47 (dd, J=9.6, 6.0 Hz, 1H), 4.04 (m, 1H), 3.92 (dd, J=17.2, 8.8 Hz, 1H), 3.56 (d, J=13.2 Hz, 1H), 3.35 (d, J=13.6 Hz, 1H), 2.66 (dd. J=13.2, 8.8, 1H), 2.46 (m, 3H), 2.30 (m, 2H), 2.00-1.55 (m, 8H), 1.44 (s, 9H), 1.30-1.1 (m, 2H), 1.03 (m, 6H); $^{13}$C-NMR (100 MHz, CDCl$_3$): δ: 172.2, 171.9, 170.0, 142.2, 141.2, 138.4, 129.1, 128.6, 128.4, 127.3, 127.2, 127.1, 80.6, 61.1, 58.3, 57.8, 56.8, 55.7, 46.9, 35.0, 34.5, 33.6, 33.4, 28.4, 26.6, 25.5, 10.5, 9.8.

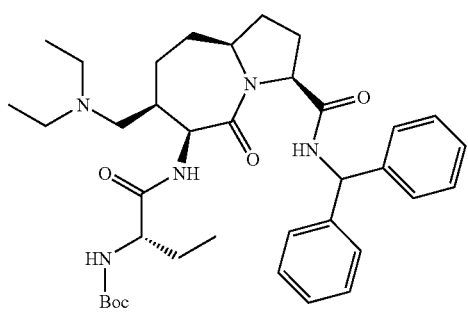

18c

18c. Biotage™ eluant conditions: 1% of MeOH and 99% of CH$_2$Cl$_2$ to 10% of MeOH and 90% of CH$_2$Cl$_2$. Yield 61% (40 mg, MW 647.40, 0.061 mmol) of pure 18c. Analytical characterization: [α]$_D^{20}$-125.0 (c 0.86, CHCl$_3$); $^1$H-NMR (400 MHz, CDCl$_3$): 9.57 (d. J=5.2 Hz, 1H), 8.20 (d, J=7.2 Hz, 1H), 7.30-7.10 (m, 10H), 6.11 (d, J=8.4 Hz, 1H), 5.14 (d, J=7.2, 1H), 4.70 (d, J=7.2 Hz, 114), 4.31 (dd, J=9.6, 5.2 Hz, 1H), 3.99 (m, 1H), 3.82 (dd, J=17.2, 8.8 Hz, 1H), 2.45 (m, 3H), 2.35 (m, 3H), 2.15 (m, 2H), 1.85-1.55 (m, 7H), 1.55 (m, 1H), 1.36 (s, 9H), 1.25-1.05 (m, 2H), 0.98 (t, J=7.6 Hz, 3H), 0.94 (t, J=7.2 Hz, 6H); $^{13}$C-NMR (100 MHz, CDCl$_3$): 172.0, 171.7, 170.2, 142.4, 141.4, 128.6, 128.3, 127.3, 127.2, 127.1, 80.3, 61.0, 58.8, 58.1, 57.4, 56.9, 55.6, 46.1, 35.2, 33.6, 33.4, 28.4, 27.1, 25.5, 11.2, 9.7.

1.18 General Procedure for the Synthesis of Compounds 19 (Scheme 14)

Scheme 14

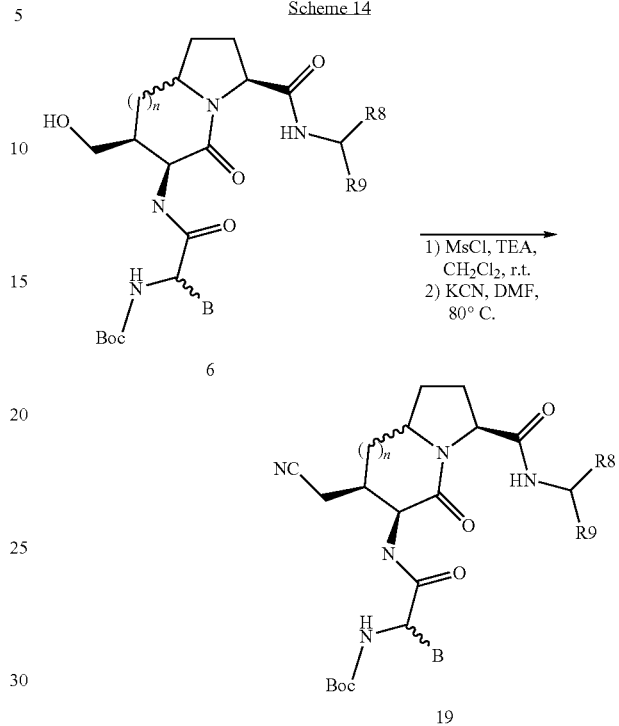

Dry TEA (4.0 mmol) and MsCl (4.0 mmol) were added to stirred solutions of compounds 6 (1.0 mmol) in dry CH$_2$Cl$_2$ (4 ml) under argon at 0° C. The reaction mixtures were stirred at room temperature overnight. After reaction completion, the resulting mixtures were diluted with CH$_2$Cl$_2$ (20 ml) and washed with saturated solutions of NH$_4$Cl (3×20 ml). The combined organic layers were dried over Na$_2$SO$_4$, and then the solvent removed under reduced pressure. The crude products were dissolved in dry DMF (10 ml) under argon at room temperature, and then KCN (15.0 mmol) was added. The reaction mixtures were left stirring at 80° C. overnight. After reaction completion, the solvent was removed under reduced pressure, the crude products were diluted with CH$_2$Cl$_2$ (20 ml) and washed with water (3×20 ml). The organic layers were dried over Na$_2$SO$_4$, and then the solvent removed under reduced pressure. Finally, the crude products were purified either by flash chromatography or by Biotage™ flash chromatography.

Compound 19a was synthesized by the general procedure described above.

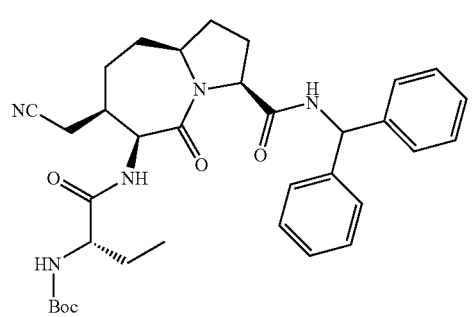

19a

19a. Biotage™ eluant conditions: 1% of MeOH and 99% of CH$_2$Cl$_2$ to 10% of MeOH and 90% of CH$_2$Cl$_2$. Yield 51%

(31 mg, MW 601.33, 0.051 mmol) of pure 19a. Analytical characterization: $[\alpha]_D^{20}$-69.7 (c 1.19, CHCl$_3$); $^1$H-NMR (400 MHz, CDCl$_3$): δ: 7.82 (d, J=8.8 Hz, 1H), 7.40-7.15 (m, 11H), 6.24 (d, J=8.8 Hz, 1H), 4.98 (bd. J=7.2 Hz, 1H), 4.75 (d, J=7.6 Hz, 1H), 4.54 (dd, J=10.0, 8.0 Hz, 1H), 4.01 (m, 1H), 3.84 (dd, J=17.6, 9.2 Hz, 1H), 2.65 (m, 1H), 2.45 (m, 1H), 2.35-2.10 (m, 3H), 2.15 (m, 1H), 2.00-1.55 (m, 9H), 1.48 (s, 9H), 1.35-1.15 (m, 2H), 0.93 (t, J=7.2 Hz, 3H); $^{13}$C-NMR (100 MHz, CDCl$_3$): δ: 173.0, 170.5, 169.2, 142.1, 141.0, 128.8, 128.6, 127.8, 127.4, 127.3, 127.2, 80.4, 61.0, 58.8, 56.8, 54.2, 37.7, 34.4, 34.0, 33.2, 28.3, 27.9, 26.0, 25.5, 25.2, 20.7, 10.3.

Additional compounds of general structure 19 are:

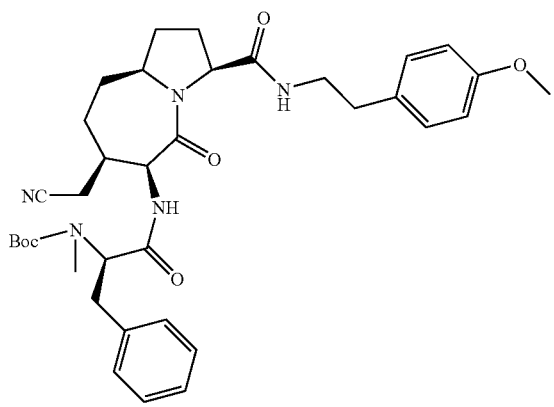

19b

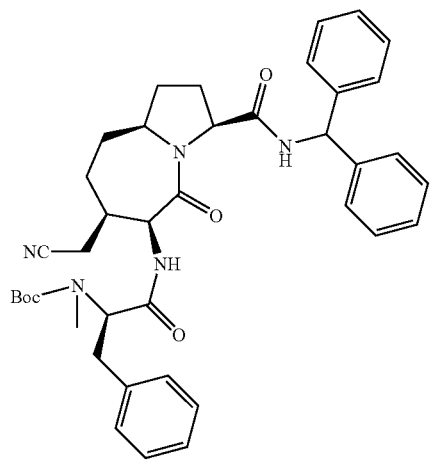

19c

19b. Biotage™ eluant conditions: 10% of AcOEt and 90% of Petroleum ether to 100% of AcOEt and 0% of Petroleum ether 10 VC. Yield 46% (297 mg, MW 645.35, 0.46 mmol) of pure 19b. Analytical characterization: $[\alpha]_D^{20}$-106.0 (c 0.93, CHCl$_3$); $^1$H-NMR (400 MHz, CDCl$_3$): (signals are split due to amide isomerism) δ: 7.32-7.21 (m, 6H), 7.13 (d, J=8.4 Hz, 2H), 6.87 (d, J=7.6 Hz, 2H), 6.65 (m 1H), 4.88 (m, 1H), 4.49 (m, 2H), 3.81-3.77 (m, 4H), 3.65-3.50 (m, 1H), 3.50-3.35 (m, 2H), 3.05-2.85 (m, 1H), 2.85-2.68 (m, 5H), 2.37 (m, 1H), 2.28-2.22 (m, 2H), 2.21-2.05 (m, 2H), 1.95-1.55 (m, 5H), 1.43-1.37 (2s, 9H), 1.25 (m, 1H); $^1$H-NMR (600 MHz, DMSO-d6, 358K): δ: 7.72 (d, J=7.8 Hz, 1H), 7.64 (bs, 1H), 7.29 (t, J=7.2 Hz, 2H), 7.25 (d, J=7.2 Hz, 2H), 7.21 (t, 7.2 Hz, 1H), 7.16 (d, J=8.4 Hz, 2H), 6.86 (d, J=8.4 Hz, 2H), 4.91 (bs, 1H), 4.54 (t, J=9.0 Hz, 1H), 4.41 (dd, J=7.8, 3.6 Hz, 1H), 3.99 (dd, J=15.0, 7.8 Hz, 1H), 3.76 (s, 3H), 3.32 (m, 2H), 3.27 (dd, J=14.4, 5.4 Hz, 1H), 2.91 (dd, J=13.8 Hz, 10.8 Hz, 1H), 2.74 (s, 3H), 2.70 (t, J=6.6 Hz, 2H), 2.56 (dd, J=17.4, 4.8 Hz, 1H), 2.38 (dd, J=16.8, 8.4 Hz, 1H), 2.18 (m, 2H), 1.96 (m, 2H), 1.85 (m, 2H), 1.78-1.64 (m, 3H), 1.31 (s, 9H); $^{13}$C-NMR (100 MHz, CDCl$_3$): (signals are split due to amide isomerism): δ: 171.3, 170.5, 170.1, 158.3, 137.5, 137.4, 130.5, 129.2, 128.7, 128.5, 128.3, 127.4, 126.9, 118.7, 114.0, 81.0, 80.6, 61.6, 61.4, 60.8, 60.7, 59.3, 58.8, 55.4, 54.4, 54.2, 40.7, 40.3, 37.5, 37.3, 34.4, 33.9, 33.1, 32.0, 28.3, 26.2, 26.0, 20.9, 20.7.

19c. Biotage™ eluant conditions: 10% of AcOEt and 90% of Petroleum ether to 100% of AcOEt and 0% of Petroleum ether 10 VC. Yield 43% (291 mg, MW 677.36, 0.43 mmol) of pure 19c. Analytical characterization: $[\alpha]_D^{20}$-89.3 (c 1.07, CHCl$_3$); $^1$H-NMR (400 MHz, CDCl$_3$): (signals are split due to amide isomerism) δ: 7.81 (bs, 1H), 7.38-7.23 (m, 16H), 6.23 (d, J=8.8 Hz, 1H), 4.88 (m, 1H), 4.73 (d, J=7.2 Hz, 1H), 4.50 (t, J=8.4 Hz, 1H), 3.83 (bs, 1H), 3.36 (dd, J=14.0, 6.4 Hz, 1H), 3.05-285 (2m, 1H), 2.84-2.75 (2s, 3H), 2.45 (dd, J=12.0, 6.8 Hz, 1H), 2.35-2.00 (m, 4H), 2.00-1.40 (m, 14H), 1.15 (m, 1H); $^1$H-NMR (600 MHz, DMSO-d$_6$, 358K): 8.61 (d, J=7.8 Hz, 1H), 7.76 (d, J=8.4 Hz, 1H), 7.40-7.19 (m, 15H), 6.10 (d, J=8.4 Hz, 1H), 4.91 (bs, 1H), 4.64 (dd, J=11.4, 3.6 Hz, 1H), 4.55 (t, J=9.6 Hz, 1H), 4.00 (dd, J=15.0, 7.2 hz, 1H), 3.25 (dd, J=14.4, 5.4 Hz, 1H), 2.90 (dd, J=14.4, 10.8 Hz, 1H), 2.73 (s, 3H), 2.54 (dd, J=21.6, 4.8 Hz, 1H), 2.36 (dd, J=16.8, 7.8 Hz, 1H), 2.20 (m, 1H), 2.12 (m, 1H), 2.03 (m, 1H), 1.95-1.55 (m, 6H), 1.31 (s, 9H); $^{13}$C-NMR (100 MHz, CDCl$_3$): (signals are split due to amide isomerism) δ: 171.3, 170.9, 170.5, 170.2, 169.3, 142.1, 141.0, 137.3, 129.2, 128.8, 128.7, 128.4, 127.8, 127.7, 127.4, 127.0, 126.9, 126.8, 118.5, 81.1, 80.6, 61.0, 60.9, 59.7, 58.7, 56.8, 54.2, 37.5, 37.2, 34.4, 34.2, 33.9, 33.2, 31.9, 30.4, 29.7, 28.7, 28.2, 25.5, 23.9, 20.8, 14.2, 13.6.

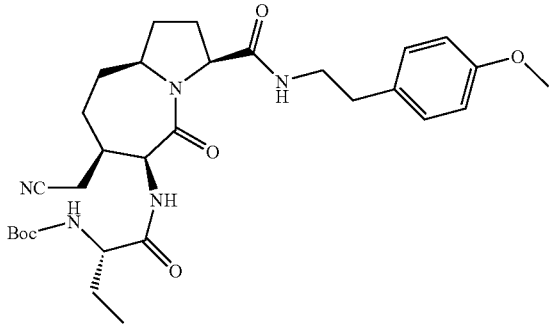

19d

19d. Biotage™ eluant conditions: 10% of AcOEt and 90% of Petroleum ether to 100% of AcOEt and 0% of Petroleum ether 10 VC. Yield 51.8% (295 mg, MW 569.32, 0.52 mmol) of pure 19d. Analytical characterization: $[\alpha]_D^{20}$-68.7 (c 1.23, CHCl$_3$); $^1$H-NMR (400 MHz, CDCl$_3$): δ: 7.16 (d, J=8.4 Hz, 2H), 6.90 (d, J=8.4 Hz, 2H), 6.71 (bs, 1H), 5.05 (d, J=6.5 Hz, 1H), 4.52 (m 2H), 4.04 (m, 1H), 3.79 (m, 4H), 3.61 (m, 1H), 3.50 (m, 1H), 2.80 (m, 2H), 2.75 (dd, J=12.0, 6.5 Hz, 1H), 2.40-1.55 (m, 11H), 1.49 (s, 9H), 1.30 (m, 1H), 0.99 (t, J=7.2 Hz, 3H); $^{13}$C-NMR (100 MHz, CDCl$_3$): δ: 173.0, 170.5, 170.1, 158.3, 130.6, 129.8, 119.0, 114.1, 80.6, 61.4, 58.9, 56.6, 55.5, 54.2, 40.2, 37.7, 34.4, 34.1, 33.1, 28.2, 26.2, 25.4, 20.8, 10.3

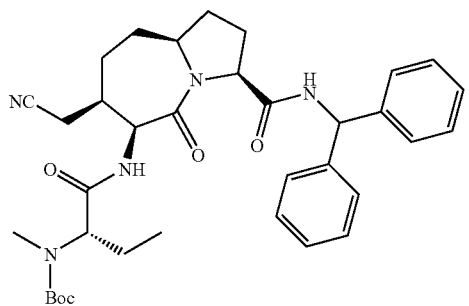

19e

19e. Biotage™ eluant conditions: 60% of EtOAc and 40% of Petroleum ether to 100% of EtOAc 10 VC. Yield 72.5% (196 mg, MW 615, 0.32 mmol) of pure 19e. Analytical characterization: $[α]_D^{20}$-104.6 (c 0.002, CHCl$_3$); $^1$H-NMR (400 MHz, CDCl$_3$): δ: 7.74 (bs, 1H), 7.39-7.11 (m, 11H), 6.16 (d. J=88.77 Hz, 1H), 4.66 (d, J=7.80 Hz, 1H), 4.44 (t, J=8.84 Hz, 1H), 4.33 (bs, 1H), 3.74 (dd, J=9.27, 17.69 Hz, 1H), 2.79 (s, 3H), 2.65 (m, 1H), 2.46 (m, 1H), 2.37-2.10 (m, 3H), 2.00-1.55 (m, 6H), 1.43 (s, 9H), 1.32 (m, 1H), 1.06 (m, 1H), 0.85 (t, J=7.37 Hz, 3H); $^{13}$C-NMR (100 MHz, CDCl$_3$): δ: 172.3, 170.6, 169.5, 142.2, 141.0, 128.7, 128.6, 127.3, 127.2, 80.5, 61.0, 60.5, 58.8, 56.8, 54.0, 37.4, 34.4, 34.0, 33.2, 30.4, 28.4, 25.5, 21.4, 20.7, 10.7.

1.19 General Procedure for the Synthesis of Compounds 20 (Scheme 15)

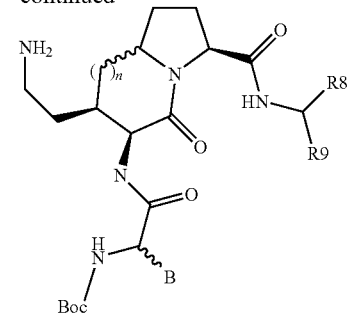

20

Additional compounds of general structure 20 are:

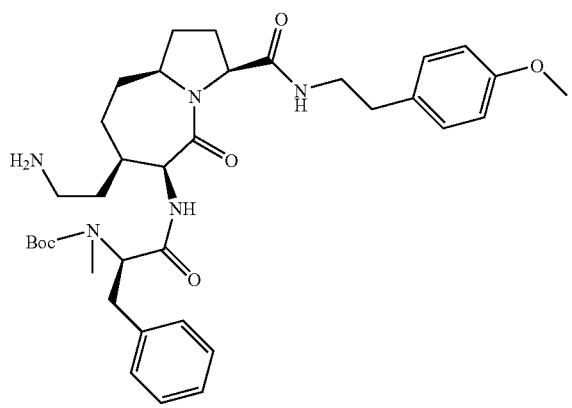

20b

Compounds 19 were converted to the corresponding amines 20 by continuous flow hydrogenation using the H-Cube™ system developed by Thales Nanotechnology. The hydrogenation reaction was performed using a Raney nickel catalyst cartridge column (CatCart™). The reactor pressure and temperature were fixed at 60 bar and 45° C. Under these conditions, a solution of compounds 19 (0.1 mmol) in EtOH (150 ml) was flowed through the system with a flow rate of 0.5 ml/min. Finally, the solvent was removed under reduced pressure. The crude products were not requiring any further purification.

Compound 20a was synthesized by the general procedure described above.

Scheme 15

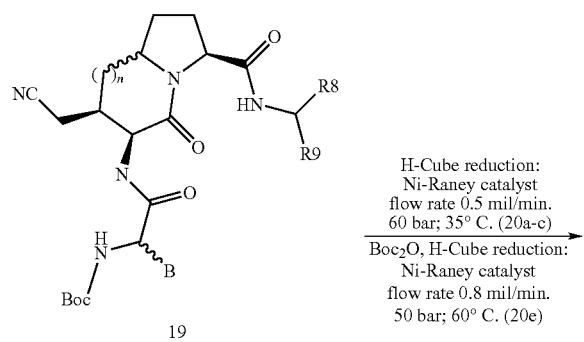

19

H-Cube reduction:
Ni-Raney catalyst
flow rate 0.5 mil/min.
60 bar; 35° C. (20a-c)

Boc$_2$O, H-Cube reduction:
Ni-Raney catalyst
flow rate 0.8 mil/min.
50 bar; 60° C. (20e)

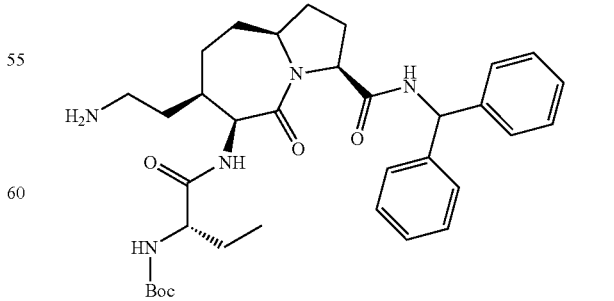

20a

20a. Yield 95% (57 mg, MW 605.36, 0.095 mmol) of pure 20a. Analytical characterization: $[α]_D^{20}$-65.7 (c 1.25, CHCl$_3$); $^1$H-NMR (400 MHz, CDCl$_3$): δ: 7.92 (d, J=8.0 Hz, 1H), 7.51 (d, J=8.0, 1H), 7.40-7.15 (m, 10H), 6.16 (d, J=8.8 Hz, 1H), 5.72 (d. J=7.6 Hz, 1H), 4.67 (d, J=5.6 Hz, 1H), 4.55 (dd, J=10.0, 8.0 Hz, 1H), 4.26 (m, 1H), 3.86 (dd, J=17.6, 9.2 Hz, 1H), 2.69 (m, 1H), 2.41 (m, 1H), 2.22 (m, 2H), 2.00-1.10 (m, 7H), 1.45 (m, 2H), 1.42 (s, 9H), 1.35-1.15 (m, 2H), 1.00 (t, J=7.2 Hz, 3H); $^{13}$C-NMR (100 MHz, CDCl$_3$): δ: 172.5, 171.3, 170.9, 156.3, 141.4, 128.8, 128.6, 127.6, 127.5, 127.2, 80.0, 61.5, 58.5, 57.4, 56.0, 54.8, 37.0, 35.8, 33.4, 33.2, 32.8, 28.3, 27.0, 26.3, 25.8, 10.2.

Additional compounds of general structure 20 are:

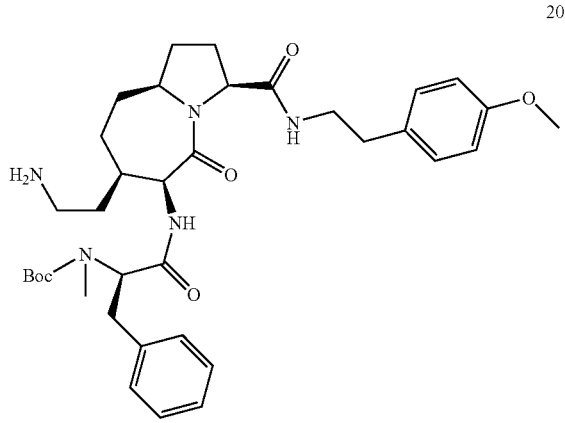 [SMILES: COc1ccc(CCNC(=O)[C@@H]2CC[C@@H]3CC[C@H](CCN)[C@H](NC(=O)[C@@H](Cc4ccccc4)N(C)C(=O)OC(C)(C)C)C(=O)N32)cc1]

20b

20b. HPLC eluant conditions: from 85% of H$_2$O (0.1% HCOOH) and 15% of CH$_3$CN (0.1% HCOOH) to 70% of H$_2$O (0.1% HCOOH) and 30% of CH$_3$CN (0.1% HCOOH), flow rate 20 ml/min., 10 min. runs. Yield 58.0% (392 mg, MW 677.36, 0.58 mmol) of pure 20b. Analytical characterization: [α]$_D^{20}$-127.2 (c 0.90, MeOH); $^1$H-NMR (400 MHz, CDCl$_3$): (signals are split due to amide isomerism): δ: 7.55 (2bs, 1H), 7.28-7.15 (m 5H), 7.12 (d, J=8.0 Hz, 2H), 6.83 (d, J=8.4 Hz, 2H), 5.02 (bs, 1H), 4.58-4.46 (m, 2H), 3.85-3.80 (m, 4H), 3.55-3.30 (m, 2H), 2.95 (m 2H), 2.75 (m, 4H), 2.30-1.45 (m, 14H), 1.31 (2s, 9H); $^{13}$C-NMR (100 MHz, CDCl$_3$): signals are split due to amide isomerism): δ: 171.3, 171.1, 158.2, 130.7, 129.8, 129.3, 128.4, 126.5, 114.0, 80.5, 61.7, 61.4, 58.7, 55.3, 55.0, 40.6, 40.7, 34.4, 33.2, 31.2, 28.3, 27.4.

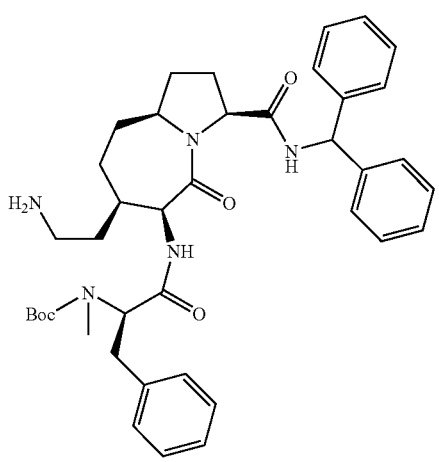

20c

20c. HPLC eluant conditions: from 80% of H$_2$O (0.1% HCOOH) and 20% of CH$_3$CN (0.1% HCOOH) to 70% of H$_2$O (0.1% HCOOH) and 30% of CH$_3$CN (0.1% HCOOH), flow rate 20 ml/min., 10 min. runs. Yield 70.0% (480 mg, MW 681.39, 0.07 mmol) of pure 20c. Analytical characterization: [α]$_D^{20}$-100.0 (c 1.05, MeOH); $^1$H-NMR (400 MHz, CDCl$_3$): (signals are split due to amide isomerism): δ: 8.25 (bs, 1H), 7.61-7.46 (1bs, 1H), 7.24-7.10 (m, 15H), 6.08 (d, J=8.4 Hz, 1H), 4.84 (m, 1H), 4.61-4.44 (m, 2H), 3.73 (bs, 1H), 3.33 (m, 1H), 2.91 (m, 1H), 2.75-2.50 (m, 4H), 2.16 (m, 2H), 1.90-1.55 (m, 4H), 1.45-1.00 (m, 15H); $^{13}$C-NMR (100 MHz, CDCl$_3$): (signals are split due to amide isomerism): δ: 129.2, 128.6, 128.4, 127.5, 127.4, 126.5, 80.5, 61.4, 58.5, 57.2, 54.8, 34.2, 33.3, 31.2, 29.9, 26.4.

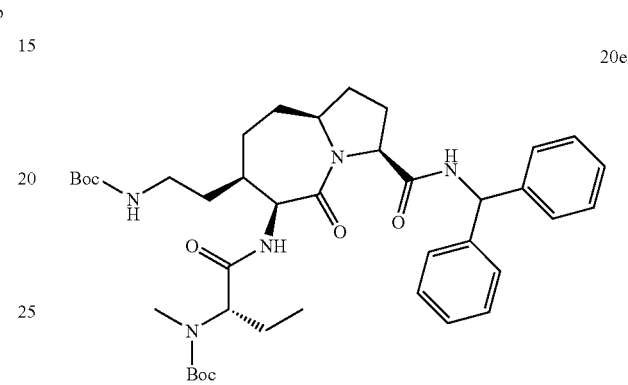

20e

20e. Biotage™ eluant conditions: 15% of EtOAc and 85% of Petroleum ether to 100% of EtOAc 10 VC. Yield 61% (71 mg, MW 719, 0.10 mmol) of pure Analytical characterization: [α]$_D^{20}$-102.32 (c 0.002, CHCl$_3$); $^1$H-NMR (400 MHz, CDCl$_3$): δ: 7.92 (bs, 1H), 7.29-7.11 (m, 11H), 6.86 (bs, 1H), 6.16 (d, J=8.8 Hz, 1H), 4.65 (d, J=7.4 Hz, 1H), 4.48 (t, J=9.2 Hz, 1H), 4.39 (bs, 1H), 3.76 (m, 1H), 3.01 (m, 1H), 2.87 (m, 1H), 2.77 (s, 3H), 2.38 (m, 1H), 2.17 (m, 1H), 1.80-1.50 (m, 8H), 1.43 (s, 9H), 1.35 (s, 9H), 1.26 (m, 1H), 1.15-1.00 (m, 2H), 0.85 (m, 3H); $^{13}$C-NMR (100 MHz, CDCl$_3$): δ: 172.4, 169.4, 155.9, 142.2, 141.2, 128.6, 128.6, 127.4, 127.3, 80.5, 61.0, 60.3, 58.8, 56.8, 54.6, 38.6, 37.5, 34.6, 33.4, 33.1, 32.3, 30.4, 28.4, 25.6, 21.6, 10.7.

1.20 General Procedure for the Synthesis of Compounds 21 (Scheme 16)

Scheme 16

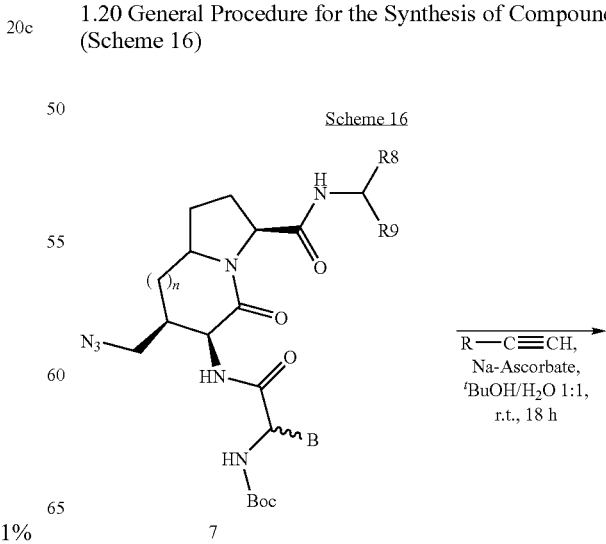

7

-continued

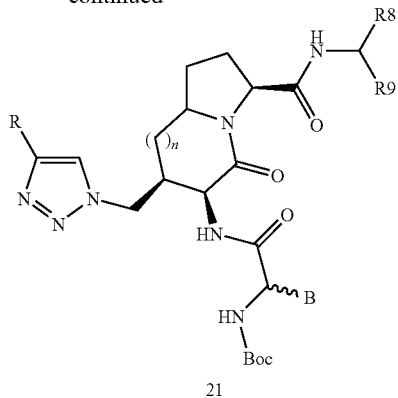

21

A 0.9 M water solution of sodium ascorbate (45 μl, 0.4 mmol) and a 0.3 M water solution of Cu(OAc)$_2$ (65 μl, 0.02 mmol) were sequentially added to stirred solutions of compounds 7 (0.10 mmol) and of an alkyne (0.10 mmol) in a 1:1 mixture of H$_2$O/$^t$BuOH (300 μl). The reaction mixtures were stirred overnight at room temperature and then the solvent was removed under reduced pressure. Finally, the residues were purified either by flash chromatography or by chromatography on a C$_{18}$ reverse phase semi-preparative HPLC column.

Compound 21a was synthesized by the general procedure described above.

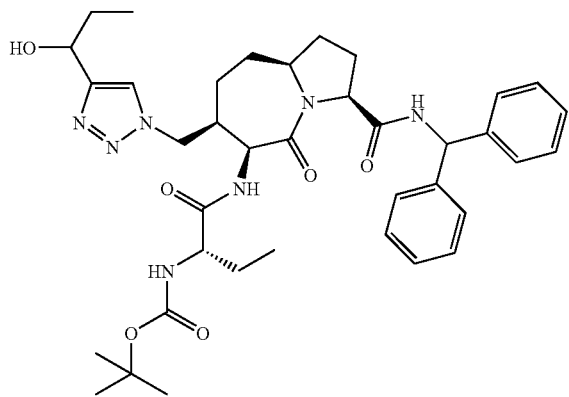

21a

21a. Biotage™ eluant conditions: 1% of MeOH and 99% of CH$_2$Cl$_2$ to 10% of MeOH and 90% of CH$_2$Cl$_2$. Yield 58% (41 mg, MW 701.39, 0.058 mmol) of pure 21a. Analytical characterization: [α]$_D^{20}$-50.0 (c 0.88, CHCl$_3$); $^1$H-NMR (400 MHz, CDCl$_3$): 7.75 (dd, J=8.4, 2.8 Hz, 1H), 7.35-7.00 (m, 11H), 6.11 (d, J=8.4 Hz, 1H), 4.99 (d. J=6.4 Hz, 1H), 4.76 (bs, 1H), 4.63 (m, 2H), 4.43 (m, 1H), 4.08 (m, 1H), 3.92 (m, 1H), 2.71 (m, 1H), 2.32 (m, 1H), 2.12 (m, 1H), 2.05 (m, 1H), 1.95-1.45 (m, 11H), 1.32 (s, 9H), 1.18 (s, 3H), 1.15-1.05 (m, 1H), 1.00-0.85 (m, 6H); $^{13}$C-NMR (100 MHz, CDCl$_3$): 172.9, 170.7, 169.3, 141.8, 141.3, 128.7, 127.5, 127.3, 127.1, 80.3, 68.4, 61.2, 58.8, 56.8, 56.3, 54.0, 52.2, 40.3, 33.8, 33.7, 31.7, 30.3, 29.7, 28.3, 25.7, 10.2, 9.8.

1.21 General Procedure for the Boc-Deprotection of Compounds 4-21

Method A: A 3N solution of HCl in MeOH (0.5 ml) was added to stirred solutions of compounds 4-21 (varying amounts, comprised between 0.018 and 0.090 mmol) in MeOH (2 ml), except for compounds treated as in Methods B-D. The reaction mixtures were left stirring at room temperature overnight and then concentrated under reduced pressure. When the crude was not sufficiently pure, the residues were purified by chromatography on a C$_{18}$ reverse phase semi-preparative HPLC column and then lyophilized.

Method B: TFA (450 μl, 5.0 mmol) was added to a stirred solutions of compounds 9 and 12 (0.10 mmol) in DCM (2 ml). The reaction mixtures were left stirring at room temperature overnight and then concentrated under reduced pressure. When the crude was not sufficiently pure, the residues were purified by chromatography on a C$_{18}$ reverse phase semi-preparative HPLC column and then lyophilized.

Method C: Formic acid (1 ml) was added to compounds 6b-6g (varying amounts, comprised between 0.018 and 0.090 mmol). The reaction mixtures were left stirring at room temperature overnight and then concentrated under reduced pressure. The crude products were treated with a 1M solution of NH$_3$ in MeOH (2 ml) and the reaction mixtures were left stirring at room temperature overnight and then concentrated under reduced pressure. The residues were purified by chromatography on a C$_{18}$ reverse phase semi-preparative hplc column and then lyophilized.

Method D: Formic acid (1 ml) was added to compounds 8b-8f and 20b,c (varying amounts, comprised between 0.018 and 0.090 mmol). The reaction mixtures were left stirring at room temperature overnight and then concentrated under reduced pressure. When the crude was not sufficiently pure, the residues were purified by chromatography on a C$_{18}$ reverse phase semi-preparative hplc column and then lyophilized.

Compounds 24a to 39a were synthesized by the general procedure described above.

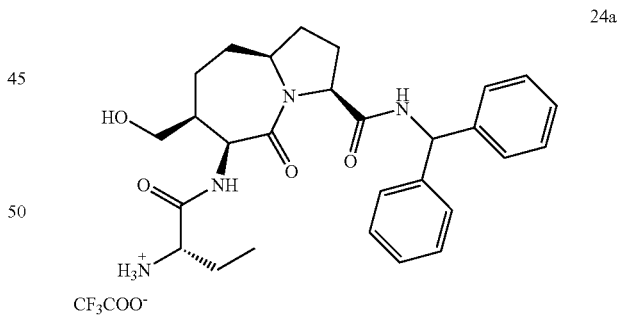

24a 24a, from 6a (0.050 mmol). HPLC eluant conditions: from 80% of H$_2$O (0.1% TFA) and 20% of CH$_3$CN to 40% of H$_2$O (0.1% TFA) and 60% of CH$_3$CN, flow rate 20 ml/min., 10 min. runs. Yield 73% (22 mg, MW 606.27, 0.036 mmol) of pure 24a. Analytical characterization: [α]$_D^{20}$-52.6 (c 0.46, H$_2$O); $^1$H NMR (400 MHz, D70): δ: 7.43-7.28 (m, 10H), 6.05 (s, 1H), 4.65 (m, 1H), 4.54 (m, 1H), 4.01 (t, J=6.4 Hz, 1H), 3.59 (d, J=4.0 Hz, 1H), 2.25 (m, 1H), 2.15 (m, 1H), 2.05-1.80 (m, 5H), 1.80-1.67 (m, 3H), 1.60 (m, 1H), 1.01 (t, J=7.5 Hz, 3H); $^{13}$C NMR (100 MHz, D$_2$O): δ: 173.0, 171.1, 169.5, 141.0, 140.8, 129.0, 128.9, 127.8, 127.4, 127.2, 63.2, 62.0, 58.7, 57.7, 54.4, 54.3, 39.0, 32.3, 31.1, 29.3, 27.9, 24.4, 8.5.

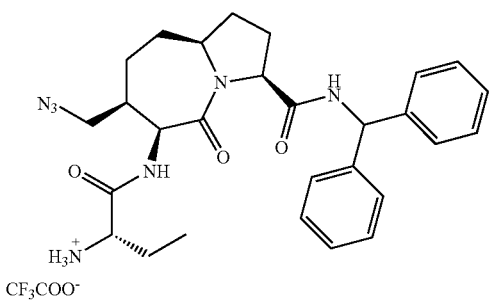

25a

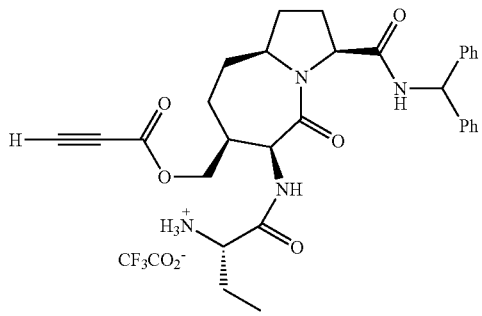

27a 27a, from 9a (0.050 mmol). The crude product did not require HPLC purification. Yield 94% (31 mg, MW 658.26, 0.047 mmol) of pure 27a. Analytical characterization: $[\alpha]_D^{20}$-65.3 (c 1.10, MeOH); $^1$H-NMR (400 MHz, CDCl$_3$): δ: 7.30-7.22 (m, 10H), 5.97 (s, 1H), 4.65 (m, 1H), 4.60 (t, J=7.8, 1H), 4.21 (m, 1H), 4.14 (m, 1H), 3.94 (m, 2H), 2.61-1.50 (m, 12H), 0.91 (t, J=7.2, 3H); $^{13}$C-NMR (100 MHz, CDCl$_3$): 173.0, 170.4, 163.4, 162.4, 141.0, 140.8, 129.0, 128.9, 127.8, 127.4, 127.2, 78.2, 67.9, 62.0, 58.8, 57.7, 54.3, 54.6, 37.0, 32.3, 31.0, 29.5, 27.9, 24.4, 8.3

25a, from 7a (0.057 mmol). HPLC eluant conditions: from 80% of H$_2$O (0.1% TFA) and 20% of CH$_3$CN to 40% of H$_2$O (0.1% TFA) and 60% of CH$_3$CN, flow rate 20 ml/min., 10 min. runs. Yield 45% (16 mg, MW 631.34, 0.025 mmol) of pure 25a. Analytical characterization: $[\alpha]_D^{20}$-151.1 (c 0.44, H$_2$O); $^1$H-NMR (400 MHz, D$_2$O): δ: 7.28 (m, 10H), 5.98 (s, 1H), 4.62 (m, 1H), 4.0 (m, 2H), 3.36 (m, 2H), 2.25-1.45 (m, 11H), 0.95 (t, J=7.6 Hz, 3H); $^{13}$C-NMR (100 MHz, D$_2$O): δ: 172.8, 170.5, 169.4, 141.0, 140.8, 128.9, 128.8, 127.8, 127.4, 127.1, 61.9, 58.7, 57.6, 54.3, 54.2, 53.9, 37.5, 32.3, 31.0, 30.3, 29.6, 27.8, 24.4, 8.3.

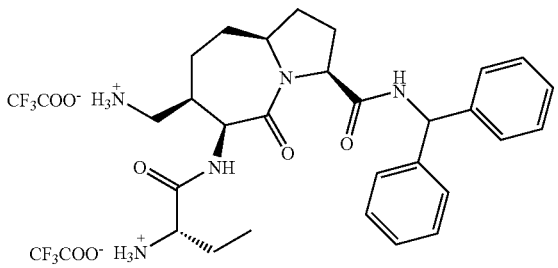

26a

28a 28a, from 10a (0.050 mmol). The crude product did not require HPLC purification. Yield 96% (28 mg, MW 583.26, 0.048 mmol) of pure 28a. Analytical characterization: $[\alpha]_D^{20}$-67.4 (c 0.90, MeOH); $^1$H-NMR (400 MHz, CDCl$_3$): δ: 7.39-7.29 (m, 10H), 6.04 (s, 1H), 4.65 (d, J=9.6, 1H), 4.54 (m, 1H), 4.00 (m, 2H), 3.45 (s, 1H), 3.33 (m, 2H), 2.27-1.55 (m, 11H), 0.98 (t. J=10.8, 3H). $^{13}$C-NMR (100 MHz, CDCl$_3$): 173.0, 170.5, 169.5, 166.5, 141.0, 140.8, 129.0, 128.9, 127.8, 127.4, 127.2, 84.2, 78.0, 62.0, 58.7, 57.7, 54.6, 54.4, 41.0, 37.9, 32.4, 30.8, 29.8, 27.9, 24.3, 8.5

26a, from 8a (0.049 mmol). HPLC eluant conditions: from 85% of H$_2$O (0.1% TFA) and 15% of CH$_3$CN to 70% of H$_2$O (0.1% TFA) and 30% of CH$_3$CN, flow rate 20 ml/min., 10 min. runs. Yield 37% (13 mg, MW 718.65, 0.018 mmol) of pure 26a. Analytical characterization: $[\alpha]_D^{20}$-59.5 (c 0.42, H$_2$O); $^1$H-NMR (400 MHz, H$_2$O-D$_2$O 90:10): δ: 9.43 (d, J=6.8 Hz, 1H), 7.27 (m, 10H), 5.96 (s, 1H), 4.7-4.5 (m, 1H), 4.47 (d, J=6.8 Hz, 1H), 4.0 (t, J=5.6 Hz, 2H), 3.08 (d, J=10.8 Hz, 1H), 2.85 (t, J=10.0 Hz, 1H), 2.21-1.75 (m, 8H), 1.75-1.50 (m, 3H), 0.91 (t, J=7.2 Hz, 3H); $^{13}$C-NMR (100 MHz, H$_2$O-D$_2$O 90:10): δ: 173.0, 170.4, 169.4, 140.9, 140.7, 129.0, 128.8, 127.8, 127.3, 127.1, 61.9, 58.3, 57.8, 54.5, 54.1, 41.0, 36.3, 32.2, 30.0, 28.4, 28.0, 24.6, 8.4.

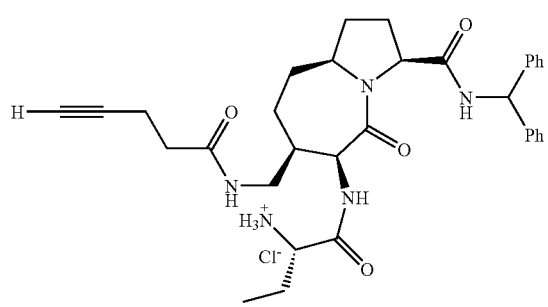

28b 28b, from 10b (0.055 mmol). The crude product did not require HPLC purification. Yield 96% (32 mg, MW 607.30, 0.053 mmol) of pure 28a. Analytical characterization: [α]$_D^{20}$-62.0 (c 1.45, MeOH); $^1$H-NMR (400 MHz, CDCl$_3$): δ: 7.40-7.20 (m, 10H), 5.98 (s, 1H); 4.56 (d. J=10.0, 1H), 4.47 (bs, 1H), 3.97 (m, 2H), 3.35 (m, 1H), 3.10 (m, 1H), 2.40-2.30 (m, 4H), 2.29 (s, 1H), 2.25-1.45 (m, 11H), 0.96 (t, J=10.8, 3H). $^{13}$C-NMR (100 MHz, CDCl$_3$): 174.8, 172.9, 170.5, 169.5, 141.0, 140.8, 129.0, 128.9, 127.8, 127.4, 127.2, 70.3, 61.9, 58.6, 57.6, 54.5, 54.3, 41.0, 37.7, 34.5, 32.4, 30.6, 29.3, 27.8, 24.4, 14.6, 8.5

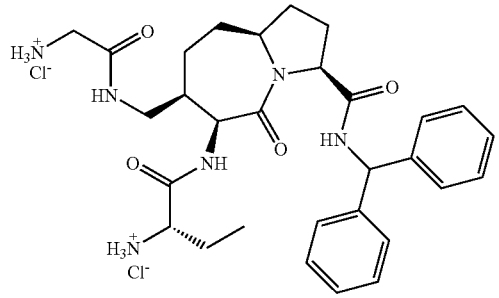

29a 29a, from 11a (0.080 mmol). The crude product did not require HPLC purification. Yield 69% (34 mg, MW 620.27, 0.055 mmol) of pure 29a. Analytical characterization: [α]$_D^{20}$-49.4 (c 0.85, H$_2$O); $^1$H-NMR (400 MHz, D$_2$O): δ: 7.40-7.28 (m, 10H), 6.02 (s, 1H), 4.60 (d, J=10.4 Hz, 1H), 4.51 (dd, J=8.0, 5.6 Hz, 1H), 4.03 (m, 2H), 3.74 (s, 2H), 3.34 (dd, J=14.0, 4.0 Hz, 1H), 3.18 (dd, J=14.0, 8.4 Hz, 1H), 2.26-2.10 (m, 2H), 2.00-1.75 (m, 6H), 1.74-1.42 (m, 3H), 0.97 (t, J=7.6 Hz, 3H); $^{13}$C-NMR (100 MHz, D$_2$O): δ: 173.0, 170.4, 169.7, 167.1, 141.0, 140.8, 129.0, 128.9, 127.9, 127.8, 127.2, 62.0, 58.6, 57.7, 54.5, 54.4, 41.1, 40.5, 37.6, 32.3, 30.4, 29.1, 28.0, 24.4, 8.5.

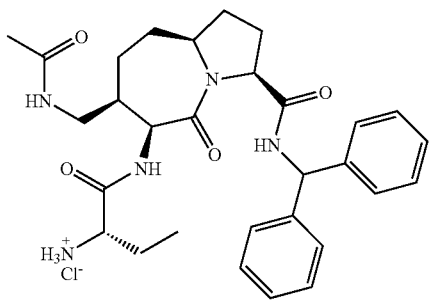

29b 29b, from 11b (0.038 mmol). The crude product did not require HPLC purification. Yield 97% (21 mg, MW 569.28, 0.037 mmol) of pure 29b. Analytical characterization: [α]$_D^{20}$-62.5 (c 0.56, MeOH); $^1$H-NMR (400 MHz, D$_2$O): δ: 7.38-7.28 (m, 10H), 6.06 (s, 1H), 4.60 (d, J=10.4 Hz, 1H), 4.51 (dd, J=8.0, 5.2 Hz, 1H), 4.00 (m, 2H), 3.27 (dd, J=14.0, 4.0 Hz, 1H), 3.13 (dd, J=14, 8.4 Hz, 1H), 2.20-1.45 (m, 14H), 0.97 (t, J=7.2 Hz, 3H); $^{13}$C-NMR (100 MHz, D$_2$O): δ: 174.2, 173.0, 170.6, 169.6, 141.0, 140.8, 129.0, 128.9, 127.8, 127.4, 127.2, 61.9, 58.6, 57.7, 54.5, 41.1, 37.6, 32.4, 30.6, 29.4, 27.9, 24.4, 22.0, 8.5.

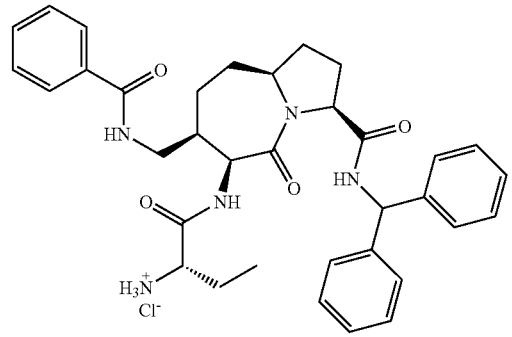

29c 29c, from 11c (0.062 mmol). The crude product did not require HPLC purification. Yield 77% (30 mg, MW 631.30, 0.048 mmol) of pure 29c. Analytical characterization: [α]$_D^{20}$-48.6 (c 1.46, MeOH); $^1$H-NMR (400 MHz, D$_2$O): δ: 7.71 (d, J=8.4 Hz, 2H), 7.58 (d, J=8.4 Hz, 1H), 7.49 (m, 2H), 7.32-7.05 (m, 10H), 6.04 (s, 1H), 4.54 (dd, J=8.0, 5.6 Hz, 1H), 4.07 (m, 1H), 4.00 (m, 1H), 3.52 (dd, J=14.0, 4.4 Hz, 1H), 3.34 (dd, J=14.0, 8.4 Hz, 1H), 2.25-1.26 (m, 11H), 0.79 (t, J=7.6 Hz, 3H); $^{13}$C-NMR (100 MHz, D$_2$O): δ: 172.8, 170.5, 169.6, 141.0, 140.9, 132.3, 129.0, 128.9, 127.8, 127.4, 127.2, 127.1, 61.9, 58.6, 57.7, 54.6, 54.5, 41.6, 37.8, 32.4, 30.7, 29.5, 27.8, 24.4, 8.5.

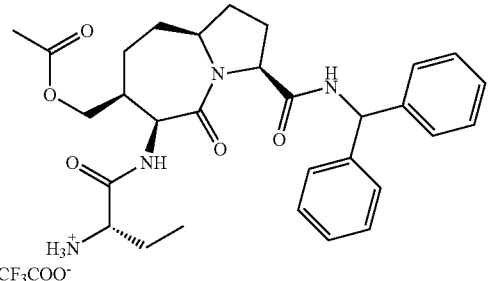

30a 30a, from 12a (0.052 mmol). HPLC eluant conditions: from 70% of H$_2$O (0.1% TFA) and 30% of CH$_3$CN to 40% of H$_2$O (0.1% TFA) and 60% of CH$_3$CN, flow rate 20 ml/min., 10 min. runs. Yield 50% (17 mg, MW 648.28, 0.026 mmol) of pure 30a. Analytical characterization: [α]$_D^{20}$-43.8 (c 0.68, H$_2$O); $^1$H NMR (400 MHz, D$_2$O): δ: 7.40-7.26 (m, 10H), 6.02 (s, 1H), 4.71 (m, 1H), 4.51 (dd, J=7.2, 6.0 Hz, 1H), 4.11 (dd, J=11.0, 5.4 Hz, 1H), 4.06-3.96 (m, 3H), 2.21 (m, 1H), 2.13 (m, 1H), 2.03 (s, 3H), 2.00-1.65 (m, 6H), 1.57 (m, 1H), 0.96 (t, J=7.6 Hz, 3H); $^{13}$C NMR (100 MHz, D$_2$O) δ: 175.0, 173.0, 170.5, 169.3, 141.0, 140.8, 129.0, 128.9, 127.8, 127.4, 127.2, 66.1, 62.0, 58.8, 57.7, 54.3, 53.6, 37.0, 32.3, 31.0, 29.5, 27.9, 24.4, 20.4, 8.3.

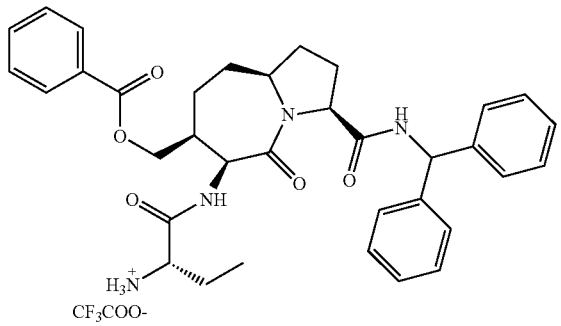

30b

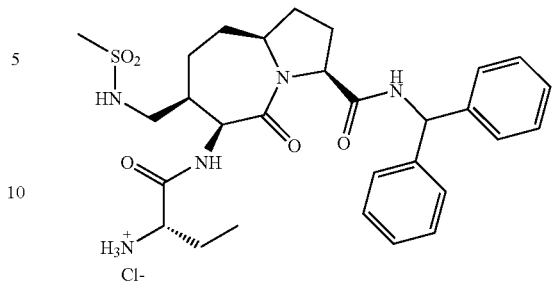

31a 30b, from 12b (0.020 mmol). The crude product did not require HPLC purification. Yield 90% (13 mg, MW 710.30, 0.018 mmol) of pure 30b. Analytical characterization: $[\alpha]_D^{20}$-59.2 (c 1.47, MeOH); $^1$H-NMR (400 MHz, D$_2$O): δ: 7.96 (d, J=7.6 Hz, 2H), 7.62 (t, J=7.6 Hz, 2H), 7.47 (t, J=7.6 Hz, 1H), 7.36-7.20 (m, 10H), 6.0 (s, 1H), 4.79 (d, J=10.0 Hz, 1H), 4.50 (dd, J=8.0, 5.2 Hz, 1H), 4.30 (dq, J=11.6, 5.6 Hz, 1H), 4.05 (q, J=8.8 Hz, 1H), 3.90 (t, J=6.4 Hz, 1H), 2.25-1.55 (m, 12H), 0.90 (t, J=7.6 Hz, 3H); $^{13}$C-NMR (100 MHz, D$_2$O): δ: 173.0, 170.6, 169.2, 140.9, 134.0, 129.5, 129.2, 129.0, 128.9, 128.8, 127.8, 127.4, 127.1, 66.6, 62.0, 58.8, 57.7, 54.3, 53.7, 38.7, 37.1, 32.3, 31.1, 27.9, 24.3, 8.3.

31a, from 13a. (0.050 mmol). The crude product did not require HPLC purification. Yield 90% (25 mg, MW 555.30, 0.045 mmol) of pure 31a. Analytical characterization: $[\alpha]_D^{20}$-62.5 (c 1.12, MeOH); $^1$H-NMR (400 MHz, D$_2$O): δ: 7.35-7.26 (m, 10H), 6.02 (s, 1H), 4.66 (d, J=10.0 Hz, 1H), 4.51 (m, 1H), 3.99 (m, 2H), 3.12 (m, 2H), 3.12 (m, 2H), 2.99 (s, 3H), 2.22-2.11 (m, 2H), 1.96-1.55 (m, 9H), 0.98 (t, J=7.6 Hz, 3H); $^{13}$C-NMR (100 MHz, D$_2$O): δ: 173.0, 170.8, 169.5, 141.0, 140.8, 129.0, 128.9, 127.8, 127.4, 127.2, 62.0, 58.6, 57.7, 54.6, 54.2, 45.0, 38.7, 37.3, 32.3 30.9, 30.0, 27.9, 24.4, 8.5.

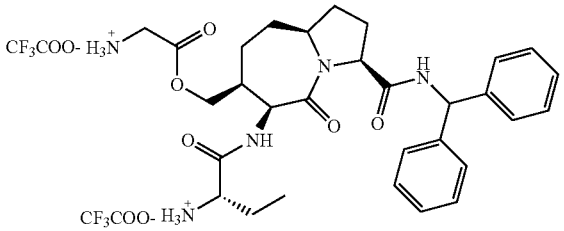

30c

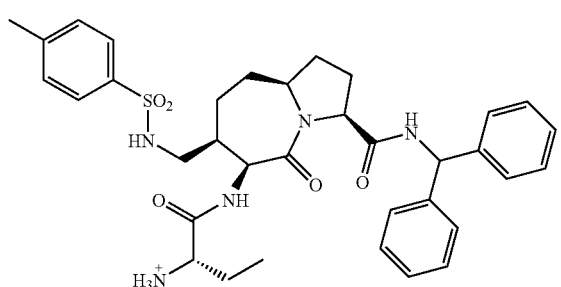

31b 30c, from 12c (0.022 mmol). The crude product did not require HPLC. Yield 94% (16 mg, MW 777.30, 0.021 mmol) of pure 30c. Analytical characterization: $[\alpha]_D^{20}$-43.4 (c 0.68, MeOH); $^1$H-NMR (400 MHz, D$_2$O): δ: 7.36-7.20 (m, 10H), 5.98 (s, 1H), 4.65 (m, 1H), 4.48 (dd. J=8.0, 5.6 Hz, 1H), 4.19 (m, 2H), 3.96 (m, 2H), 3.85 (s, 1H), 2.20-1.55 (m, 12H), 0.92 (t, J=7.6 Hz, 3H); $^{13}$C-NMR (100 MHz, D$_2$O): δ: 173.0, 170.3, 169.4, 140.8, 129.0, 128.9, 127.8, 127.4, 127.1, 67.5, 62.0, 58.8, 57.7, 54.3, 53.4, 40.1, 38.7, 37.0, 32.3, 30.9, 29.4, 28.0, 24.4, 8.3.

31b, from 13b (0.060 mmol). The crude product did not require HPLC purification. Yield 90% (34 mg, MW 631.33, 0.054 mmol) of pure 31b. Analytical characterization: $[\alpha]_D^{20}$-65.0 (c 1.64, MeOH); $^1$H-NMR (400 MHz, D$_2$O): δ: 7.69 (d, J=8.4 Hz, 2H), 7.42-7.88 (m, 12H), 6.02 (s, 1H), 4.65 (d, J=10.0 Hz, 1H), 4.51 (dd, J=8.0, 5.2 Hz, 1H), 4.00 (m, 2H), 2.96 (dd, J=13.2, 6.0 Hz, 1H), 2.85 (dd, J=13.6, 4.4 Hz, 1H), 2.37 (s, 3H), 2.26-2.09 (m, 2H), 2.00-1.45 (m, 9H), 0.99 (t, J=7.6 Hz, 3H); $^{13}$C-NMR (100 MHz, D$_2$O): δ: 173.0, 170.7, 169.3, 145.1, 141.0, 130.1, 129.0, 128.9, 127.8, 127.4, 127.2, 126.7, 62.0, 58.6, 57.7, 54.6, 54.3, 45.2, 37.0, 32.3, 31.4, 30.5, 27.9, 24.4, 20.7, 8.5.

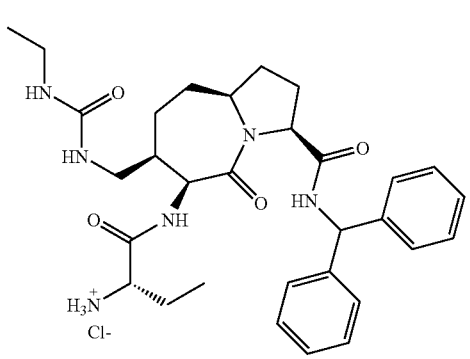

32a

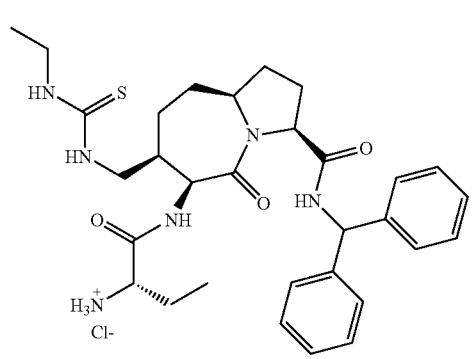

32c 32a, from 14a (0.042 mmol). The crude product did not require HPLC purification. Yield 91% (23 mg, MW 598.31, 0.038 mmol) of pure 32b. Analytical characterization: $[\alpha]_D^{20}$-58.6 (c 1.45, MeOH); $^1$H-NMR (400 MHz, D$_2$O): δ: 7.35-7.25 (m, 10H), 5.99 (s, 1H), 4.56 (d, J=10.0 Hz, 1H), 4.47 (bs, 1H), 3.95 (m, 2H), 3.20 (dd, J=14.0, 3.6 Hz, 1H), 3.02 (m, 3H), 2.25-2.05 (m, 2H), 2.00-1.65 (m, 7H), 1.60-1.50 (m, 2H), 0.98 (t, J=7.2 Hz, 3H), 0.95 (t, J=7.6 Hz, 3H); $^{13}$C-NMR (100 MHz, D$_2$O): δ: 173.0, 170.7, 169.4, 160.4, 141.0, 140.8, 129.0, 128.9, 127.8, 127.4, 127.2, 61.9, 58.6, 57.7, 54.5, 41.6, 38.0, 35.0, 32.3, 30.6, 29.2, 27.8, 24.3, 14.5, 8.5.

32c, from 14c (0.040 mmol). The crude product did not require HPLC purification. Yield 98% (24 mg, MW 614.76, 0.039 mmol) of pure 32c. Analytical characterization: $[\alpha]_D^{20}$-59.6 (c 0.91, CH$_3$OH); $^1$H-NMR (400 MHz, D$_2$O): δ: 7.39-7.27 (m, 10H), 6.02 (s, 1H), 4.65 (d, J=10.0 Hz, 1H), 4.51 (dd, J=8.0, 5.6 Hz, 1H), 4.03 (m, 2H), 3.65 (m, 1H), 3.45-3.15 (m, 3H), 2.30-2.10 (m, 2H), 2.10-1.80 (m, 6H), 1.80-1.45 (m, 3H), 1.09 (t, J=7.2 Hz, 3H), 0.97 (t. J=7.6 Hz, 3H); $^{13}$C-NMR (100 MHz, D$_2$O): δ: 173.0, 170.5, 169.6, 141.0, 140.7, 129.0, 128.9, 127.9, 127.4, 127.2, 61.9, 58.5, 57.7, 54.7, 54.5, 43.9, 37.5, 32.4, 30.5, 29.0, 27.8, 24.4, 13.5, 8.4

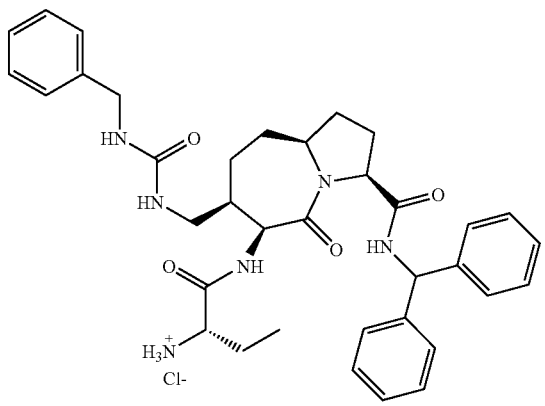

32b

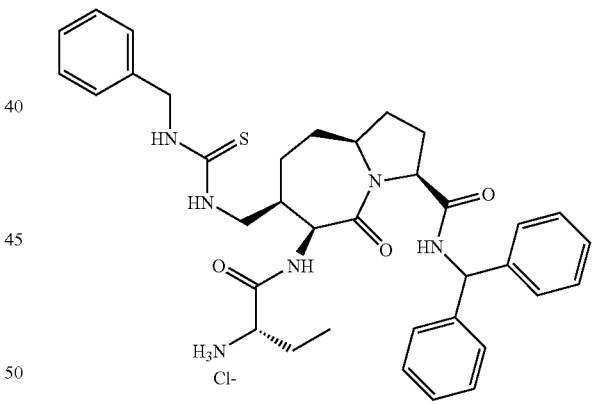

32d 32b, from 14b (0.045 mmol). The crude product did not require HPLC purification. Yield 98% (29 mg, MW 660.32, 0.044 mmol) of pure 32b. Analytical characterization: $[\alpha]_D^{20}$-60.6 (c 1.65, MeOH); $^1$H-NMR (400 MHz, D$_2$O): δ: 7.40-7.20 (m, 15H), 6.00 (s, 1H), 4.52 (d, J=10.0 Hz, 1H), 4.47 (m, 1H), 4.21 (s, 2H), 3.90 (bs, 1H), 3.85 (m, 1H), 3.19 (d, J=11.2, 1H), 3.05 (m, 1H), 2.25-2.05 (m, 2H), 2.00-1.60 (m, 7H), 1.55-1.35 (m, 2H), 0.93 (t, J=7.6 Hz, 3H); $^{13}$C-NMR (100 MHz, D$_2$O): δ: 172.9, 170.8, 169.4, 160.3, 141.0, 140.9, 139.6, 129.0, 128.9, 128.8, 127.8, 127.4, 127.3, 127.2, 126.9, 61.9, 58.6, 57.7, 54.5, 54.4, 43.5, 41.6, 38.2, 32.4, 30.8, 29.4, 27.8, 24.3, 8.5.

32d, from 14d (0.055 mmol). The crude product did not require HPLC purification. Yield 94% (35 mg. MW 676.30, 0.052 mmol) of pure 32d. Analytical characterization: $[\alpha]_D^2$-61.8 (c 0.82, MeOH); $^1$H-NMR (400 MHz, D$_2$O): δ: 7.37-7.27 (m, 15H), 6.02 (s, 1H), 4.60-4.40 (m, 3H), 4.05-3.85 (m, 2H), 3.65 (m, 2H), 3.45-3.25 (m, 2H), 2.30-1.30 (m, 11H), 0.97 (t, J=7.6 Hz, 3H); $^{13}$C-NMR (100 MHz, D$_2$O): δ: 173.0, 170.5, 169.6, 141.0, 140.7, 129.0, 128.9, 127.9, 127.7, 127.4, 127.2, 127.0, 61.9, 58.6, 57.7, 54.5, 54.2, 51.3, 43.8, 35.6, 32.3, 28.7, 27.7, 24.4, 8.4

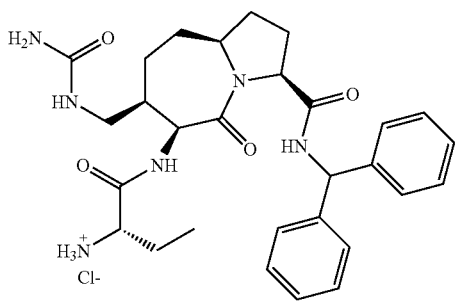

33a 33a, from 15a (0.034 mmol). The crude product did not require HPLC purification. Yield 97% (19 mg, MW 570.28, 0.033 mmol) of pure 33a. Analytical characterization: $[\alpha]_D^2$-64.8 (c 0.98, H$_2$O); $^1$H-NMR (400 MHz, D$_2$O): δ: 7.40-7.20 (m, 10H), 6.00 (s, 1H), 4.58 (d, J=10.0 Hz, 1H), 4.48 (dd, J=8.0, 5.2 Hz, 1H), 3.96 (m, 2H), 3.16 (dd, J=14.4, 4.4 Hz, 1H), 3.07 (dd, J=14.4, 7.2 Hz, 1H), 2.25-2.05 (m, 2H), 2.00-1.45 (m, 10H), 0.95 (t, J=7.6 Hz, 3H); $^{13}$C-NMR (100 MHz, D$_2$O): δ: 173.0, 170.8, 169.4, 161.3, 141.0, 140.9, 129.0, 128.9, 127.8, 127.4, 127.2, 61.9, 58.6, 57.7, 54.6, 54.4, 41.8, 37.9, 32.4, 30.8, 29.5, 27.9, 24.3, 8.5.

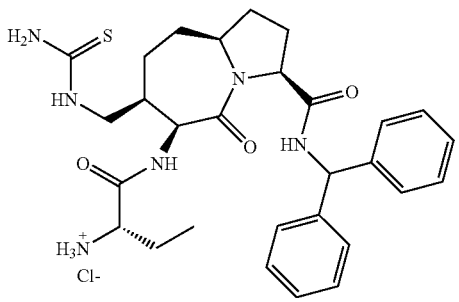

33b 33b, from 15b (0.067 mmol). The crude product did not require HPLC purification. Yield 79% (31 mg, MW 586.25, 0.053 mmol) of pure 33b. Analytical characterization: $[\alpha]_D^{20}$-66.2 (c 1.02, H$_2$O); $^1$H-NMR (400 MHz, D$_2$O): δ: 7.44-7.20 (m, 10H), 6.01 (bs, 1H), 4.65 (d, J=9.4 Hz, 1H), 4.50 (m, 1H), 4.03 (m, 2H), 3.50 (m, 1H), 3.28 (m, 1H), 2.30-2.10 (m, 2H), 2.05-1.75 (m, 6H), 1.75-1.45 (m, 10H), 0.96 (t, J=7.6 Hz, 3H); $^{13}$C-NMR (100 MHz, D$_2$O): δ: 173.0, 170.8, 141.0, 140.9, 129.0, 128.9, 127.9, 127.4, 127.2, 61.9, 58.4, 57.7, 54.6, 54.4, 41.8, 32.3, 30.8, 28.0, 27.9, 24.4, 8.5.

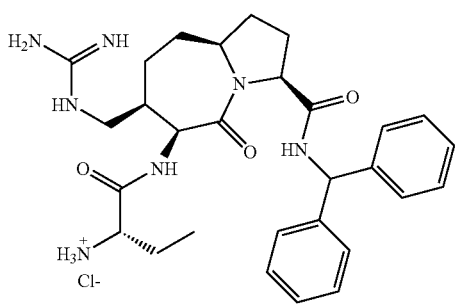

34a 34a, from 16a (0.030 mmol). The crude product did not require HPLC purification. Quantitative yield (17 mg, MW 569.29, 0.030 mmol) of pure 34a. Analytical characterization: $[\alpha]_D^{20}$-44.6 (c 0.63, MeOH); $^1$H-NMR (400 MHz, D$_2$O): δ: 8.84 (d, J=7.2 Hz, 1H), 7.52 (bs, 1H), 7.40-7.18 (m, 10H), 5.97 (d, J=7.2 Hz, 1H), 4.58 (m, 1H), 4.47 (t, J=7.2 Hz, 1H), 4.58 (m, 1H), 4.47 (t, J=6.0 Hz, 1H), 3.27 (dd, J=14.4, 4.0 Hz, 1H), 3.02 (dd, J=14.0, 9.2 Hz, 1H), 2.26-1.43 (m, 11H), 0.92 (t, J=7.6 Hz, 3H); $^{13}$C-NMR (100 MHz, D$_2$O): 173.0, 170.1, 169.4, 156.9, 140.9, 140.7, 128.9, 128.8, 127.8, 127.7, 127.3, 127.1, 61.9, 58.5, 57.7, 54.4, 43.0, 36.9, 32.2, 30.5, 29.2, 27.9, 24.4, 8.4.

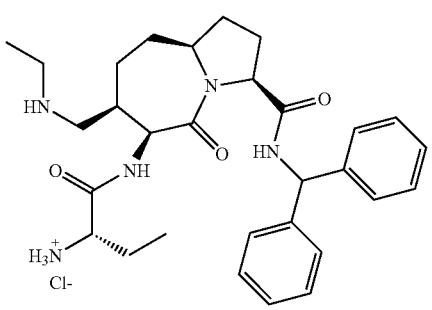

35a 35a, from 17a (0.050 mmol). The crude product did not require HPLC purification. Yield 90% (25 mg, MW 555.32, 0.045 mmol) of pure 35a. Analytical characterization: $[\alpha]_D^{20}$-53.8 (c 0.65, MeOH); $^1$H-NMR (400 MHz, D$_2$O): 7.40-7.28 (m, 10H), 6.03 (s, 1H), 4.66 (d, J=10.4 Hz, 1H), 4.52 (dd, J=8.0, 5.6 Hz, 1H), 4.06 (m, 1H), 3.15-2.98 (m, 4H), 2.21-2.04 (m, 4H), 2.00-1.85 (m, 4H), 1.78-1.60 (m, 3H), 1.23 (t, J=7.2 Hz, 3H), 0.97 (t, J=7.6 Hz, 3H); $^{13}$C-NMR (100 MHz, D$_2$O): 173.0, 170.1, 169.3, 141.0, 140.7, 129.0, 128.9, 127.9, 127.8, 127.4, 127.2, 61.9, 58.3, 57.8, 54.3, 54.1, 43.9, 35.7, 32.2, 29.8, 28.5, 28.1, 24.4, 10.5, 8.4

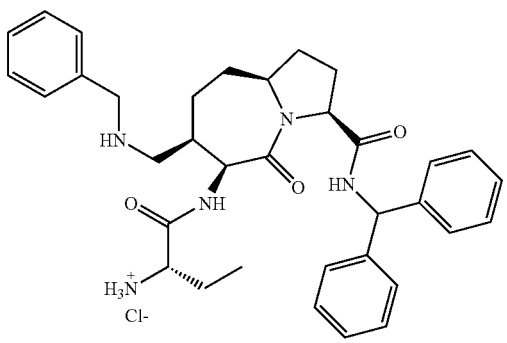

35b 35b, from 17b (0.070 mmol). The crude product did not require HPLC purification. Yield 98% (42 mg, MW 617.74, 0.068 mmol) of pure 35b. Analytical characterization: $[\alpha]_D^{20}$-47.9 (c 1.42, MeOH); $^1$H-NMR (400 MHz, D$_2$O): 8.94 (d, J=7.2 Hz, 1H), 7.48-7.27 (m, 15H), 6.02 (s, 1H), 4.63 (d, J=8.4 Hz, 1H), 4.50 (dd, J=7.6, 5.6 Hz, 1H), 4.21 (d, J=5.2 Hz, 2H), 4.03 (m, 1H), 3.95 (t, J=6.4 Hz, 1H), 3.19 (dd, J=13.2, 3.6 Hz, 1H), 3.04 (dd, J=13.2, 9.6 Hz, 1H), 2.20-2.05 (m, 4H), 2.00-1.80 (m, 4H), 1.75-1.55 (m, 3H), 0.96 (t, J=7.2 Hz, 3H); $^{13}$C-NMR (100 MHz, D$_2$O): 172.9, 170.9, 169.2, 141.0, 140.8, 130.4, 130.0, 129.9, 129.4, 129.0, 128.9, 127.9, 127.4, 127.3, 62.0, 58.3, 57.8, 54.4, 54.2, 51.8, 48.5, 35.6, 32.3, 29.8, 28.7, 28.1, 24.4, 8.5.

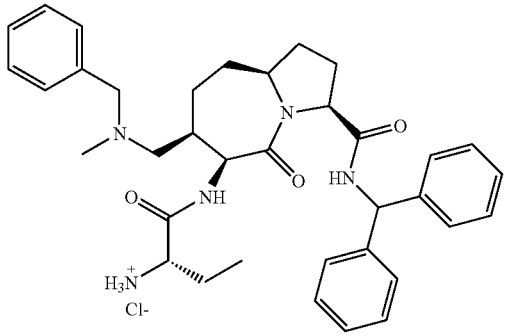

36a 36a, from 18a (0.075 mmol). The crude product did not require HPLC purification. Yield 96% (43 mg, MW 595.35, 0.072 mmol) of pure 36a. Analytical characterization: $[\alpha]_D^{20}$-56.3 (c 0.80, MeOH); $^1$H-NMR (400 MHz, D$_2$O): 8.93 (d, J=7.6 Hz, 1H), 7.48-7.27 (m, 15H), 6.02 (s, 1H), 4.55-4.10 (m, 3H), 4.26 (m, 1H), 3.98 (m, 2H), 3.09 (m, 1H), 2.86 (bs, 3H), 2.20-1.40 (m, 11H), 0.96 (t, J=7.2 Hz, 3H); $^{13}$C-NMR (100 MHz, D$_2$O): 172.9, 170.1, 168.9, 141.0, 140.8, 131.2, 130.5, 129.5, 129.5, 129.0, 128.9, 127.9, 127.5, 127.3, 61.9, 58.7, 57.8, 56.2, 54.4, 54.2, 53.9, 40.8, 34.0, 32.3, 29.8, 28.7, 28.1, 24.4, 8.5.

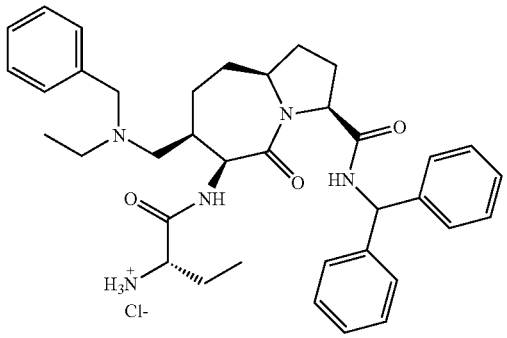

36b 36b, from 18b (0.080 mmol). The crude product did not require HPLC purification. Yield 94% (46 mg, MW 609.37, 0.076 mmol) of pure 36b. Analytical characterization: $[\alpha]_D^{20}$-61.5 (c 1.22, MeOH); $^1$H-NMR (400 MHz, D$_2$O): 8.94 (d, J=7.2 Hz, 1H), 7.48-7.27 (m, 15H), 6.02 (s, 1H), 4.50 (m, 2H), 4.40-4.20 (m, 1H), 4.05 (m, 1H), 3.90 (m, 1H), 3.40-3.05 (m, 4H), 2.35-1.55 (m, 10H), 1.33 (m, 4H), 0.96 (t, J=7.2 Hz, 3H); $^{13}$C-NMR (100 MHz, D$_2$O): 172.9, 170.9, 169.2, 141.0, 140.8, 130.4, 130.0, 129.9, 129.4, 129.0, 128.9, 127.9, 127.4, 127.3, 61.8, 58.3, 57.8, 54.3, 54.0, 53.7, 49.8, 34.4, 32.2, 28.8, 28.4, 28.1, 24.4, 8.4, 8.1.

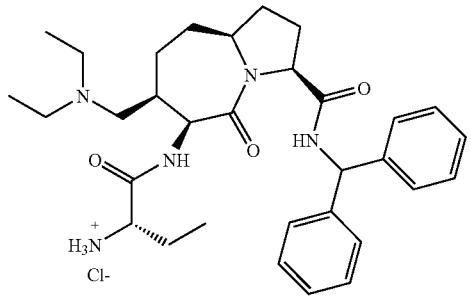

36c 36c, from 18c (0.040 mmol). The crude product did not require HPLC purification. Yield 98% (23 mg, MW 583.33, 0.039 mmol) of pure 36c. Analytical characterization: $[\alpha]_D^{20}$-57.0 (c 1.21, MeOH); $^1$H-NMR (400 MHz, D$_2$O): 7.40-7.28 (m, 10H), 6.03 (s, 1H), 4.66 (d, J=10.0 Hz, 1H), 4.52 (dd, J=8.0, 5.6 Hz, 1H), 4.06 (m, 2H), 3.30-3.12 (m, 6H), 2.27-2.10 (m, 4H), 2.00-1.85 (m, 4H), 1.78-1.60 (m, 3H), 1.23 (m, 6H), 0.97 (t, J=7.6 Hz, 3H); $^{13}$C-NMR (100 MHz, D$_2$O): 172.9, 170.2, 169.0, 141.0, 140.7, 129.0, 128.9, 127.9, 127.8, 127.4, 127.2, 61.9, 58.0, 57.7, 54.3, 54.0, 53.8, 49.5, 46.8, 34.0, 32.2, 29.3, 28.5, 28.1, 24.4, 8.5, 7.5

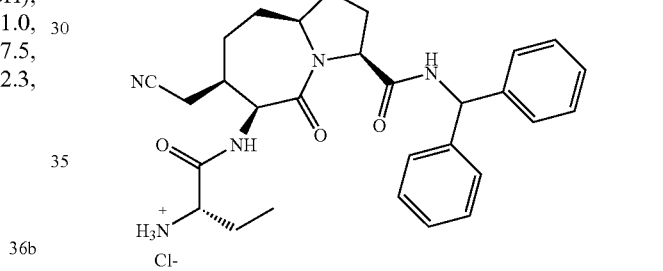

37a 37a, from 19a (0.018 mmol). The crude product did not require HPLC purification. Quantitative yield (10 mg, MW 537.25, 0.018 mmol) of pure 37a. Analytical characterization: $[\alpha]_D^{20}$-134.7 (c 0.23, MeOH); $^1$H-NMR (400 MHz, D$_2$O): 7.40-7.25 (m, 10H), 6.02 (s, 1H), 4.70 (m, 1H), 4.52 (dd, J=8.0, 4.8 Hz, 1H), 4.04 (m, 2H), 2.58 (d, J=5.2 Hz, 2H), 2.30-1.55 (m, 11H), 0.96 (t, J=7.6 Hz, 3H); $^{13}$C-NMR (100 MHz, D$_2$O): 172.9, 170.0, 169.8, 141.0, 140.8, 129.0, 128.9, 127.9, 127.4, 127.2, 119.9, 62.1, 58.9, 57.7, 54.9, 54.3, 34.6, 32.8, 32.3, 31.4, 28.0, 24.4, 21.3, 8.4.

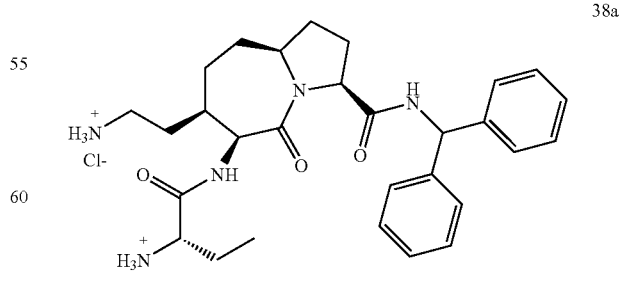

38a 38a, from 20a (0.020 mmol). The crude product did not require HPLC purification. Quantitative yield (12 mg, MW 577.63, 0.020 mmol) of pure 38a. Analytical characterization: $[\alpha]_D^{20}$-61.4 (c 0.44, H$_2$O); $^1$H-NMR (400 MHz, D$_2$O): 8.87 (d, J=7.6 Hz, 1H), 7.40-7.25 (m, 10H), 4.57 (d. J=9.6 Hz, 1H), 4.47 (dd, J=7.6, 5.6 Hz, 1H), 4.03 (m, 2H), 3.05-2.85 (m, 2H), 2.35-2.10 (m, 2H), 2.05-1.65 (m, 8H), 1.65-1.50 (m, 3H), 0.96 (t, J=7.6 Hz, 3H); $^{13}$C-NMR (100 MHz, D$_2$O): 173.1, 170.5, 169.7, 141.0, 140.8, 129.0, 128.9, 127.9, 127.9, 127.4, 127.2, 61.9, 58.4, 57.7, 56.0, 54.3, 37.3, 35.2, 32.3, 30.2, 29.8, 29.2, 28.0, 24.5, 8.4.

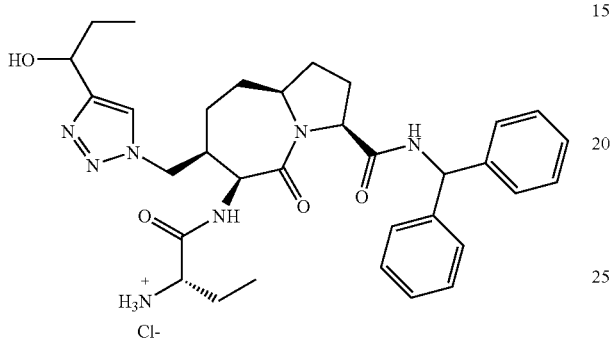

39a 39a, from 21a (0.038 mmol). The crude product did not require HPLC purification. Quantitative yield (25 mg, MW 637.32, 0.038 mmol) of pure 39a. Analytical characterization: $[\alpha]_D^{20}$-71.1 (c 1.40, MeOH); $^1$H-NMR (400 MHz, D$_2$O): 7.92 (s, 1H), 7.35-7.20 (m, 10H), 5.99 (s, 1H), 4.76 (m, 2H), 4.53 (dd, J=14.0, 5.2 Hz, 1H), 4.48 (m, 1H), 4.33 (dd, J=14.4, 8.4 Hz, 1H), 4.00 (bs, 1H), 3.93 (m, 1H), 2.30-2.05 (m, 3H), 1.95-1.60 (m, 8H), 1.55-1.35 (m, 2H), 0.95 (t, J=7.2 Hz, 3H), 0.81 (t, J=7.2 Hz, 3H) $^{13}$C-NMR (100 MHz, D$_2$O): 172.8, 169.8, 169.6, 1410, 140.9, 129.0, 128.9, 127.8, 127.4, 127.2, 67.3, 61.9, 58.2, 57.7, 54.4, 52.2, 38.3, 32.2, 29.8, 29.2, 28.3, 27.9, 24.4, 9.0, 8.4

Additional compounds 24b to 38c were synthesized by the general procedures described above.

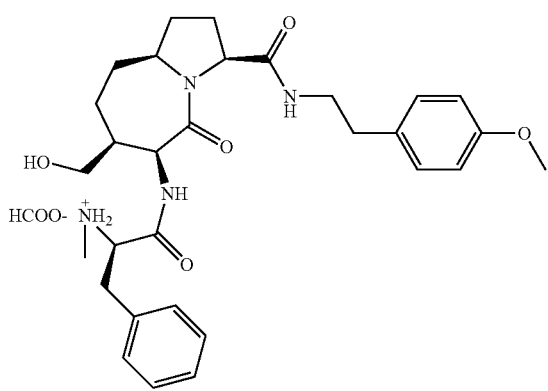

24b 24b, from 6b (0.050 mmol). HPLC eluant conditions: from 95% of H$_2$O (0.1% HCOOH) and 5% of CH$_3$CN (0.1% HCOOH) to 85% of H$_2$O (0.1% HCOOH) and 15% of CH$_3$CN (0.1% HCOOH), flow rate 20 ml/min., 10 min. runs. Yield 66% (19.2 mg, MW 582.40, 0.033 mmol) of pure 24b. Analytical characterization: $[\alpha]_D^{20}$-111.6 (c 1.34, MeOH); $^1$H-NMR (400 MHz, D$_2$O): δ: 8.38 (bs, 1H), 7.38-7.28 (m, 3H), 7.21 (d, J=6.8 Hz, 2H), 7.13 (d, J=8.4 Hz, 2H), 6.87 (d, J=8.4 Hz, 2H), 4.21 (m 2H), 4.10 (dd, J=10, 5.2 Hz, 1H), 3.86 (m, 1H), 3.73 (s, 3H), 3.48 (m, 1H), 3.32-3.22 (m, 2H), 3.00 (dd, J=13.2, 10.2, 1H), 2.82 (m, 1H), 2.71 (m, 3H), 2.65 (s, 3H), 2.08 (m, 1H), 1.93-1.84 (m, 2H), 1.72 (m, 1H), 1.66 (m, 1H), 1.51-1.44 (m, 3H), 1.35 (m, 1H); $^{13}$C NMR (100 MHz, D$_2$O): δ: 173.3, 170.4, 167.8, 157.4, 133.6, 131.7, 130.1, 129.3, 129.0, 128.0, 114.1, 63.1, 62.2, 62.1, 58.4, 55.4, 54.7, 40.1, 38.0, 36.0, 33.5, 32.2, 31.7, 30.3, 28.0, 27.1.

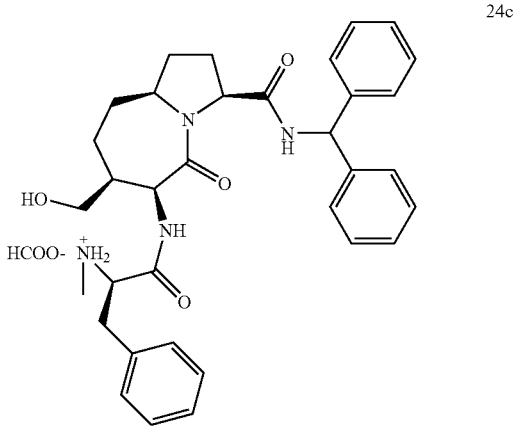 [SMILES: "HCOO-" ; CN[C@H](Cc1ccccc1)C(=O)N[C@@H]1C(=O)N2[C@@H](CC[C@@H]1CO)CC[C@H]2C(=O)NC(c1ccccc1)c1ccccc1]

24c 24c, from 6c (0.050 mmol). HPLC eluant conditions: from 80% of H$_2$O (0.1% HCOOH) and 20% of CH$_3$CN (0.1% HCOOH) to 65% of H$_2$O (0.1% HCOOH) and 35% of CH$_3$CN (0.1% HCOOH), flow rate 20 ml/min., 10 min. runs. Yield 80% (24.6 mg. MW 614.31, 0.040 mmol) of pure 24c. Analytical characterization: $[\alpha]_D^{20}$-91.4 (c 0.93, MeOH); $^1$H NMR (400 MHz, D$_2$O): δ: 8.38 (bs, 1H), 7.37-7.25 (m, 13H), 7.19 (d, J=6.8 Hz, 2H), 6.0 (s, 1H), 4.47 (dd, J=8.0, 5.2 Hz, 1H), 4.24 (d, J=9.6 Hz, 1H), 3.95 (m, 1H), 3.55 (m, 1H), 3.04 (dd, J=14.0, 8.0 Hz, 1H), 2.80 (m, 2H), 2.67 (dd. J=10.8, 4.0 Hz, 1H), 2.33 (s, 3H), 2.19 (m, 2H), 1.95-1.62 (m, 4H), 1.45 (m, 3H); $^1$H NMR (400 MHz, DMSO-d$_6$): δ: 8.86 (d, J=8.4 Hz, 1H), 8.23 (d, J=8.4 Hz, 1H), 7.36-7.19 (m, 15H), 6.08 (d, J=5.2, 1H), 4.57 (dd, J=8.0 Hz, 1H), 4.39 (t, J=8.4 Hz, 1H), 3.95 (m, 1H), 3.33 (m, 1H), 3.22 (dd. J=8.4, 5.2 Hz, 1H), 3.15 (m, 1H), 2.86 (dd, J=10.8, 4.0 Hz, 1H), 2.63 (dd, J=14.0, 8.0 Hz, 1H), 2.18 (s, 3H), 2.15 (m, 1H), 2.08-2.01 (m, 2H), 1.84-1.74 (m, 2H), 1.69-1.62 (m, 4H); $^{13}$C NMR (100 MHz, DMSO-d$_6$): δ: 173.7, 171.2, 170.0, 143.2, 142.8, 139.0, 129.6, 128.9, 128.8, 128.6, 127.9, 127.5, 126.6, 65.7, 62.9, 61.2, 58.0, 56.3, 53.4, 40.9, 35.0, 33.0, 32.2, 30.0, 28.5.

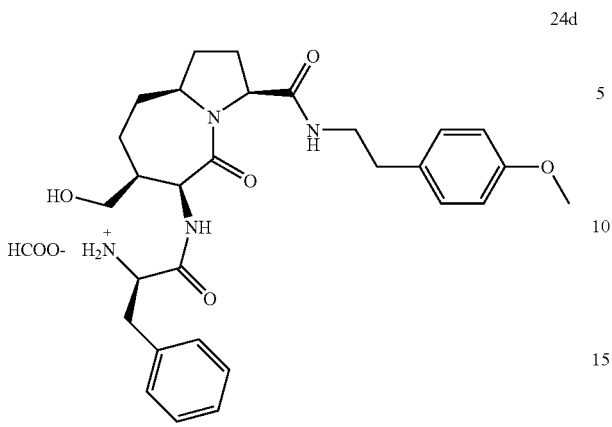

24d, from 6d (0.050 mmol). HPLC eluant conditions: from 95% of $H_2O$ (0.1% HCOOH) and 5% of $CH_3CN$ (0.1% HCOOH) to 85% of $H_2O$ (0.1% HCOOH) and 15% of $CH_3CN$ (0.1% HCOOH), flow rate 20 ml/min., 10 min. runs. Yield 44% (12.5 mg, MW 568.29, 0.022 mmol) of pure 24d. Analytical characterization: $[\alpha]_D^{20}$-81.4 (c 0.92, MeOH); $^1H$ NMR (400 MHz, $D_2O$): δ: 8.38 (bs, 1H), 7.40-7.32 (m, 3H), 7.24 (d, J=7.2 Hz, 2H), 7.14 (d, J=8.0 Hz, 2H), 6.88 (d, J=8.4 Hz, 2H), 4.29 (d, J=9.6 Hz, 1H), 4.25 (m, 2H), 3.87 (m, 1H), 3.74 (s, 3H), 3.45 (m, 1H), 3.30 (m, 1H), 3.15 (m, 2H), 2.98 (m, 1H), 2.85 (dd, J=10.8, 3.6 Hz, 1H), 2.70 (m, 2H), 2.09 (m, 1H), 1.92 (m, 2H), 1.75 (m, 1H), 1.67 (m, 1H), 1.51 (m, 3H), 1.32 (m, 1H); $^{13}C$ NMR (100 MHz, $D_2O$): δ: 173.4, 170.9, 168.7, 157.4, 133.7, 131.7, 130.1, 129.3, 129.1, 128.0, 114.1, 62.5, 62.2, 58.4, 55.4, 54.8, 54.4, 40.7, 40.1, 38.2, 36.8, 33.5, 32.2, 30.5, 28.3, 27.9.

24f, from 6f (0.050 mmol). HPLC eluant conditions: from 80% of $H_2O$ (0.1% HCOOH) and 20% of $CH_3CN$ (0.1% HCOOH) to 60% of $H_2O$ (0.1% HCOOH) and 40% of $CH_3CN$ (0.1% HCOOH), flow rate 20 ml/min., 10 min. runs. Yield 42% (12.6 mg, MW 600.30, 0.021 mmol) of pure 24d. Analytical characterization: $[\alpha]_D^{20}$-111.9 (c 0.76, MeOH); $^1H$ NMR (400 MHz, $CD_3OD$): δ: 7.45-7.32 (m, 15H), 6.23 (s, 1H), 4.73 (dd, J=7.6, 4.0 Hz, 1H) 4.57 (d, J=9.2 Hz, 1H), 4.10 (m, 1H), 3.74 (t, J=7.2 Hz, 1H), 3.34 (m, 2H), 3.12 (dd, J=13.6, 6.8 Hz, 1H), 2.89 (dd, J=13.6, 8.0 Hz, 1H), 2.34 (m, 1H), 2.16 (m, 3H), 2.00-1.85 (m, 2H), 1.75 (m, 3H); $^{13}C$ NMR (100 MHz, $CD_3OD$): δ: 175.7, 171.8, 171.0, 141.7, 137.8, 129.2, 128.2, 127.5, 127.4, 127.2, 127.1, 127.0, 126.9, 126.5, 63.4, 61.7, 58.5, 57.0, 56.7, 54.2, 40.5, 40.0, 32.7, 32.3, 30.1, 27.6.

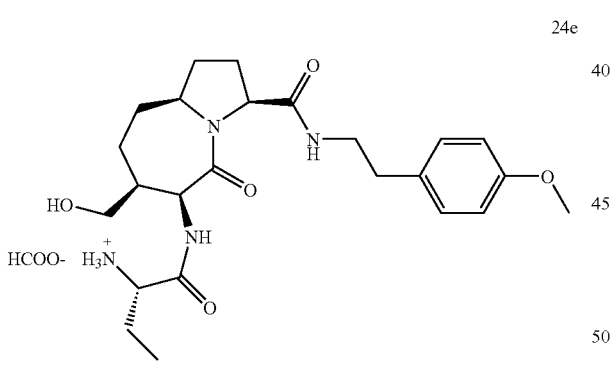

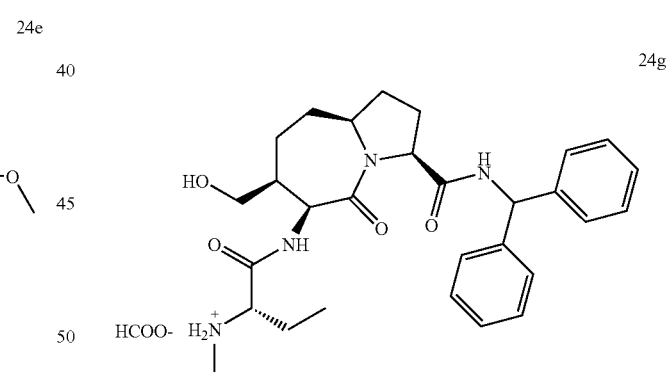

24e, from 6e (0.050 mmol). HPLC eluant conditions: from 90% of $H_2O$ (0.1% HCOOH) and 10% of $CH_3CN$ (0.1% HCOOH) to 75% of $H_2O$ (0.1% HCOOH) and 15% of $CH_3CN$ (0.1% HCOOH), flow rate 20 ml/min., 10 min. runs. Yield 66% (16.7 mg, MW 506.28, 0.033 mmol) of pure 24e. Analytical characterization: $[\alpha]_D^{20}$-67.7 (c 1.10, MeOH); $^1H$ NMR (400 MHz, $D_2O$): δ: 8.38 (bs, 1H), 7.16 (d, J=8 Hz, 2H), 6.90 (d. J=8 Hz, 2H), 4.54 (d, J=9.2 Hz, 1H), 4.26 (dd, J=8.0, 4.4 Hz, 1H), 3.92 (m, 2H), 3.75 (s, 3H), 3.55 (m, 3H), 3.37 (m 1H), 2.77 (m, 2H), 2.15 (m, 1H), 2.00-1.60 (m, 8H), 1.55 (m, 1H), 1.45 (m, 1H), 0.89 (t. J=7.2 Hz, 3H); $^{13}C$ NMR (100 MHz, $D_2O$): δ: 173.4, 171.3, 157.4, 131.7, 130.1, 114.1, 63.1, 62.2, 58.8, 55.4, 54.5, 54.2, 40.1, 38.9, 33.5, 32.2, 29.6, 27.9, 24.6.

24g, from 6g (0.050 mmol). HPLC eluant conditions: from 80% of $H_2O$ (0.1% HCOOH) and 20% of $CH_3CN$ (0.1% HCOOH) to 60% of $H_2O$ (0.1% HCOOH) and 40% of $CH_3CN$ (0.1% HCOOH), flow rate 20 ml/min., 10 min. runs. Yield 73.6% (20 mg, MW 552.28, 0.036 mmol) of pure 24g. Analytical characterization: $[\alpha]_D^{20}$-83.3° (c 0.01, MeOH); $^1H$ NMR (400 MHz, $D_2O$): δ: 7.40-7.28 (m, 10H), 6.06 (s, 1H), 4.69 (m, 1H), 4.55 (dd, J=5.50, 8.25 Hz, 1H), 4.06 (m, 1H), 3.90 (dd, J=5.29, 7.19 Hz, 1H), 3.59 (d, J=4.87 Hz, 2H), 2.68 (s, 3H), 2.26 (m, 1H), 2.19 (m, 1H), 2.00-1.80 (m, 6H), 1.80-1.55 (m, 3H), 0.98 (t, J=7.19 Hz, 3H); $^{13}C$ NMR (100 MHz, $D_2O$): δ: 173.0, 170.9, 168.3, 141.0, 140.8, 129.0, 128.9, 127.4, 127.2, 65.0, 63.2, 62.8, 62.0, 58.7, 57.7, 54.5, 38.9, 32.3, 31.5, 31.0, 29.2, 28.0, 23.4, 8.2

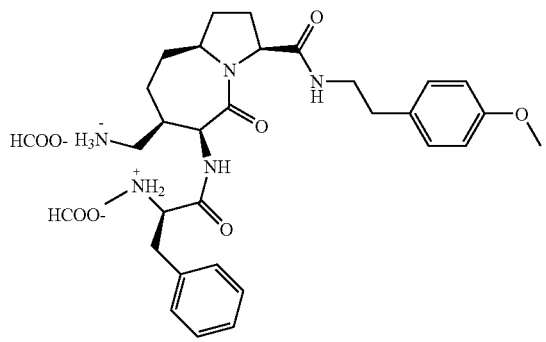

26b

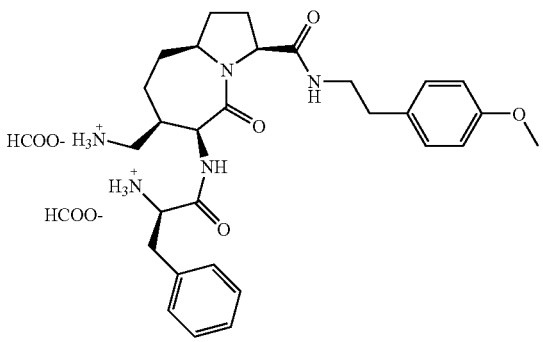

26d 26b, from 8b (0.050 mmol). HPLC eluant conditions: from 95% of H$_2$O (0.1% HCOOH) and 5% of CH$_3$CN (0.1% HCOOH) to 85% of H$_2$O (0.1% HCOOH) and 15% of CH$_3$CN (0.1% HCOOH), flow rate 20 ml/min., 10 min. runs. Yield 42% (13.1 mg. MW 626.34, 0.021 mmol) of pure 26b. Analytical characterization: $[\alpha]_D^{20}$-71.7 (c 0.90, MeOH); $^1$H NMR (400 MHz, D$_2$O): δ: 8.38 (bs, 2H), 7.35 (m, 3H), 7.23 (d, J=6.8 Hz, 2H), 7.14 (d, J=8.4 Hz, 2H), 6.88 (d, J=8.8 Hz, 2H), 4.30 (d, J=10 Hz, 1H), 4.21 (dd, J=7.6, 4.8 Hz, 1H), 3.92 (m, 2H), 3.74 (s, 3H), 3.49 (m, 1H), 3.24 (m, 2H), 3.93 (m, 1H), 2.75 (m, 2H), 2.53 (s, 3H), 2.21 (m, 1H), 2.13 (m, 1H), 1.96 (m, 3H), 1.75 (m, 2H), 1.70-1.40 (m, 4H); $^{13}$C NMR (100 MHz, D$_2$O): δ: 173.3, 169.0, 157.4, 135.2, 131.8, 130.2, 129.4, 129.1, 127.5, 114.1, 69.7, 63.9, 62.0, 57.8, 55.4, 53.9, 40.3, 39.7, 38.7, 36.9, 35.1, 33.6, 32.1, 29.6, 29.2, 28.1, 27.0.

26d, from 8d (0.050 mmol). HPLC eluant conditions: from 95% of H$_2$O (0.1% HCOOH) and 5% of CH$_3$CN (0.1% HCOOH) to 75% of H$_2$O (0.1% HCOOH) and 25% of CH$_3$CN (0.1% HCOOH), flow rate 20 ml/min., 10 min. runs. Yield 40% (12.6 mg, MW 613.32, 0.020 mmol) of pure 26d. Analytical characterization: $[\alpha]°$-94.0 (c 0.90, MeOH); NMR (400 MHz, D$_2$O): δ: 8.38 (bs, 2H), 7.39-7.32 (m, 3H), 7.25 (d, J=7.6 Hz, 2H), 7.15 (d, J=7.6 Hz, 2H), 6.89 (d, J=7.6 Hz, 2H), 4.36 (d, J=10.4 Hz, 1H), 4.24 (t, J=6.8 Hz, 1H), 4.13 (t, J=7.6 Hz, 1H), 3.94 (m, 1H), 3.74 (s, 3H), 3.49 (m, 1H), 3.25 (dd, J=14.0, 6.8 Hz, 1H), 3.15 (dd, J=13.6, 6.8 Hz, 1H), 3.02 (m, 1H), 2.71 (m, 2H), 2.35 (t, J=12.0 Hz, 1H), 2.21 (bd, J=22.4 Hz, 1H), 2.13 (m, 1H), 1.96 (m, 2H), 1.78 (m, 2H), 1.65-1.45 (m, 4H); $^{13}$C NMR (100 MHz, D$_2$O): δ: 173.3, 169.3, 157.4, 134.9, 131.9, 130.2, 129.2, 127.7, 114.1, 62.1, 58.0, 55.5, 55.2, 54.0, 40.3, 39.9, 37.6, 35.3, 33.6, 32.2, 29.4, 28.1, 27.4.

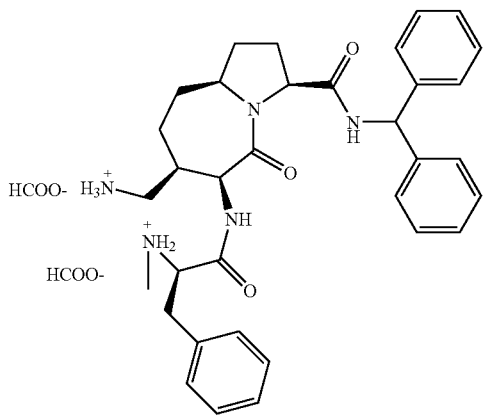

26c

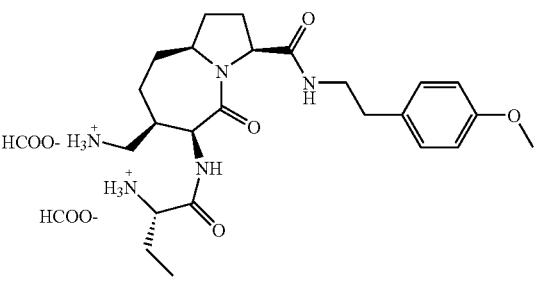

26e 26c, from 8c (0.050 mmol). HPLC eluant conditions: from 90% of H$_2$O (0.1% HCOOH) and 10% of CH$_3$CN (0.1% HCOOH) to 70% of H$_2$O (0.1% HCOOH) and 30% of CH$_3$CN (0.1% HCOOH), flow rate 20 ml/min., 10 min. runs. Yield 78% (25.7 mg, MW 659.34, 0.039 mmol) of pure 26c. Analytical characterization: $[\alpha]_D^{20}$-73.5 (c 1.15, MeOH); $^1$H NMR (400 MHz, D$_2$O): δ: 8.38 (bs, 2H), 7.36-7.24 (m, 15H), 5.97 (s, 1H), 4.46 (m, 1H), 4.32 (d, J=10.4 Hz, 1H), 3.98 (m, 1H), 3.90 (dd, J=10.4, 5.2 Hz, 1H), 3.22 (dd, J=13.2, 5.2 Hz, 1H), 2.89 (dd, J=13.2, 10.8 Hz, 1H), 2.53 (s, 3H), 2.15 (m, 3H), 2.00-1.85 (m, 3H), 1.85-1.60 (m, 3H), 1.55-1.40 (m, 2H); $^{13}$C NMR (100 MHz, D$_2$O): δ: 173.0, 170.8, 169.2, 140.9, 140.6, 135.2, 129.4, 129.2, 129.0, 128.8, 127.8, 127.4, 127.1, 63.7, 61.8, 57.9, 57.7, 54.0, 39.7, 37.7, 36.7, 35.0, 32.2, 29.0, 28.0, 26.8.

26e, from 8e (0.050 mmol). HPLC eluant conditions: from 95% of H$_2$O (0.1% HCOOH) and 5% of CH$_3$CN to 85% of H$_2$O (0.1% HCOOH) and 15% of CH$_3$CN (0.1% HCOOH), flow rate 20 ml/min., 10 min. runs. Yield 38% (10.5 mg, MW 551.3, 0.019 mmol) of pure 26e. Analytical characterization: $[\alpha]_D^{20}$-82.1 (c 1.20, MeOH); $^1$H NMR (400 MHz, D$_2$O): δ: 8.38 (bs, 2H), 7.16 (d, J=8.4 Hz, 2H), 6.90 (d, J=8.8 Hz, 2H), 4.62 (d, J=10.0 Hz, 1H), 4.25 (dd, J=8.0, 5.2 Hz, 1H), 4.00 (m, 2H), 3.75 (s, 3H), 3.55 (m, 1H), 3.28 (m, 1H), 3.11 (dd, J=13.2, 3.6 Hz, 1H), 2.88 (dd, J=13.2, 9.6 Hz, 1H), 2.72 (m, 2H), 2.20-1.80 (m, 7H), 1.73-1.50 (m, 4H), 0.92 (t, J=7.6 Hz, 3H); $^{13}$C NMR (100 MHz, D$_2$O): δ: 173.3, 170.2, 169.4, 157.4, 131.8, 130.2, 114.1, 62.1, 58.4, 55.4, 54.3, 54.0, 40.9, 40.3, 36.2, 33.6, 32.1, 30.1, 28.6, 28.1, 24.4, 8.3.

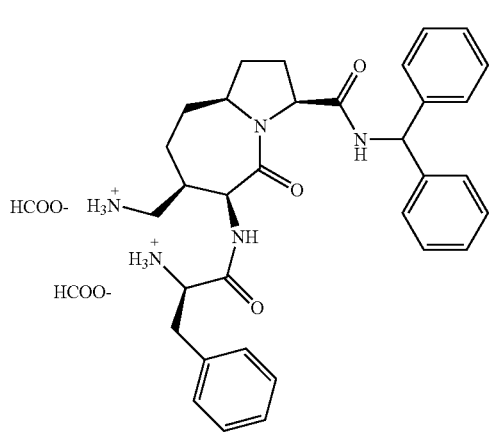

26f

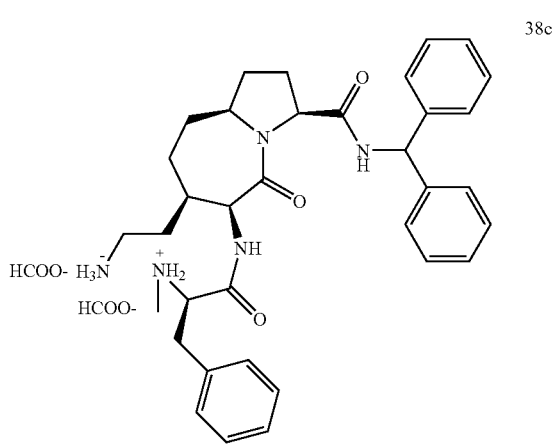

38c 26f, from 8f (0.050 mmol). HPLC eluant conditions: from 95% of H$_2$O (0.1% HCOOH) and 5% of CH$_3$CN (0.1% HCOOH) to 85% of H$_2$O (0.1% HCOOH) and 15% of CH$_3$CN (0.1% HCOOH), flow rate 20 ml/min. 10 min. runs. Yield 28% (9.0 mg, MW 645.33, 0.014 mmol) of pure 26e. Analytical characterization: $[\alpha]_D^{20}$-79.6 (c 0.81, MeOH); $^1$H NMR (400 MHz, D$_2$O): δ: 8.38 (bs, 2H), 7.40-7.24 (m, 15H), 5.98 (s, 1H), 4.47 (m, 1H), 4.37 (d, J=10.0 Hz, 1H), 4.07 (t, J=8.0 Hz, 1H), 3.99 (bs, 1H), 3.13 (dd, J=13.2, 6.4 Hz, 1H), 2.99 (m, 1H), 2.35 (t, J=12.0 Hz, 1H), 2.15 (m, 3H), 2.05-1.88 (m, 2H), 1.83-1.68 (m, 3H), 1.52 (m, 2H); $^{13}$C NMR (100 MHz, D$_2$O): δ: 173.0, 171.8, 169.2, 140.9, 140.7, 135.2, 129.4, 129.2, 129.0, 128.9, 127.8, 127.6, 127.3, 127.2, 61.9, 57.9, 57.7, 55.4, 53.9, 39.8, 38.0, 35.3, 32.3, 29.2, 28.0, 27.1.

38c, from 20c (0.050 mmol). HPLC eluant conditions: from 85% of H$_2$O (0.1% HCOOH) and 15% of CH$_3$CN (0.1% HCOOH) to 65% of H$_2$O (0.1% HCOOH) and 35% of CH$_3$CN (0.1% HCOOH), flow rate 20 ml/min., 10 min. runs. Yield 66% (22 mg, MW 673.36, 0.033 mmol) of pure 38c. Analytical characterization: $[\alpha]_D^{20}$-77.7 (c 0.47, MeOH); $^1$H NMR (400 MHz, D$_2$O): δ: 8.38 (bs, 2H), 7.35-1.19 (m, 15H), 5.98 (s, 1H), 4.45 (t, J=5.2 Hz, 1H), 4.31 (d, J=9.6 Hz, 1H), 3.98 (m, 1H), 3.46 (dd, J=9.6, 5.6 Hz, 1H), 2.95 (dd, J=13.2, 5.6 Hz, 1H), 2.75 (dd, J=13.2, 12.0 Hz, 1H), 2.63 (m, 2H), 2.24 (s, 3H), 2.21-1.12 (m, 2H), 1.90 (m, 2H), 1.68 (m, 2H), 1.44 (m, 3H), 0.97 (m, 2H); $^{13}$C NMR (100 MHz, D$_2$O): δ: 175.4, 173.1, 170.6, 141.0, 140.7, 137.2, 129.4, 129.0, 128.9, 128.8, 127.8, 127.4, 127.2, 126.8, 65.1, 61.7, 58.1, 57.7, 55.7, 38.5, 37.2, 34.2, 33.0, 32.3, 29.9, 29.3, 28.0.

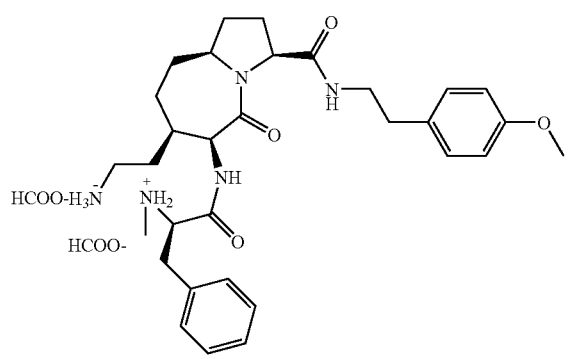

38b

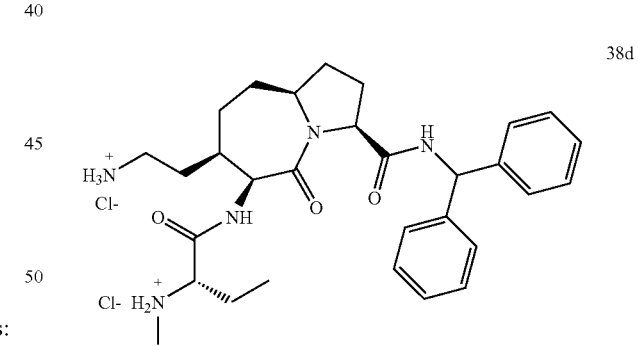

38d 38b, from 20b (0.050 mmol). HPLC eluant conditions: from 90% of H$_2$O (0.1% HCOOH) and 10% of CH$_3$CN (0.1% HCOOH) to 70% of H$_2$O (0.1% HCOOH) and 30% of CH$_3$CN (0.1% HCOOH), flow rate 20 ml/min., 10 min. runs. Yield 52% (16.7 mg, MW 641.74, 0.026 mmol) of pure 38b. Analytical characterization: $[\alpha]_D^{20}$-79.1 (c 0.43, MeOH); $^1$H NMR (400 MHz, D$_2$O): δ: 8.38 (bs, 2H), 7.25 (m, 3H), 7.20 (d, J=7.6 Hz, 2H), 7.05 (d, J=8.4 Hz, 2H), 6.08 (d, J=8.4 Hz, 2H), 4.20 (d, J=9.6 Hz, 1H), 4.13 (dd, J=8.0, 5.2 hz, 1H), 3.99 (dd, J=9.6, 5.6 Hz, 1H), 3.83 (m, 1H), 3.65 (s, 3H), 3.45 (m, 1H), 3.15 (m, 2H), 2.96 (dd, J=13.2, 10.0, 1H), 2.7-2.50 (m, 7H), 2.02 (m, 1H), 1.84 (m, 2H), 1.66 (m, 1H), 1.54 (m, 1H), 1.43 (m, 2H), 1.32 (m, 2H), 0.95 (m, 2H); $^{13}$C NMR (100 MHz, D$_2$O): δ: 173.4, 170.0, 168.6, 157.4, 134.1, 131.8, 130.2, 129.5, 129.2, 127.7, 114.1, 63.1, 62.0, 58.0, 56.4, 55.4, 40.2, 37.0, 36.2, 33.9, 33.6, 32.2, 31.8, 29.7, 29.1, 28.6, 28.1.

38d, from 20e (0.070 mmol). The crude product did not require HPLC purification. Quantitative yield (38 mg, MW 592.63, 0.064 mmol) of pure 38d. Analytical characterization: $[\alpha]_D^{20}$-68.6 (c 0.01, MeOH); $^1$H-NMR (400 MHz, D$_2$O): δ: 7.40-7.20 (m, 10H), 6.05 (s, J=7.3 Hz, 1H), 4.63 (m, 1H), 4.51 (t, J=6.9 Hz, 1H), 4.08 (m, 1H), 3.95 (t, J=5.6 Hz, 1H), 3.05 (m, 1H), 2.95 (m, 1H), 2.68 (s, 3H), 2.30-2.10 (m, 2H), 2.08-1.65 (m, 9H), 1.63-1.55 (m, 2H), 0.97 (t, J=7.3 Hz, 3H); $^{13}$C-NMR (100 MHz, D$_2$O): δ: 173.0, 170.3, 168.6, 141.0, 140.8, 129.0, 128.9, 127.5, 127.4, 127.2, 62.7, 61.8, 60.8, 58.4, 57.7, 56.2, 37.4, 35.1, 32.3, 31.7, 30.1, 29.6, 29.2, 28.1, 23.5, 8.2.

Example 2

Synthesis of Hetero- and Homodimeric Smac Mimetics with [4.3.0] and [5.3.0] Bicyclic Lactam Systems 2.1 General procedure for the synthesis of heterodimeric compounds 41 (Scheme 17)

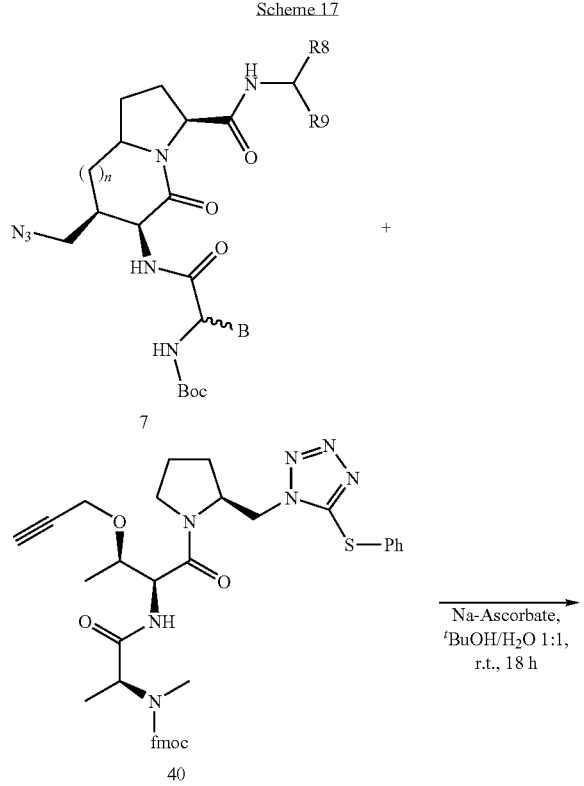

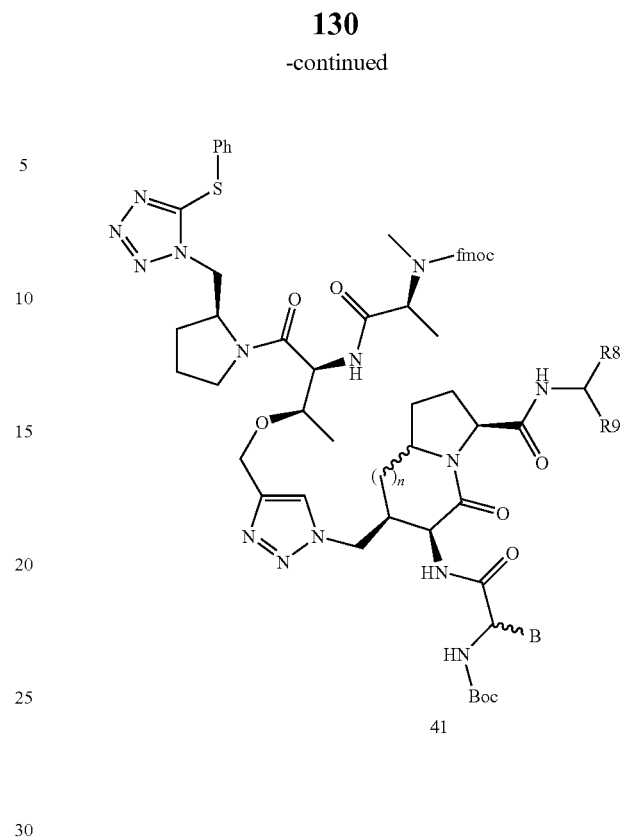

A 0.9 M water solution of Sodium Ascorbate (45 μl; 0.4 mmol) and a 0.3 M water solution of Cu(OAc), (65 μl; 0.02 mmol) were added to stirred solutions of compounds 7 (0.10 mmol) and of the alkyne 40² (0.10 mmol) in a 1:1 mixture of H₂O/ᵗBuOH (300 μl). The reaction mixtures were stirred overnight at room temperature, and then the solvent was removed under reduced pressure. Finally, the residues were purified either by flash chromatography or by Biotage™ flash chromatography.

Compound 41a was synthesized by the general procedure described above.

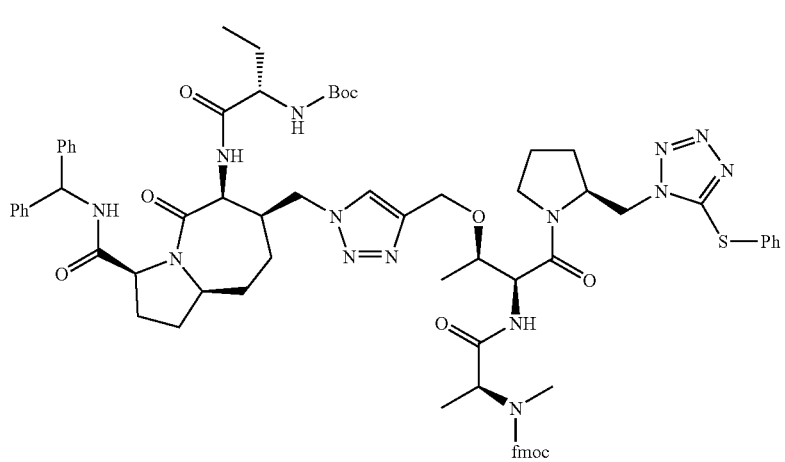

41a. Eluant mixture: CH$_2$Cl$_2$/MeOH 95:5. Yield 57% (76 mg, MW 1324.62, 0.057 mmol) of pure 41a. Analytical characterization: [α]$_D^{20}$-55.6 (c 0.54, MeOH); $^1$H-NMR (400 MHz, CDCl$_3$): δ: 7.83 (d, J=7.2 Hz, 1H), 7.76 (d. J=7.2 Hz, 2H), 7.57 (m, 5H), 7.49 (bd, 1H), 7.45-7.13 (m, 18H), 7.09 (bd, 1H), 6.17 (d, J=8.2 Hz, 1H), 5.23 (bd, J=7.2 Hz, 1H), 4.9-4.6 (m, 7H), 4.6-4.35 (m, 7H), 4.28 (t, J=7.5 Hz, 1H), 4.23-3.90 (m, 3H), 3.90-3.50 (m, 4H), 2.38 (m, 1H), 2.21 (m, 1H), 2.02 (m, 1H), 1.94-1.45 (m, 13H), 1.43-1.32 (m, 14H), 1.30-1.05 (m, 6H), 0.93 (t, 3H); $^{13}$C-NMR (100 MHz, CDCl$_3$): δ: 173.0, 171.2, 170.7, 169.4, 169.3, 155.3, 153.3, 143.9, 141.8, 141.3, 133.0, 129.8, 129.7, 128.8, 127.7, 127.5, 127.4, 127.3, 127.2, 127.1, 125.0, 120.0, 80.1, 74.6, 68.0, 62.6, 61.2, 58.7, 56.8, 56.4, 56.3, 54.6, 53.7, 51.8, 48.4, 47.7, 47.2, 40.4, 33.5, 33.2, 31.1, 30.1, 28.5, 27.2, 26.0, 25.6, 24.0, 16.3, 14.0, 10.2.

2.2 General Procedure for the Synthesis of Homodimeric Compounds 42 (Scheme 18)

Scheme 18

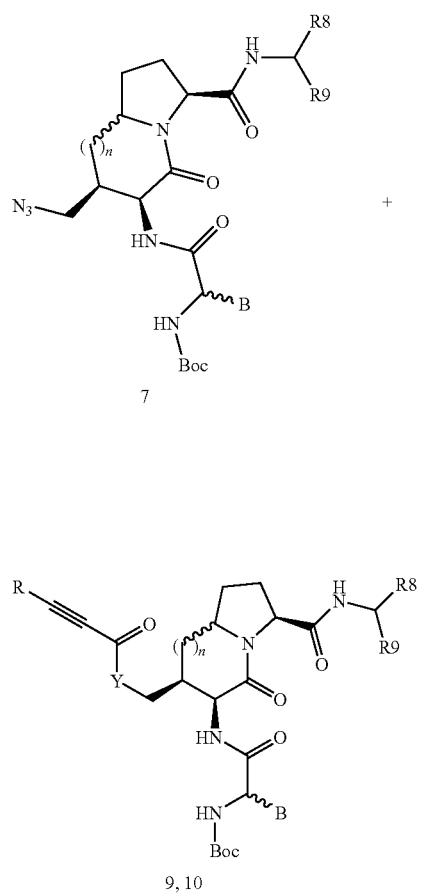

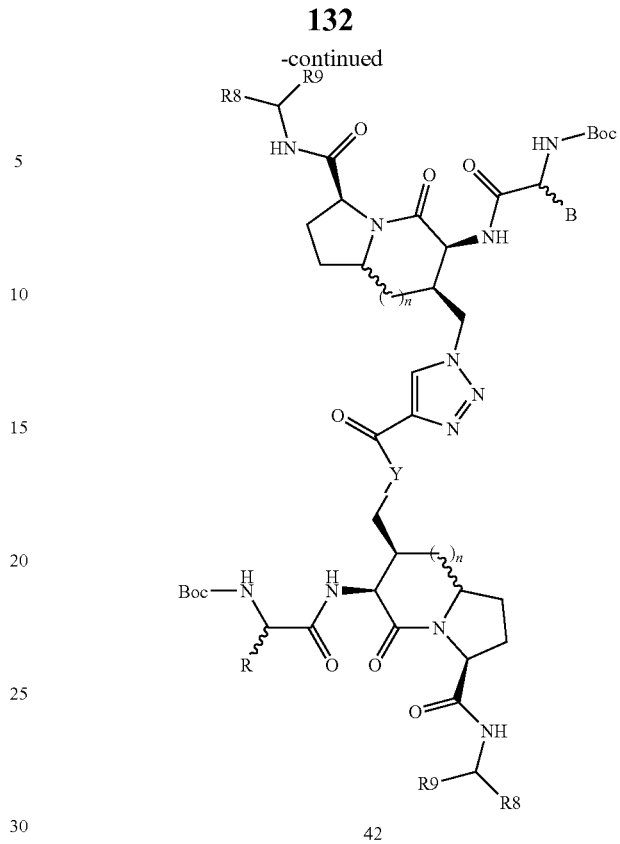

A 0.9 M water solution of sodium ascorbate (45 μl, 0.4 mmol) and a 0.3 M water solution of Cu(OAc)$_2$ (65 μl, 0.02 mmol) were sequentially added to a stirred solution of compounds 7 (0.10 mmol) and the compounds 9 (Y=O) or 10 (Y=NH) (0.10 mmol) in a 1:1 mixture of H$_2$O/$^t$BuOH (300 μl). The reaction mixtures were stirred overnight at room temperature and then the solvent was removed under reduced pressure. Finally, the residues were purified by Biotage™ flash chromatography or by chromatography on a C$_{18}$ reverse phase semi-preparative HPLC column.

Compounds 42a and 42b were synthesized by the general procedure described above.

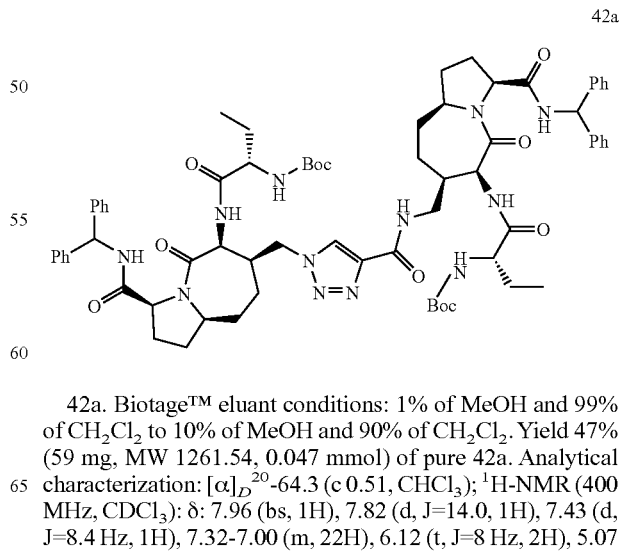

42a. Biotage™ eluant conditions: 1% of MeOH and 99% of CH$_2$Cl$_2$ to 10% of MeOH and 90% of CH$_2$Cl$_2$. Yield 47% (59 mg, MW 1261.54, 0.047 mmol) of pure 42a. Analytical characterization: [α]$_D^{20}$-64.3 (c 0.51, CHCl$_3$); $^1$H-NMR (400 MHz, CDCl$_3$): δ: 7.96 (bs, 1H), 7.82 (d, J=14.0, 1H), 7.43 (d, J=8.4 Hz, 1H), 7.32-7.00 (m, 22H), 6.12 (t, J=8 Hz, 2H), 5.07

(d, J=5.6 Hz, 1H), 4.91 (d, J=11.2 Hz, 1H), 4.64 (t, J=6.4 Hz, 2H), 4.55 (m, 3H), 4.14 (t, J=11.6 Hz, 1H), 3.98 (m, 2H), 3.73 (m, 3H), 3.14 (d, J=12.0 Hz, 1H), 2.34 (m, 2H), 2.16 (m, 2H), 2.0-1.40 (m, 22H), 1.31 (s, 18H), 1.19 (s, 2H), 1.20-0.95 (m, 6H), 0.90 (m, 6H); $^{13}$C-NMR (100 MHz, CDCl$_3$): δ: 173.1, 171.7, 170.6, 169.4, 169.2, 160.4, 142.1, 141.8, 141.0, 128.8, 128.7, 127.7, 127.5, 127.4, 127.2, 127.1, 61.3, 61.1, 58.8, 58.7, 56.8, 56.7, 54.0, 53.7, 40.7, 40.6, 40.2, 34.4, 33.8, 33.3, 33.2, 31.4, 25.7, 25.5, 25.4, 10.3, 10.2.

7.45-7.15 (m, 24H), 6.21 (m, 2H), 5.02 (m, 2H), 4.72 (d, J=7.2 Hz, 2H), 4.66 (t, J=8.4 Hz, 1H), 4.51 (m, 2H), 4.04 (m, 3H), 3.80 (m, 2H), 3.54 (m, 1H), 3.06 (m, 3H), 2.65 (t, J=7.6 Hz, 2H), 2.44 (m, 2H), 2.25 (m, 2H), 2.05-1.50 (m, 17H), 1.44 (s, 9H), 1.42 (s, 9H), 1.10 (m, 2H), 0.98 (t, J=7.6 Hz, 6H); $^{13}$C-NMR (100 MHz, CDCl$_3$): δ: 172.9, 172.1, 171.7, 170.8, 169.4, 169.2, 142.0, 141.8, 141.3, 128.7, 128.6, 127.6, 127.5, 127.4, 127.3, 127.2, 127.1, 61.2, 61.1, 58.8, 56.9, 56.8, 54.1, 53.7, 51.6, 40.5, 40.0, 35.8, 34.5, 33.8, 33.3, 33.2, 31.8, 31.3, 28.3, 25.8, 25.6, 25.3, 21.7, 10.2.

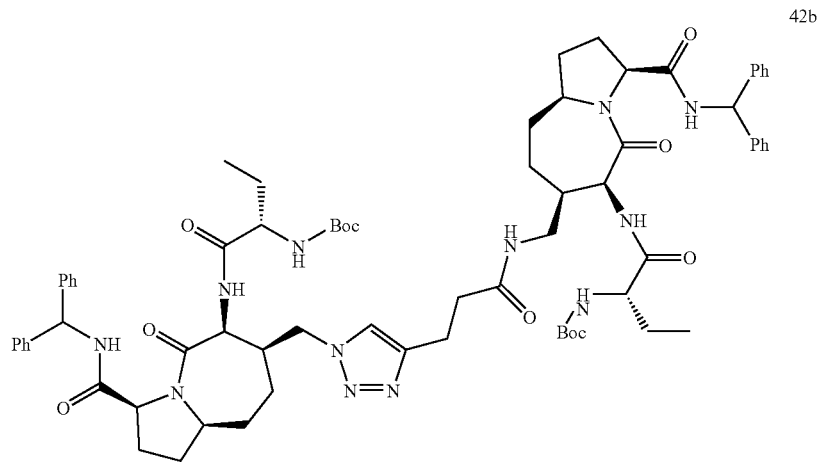 [SMILES: CC[C@H](NC(=O)OC(C)(C)C)C(=O)N[C@@H]1C(=O)N2[C@@H](CC[C@@H]1CNC(=O)CCc1cn(C[C@H]3CC[C@H]4CC[C@@H](C(=O)NC(c5ccccc5)c5ccccc5)N4C(=O)[C@H]3NC(=O)[C@H](CC)NC(=O)OC(C)(C)C)nn1)CC[C@H]2C(=O)NC(c1ccccc1)c1ccccc1]

42b. Biotage™ eluant conditions: 1% of MeOH and 99% of CH$_2$Cl$_2$ to 10% of MeOH and 90% of CH$_2$Cl$_2$. Yield 54% (70 mg, MW 1288.70, 0.054 mmol) of pure 42b. Analytical characterization: [α]$_D^{20}$ -66.2 (c 1.06, CHCl$_3$); $^1$H-NMR (400 MHz, CDCl$_3$): δ: 7.95 (d, J=8.4 Hz, 1H), 7.82 (d, J=8.4 Hz, 1H),

2.3 General Procedure for the Synthesis of Homodimeric Compounds 43 (Scheme 19)

Scheme 19

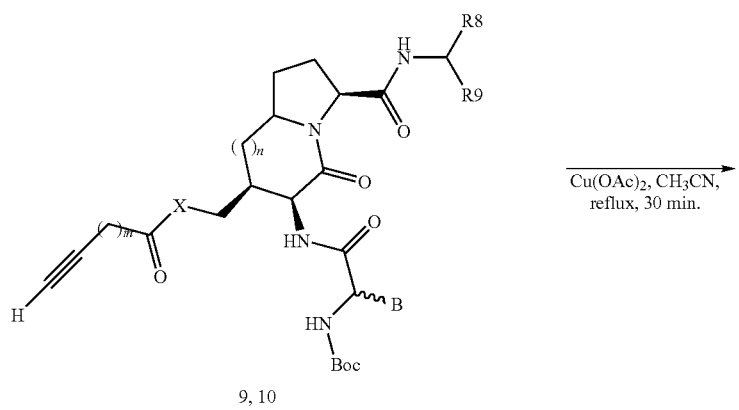

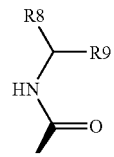

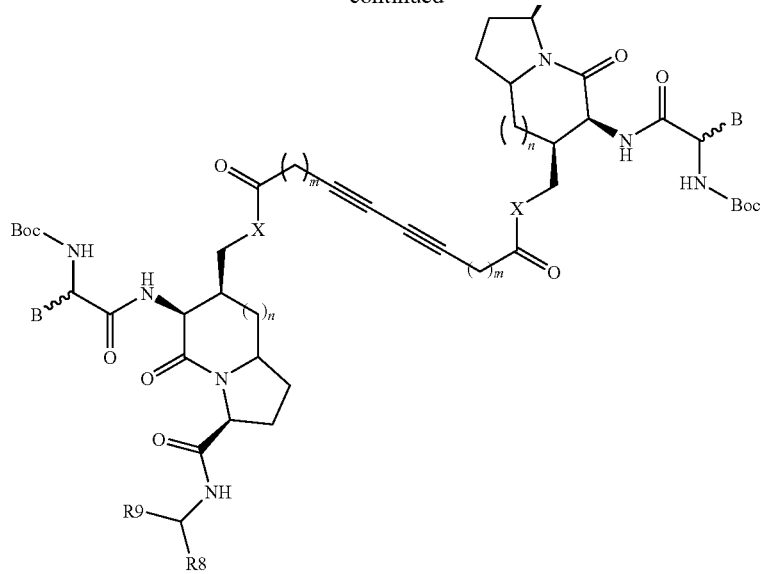

43

Stirred solution of compounds 9 (X=O) or 10 (X=NH) (0.10 mmol) and Cu(OAc)$_2$ (0.70 mmol) were refluxed for 30 min. After reaction completion, the solvent was removed under reduced pressure, the residues were dissolved in CH$_2$Cl$_2$ and Cu(II) salts were removed by filtering over a short pad of silica gel eluting with CH$_2$Cl$_2$/MeOH (90:10). Finally, the crude products were purified either by Biotage™ flash chromatography or by chromatography on a C18 reverse phase semi-preparative HPLC column.

Compound 43a was synthesized by the general procedure described above.

171.7, 170.8, 169.4, 141.2, 140.8, 128.6, 127.5, 127.4, 127.4, 127.2, 80.5, 66.0, 61.2, 58.9, 57.0, 56.8, 54.0, 41.3, 40.0, 35.3, 34.5, 33.2, 28.3, 25.7, 25.2, 15.9, 10.3.

2.4 General Procedure for the Fmoc-Deprotection of Compounds 41

Compounds 41 (varying amounts between 0.006 and 0.045 mmol) were treated with a 20% solution of piperidine in CH$_2$Cl$_2$ (2 ml). The reaction mixtures were stirred for 30 min. at room temperature. and then concentrated in vacuo. Finally,

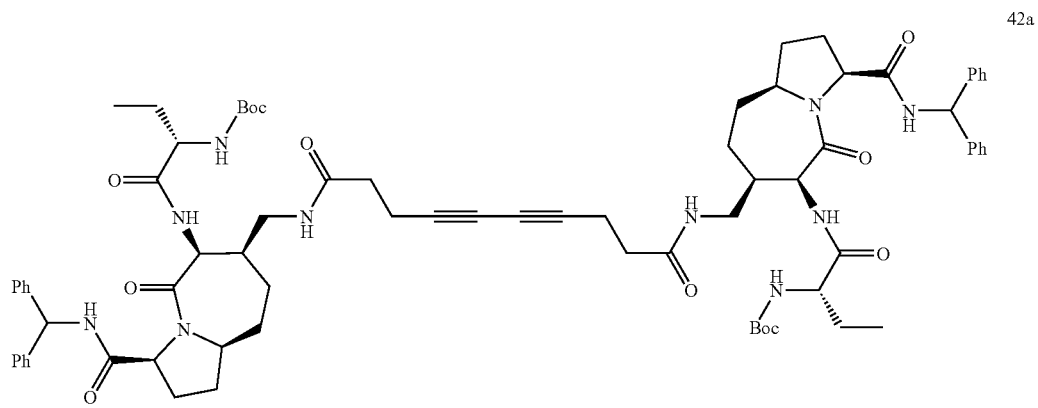 [SMILES: CC[C@H](NC(=O)OC(C)(C)C)C(=O)N[C@@H]1C(=O)N2[C@@H](CC[C@@H]1CNC(=O)CCC#CC#CCCC(=O)NC[C@H]1CC[C@H]3CC[C@@H](C(=O)NC(c4ccccc4)c4ccccc4)N3C(=O)[C@H]1NC(=O)[C@H](CC)NC(=O)OC(C)(C)C)CC[C@H]2C(=O)NC(c1ccccc1)c1ccccc1]

42a

43a. Biotage™ eluant conditions: 1% of MeOH and 99% of CH$_2$Cl$_2$ to 10% of MeOH and 90% of CH$_2$Cl$_2$. Yield 36% (48 mg, MW 1340.72, 0.036 mmol) of pure 43a. Analytical characterization: $[\alpha]_D^{20}$-69.3 (c 0.96, CHCl$_3$); $^1$H-NMR (400 MHz. CDCl$_3$): δ: 7.90 (d, J=6.8 Hz, 2H), 7.36-7.16 (m, 25H), 6.22 (d, J=8.0 Hz, 1H), 5.05 (bd, J=6.4 Hz, 2H), 4.72 (d, J=8.0 Hz, 2H), 4.49 (t, J=9.6 Hz, 2H), 3.98 (dd, J=13.6, 7.6 Hz, 2H), 3.81 (dd, J=17.6, 8.8, 2H), 3.58 (m, 2H), 3.01 (m, 1H), 2.58 (m, 4H), 2.40 (m, 6H), 2.25 (m, 2H), 1.95-1.80 (m, 8H), 1.75-1.55 (m, 10H), 1.45 (s, 18H), 1.30-1.10 (m, 4H), 1.00 (t, J=7.6 Hz, 6H); $^{13}$C-NMR (100 MHz, CDCl$_3$): δ: 173.6, the residues were purified by chromatography on a C$_{18}$ reverse phase semi-preparative HPLC column.

2.5 General Procedure for the Boc-Deprotection Reaction of Compounds de-Fmoc 41, 42 and 43

A 3N solution of HCl in MeOH (0.5 ml) was added to stirred solutions of compounds 42, 43 and of compounds resulting from Fmoc deprotection of compounds 41 as in 2.4 (varying amounts between 0.006 and 0.045 mmol) in MeOH (2 ml). The reaction mixtures were left stirring at room temperature overnight and then concentrated under reduced pressure. Finally, the residues were purified by chromatography on a $C_{18}$ reverse phase semi-preparative HPLC column, and then lyophilized.

Compounds 44a to 46a were synthesized by the general procedure described above.

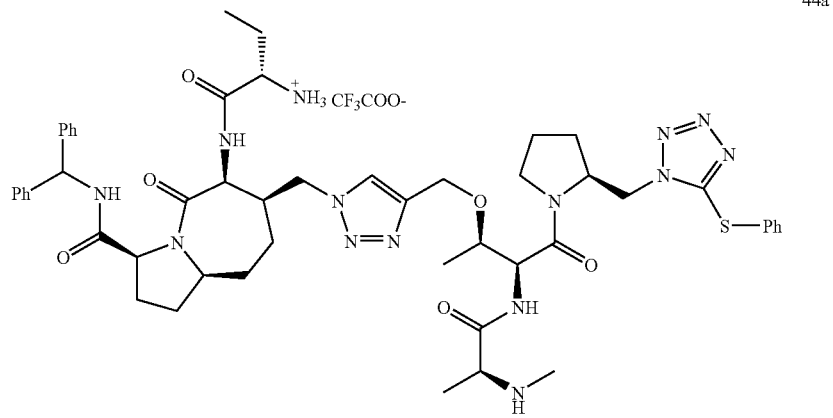

44a 44a, from 41a (0.045 mmol) HPLC eluant conditions: from 80% of $H_2O$ (0.1% TFA) and 20% of $CH_3CN$ to 50% of $H_2O$ (0.1% TFA) and 50% of $CH_3CN$, flow rate 20 ml/min., 10 min. runs. Yield 90% (45 mg, MW 1116.5, 0.040 mmol) of pure 44a. Analytical characterization: $[\alpha]_D^{20}$-29.0 (c 0.88, $H_2O$); $^1$H-NMR (400 MHz, $D_2O$): δ: 7.86 (s, 1H); 7.43-7.05 (m, 15H), 5.91 (s, 1H), 4.63-4.10 (m, 10H), 3.89 (m, 4H), 3.48 (m, 2H), 2.59 (s, 3H), 2.25-1.60 (m, 13H), 1.47 (d, J=7.2, 3H), 1.23 (d, J=6.4, 2H), 0.96 (m, 3H); $^{13}$C-NMR (100 MHz, $D_2O$): δ: 172.0, 169.7, 169.5, 154.7, 144.5, 141.2, 141.0, 134.0, 133.3, 130.2, 130.0, 128.7, 127.6, 127.3, 127.0, 126.6, 125.2, 74.0, 61.9, 61.5, 58.1, 57.4, 57.0, 56.5, 56.0, 54.3, 54.1, 51.8, 48.9, 47.6, 38.6, 32.3, 31.0, 30.3, 28.6, 27.7, 26.9, 24.4, 23.5, 16.0, 15.3, 8.4.

45a, from 42a (0.006 mmol). The crude product did not require HPLC purification. Yield 92% (6 mg, MW 1096.54, 0.0055 mmol) of pure 45a. Analytical characterization: $[\alpha]_D^{20}$-39.1 (c 0.23, $H_2O$); $^1$H-NMR (400 MHz, $D_2O$): δ: 8.78 (d, J=7.2 Hz, 1H), 8.73 (d, J=7.2 Hz, 1H), 8.35 (s, 1H), 7.32-7.18 (m, 20H), 5.97 (m, 1H), 4.61 (m, 2H), 4.58 (m, 2H), 4.48 (m, 1H), 4.35 (m, 1H), 3.9 (m, 4H), 3.50 (dd, J=13.6, 8.4 Hz, 1H), 3.28 (dd, J=12.8, 8.4 Hz, 1H), 2.25-2.35 (m, 24H), 0.95 (m, 6H); $^{13}$C-NMR (100 MHz, $D_2O$): δ: 172.7, 170.5, 169.8, 169.7, 161.9, 142.2, 141.0, 140.9, 129.0, 128.9, 127.8, 127.4, 127.1, 61.9, 58.6, 58.4, 57.6, 54.5, 54.4, 54.3, 52.3, 41.0, 38.6, 38.1, 32.4, 32.3, 30.6, 27.8, 24.4, 8.5, 8.4.

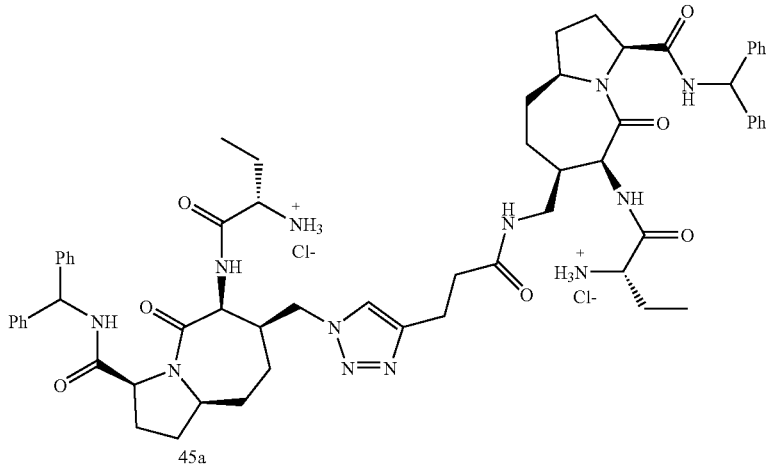

45a

45b

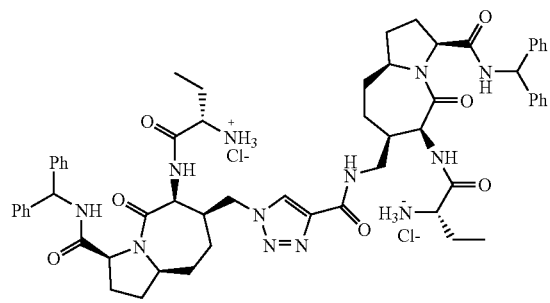

45b, from 42b (0.017 mmol). The crude product did not require HPLC purification. Quantitative yield (20 mg, MW 1160.27, 0.017 mmol) of pure 45b. Analytical characterization: $[\alpha]_D^{20}$-36.8 (c 0.98, $H_2O$); $^1$H-NMR (400 MHz, $D_2O$): δ: 7.61 (s, 1H), 7.40-7.15 (m, 20H), 6.00 (s, 1H), 5.96 (s, 1H), 4.65 (m, 1H), 4.48-4.40 (m, 4H), 3.97 (m, 2H), 3.86 (bs, 2H), 3.27 (m, 1H), 2.91 (m, 3H), 2.51 (m, 2H), 2.15-1.15 (m, 24H), 0.94 (m, 6H); $^{13}$C-NMR (100 MHz, $D_2O$): δ: 174.9, 172.4, 172.3, 170.0, 169.8, 169.6, 169.5, 146.5, 141.2, 141.0, 129.0, 128.9, 128.7, 127.8, 127.4, 127.2, 127.1, 61.7, 61.6, 58.2, 57.4, 54.4, 54.3, 54.2, 51.7, 40.7, 38.2, 37.6, 35.1, 32.5, 32.3, 30.0, 27.9, 27.8, 24.4, 210, 8.5.

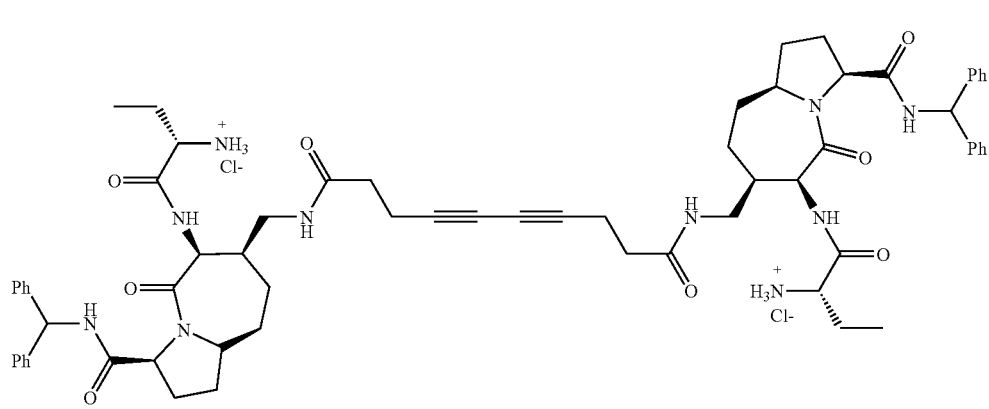

46a 46a, from 43a (0.014 mmol). The crude product did not require HPLC purification. Quantitative yield (17 mg, MW 1212.58, 0.014 mmol) of pure 46a. Analytical characterization: $[\alpha]_D^{20}$-43.1 (c 0.90, $H_2O$); $^1$H-NMR (400 MHz, $D_2O$): δ: 7.35-7.20 (m, 20H), 5.95 (s, 2H), 4.56 (d, J=10.4 Hz, 2H), 4.50 (dd, J=7.6, 4.8 Hz, 2H), 3.98 (m, 4H), 3.23 (dd, J=13.6, 3.2 Hz, 2H), 3.06 (m, 2H), 2.45-2.30 (m, 4H), 2.25-1.40 (m, 26H), 0.97 (t, J=7.2 Hz, 6H); $^{13}$C-NMR (100 MHz, $D_2O$): δ: 174.3, 172.4, 170.4, 169.6, 141.1, 140.9, 129.0, 128.9, 127.9, 127.8, 127.4, 127.0, 65.8, 61.7, 58.4, 57.7, 54.5, 54.4, 40.7, 37.6, 34.3, 32.6, 30.7, 27.8, 24.4, 15.5, 8.5.

Example 3

Fluorescence Polarization Assay 3.1 Cloning, Expression and Purification of Human MAP BIR3

A pET28 vector (Novagen) with the cDNA coding for human XIAP BIR3 domain from residue 241 to 356 was used to transform *Escherichia coli* strain BL21. Protein expression was induced by adding isopropyl-β-D-thiogalactopyranoside (IPTG) to a final concentration of 1 mM and 100 μM zinc acetate (ZnAc) for 3 hours at 37° C. Bacteria grown in LB medium plus kanamycin were harvested, resuspended in a buffer containing 50 mM Tris HCl pH 7.5, 200 mM NaCl, 50 μM ZnAc and protease inhibitors, treated with 100 μg/ml lysozyme for 30 minutes in ice and then lysed by sonication. After elimination of debris by centrifugation, recombinant protein was purified using Ni-NTA (His-trap Ffcrude, Ge-Healthcare) followed by gel filtration (Superdex 200, Ge-Healthcare). BIR3-His-tag was eluted with 250 mM imidazole and thereafter stored in 20 mM Tris pH 7.5, 200 mM NaCl, 50 μM ZnAc, and 10 mM Dithiothreitol.

3.2 Saturation Binding Experiment

Fluorescent polarization experiments were performed in black, flat-bottom 96-well microplates (PBI) and fluorescent polarization was measured by Ultra plate reader (Tecan). Fluorescent-labelled Smac peptide [AbuRPF-K(5-Fam)-$NH_2$] (FITC-SMAC) to a final concentration of 5 nM and increasing concentration of BIR3-His-tag from 0 to 20 μM were added to an assay buffer. The final volume in each well was 125 μl, with the assay buffer consisting of 100 mM potassium phosphate, pH 7.5; 100 μg/ml bovine γ-globulin; 0.02% sodium azide. After a 15 min shaking, the plate was incubated for 3 hours at room temperature. Fluorescence polarization was measured at an excitation and emission wavelengths of 485 nm and 530 nm respectively. The equilibrium binding graphs were constructed by plotting millipolarization units (mP) as function of the XIAP BIR3 concentration. Data were analyzed using Prism 4.0 software (Graphpad Software).

3.3 Competitive Binding Experiments

SMAC-mimic compounds were evaluated for their ability to displace FITC-SMAC probe from recombinant protein. 5 mM of FITC-SMAC, XIAP BIR3-His-tag and serial dilutions of the SMAC-mimic compounds (concentrations ranging from 4 μM to 0.4 nM) were added to each well to a final volume of 125 μl in the assay buffer described above. The concentration of BIR3-His-tag used was 60 nM, able to bind more than 50% of the ligand in the saturation binding experiment. After being mixed for 15 minutes on a shaker and incubated 3 hours at room temperature, fluorescent polarization was measured by Ultra plate reader (Tecan). All SMAC-mimics and the fluorescent peptide were stocked in DMSO.

3.4 Binding Affinities for BIR3Domain of Map of Homo- and Heterodimeric Smac Mimetics with [4.3.0] and [5.3.0] Bicyclic Lactam Systems The IC50s of some examples are reported in the Table below, as an average value from three independent measurements, together with their standard deviation.

| Compound No. | IC50(av) [nM] | RSD % |
| --- | --- | --- |
| 24a | 275 | 7.1% |
| 24c | 997 | 14.3% |
| 25a | 406 | 8.1% |
| 24g | 211 | 7.0% |
| 26a | 967 | 5.4% |
| 26c | 508 | 12.2% |
| 29a | 445 | 14.7% |
| 29b | 296 | 15.9% |
| 29c | 428 | 11.5% |
| 30a | 334 | 18.4% |
| 30b | 259 | 12.5% |
| 31a | 611 | 26.1% |
| 31b | 356 | 11.5% |
| 32a | 511 | 7.9% |
| 32b | 297 | 11.8% |
| 32c | 237 | 8.8% |

| Compound No. | IC50(av) [nM] | RSD % |
|---|---|---|
| 32d | 330 | 3.4% |
| 33a | 380 | 5.8% |
| 33b | 345 | 0.8% |
| 34a | 221 | 13.6% |
| 35a | 4428 | 54.5% |
| 35b | 242 | 10.4% |
| 36a | 318 | 4.3% |
| 36b | 646 | 3.8% |
| 36c | 440 | 12.0% |
| 37a | 370 | 4.0% |
| 38a | 324 | 6.1% |
| 38c | 352 | 8.9% |
| 38d | 143 | 6.9% |
| 39a | 248 | 2.1% |
| 44a | 245 | 15.0% |
| 45a | 352 | 10.9% |
| 45b | 308 | 19.7% |
| 46a | 372 | 8.0% |

The values of the tested compounds clearly show high potency (nanomolar) on the relevant in vitro assay, with an indication of structure-activity relationships among congeners.

3.5 Cloning, Expression and Purification of Human Map Linker-BIR2-BIR3

A pET28 vector (Novagen) with the cDNA coding for human XIAP from residue 124 to 356 (linker-BIR2-BIR3), coding for BIR2 and BIR3 domains and the linker region preceding BIR2, was used to transform *Escherichia coli* strain BL21. Protein expression was induced by adding isopropyl-β-D-thiogalactopyranoside (IPTG) to a final concentration of 1 mM and 100 µM zinc acetate (ZnAc) for 3 hours at 37° C. Bacteria grown in LB medium plus kanamycin were harvested, resuspended in a buffer containing 50 mM Tris HCl pH 7.5, 200 mM NaCl, 50 µl\/1 ZnAc and protease inhibitors, treated with 100 µg/ml lysozyme for 30 minutes in ice and then lysed by sonication. After elimination of debris by centrifugation, recombinant protein was purified using Ni-NTA (His-trap Ffcrude, Ge-Healthcare) followed by gel filtration (Superdex 200, Ge-Healthcare). The linker-BIR2-BIR3-His-tag was eluted with 250 mM imidazole and thereafter stored in 20 mM Tris pH 7.5, 200 mM NaCl, 50 µM ZnAc, and 10 mM Dithiothreitol.

3.6 Saturation Binding Experiment—Human Map Linker-BIR2-BIR3

Fluorescent polarization experiments were performed in black, flat-bottom 96-well microplates (PBI) and fluorescent polarization was measured by Ultra plate reader (Tecan). Fluorescent-labelled dimeric Smac peptide SMAC-1F (Nikolovska-Coleska et al., Analyt. Biochem. 374:87, 2008) to a final concentration of 1 nM and increasing concentration of linker-BIR2-BIR3-His-tag from 0 to 2 µM were added to an assay buffer. The final volume in each well was 125 µl, with the assay buffer consisting of 100 mM potassium phosphate, pH 7.5; 100 µg/ml bovine γ-globulin; 0.02% sodium azide. After a 15 minutes shaking, the plate was incubated for 3 hours at room temperature. Fluorescence polarization was measured at an excitation and emission wavelengths of 485 nm and 530 nm respectively. The equilibrium binding graphs were constructed by plotting millipolarization units (mP) as function of the XIAP linker-BIR2-BIR3 concentration. Data were analyzed using Prism 4.0 software (Graphpad Software).

3.7 Competitive Binding Experiments—Human Map Linker-BIR2-BIR3

SMAC-mimic compounds were evaluated for their ability to displace SMAC-1F probe from recombinant protein. 1 nM of SMAC-1F, 3 nM of XIAP linker-BIR2-BIR3-His-tag and serial dilutions of the SMAC-mimic compounds (concentrations ranging from 2 µM to 0.4 nM) were added to each well to a final volume of 125 µl in the assay buffer described above. After being mixed for 15 minutes on a shaker and incubated 3 hours at room temperature, fluorescent polarization was measured by Ultra plate reader (Tecan). All SMAC-mimics and the fluorescent peptide were stocked in DMSO.

3.8 Binding Affinities for the Linker-BIR2-BIR3Domains of Map of Homo- and Heterodimeric Smac Mimetics with [4.3.0] and [5.3.0] Bicyclic Lactam Systems The IC50s of some examples are reported in the Table below, as an average value from three independent measurements, together with their standard deviation.

| Compound No. | IC50(av) [nM] | RSD % |
|---|---|---|
| 46a | 3.9 | 18.0 |
| 45b | 7.1 | 15.9 |
| 44a | 5.4 | 19.8 |
| 45a | 12.6 | 17.7 |
| 30a | 321 | 58.9 |
| 32d | 54 | 18.2 |
| 32c | 83 | 15.6 |
| 35b | 72 | 20.2 |
| 33b | 54 | 21.2 |
| 38d | 85 | 21.7 |
| 38a | 85 | 30.7 |
| 32b | 97 | 21.6 |
| 35a | 92 | 15.7 |
| 36c | 114 | 25.4 |
| 26a | 111 | 21.4 |
| 29c | 109 | 30.0 |
| 30b | 147 | 27.3 |
| 29b | 187 | 26.9 |
| 39a | 221 | 22.9 |
| 24g | 204 | 20.9 |
| 29a | 149 | 25.3 |
| 36a | 154 | 22.5 |
| 36b | 109 | 21.4 |
| 31b | 162 | 30.6 |
| 33a | 236 | 24.1 |
| 32a | 192 | 29.7 |
| 31a | 238 | 28.9 |
| 34a | 389 | 30.3 |
| 25a | 238 | 24.9 |
| 24a | 288 | 30.8 |
| 38c | 389 | 40.3 |
| 37a | 239 | 25.6 |
| 26c | 869 | 48.8 |
| 24c | 2124 | 59.9 |

The values of the tested compounds clearly show high potency (nanomolar) on the relevant in vitro assay, with an indication of structure-activity relationships among congeners.

Example 4

Cellular Cytotoxicity Assays—Tumor Cell Lines 4.1 Cells and Treatments

The human promyelocytic and chronic myeloid leukemia cell lines HL60 and K562, respectively, were obtained from Interlab Cell Line Collection (ICLC, Genova, Italy). The multiple myeloma (MM) cell line KMS26 was kindly provided by Dr. T. Otsuki, Kawasaki Medical School, Okayama, Japan, while the ARH77 cell line was obtained from American Type Culture Collection (ATCC), Rockville, Md., US. The myeloid cell lines (K562 and HL60) were cultured in RPMI 1640 medium, while the multiple myeloma cell lines (KMS26 and ARH77) were cultured in Icove's Modified Dulbecco's medium (IMDM), both supplemented with 10% fetal bovine serum (FBS) at 37° C. and 5% $CO_2$ in fully humidified atmosphere. Cells were cultured at densities ranging between 1 and $2 \times 10^5$ cells per ml. CD34 cells were selected from cytokine stimulated peripheral blood (PBSC) of normal donors after informed consent.

4.2 Single and Combined Cytotoxicity Assays

The effect of SMAC-mimic compounds on cell growth was evaluated by means of colorimetric assay for the quantification of cell proliferation and viability based on the cleavage of the WST-1 tetrazolium salt by mitochondrial dehydrogenases in viable cells. Briefly, after 24, 48 and 72 hours-treatment with Smac-mimic compounds, 10 μl of WST-1 were added to each of the 96 well culture plates containing 100 μl of cell suspension. After 4 hours incubation at 37° C., plates were evaluated by means of 1420 VICTOR multilabel counter (EG&G Wallac, Finland) and data expressed as mean percentage of 3 replicates normalized to the untreated control.

4.3 Cytotoxicity of Smac Mimetics—Standalone

HL60 and K562 human cell lines were cultured in RPMI 1640 culture medium supplemented with 10% FBS while the ARH77 and KMS26 cell lines were cultured in IMDM culture medium supplemented with 10% FBS. All the cell lines were grown at density of $1 \times 10^5$ cells per ml and seeded (100 μl of cell suspension/well) on 96-well microtiter plates with or without escalating doses of SMAC-mimic compounds. Cells were incubated at 37° C. in a 5% $CO_2$ fully humidified atmosphere and examined at 24, 48 and 72 hours for cytotoxicity with the WST-1 colorimetric assay. Briefly, 10 μl of WST-1 were added to each of the 96-well culture plates containing 100 μl of cell suspension/well. After 4 h incubation at 37° C., plates were evaluated by means of 1420 VICTOR multilabel counter (EG&G Wallac, Finland). Data are expressed as mean percentage of three replicates normalized to the untreated control. An $IC_{50}$ value was calculated as the concentration of compound inhibiting growth by 50%, relative to control cultures.

| HL60 | IC50 (nM) | | |
|---|---|---|---|
| | 24 hrs | 48 hrs | 72 hrs |
| 24a | >10.000 | 781.7 | 98.1 |
| 30a | >10.000 | 1790 | 623.1 |
| 23a | >10.000 | >10.000 | >10.000 |
| 26a | 54.8 | 14.7 | 8.2 |
| 25a | >10.000 | 3321 | 1.8 |
| 44a | 2.3 | 1.6 | 0.6 |
| 22a | 2172 | 2500 | 2025 |

In the HL60 cells, the most potent compound was SMAC012, exhibiting an $IC_{50}$ of 2.3 nM at already 24 hours, followed by SMAC010 ($IC_{50}$ 54.8 at 24 hours).

| K562 | IC50 (nM) | | |
|---|---|---|---|
| | 24 hrs | 48 hrs | 72 hrs |
| 24a | >10.000 | >10.000 | >10.000 |
| 30a | >10.000 | >10.000 | >10.000 |
| 23a | 4100 | 1695 | 1265 |
| 26a | 593 | 0.06 | 0.08 |
| 25a | 4776 | 3948 | 2127 |
| 44a | 22 | 5.3 | 0.02 |
| 22a | 99.8 | 101 | 209 |

As for K562, the most cytotoxic compound was SMAC013, showing an $IC_{50}$ of 4.6 nM at 24 hrs, followed by SMAC012 ($IC_{50}$ 22 nM at 24 hrs).

Cytotoxicity on multiple myeloma cell lines was measured only for the most potent Smac mimic compounds.

| ARH77 | IC50 (nM) | | |
|---|---|---|---|
| | 24 hrs | 48 hrs | 72 hrs |
| 24a | >10.000 | >10.000 | >10.000 |
| 26a | >10.000 | >10.000 | >10.000 |
| 44a | >10.000 | >10.000 | >10.000 |

The ARH77 cell line was resistant to all the tested compounds.

| KMS26 | IC50 (nM) | | |
|---|---|---|---|
| | 24 hrs | 48 hrs | 72 hrs |
| 24a | >10.000 | 0.03 | 16.7 |
| 26a | >10.000 | 0.002 | 62.3 |
| 44a | 346 | 0.03 | 59.4 |

Interesting activities were observed on KMS26. The most cytotoxic compound was SMAC010, showing an $IC_{50}$ of 0.002 nM at 48 hours, followed by SMAC012 ($IC_{50}$ 346 nM at 24 hours and 0.03 nM at 48 hours).

4.4 Cytotoxicity of Smac Mimetics—Combination Treatments with Cytotoxic Agents The cytotoxicity of Smac mimic compounds was also tested on the same cell lines in combination with the chemotherapeutic cytotoxic agents taxol (Sigma, St. Louis, Mo. U.S.A.) and cisplatinum (Bristol-Myers Squibb, New York, N.Y., U.S.A.). Escalating doses of each drug was added simultaneously to the cell cultures and the effects were evaluated after 24, 48 and 72 hours-treatment by means of the WST-1 colorimetric assay. The effect of the combination of Smac-mimic compounds (A) with other drugs (B) was evaluated according to the method of Kerni et al. (Kern D H, Morgan C R, Hildebrand-Zanki S U, *In vitro pharmacodynamics of 1-beta-arabinofuranosylcytosine: synergy of antitumor activity with cis-diamminechloroplatinum. Cancer Res* 1988; 48: 117-21). An R index of 1 (additive effect) or lower indicated the absence of synergism. Synergism was defined as any value of R greater than 1 (Romanelli S. Perego P, Pratesi G, Carenini N, Tortoreto M. Zuino F. *In vitro and in vivo interactions between cisplatin and topotecan in ovarian carcinoma systems. Cancer Chemother Pharmacol* 1988; 41: 385-90).

Herein after the combination of drugs which showed synergistic effect are summarized:

| HL60 72 hrs | | | |
|---|---|---|---|
| 24a | 10 nM | Cisplatinum 100 ng/ml | 24a + Cisplatinum |
| | 110 | 84 | 43 |

| K562 72 hrs | | | |
|---|---|---|---|
| 24a | 50 nM | Cisplatinum 10 ng/ml | 24a + Cisplatinum |
| | 90 | 99 | 48 |

| K562 72 hrs | | | |
|---|---|---|---|
| 44a | 0.1 nM | Cisplatinum 100 ng/ml | 44a + Cisplatinum |
| | 89 | 79 | 30 |

| K562 72 hrs | | | |
|---|---|---|---|
| 44a | 0.1 nM | Taxol 100 nM | 44a + Taxol |
| | 89 | 69 | 27 |

4.5 Cells and Treatments—MDA-MB-231 Cells

MDA-MB-231 (adherent breast epithelial adenocarcinoma cells) were purchased from Istituto Zooprofilattico di Brescia (www.bs.izs.it). Reagents for cell culture were purchased from Sigma unless otherwise indicated below. Cells were grown on Plastic Petri dishes (Falcon) in RPMI 1640 medium supplemented with 2 mM L-glutamine, Penicillin (100 U/ml)/Streptomicin (100 µg/ml), 10% Fetal Bovine Serum. A subcultivation ratio of 1:4 was used. Cells were maintained at 37° C. in an atmosphere of 95% air and 5% $CO_2$.

4.6 Standalone Cytotoxicity Assays—MDA-MB-231 Cells

The cellular growth inhibitory effect of our compounds was evaluated using the MTT assay (Sigma). After 96 hours of treatment, 10 µl of MTT reagent solution (5 mg of MTT powder/ml diluted in Phosphate Buffer Salt saline solution) were added in each well and allowed to react for 3 hours in the incubator. After 3 hours cells were solubilized in Lysis Buffer (10% SDS/0.1% HCl in water, 100 µl for each well) for 24 hours at 37° C. Finally, the absorbance was measured at 570 nm using a multiplate reader. Absorbance values were collected and $IC_{50}/IC_{80}$ values were determined using GraphPad Prism 5 software. The experiments were repeated twice.

4.6 Cytotoxicity of Smac Mimetics—Standalone—MDA-MB-231 Cells

MDA-MB-231 cells were seeded in 96-well flat bottom cell culture plates at a density of 5000 cells/well in 100 µl of culture medium and allowed to adhere for 24 hours in the incubator. After 24 hours MDA-MB-231 cells were exposed to the compounds at various concentrations for 96 hours in the incubator (50 nM, 100 nM, 200 nM, 500 nM, 1 µM, 5 µM, 10 µM, 50 µM and 100 µM). Each point was done in triplicate.

After 96 hours of treatment, 10 µl of MTT reagent solution (5 mg of MTT powder/ml diluted in Phosphate Buffer Salt saline solution) were added in each well and allowed to react for 3 hours in the incubator. After 3 hours cells were solubilized in Lysis Buffer (10% SDS/0.1% HCl in water, 100 µl for each well) for 24 hours at 37° C. Finally, the absorbance was measured at 570 nm using a multiplate reader. Absorbance values were collected and $IC_{50}/IC_{80}$ values were determined using GraphPad Prism 5 software. The experiments were repeated twice.

MDA-MB-231 Cells

| Compound | $IC_{50}$ (µM ± standard Deviation) | $IC_{80}$ (µM ± standard Deviation) |
|---|---|---|
| 24a | 1.026 ± 0.68 | 3.9 ± 0.07 |
| 44a | 0.168 ± 0.002 | 0.288 ± 0.003 |
| 38a | 12.9 ± 0.3 | 33.9 ± 0.7 |
| 46a | 0.116 ± 0.002 | 0.170 ± 0.002 |
| 24g | 0.237 ± 0.003 | 0.870 ± 0.004 |
| 38d | 2.3 ± 1.2 | 14.8 ± 1.0 |

Example 5

Cellular Cytotoxicity Assays—Human Stem Cells

5.1 Immuno-Magnetic Separation of $CD34^+$ Cells and Clonogenic Assays

Low density mononuclear cells (LD-MNC) were separated from PBSC by Ficoll-Paque gradient (Nycomed Pharma AS, Oslo, Norway) centrifugation. The recovered cells were then washed twice in Hanks' balanced salt solution (HBSS) and resuspended in IMDM 10% FBS. To isolate the $CD34^+$ cells, the LD-MNC were incubated for 15 minutes at 4° C. with an anti-CD34 monoclonal antibody, then washed and incubated for 15 minutes at 4° C. with anti-mouse immuno-magnetic beads (Miltenyi Biotec, Bergisch Gladbach, Germany). For the flow cytometry analysis, CD34-phycoerythrin conjugated antibody (HPCA-2, Becton Dickinson) was added to the cells for 15 minutes at 4° C. Viability and purity of separated cells were assessed by trypan blue dye exclusion and flow cytometry analysis respectively. For CFU-GM clonogenic assays, $5 \times 10^3$/ml $CD34^+$ cells were plated in a methylcellulose culture medium (MethoCult 4434, StemCell Technologies Inc., Vancouver, Canada) containing 0.9% methylcellulose in Iscove's MDM, 30% fetal bovine serum, 1% bovine serum albumin, 0.1 mM 2-Mercaptoethanol, 2 mM L-glutamine, 50 ng/ml rhSCF, 10 ng/ml rhGM-CSF, 10 ng/ml rhIL-3, 3 Units/ml rhEPO with different doses of Smac-mimic compounds. Triplicate dishes were incubated at 37° C. in a 5% $CO_2$ fully humidified atmosphere for 14 days. The aggregates of ≥40 and <40 cells were respectively scored as colonies and clusters.

5.2 Cytotoxicity of Smac Mimetics on CD34 Human Hemopoietic Stem Cells

CD34 stem cells were purified from human bone marrow aspirates by magnetic purification using MACS microbeads and subjected to standard CFU-GM clonogenic assays. Essentially, mononuclear cells were separated from bone marrow aspirates by Ficoll-Paque gradient centrifugation. The recovered cells were washed twice in Hanks' balanced salt solution, resuspended in IMDM 10% FBS, incubated for 15 min on ice with an anti-CD34 monoclonal antibody, washed and incubated for 15 min on ice with anti-mouse immuno-magnetic beads (Milteny Biotec, Germany). For CFU-GM clonogenic assays, $5 \times 10^3$/ml CD34+ cells were plated in a methylcellulose culture medium (MethoCult 4434. StemCell Technologies Inc., Canada) containing 0.9% methylcellulose in Iscove's MDM, 30% fetal bovine serum, 1% bovine serum albumin, $10^{-4}$M 2-Mercaptoethanol, 2 mM L-glutamine, 50 ng/ml rhSCF, 10 ng/ml rhGM-CSF, 10 ng/ml rhIL-3, 3 U/ml rhEPO without or with different doses of SMAC-mimics. Triplicate dishes were incubated at 37° C. in a 5% $CO_2$ fully humidified atmosphere for 14 days. The aggregates of >40 and <40 cells were scored as colonies and clusters, respectively.

The invention claimed is:

1. A compound of formula (I)

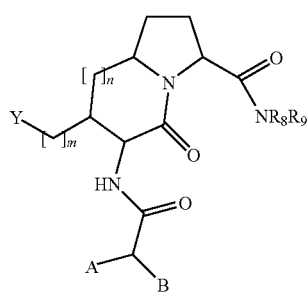

(I)

or a pharmaceutically acceptable salt or prodrug thereof, wherein:

n is 1 or 2 m is an integer from 0 to 3

A is $NR_1R_2$, or $N^+R_1R_2R_3$ $R_1$, $R_2$ and $R_3$ are, each independently,
  hydrogen;
  $C_{1-8}$ alkyl or heteroalkyl; $C_{2-8}$ alkenyl or heteroalkenyl; $C_{2-8}$ alkynyl or heteroalkynyl;
  optionally substituted aryl, alkylaryl, heteroaryl, alkylheteroaryl;
or
any two of $R_1$, $R_2$, and $R_3$ taken together with the nitrogen to which they are attached form a heterocyclic group, optionally substituted by one or more oxo, thioxo, and optionally comprising a heteroatom selected from O, S, and N, provided that the heteroatom is separated from the nitrogen atom by a least two carbon atoms;

$R_4$ and $R_5$ are each independently
  hydrogen;
  optionally substituted $C_{1-4}$ alkyl or heteroalkyl; $C_{2-5}$ alkenyl or heteroalkenyl; $C_{2-5}$ alkynyl or heteroalkynyl;
  optionally substituted aryl, alkylaryl, heteroaryl, or alkylheteroaryl;

B is
  $C_{1-4}$ alkyl; $C_{2-4}$ alkenyl; $C_{2-4}$ alkynyl;
  aryl, alkylaryl, heteroaryl or alkylheteroaryl;
  all optionally substituted by one or more halogen;

Y is selected among $OR_6$, $NHR_6$, $NR_6R_7$, $NH—S(O)_2—R_6$, $N^+(R_6)_3$, $SR_6$, $N_3$, $C(O)OR_6$, CN, $C(S)OR_6$, $C(S)NHR_6$, $C(NH)NHR_6$, $NH(CNH)NHR_6$, $NH(CS)NHR_6$, $NH(CO)NHR_6$ and

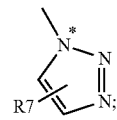

or

Y is a group of formula (II), (III) or (IV):

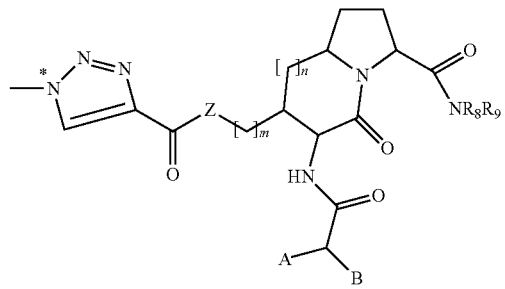

(II)

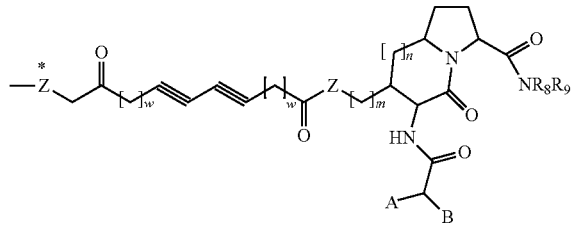

(III)

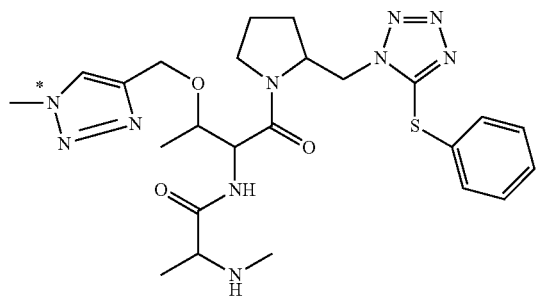

(IV)

wherein * indicates the atom is linked to the formula (I) moiety;

wherein A, B, n and m are, each independently, as previously defined; and each z is independently O, NH or S; each w is independently an integer from 1 to 4;

$R_6$ is
  hydrogen;
  optionally substituted $C_{1-8}$ alkyl; $C_{2-8}$ alkenyl; $C_{2-8}$ alkynyl;
  optionally substituted aryl; heteroaryl;

$R_7$ is
  optionally substituted $C_{1-8}$ alkyl; $C_{2-8}$ alkenyl; or $C_{2-8}$ alkynyl;

optionally substituted aryl or heteroaryl, $R_8$ and $R_9$ are each independently hydrogen;

optionally substituted $C_{1-18}$ alkyl; $C_{2-18}$ alkenyl; $C_{2-18}$ alkynyl;

optionally substituted aryl; heteroaryl.

2. A compound of formula (V)

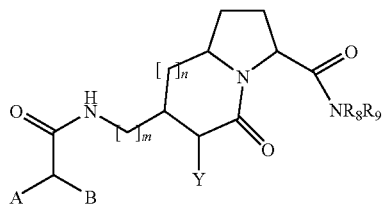

(V)

or a pharmaceutically acceptable salt or prodrug thereof, wherein the substituents are as defined in claim 1.

3. A compound according to claim 1 wherein the optionally substituted alkyl, alkenyl and alkynyl, aryl, alkylaryl, heteroaryl and alkylheteroaryl groups are substituted on the aliphatic chain by oxo or thioxo groups.

4. A compound according to claim 1 wherein the optionally substituted alkyl, alkenyl and alkynyl, aryl, alkylaryl, heteroaryl and alkylheteroaryl groups are substituted by alkyl, cycloalkyl, optionally substituted aryl, alkylaryl, heteroaryl, alkylheteroaryl, $OR_4$, $SR_4$, $NR_4R_5$ or $COOR_4$.

5. A compound according to claim 1, wherein A is $NH_2$, or —NH-Alkyl or —N(Alkyl)$_2$.

6. A compound according to claim 1, wherein B is an alkyl group or an optionally substituted alkylaryl group.

7. A compound according to claim 1, wherein n is 2.

8. A compound according to claim 1, wherein m is 1.

9. A compound according to claim 1, wherein m is 2.

10. A compound according to claim 1, wherein $NR_8R_9$ is a NH-alkyl group, said alkyl optionally substituted by one or more aryl group.

11. A compound of formula (I) according to claim 1, which is

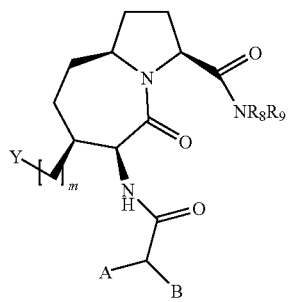

wherein the substituents are as defined in claim 1 and the wedge-shaped bonds indicate that the substituents are positioned above the plane.

12. A compound of formula (I) according to claim 1, which is

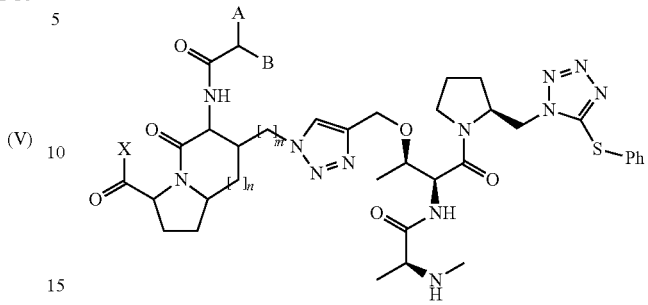

wherein X is $NR_8R_9$, the other substituents are as defined in claim 1 and the wedge-shaped bonds indicate that the substituents are positioned above the plane.

13. A compound of formula (I) according to claim 1, which is

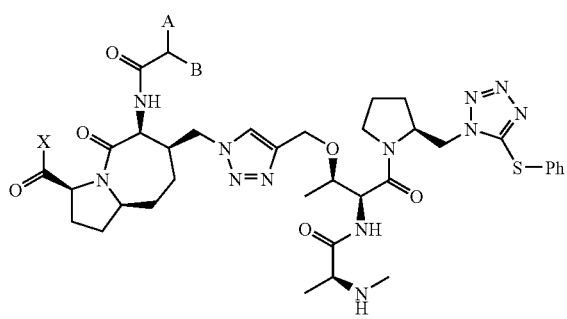

wherein X is $NR_8R_9$, the other substituents are as defined above and the wedge-shaped bonds indicate that the substituents are positioned above the plane.

14. A compound according to claim 1 for its use in therapy.

15. A compound according to claim 1 for its use as proapoptotic agent.

16. A pharmaceutical composition comprising as the active ingredient, at least one compound according to claim 1.

17. A combination of an effective amount of a compound of formula (I) and (V) and at least one additional therapeutic agent selected among chemotherapeutics; apoptosis modulators; antimicrobial, antiviral, antifungal and anti-inflammatory agents.

18. A combination of an effective amount of a compound of formula (I) and (V) and at least one additional therapeutic agent selected among chemotherapeutics and apoptosis modulators for treating cancer.

19. A method for leukemia and myeloma which comprises administering to a subject in need thereof a compound according to claim 1.

* * * * *